US008900791B2

(12) United States Patent
Tsuchimura et al.

(10) Patent No.: US 8,900,791 B2
(45) Date of Patent: Dec. 2, 2014

(54) ACTINIC RAY-SENSITIVE OR RADIATION-SENSITIVE RESIN COMPOSITION AND METHOD OF FORMING PATTERN WITH THE COMPOSITION

(75) Inventors: Tomotaka Tsuchimura, Haibara-gun (JP); Koji Shirakawa, Haibara-gun (JP); Toru Tsuchihashi, Haibara-gun (JP); Hideaki Tsubaki, Haibara-gun (JP)

(73) Assignee: FUJIFILM Corporation, Tokyo (JP)

( * ) Notice: Subject to any disclaimer, the term of this patent is extended or adjusted under 35 U.S.C. 154(b) by 489 days.

(21) Appl. No.: 13/071,153

(22) Filed: Mar. 24, 2011

(65) Prior Publication Data

US 2011/0171577 A1 Jul. 14, 2011

Related U.S. Application Data

(63) Continuation of application No. PCT/JP2009/067292, filed on Sep. 28, 2009.

(30) Foreign Application Priority Data

Sep. 26, 2008 (JP) ................................ 2008-249192
Feb. 23, 2009 (JP) ................................ 2009-039905

(51) Int. Cl.

| | |
|---|---|
| ***G03F 7/004*** | (2006.01) |
| ***G03F 7/028*** | (2006.01) |
| ***C07C 309/25*** | (2006.01) |
| ***C07C 309/28*** | (2006.01) |
| ***C07C 309/42*** | (2006.01) |
| ***C07C 309/29*** | (2006.01) |
| ***C07C 309/35*** | (2006.01) |
| ***C07C 309/38*** | (2006.01) |
| ***C07C 309/39*** | (2006.01) |
| ***C07C 309/44*** | (2006.01) |
| ***C07C 309/59*** | (2006.01) |
| ***C07C 323/66*** | (2006.01) |
| ***C07C 381/12*** | (2006.01) |
| ***C07D 209/82*** | (2006.01) |
| ***C07D 339/08*** | (2006.01) |
| ***G03F 7/038*** | (2006.01) |
| ***G03F 7/039*** | (2006.01) |

(52) U.S. Cl.

CPC ............. *C07C 309/42* (2013.01); *C07C 309/25* (2013.01); *C07C 309/29* (2013.01); *C07C 309/35* (2013.01); *C07C 309/38* (2013.01); *C07C 309/39* (2013.01); *C07C 309/44* (2013.01); *C07C 309/59* (2013.01); *C07C 323/66* (2013.01); *C07C 381/12* (2013.01); *C07C 2101/02* (2013.01); *C07C 2101/04* (2013.01); *C07C 2101/08* (2013.01); *C07C 2101/14* (2013.01); *C07C 2101/18* (2013.01); *C07C 2102/28* (2013.01); *C07C 2102/42* (2013.01); *C07C 2102/44* (2013.01); *C07C 2103/24* (2013.01); *C07C 2103/28* (2013.01); *C07C 2103/74* (2013.01); *C07D 209/82* (2013.01); *C07D 339/08* (2013.01); *G03F 7/0045* (2013.01); *G03F 7/0382* (2013.01); *G03F 7/0392* (2013.01); *G03F 7/0397* (2013.01); *Y10S 430/122* (2013.01)

USPC ......... 430/270.1; 430/325; 430/326; 430/921

(58) Field of Classification Search

USPC .............. 430/270.1, 325, 326, 913, 914, 921; 549/16, 17, 26, 43; 544/145; 546/197; 548/526; 568/21, 23, 22, 25

See application file for complete search history.

(56) References Cited

U.S. PATENT DOCUMENTS

| | | | | |
|---|---|---|---|---|
| 5,347,063 | A | 9/1994 | Shen et al. | |
| 5,679,496 | A * | 10/1997 | Ohsawa et al. | 430/270.1 |
| 6,200,729 | B1 | 3/2001 | Aoai et al. | |
| 6,265,135 | B1 | 7/2001 | Kodama et al. | |
| 6,548,221 | B2 | 4/2003 | Uetani et al. | |

(Continued)

FOREIGN PATENT DOCUMENTS

| | | |
|---|---|---|
| EP | 0 869 393 A1 | 10/1998 |
| EP | 1 480 078 A1 | 11/2004 |

(Continued)

OTHER PUBLICATIONS

Yamaguchi et al., JP2009053518A (English Translation), 2011.*

(Continued)

*Primary Examiner* — Anca Eoff
(74) *Attorney, Agent, or Firm* — Sughrue Mion, PLLC

(57) ABSTRACT

An actinic ray-sensitive or radiation-sensitive resin composition includes any of the compounds of general formula (I) below;

(I)

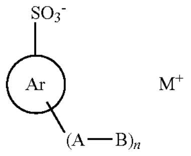

wherein:

Ar represents an aromatic ring that may have a substituent other than the -(A-B) groups;

n is an integer of 1 or greater;

A represents any one, or a combination of two or more members selected from a single bond, an alkylene group, —O—, —S—, —C(═O)—, —S(═O)—, —S(═O)$_2$— and —OS(═O)$_2$—, provided that —C(═O)O— is excluded;

B represents a group containing a hydrocarbon group having 4 or more carbon atoms wherein either a tertiary or a quaternary carbon atom is contained, when n is 2 or greater, the two or more -(A-B) groups may be identical to or different from each other; and $M^+$ represents an organic onium ion.

21 Claims, No Drawings

(56) References Cited

U.S. PATENT DOCUMENTS

| | | | | |
|---|---|---|---|---|
| 6,680,157 | B1 | 1/2004 | Fedynyshyn | |
| 7,341,817 | B2 | 3/2008 | Wada et al. | |
| 8,034,537 | B2 | 10/2011 | Fukuhara et al. | |
| 8,343,708 | B2 | 1/2013 | Fukuhara et al. | |
| 2005/0014095 | A1 | 1/2005 | Yamaguchi et al. | |
| 2005/0123859 | A1 | 6/2005 | Wada et al. | |
| 2010/0112477 | A1 | 5/2010 | Fukuhara et al. | |
| 2012/0003585 | A1* | 1/2012 | Tsubaki et al. | 430/286.1 |
| 2012/0034564 | A1 | 2/2012 | Fukuhara et al. | |

FOREIGN PATENT DOCUMENTS

| | | | | |
|---|---|---|---|---|
| EP | 1 536 285 | A2 | | 6/2005 |
| JP | 10-333326 | | * | 12/1998 |
| JP | 2000-053601 | A | | 2/2000 |
| JP | 2000-187330 | A | | 7/2000 |
| JP | 2000-267282 | A | | 9/2000 |
| JP | 2003-267949 | A | | 9/2003 |
| JP | 2005-173549 | A | | 6/2005 |
| JP | 2006-47533 | A | | 2/2006 |
| JP | 2008-268931 | A | | 11/2008 |
| JP | 2009-053518 | A | | 3/2009 |
| JP | 2009053518 | A | * | 3/2009 |

OTHER PUBLICATIONS

Japanese Office Action issued in application No. 2009-039905 dated Jun. 4, 2013.

* cited by examiner

ACTINIC RAY-SENSITIVE OR RADIATION-SENSITIVE RESIN COMPOSITION AND METHOD OF FORMING PATTERN WITH THE COMPOSITION

CROSS-REFERENCE TO RELATED APPLICATIONS

This is a Continuation Application of PCT Application No. PCT/JP2009/067292, filed Sep. 28, 2009, which was published under PCT Article 21(2) in English.

This application is based upon and claims the benefit of priority from prior Japanese Patent Applications No. 2008-249192, filed Sep. 26, 2008; and No. 2009-039905, filed Feb. 23, 2009, the entire contents of both of which are incorporated herein by reference.

BACKGROUND OF THE INVENTION

1. Field of the Invention

The present invention relates to an actinic ray-sensitive or radiation-sensitive resin composition that when exposed to actinic rays or radiation (electron beams, X-rays, EUV, UV, etc.), makes a reaction to thereby have its properties changed and also relates to a method of forming a pattern by use of the composition. More particularly, the present invention relates to an actinic ray-sensitive or radiation-sensitive resin composition employed in a semiconductor production process for an IC or the like, a circuit board production process for a liquid crystal, a thermal head or the like and other photofabrication processes as well as in lithographic printing plates and thermosetting compositions, and also relates to a method of forming a pattern by use of the composition.

In the present invention, the terms "actinic rays" and "radiation" mean, for example, a mercury lamp bright line spectrum, far-ultraviolet rays represented by an excimer laser, extreme ultraviolet rays, X-rays, electron beams and the like. In the present invention, the term "light" means actinic rays or radiation.

2. Description of the Related Art

A chemical amplification resist composition is a pattern forming material that is capable of, upon exposure to far ultraviolet rays or other radiation, generating an acid at the exposed area and, by a reaction catalyzed by the acid, changing the solubility in a developer between the area having been exposed to actinic radiation and the nonexposed area to thereby attain pattern formation on a substrate.

In using a KrF excimer laser as an exposure light source, a resin whose fundamental skeleton consists of a poly(hydroxystyrene) exhibiting a low absorption mainly in the region of 248 nm is employed as a major component of the composition. Accordingly, there can be attained a high sensitivity, high resolving power and favorable pattern formation. Thus, a system superior to the conventional naphthoquinone diazide/novolak resin system is realized.

On the other hand, in using a light source of a further shorter wavelength, for example, an ArF excimer laser (193 nm) as an exposure light source, as the compounds having aromatic groups inherently exhibit a sharp absorption in the region of 193 nm, the above-mentioned chemical amplification system has not been satisfactory.

Therefore, resists for an ArF excimer laser containing a resin with an alicyclic hydrocarbon structure have been developed.

With respect to an acid generator being a major constituent of any of the chemical amplification resists, using a triphenylsulfonium salt as the same is generally known (see, for example, patent reference 1).

However, this acid generator is unsatisfactory in many respects. Accordingly, it is desired to develop a photosensitive composition enhanced in the sensitivity, resolution, pattern profile, roughness characteristic, etc. by improving the acid generator.

In particular, the roughness characteristic and resolution become important as the pattern dimension is reduced. Accordingly, in the lithography using X-rays, electron beams or EUV, as forming a pattern reduced to several ten nanometers is targeted, it is required to ensure excellence in especially the resolution and roughness characteristic.

When use is made of, for example, a light source emitting electron beams, X-rays or EUV, the exposure is carried out in vacuum. This would cause any low-boiling-point compounds, such as solvents, and resist materials decomposed by high energy to evaporate to thereby dirty the exposure apparatus. This outgas problem is attracting greater attention. In recent years, various researches have been made on the reduction of the outgas. The researches include a proposal to inhibit the evaporation of low-molecular compounds by providing a top coat layer (see, for example, patent reference 2) and a proposal to add a radical trapping agent for inhibition of any polymer decomposition (see, for example, patent reference 3). For the acid generator as well, an ingenuity for reduction of the outgas is demanded.

PRIOR ART REFERENCES

Patent reference 1: U.S. Pat. No. 6,548,221
Patent reference 2: EP 1480078
Patent reference 3: U.S. Pat. No. 6,680,157

BRIEF SUMMARY OF THE INVENTION

It is objects of the present invention to provide an actinic ray-sensitive or radiation-sensitive resin composition excelling in the sensitivity, resolution, roughness characteristic, pattern profile and outgas characteristic and provide a method of forming a pattern by use of the composition.

These objects can be attained by using as the acid generator a novel compound obtained by introducing a specified substituent in a sulfonate anion so that the diffusion of any generated acid is inhibited to thereby enhance the resolution and roughness characteristic of the photosensitive composition.

That is, the above objects can be attained by the present invention characterized by the following features.

(1) An actinic ray-sensitive or radiation-sensitive resin composition comprising any of the compounds (A1) of general formula (I) below.

(I)

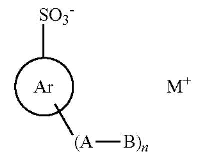

In the formula,

Ar represents an aromatic ring that may have a substituent other than the -(A-B) groups, and n is an integer of 1 or greater.

A represents any one, or a combination of two or more members selected from a single bond, an alkylene group, —O—, —S—, —C(═O)—, —S(═O)—, —S(═O)$_2$— and —OS(═O)$_2$—, provided that —C(═O)O— is excluded.

B represents a group containing a hydrocarbon group having 4 or more carbon atoms wherein either a tertiary or a quaternary carbon atom is contained.

When n is 2 or greater, the two or more -(A-B) groups may be identical to or different from each other.

$M^+$ represents an organic onium ion.

(2) The actinic ray-sensitive or radiation-sensitive resin composition according to item (1) above, wherein in the general formula (I), B represents a cycloaliphatic group having 4 or more carbon atoms.

(3) The actinic ray-sensitive or radiation-sensitive resin composition according to item (1) or (2) above, characterized by further containing a resin (B) that is decomposed by the action of an acid to thereby exhibit an increased solubility in an alkali developer.

(4) The actinic ray-sensitive or radiation-sensitive resin composition according to item (1) or (2) above, characterized by further containing a resin (C) soluble in an alkali developer and an acid crosslinking agent (D) capable of crosslinking with the resin soluble in an alkali developer by the action of an acid.

(5) The actinic ray-sensitive or radiation-sensitive resin composition according to item (3) above, wherein the resin (B) contains a repeating unit having a hydroxystyrene structure.

(6) The actinic ray-sensitive or radiation-sensitive resin composition according to item (3) above, wherein the resin (B) contains a repeating unit having a cyclic hydrocarbon structure of a single ring or multiple rings.

(7) The actinic ray-sensitive or radiation-sensitive resin composition according to item (3) above, wherein the resin (B) contains a repeating unit having an alcoholic hydroxyl group.

(8) The actinic ray-sensitive or radiation-sensitive resin composition according to item (7) above, wherein the repeating unit having an alcoholic hydroxyl group of the resin (B) is a repeating unit having at least one member selected from among a monohydroxyadamantane structure, a dihydroxyadamantane structure and a trihydroxyadamantane structure.

(9) The actinic ray-sensitive or radiation-sensitive resin composition according to item (3) above, wherein the resin (B) contains a repeating unit having a lactone structure.

(10) The actinic ray-sensitive or radiation-sensitive resin composition according to item (3) above, wherein the resin (B) is a resin containing at least one methacrylic ester repeating unit or at least one acrylic ester repeating unit.

(11) The actinic ray-sensitive or radiation-sensitive resin composition according to item (3) above, wherein the resin (B) has a fluorine atom in its principal chain or side chain.

(12) The actinic ray-sensitive or radiation-sensitive resin composition according to item (3) above, characterized in that the resin (B) has a hexafluoro-2-propanol structure.

(13) The actinic ray-sensitive or radiation-sensitive resin composition according to any of items (5) to (12) above, further containing a dissolution inhibiting compound of 3000 or less molecular weight (E) that is decomposed by the action of an acid to thereby increase the solubility in an alkali developer.

(14) The actinic ray-sensitive or radiation-sensitive resin composition according to any of items (5) to (13) above, further containing a basic compound (F) and/or a fluorinated and/or siliconized surfactant (G).

(15) The actinic ray-sensitive or radiation-sensitive resin composition according to item (5) above, wherein the resin (B) contains at least one repeating unit selected from among 2-alkyl-2-adamantyl (meth)acrylates and dialkyl(1-adamantyl)methyl (meth)acrylates, at least one repeating unit having a lactone structure and at least one repeating unit having two or more hydroxyl groups.

(16) The actinic ray-sensitive or radiation-sensitive resin composition according to item (15) above, wherein the resin (B) further contains a carboxylated repeating unit.

(17) The actinic ray-sensitive or radiation-sensitive resin composition according to item (5) above, wherein the resin (B) contains at least one repeating unit selected from among 2-alkyl-2-adamantyl (meth)acrylates and dialkyl(1-adamantyl)methyl (meth)acrylates and at least one repeating unit having a hydroxystyrene structure.

(18) A method of forming a pattern, comprising the steps of forming the actinic ray-sensitive or radiation-sensitive resin composition according to any of items (1) to (17) above into a film, exposing the film and developing the exposed film.

(19) The method of forming a pattern according to item (18) above, wherein the exposure is carried out by use of X-rays, electron beams or EUV.

(20) A compound of general formula (I) below.

(I)

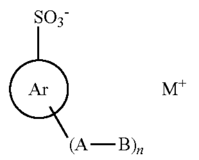

In the formula,

Ar represents an aromatic ring that may have a substituent other than the -(A-B) groups, and n is an integer of 1 or greater.

A represents any one, or a combination of two or more members selected from among a single bond, an alkylene group, —O—, —S—, —C(═O)—, —S(═O)—, —S(═O)$_2$— and —OS(═O)$_2$— (provided that —C(═O)O— is excluded).

B represents a group containing a hydrocarbon group having 4 or more carbon atoms wherein either a tertiary or a quaternary carbon atom is contained.

When n is 2 or greater, the two or more -(A-B) groups may be identical to or different from each other.

$M^+$ represents an organic onium ion.

(21) A compound of general formula (I) below that when exposed to actinic rays or radiation, generates an acid.

(I)

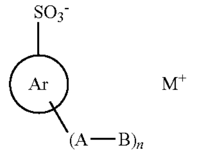

In the formula,

Ar represents an aromatic ring that may have a substituent other than the -(A-B) groups, and n is an integer of 1 or greater.

A represents any one, or a combination of two or more members selected from among a single bond, an alkylene group, —O—, —S—, —C(═O)—, —S(═O)—, —S(═O)$_2$— and —OS(═O)$_2$— (provided that —C(═O)O— is excluded).

B represents a group containing a hydrocarbon group having 4 or more carbon atoms wherein either a tertiary or a quaternary carbon atom is contained.

When n is 2 or greater, the two or more -(A-B) groups may be identical to or different from each other.

$M^+$ represents an organic onium ion.

(22) The compound of general formula (I) according to item (20) or (21) above, wherein in the general formula (I), B represents a cycloaliphatic group having 4 or more carbon atoms.

(23) The compound of general formula (I) according to any of items (20) to (22) above, wherein in the general formula (I), A represents a single bond.

Advantages of the Invention

The present invention has made it feasible to provide an actinic ray-sensitive or radiation-sensitive resin composition excelling in the sensitivity, resolution, roughness characteristic and outgas characteristic and further provide a method of forming a pattern by use of the composition.

DETAILED DESCRIPTION OF THE INVENTION

The present invention will be described in detail below.

With respect to the expression of a group (atomic group) used in this specification, the expression even when there is no mention of "substituted and unsubstituted" encompasses groups not only having no substituent but also having substituents. For example, the expression "alkyl groups" encompasses not only alkyls having no substituent (unsubstituted alkyls) but also alkyls having substituents (substituted alkyls).

The present invention is based on the finding of the novel compounds of the general formula (I) above (hereinafter also referred to as "acid generators (A1)") as compounds (acid generators) useful in an actinic ray-sensitive or radiation-sensitive resin composition that when exposed to actinic rays or radiation, generate an acid.

The photosensitive composition containing any of the acid generators (A1) may consist of either a positive photosensitive composition or a negative photosensitive composition.

The positive photosensitive composition (more preferably a positive resist composition) of the present invention may contain an acid generator (A1) and a resin (B) that is decomposed by the action of an acid to thereby exhibit an increased solubility in an alkali developer and according to necessity may further contain a dissolution inhibiting compound of 3000 or less molecular weight (E) that is decomposed by the action of an acid to thereby increase the solubility in an alkali developer.

The negative photosensitive composition (more preferably a negative resist composition) of the present invention may contain an acid generator (A1), a resin (C) soluble in an alkali developer and an acid crosslinking agent (D) capable of crosslinking with the resin soluble in an alkali developer by the action of an acid.

[1] Compounds of General Formula (I) Below (Acid Generators (A1))

(I)

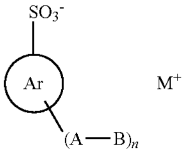

In the formula,

Ar represents an aromatic ring that may have a substituent other than the -(A-B) groups.

n is an integer of 1 or greater.

A represents any one, or a combination of two or more members selected from among a single bond, an alkylene group, —O—, —S—, —C(═O)—, —S(═O)—, —S(═O)$_2$— and —OS(═O)$_2$— (provided that —C(═O)O— is excluded).

B represents a group containing a hydrocarbon group having 4 or more carbon atoms wherein either a tertiary or a quaternary carbon atom is contained.

When n is 2 or greater, the two or more -(A-B) groups may be identical to or different from each other.

$M^+$ represents an organic onium ion.

The general formula (I) will be described in detail below.

The aromatic ring represented by Ar is preferably an aromatic ring having 6 to 30 carbon atoms. The aromatic ring may have a substituent other than the -(A-B) groups.

As the aromatic ring, there can be mentioned, for example, a benzene ring, a naphthalene ring, a pentalene ring, an indene ring, an azulene ring, a heptalene ring, an indecene ring, a perylene ring, a pentacene ring, an acenaphthalene ring, a phenanthrene ring, an anthracene ring, a naphthacene ring, a chrysene ring, a triphenylene ring, a fluorene ring, a biphenyl ring, a pyrrole ring, a furan ring, a thiophene ring, an imidazole ring, an oxazole ring, a thiazole ring, a pyridine ring, a pyrazine ring, a pyrimidine ring, a pyridazine ring, an iodolizine ring, an indole ring, a benzofuran ring, a benzothiophene ring, an isobenzofuran ring, a quinolizine ring, a quinoline ring, a phthalazine ring, a naphthyridine ring, a quinoxaline ring, a quinoxazoline ring, an isoquinoline ring, a carbazole ring, a phenanthridine ring, an acridine ring, a phenanthroline ring, a thianthrene ring, a chromene ring, a xanthene ring, a phenoxathiin ring, a phenothiazine ring, a phenazine ring or the like. Of these, a benzene ring, a naphthalene ring and an anthracene ring are preferred from the viewpoint of the simultaneous attainment of roughness improvement and sensitivity enhancement. A benzene ring is more preferred.

The aromatic ring may have a substituent other than the -(A-B) groups. As the substituent, there can be mentioned, for example, a halogen group such as a fluorine atom, a chlorine atom, a bromine atom or an iodine atom, an alkoxy group such as a methoxy group, an ethoxy group or a tert-butoxy group, an aryloxy group such as a phenoxy group or a p-tolyloxy group, an alkylthioxy group such as a methylthioxy group, an ethylthioxy group or a tert-butylthioxy group, an arylthioxy group such as a phenylthioxy group or a p-tolylthioxy group, an alkoxycarbonyl group such as a methoxycarbonyl group or a butoxycarbonyl group, a phenoxycarbonyl group, an acetoxy group, a linear or branched alkyl group such as a methyl group, an ethyl group, a propyl group, a butyl group, a heptyl group, a hexyl group, a dodecyl group or a 2-ethylhexyl group, an alkenyl group such as a vinyl group, a propenyl group or a hexenyl group, an alkynyl group such as an acetylene group, a propynyl group or a hexynyl group, an aryl group such as a phenyl group or a tolyl group, an acyl group such as a benzoyl group, an acetyl group or a toluoyl group, a hydroxyl group, a carboxyl group, a sulfonate group or the like. Of these, a linear or branched alkyl group is preferred from the viewpoint of roughness improvement.

It is preferred for A to consist of fewer atoms from the viewpoint of resolution and roughness.

Preferably, A represents a single bond, —O— or —S—. A single bond is especially preferred.

As the hydrocarbon group contained in the group containing a hydrocarbon group having 4 or more carbon atoms wherein either a tertiary or a quaternary carbon atom is contained, represented by B, there can be mentioned a noncyclic hydrocarbon group or a cycloaliphatic group.

As the noncyclic hydrocarbon group having 4 or more carbon atoms wherein either a tertiary or a quaternary carbon atom is contained, there can be mentioned a t-butyl group, a t-pentyl group, a neopentyl group, a s-butyl group, an isobutyl group, an isohexyl group, a 3,3-dimethylpentyl group, a 2-ethylhexyl group or the like. The noncyclic hydrocarbon group more preferably has 5 or more carbon atoms. The noncyclic hydrocarbon group may have a substituent. With respect to the upper limit of the number of carbon atoms of the noncyclic hydrocarbon group, the number is preferably 12 or less, more preferably 10 or less.

As the cycloaliphatic group having 4 or more carbon atoms, there can be mentioned a cycloalkyl group such as a cyclobutyl group, a cyclopentyl group, a cyclohexyl group, a cycloheptyl group or a cyclooctyl group, an adamantyl group, a norbornyl group, a bornyl group, a camphenyl group, a decahydronaphthyl group, a tricyclodecanyl group, a tetracyclodecanyl group, a camphoroyl group, a dicyclohexyl group, a pinenyl group or the like. The cycloaliphatic group may have a substituent. With respect to the upper limit of the number of carbon atoms of the cycloaliphatic group, the number is preferably 15 or less, more preferably 12 or less.

As a substituent that may be introduced in the noncyclic hydrocarbon group or cycloaliphatic group, there can be mentioned, for example, a halogen group such as a fluorine atom, a chlorine atom, a bromine atom or an iodine atom, an alkoxy group such as a methoxy group, an ethoxy group or a tert-butoxy group, an aryloxy group such as a phenoxy group or a p-tolyloxy group, an alkylthioxy group such as a methylthioxy group, an ethylthioxy group or a tert-butylthioxy group, an arylthioxy group such as a phenylthioxy group or a p-tolylthioxy group, an alkoxycarbonyl group such as a methoxycarbonyl group or a butoxycarbonyl group, a phenoxycarbonyl group, an acetoxy group, a linear or branched alkyl group such as a methyl group, an ethyl group, a propyl group, a butyl group, a heptyl group, a hexyl group, a dodecyl group or a 2-ethylhexyl group, a cycloalkyl group such as a cyclohexyl group, an alkenyl group such as a vinyl group, a propenyl group or a hexenyl group, an alkynyl group such as an acetylene group, a propynyl group or a hexynyl group, an aryl group such as a phenyl group or a tolyl group, a hydroxyl group, a carboxyl group, a sulfonate group, a carbonyl group or the like. Of these, a linear or branched alkyl group is preferred from the viewpoint of the simultaneous attainment of roughness improvement and sensitivity enhancement.

Specific examples of the groups having the above cycloaliphatic groups and noncyclic hydrocarbon groups will be shown below.

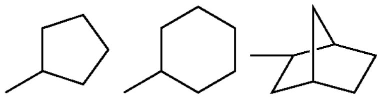

-continued

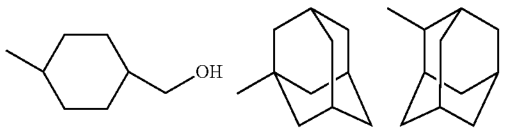

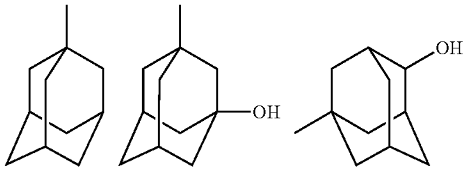

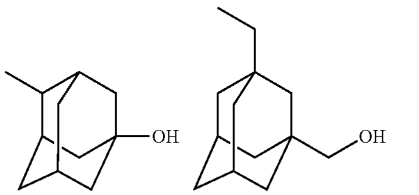

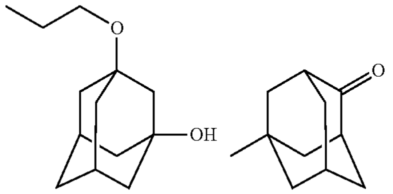

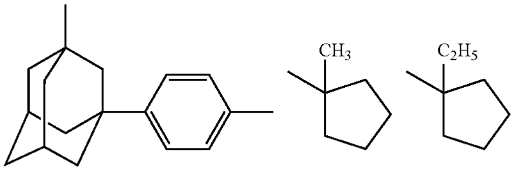

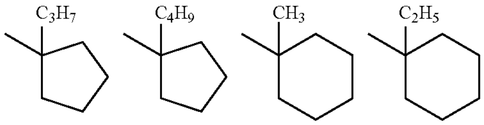

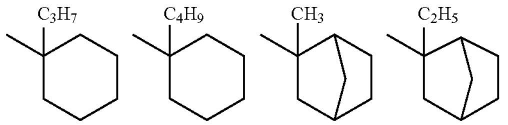

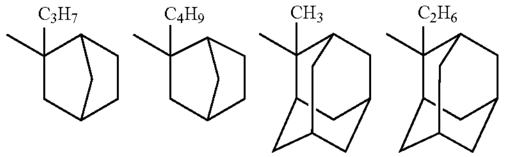

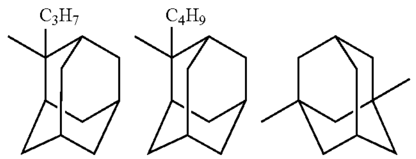

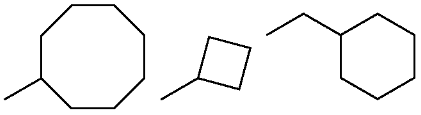

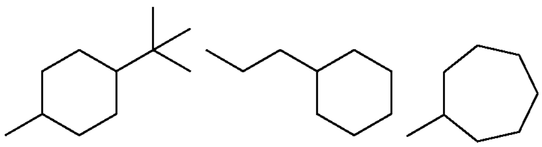

-continued
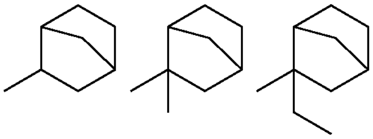
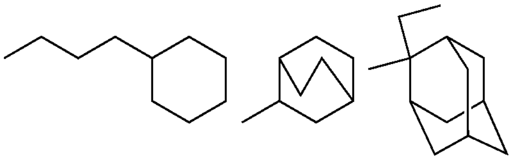
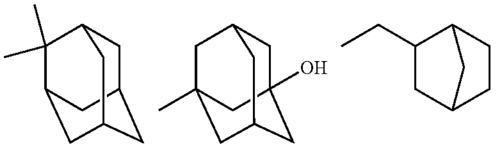
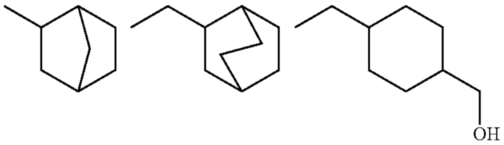
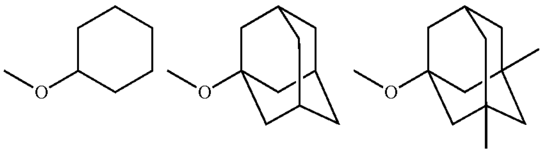
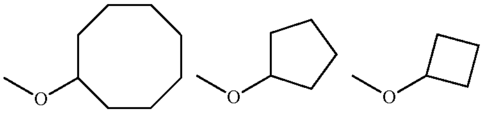
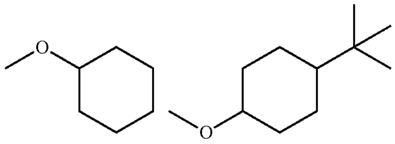
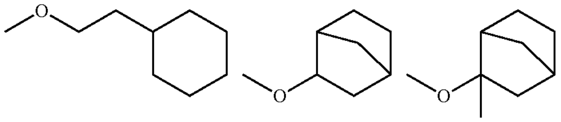
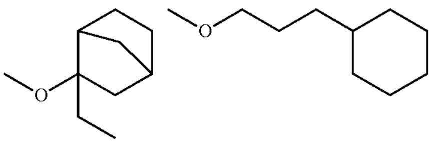
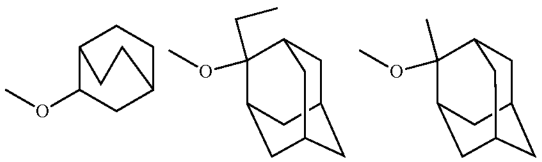
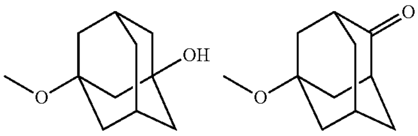
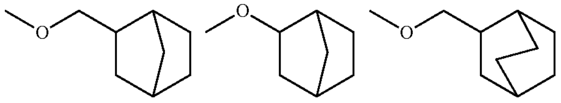
-continued
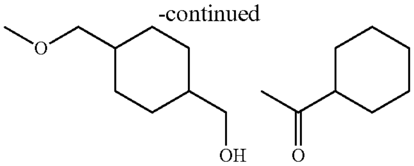
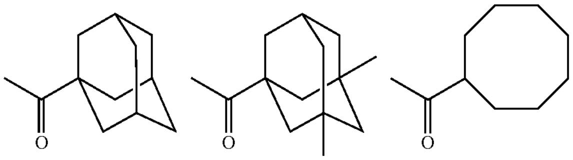
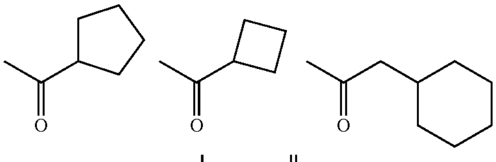
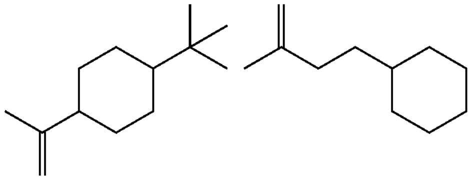
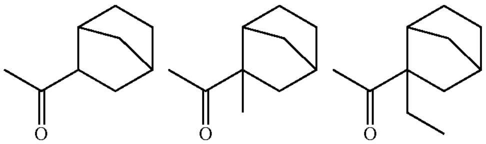
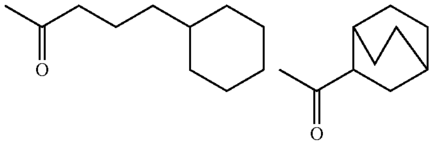
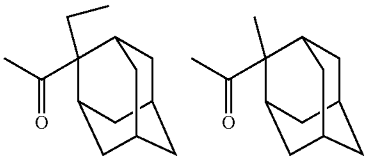
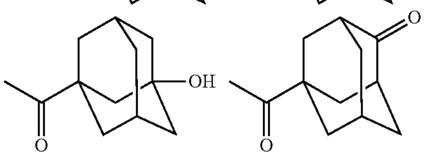
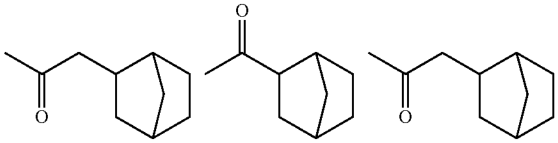
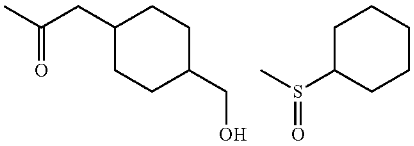
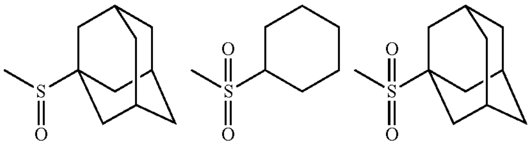
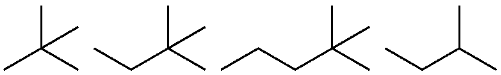

-continued
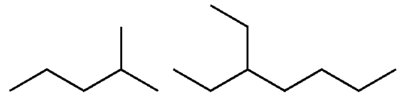
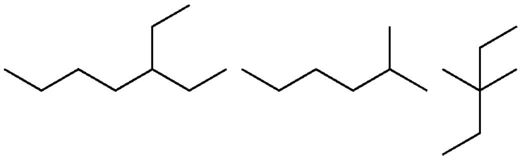
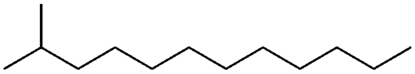
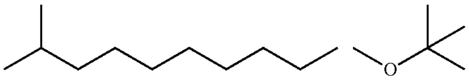
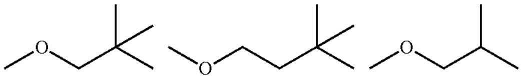
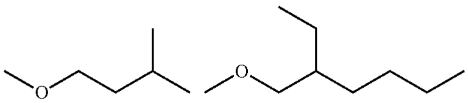
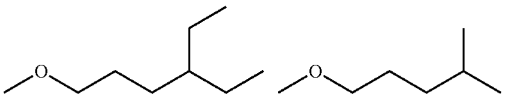
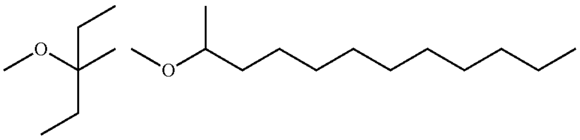
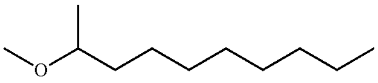
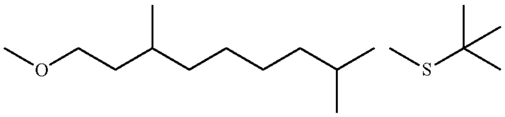
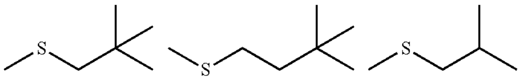
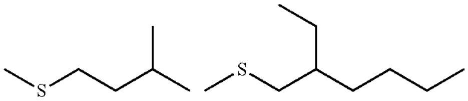
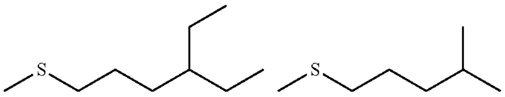
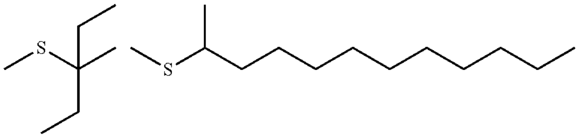
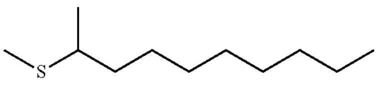
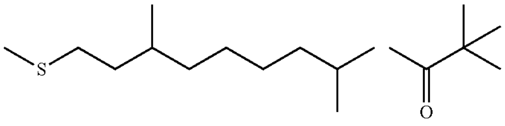
-continued
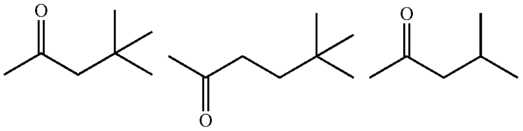
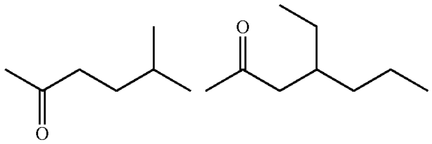
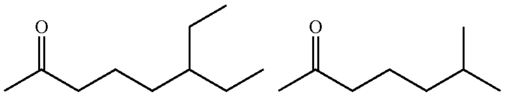
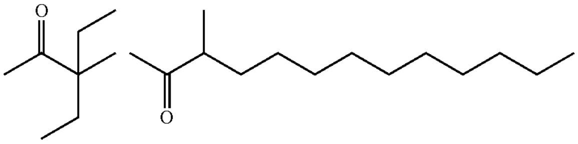
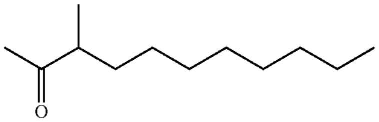
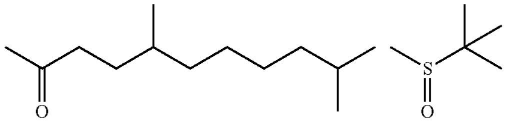
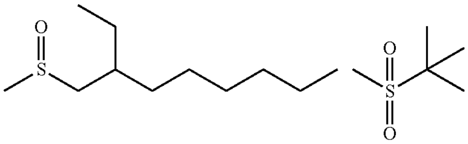
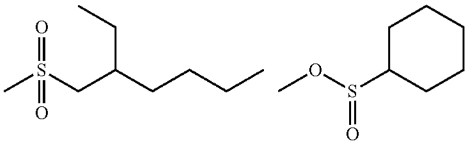
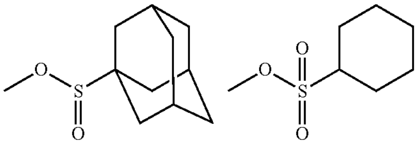
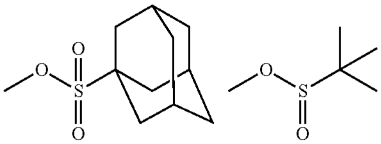
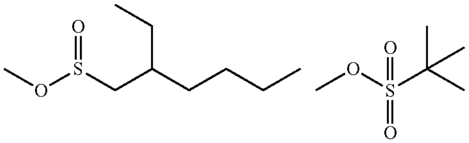
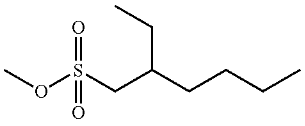
Among the above, the following structures are more preferred.

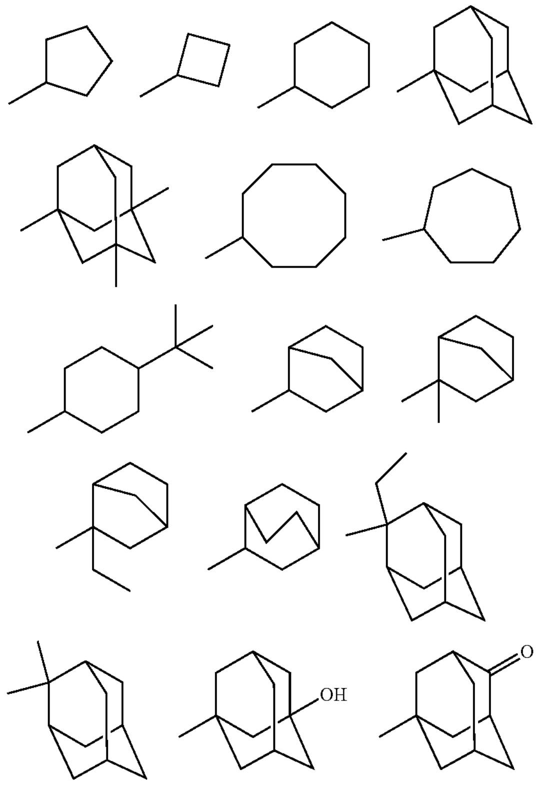

As the group containing a hydrocarbon group having 4 or more carbon atoms wherein either a tertiary or a quaternary carbon atom is contained, represented by B, the cycloaliphatic groups are preferred from the viewpoint of resolution and roughness. Among the cycloaliphatic groups, a cycloalkyl group, an adamantyl group and a norbornyl group are preferred from the viewpoint of roughness improvement. A cycloalkyl group is more preferred. Among cycloalkyl groups, a cyclohexyl group is most preferred.

In the general formula, n is an integer of 1 or greater. From the viewpoint of roughness improvement, 2 to 5 are preferred, and 2 to 4 are more preferred. Most preferably, n=3.

It is preferred for at least one o-position of the sulfonate anion to be substituted with the -(A-B) group from the viewpoint of roughness improvement. More preferably, two o-positions thereof are substituted with the -(A-B) groups.

As the sulfonate anions contained in the general formula (I), there can be mentioned the following.

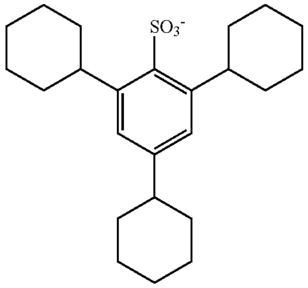

-continued

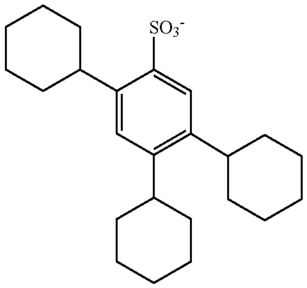

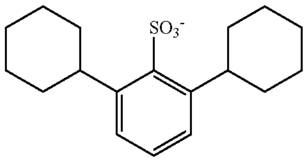

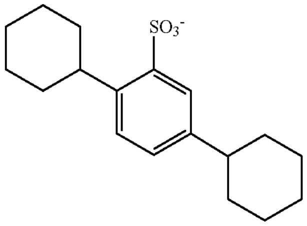

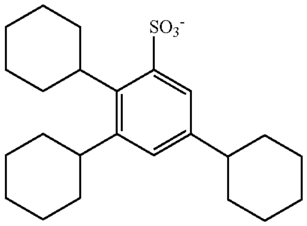

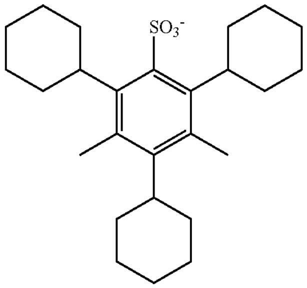

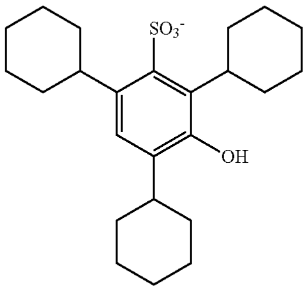

-continued
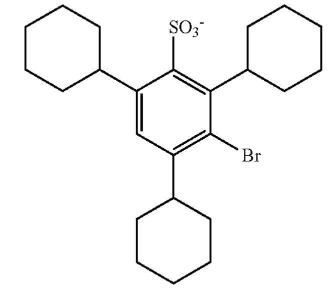
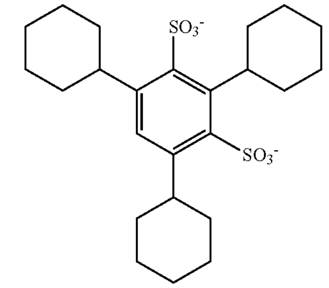
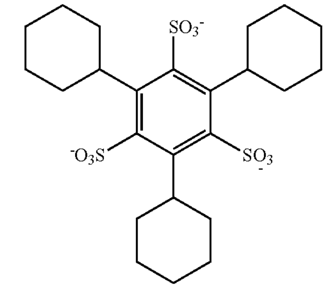
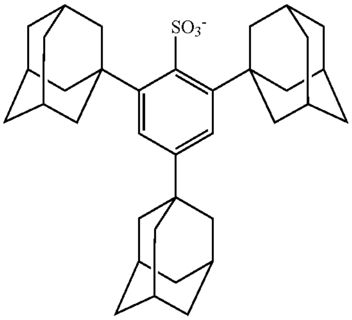
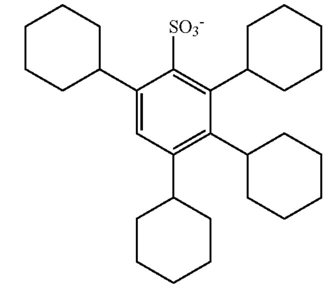
-continued
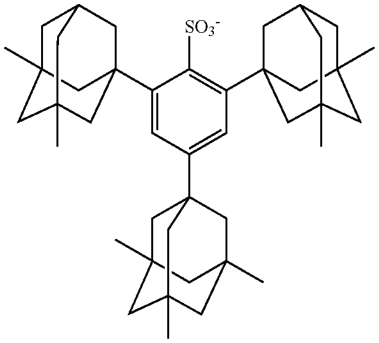
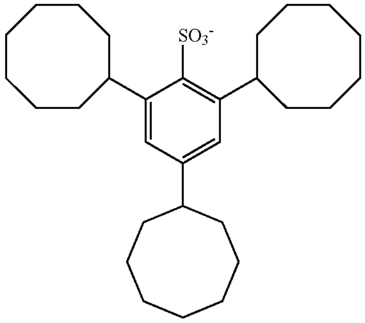
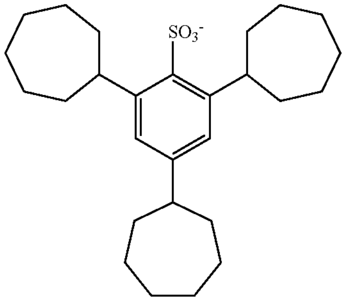
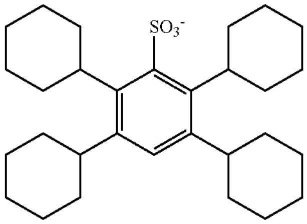
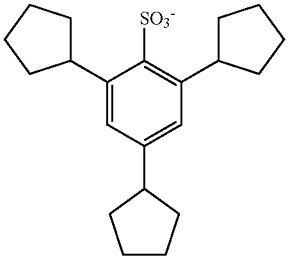
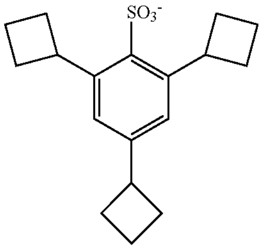

-continued
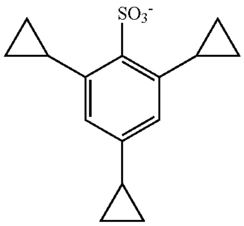
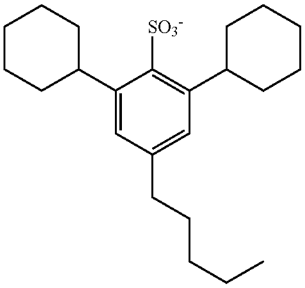
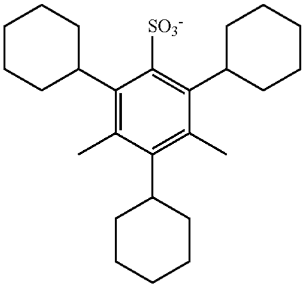
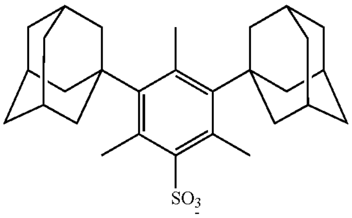
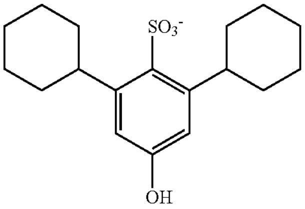
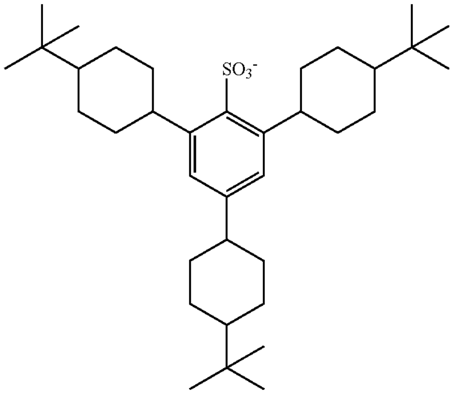
-continued
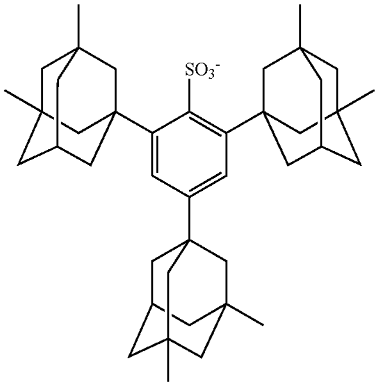
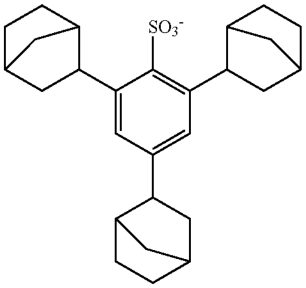
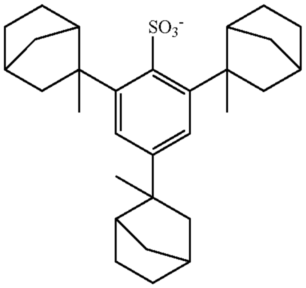
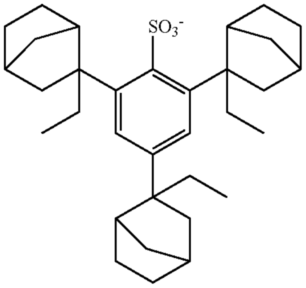
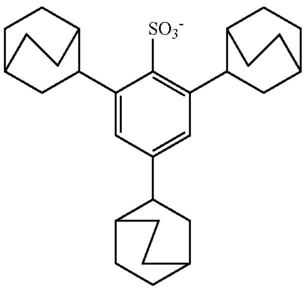

-continued
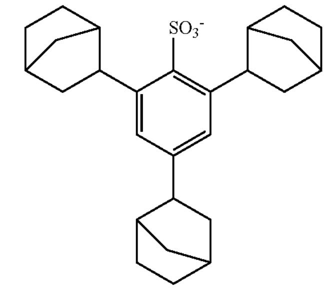
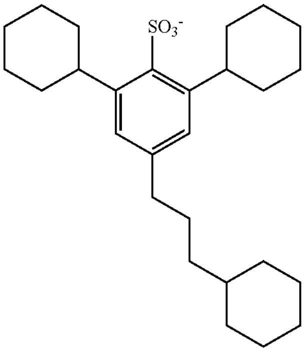
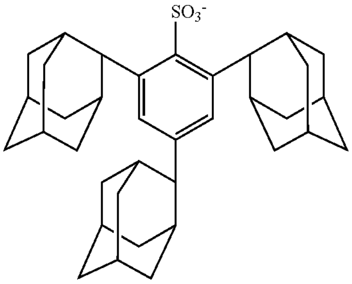
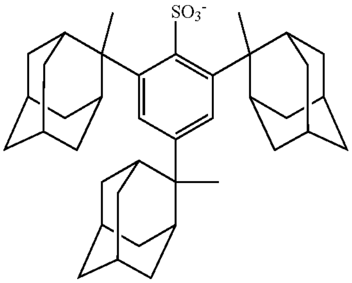
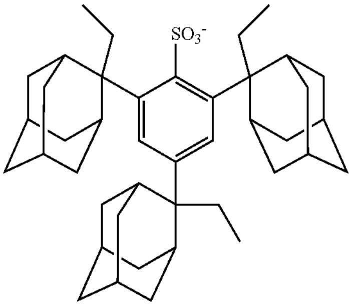
-continued
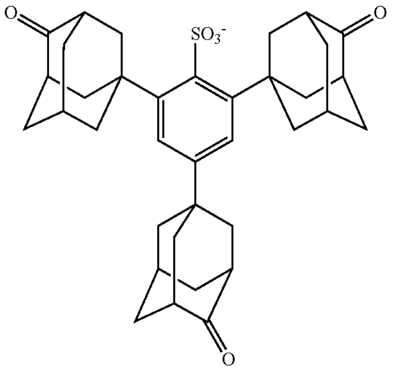
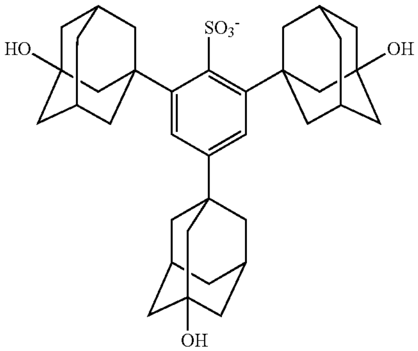
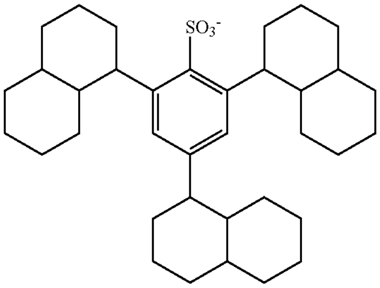
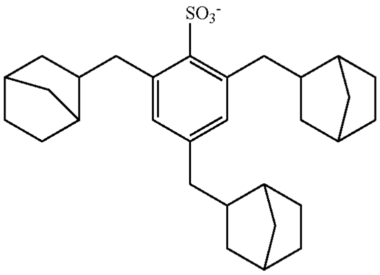
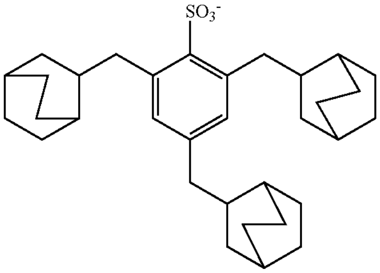

-continued
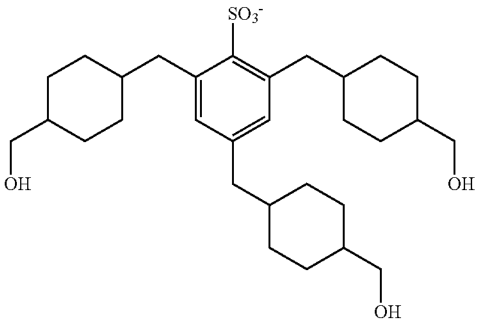
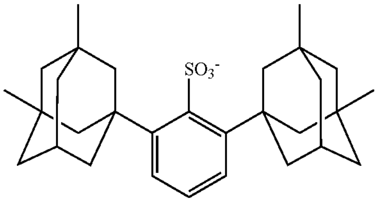
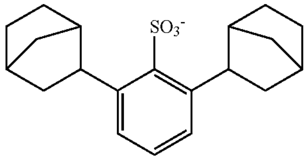
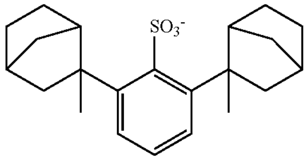
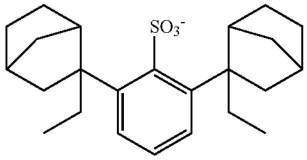
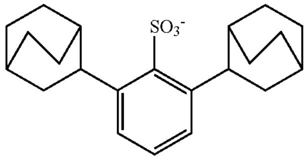
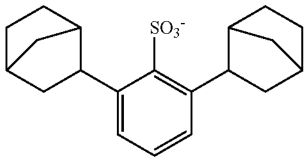
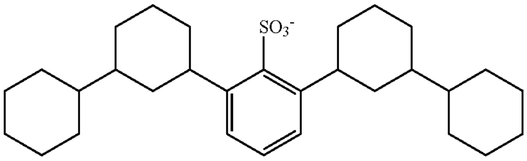
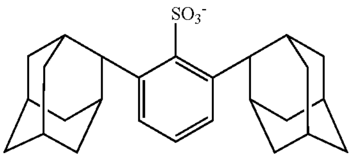
-continued
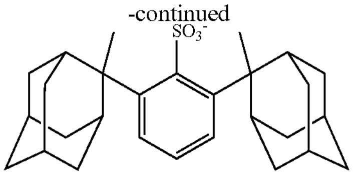
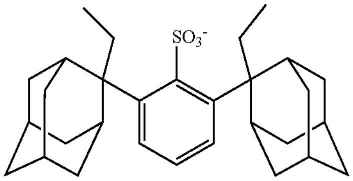
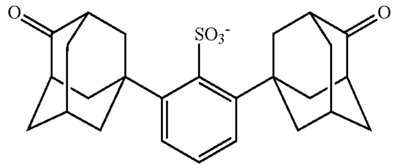
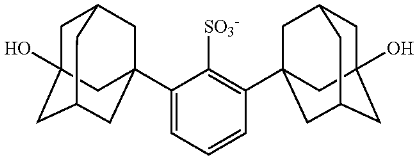
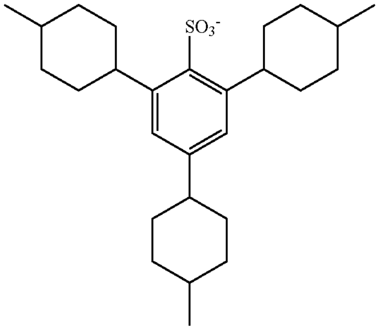
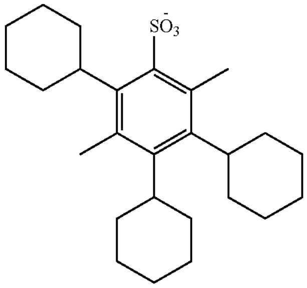
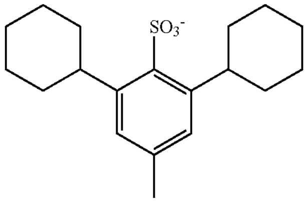
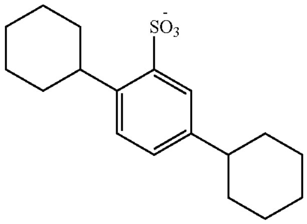

-continued
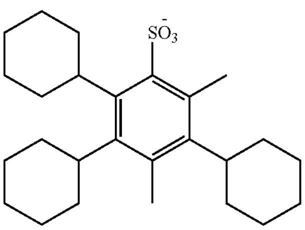
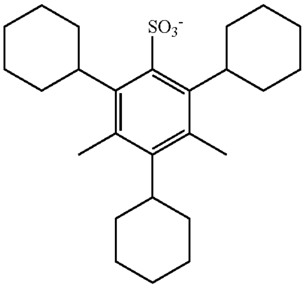
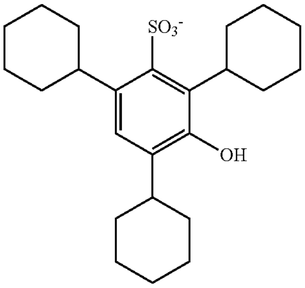
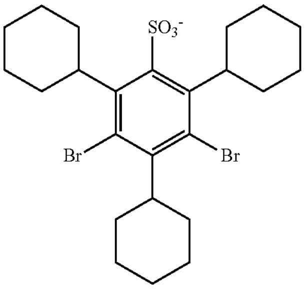
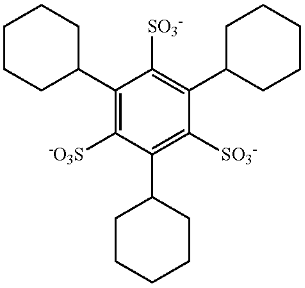
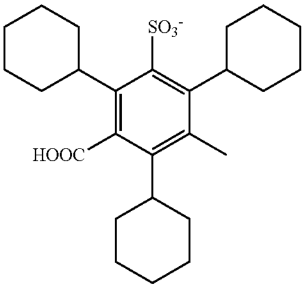
-continued
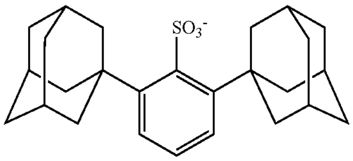
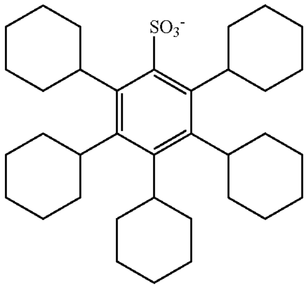
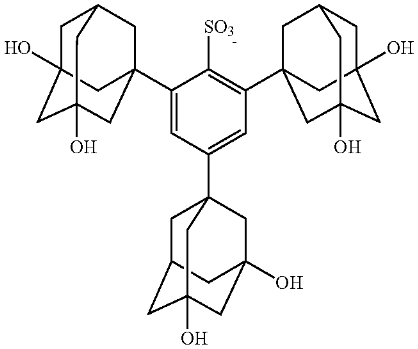
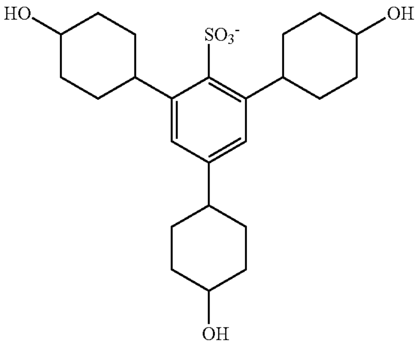
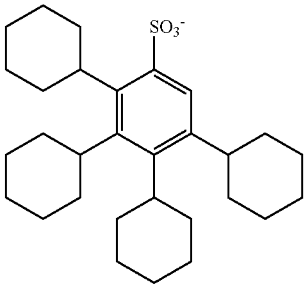
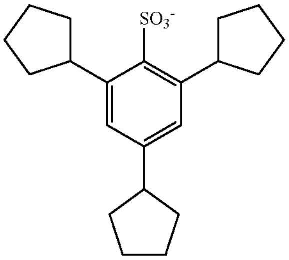

-continued
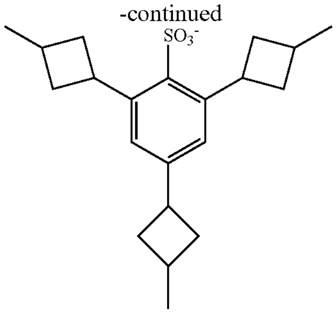
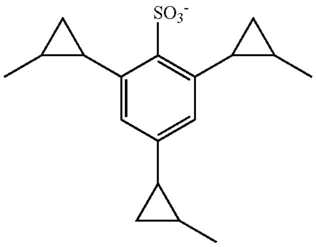
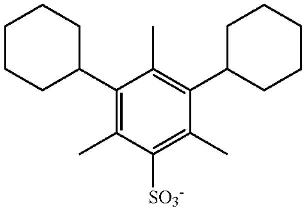
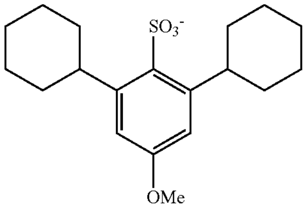
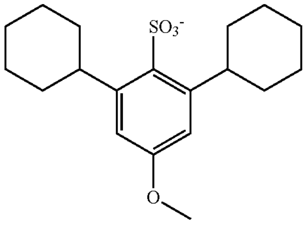
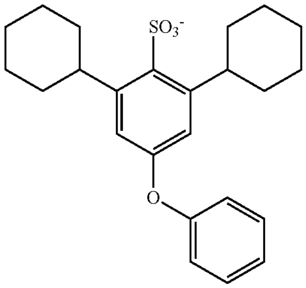
-continued
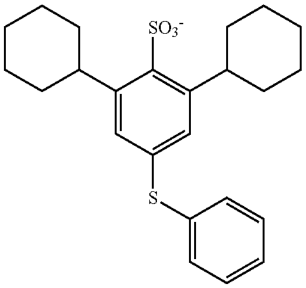
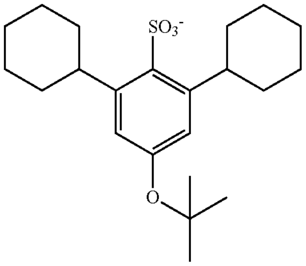
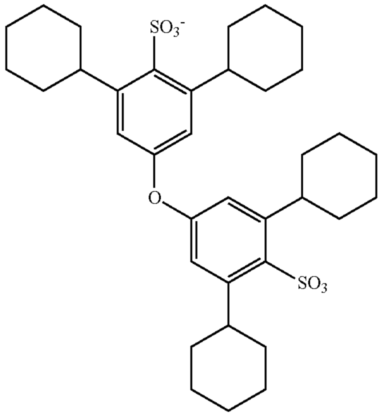
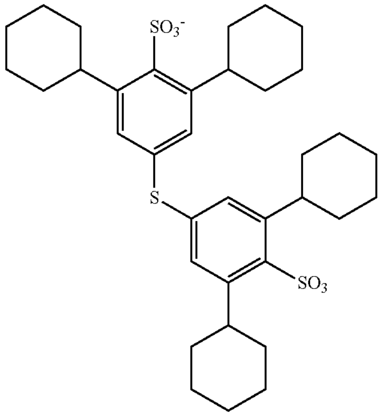
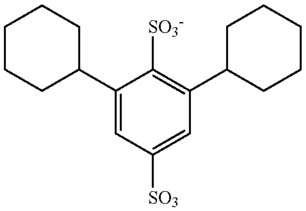

-continued
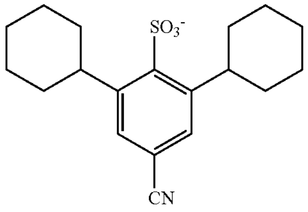
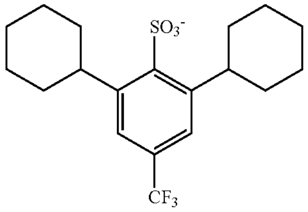
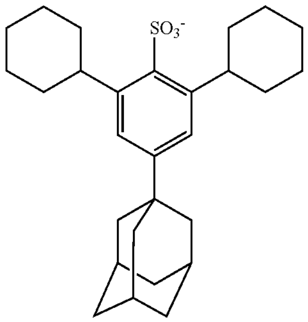
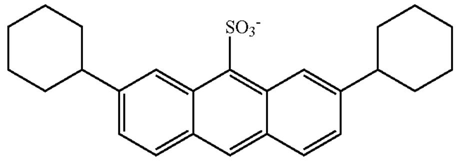
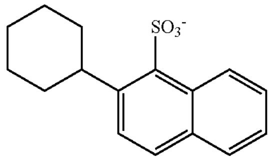
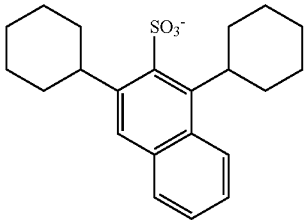
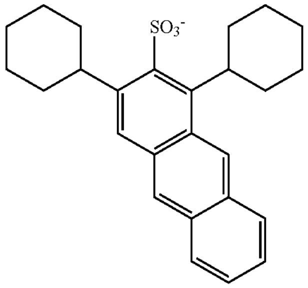
-continued
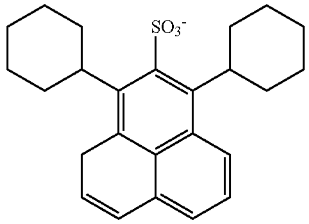
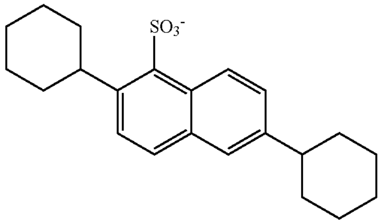
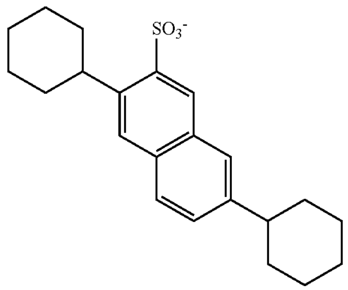
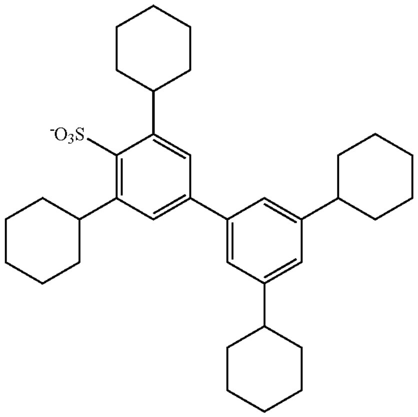
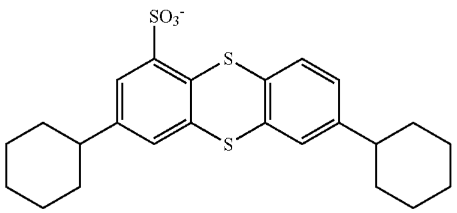
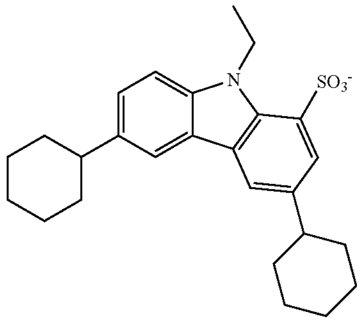

-continued

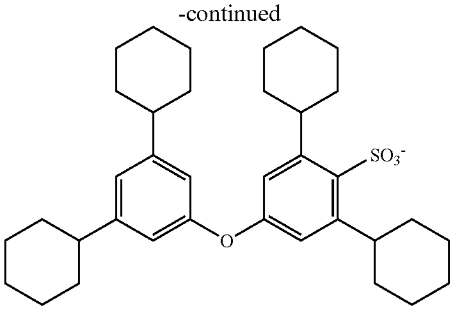

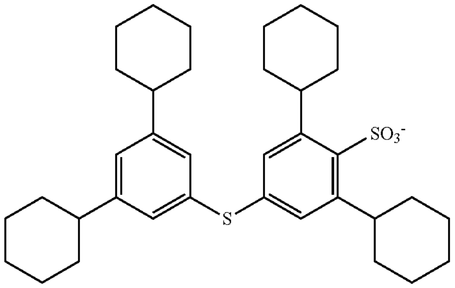

As preferred organic onium ions (counter cations) represented by $M^+$, there can be mentioned, for example, onium ions, such as iodonium, sulfonium, phosphonium, diazonium, ammonium, pyridinium, quinolinium, acridinium, oxonium, selenonium and arsonium. Among these, onium ions, such as iodonium, sulfonium, phosphonium, diazonium, quinolinium and acridinium, are preferred.

Moreover, there can be mentioned cations, such as the onium ions of Group 15 to 17 element onium salts described in, for example, JP-A-6-184170; the diazonium ions of diazonium salts described in, for example, S. I. Schlesinger, Photogr. Sci. Eng., 18, 387 (1974) and T. S. Baletal, Polymer, 21, 423 (1980); the ammonium ions of ammonium salts described in, for example, USPs 4,069,055, 4,069,056 and Re27,992 and JP-A-3-140140; the phosphonium ions of phosphonium salts described in, for example, D. C. Necker et al, Macromolecules, 17, 2468 (1984), C. S. Wen et al, Teh, Proc. Conf. Rad. Curing ASIA, p478, Tokyo, October (1988), U.S. Pat. Nos. 4,069,055 and 4,069,056 and JP-A-9-202873; the iodonium ions of iodonium salts described in, for example, J. V. Crivello et al, Macromolecules, 10(6), 1307 (1977), Chem. & Eng. News, Nov. 28, p31 (1988), EPs 104, 143, 339,049 and 410,201, and JP-A' s 2-150848 and 2-296514; the sulfonium ions of sulfonium salts described in, for example, J. V. Crivello et al, Polymer J. 17, 73 (1985), J. V. Crivello et al, J. Org. Chem., 43, 3055 (1978), W. R. Watt et al, J. Polymer Sci., Polymer Chem. Ed., 22, 1789 (1984), J. V. Crivello et al, Polymer Bull., 14, 279 (1985), J. V. Crivello et al, Macromolecules, 14(5), 1141 (1981), J. V. Crivello et al, J. Polymer Sci., Polymer Chem. Ed., 17, 2877 (1979), EPs 370,693, 161, 811, 410, 201, 339, 049, 233, 567, 297,443 and 297,442, U.S. Pat. Nos. 3,902,114, 4,933,377, 4,760,013, 4,734,444 and 2,833,827, and U.S. Pat. No. DEs 2,904,626, 3,604,580 and 3,604,581, and JP-A's 7-28237 and 8-27102; the quinolinium ions of quinolinium salts described in, for example, JP-A-9-221652; the selenonium ions of selenonium salts described in, for example, J. V. Crivello et al, Macromolecules, 10(6), 1307 (1977) and J. V. Crivello et al, J. Polymer Sci., Polymer Chem. Ed., 17, 1047 (1979); and the arsonium ions of arsonium salts described in, for example, C. S. Wen et al, Teh, Proc. Conf. Rad. Curing ASIA, p478, Tokyo, October (1988). These cations are nonlimiting.

As preferred counter cations, there can be mentioned, for example, the cations having the structures of formulae (II) to (VII) below.

$$R^1—N^+≡N \quad (II)$$

$$R^1—I^+—R^3 \quad (III)$$

(IV)

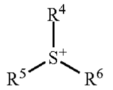

(V)

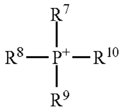

(VI)

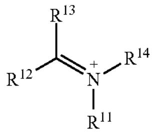

(VII)

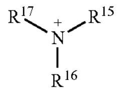

In the formulae (II) to (VII), each of $R^1$ to $R^3$ independently represents an aryl group. Each of $R^4$ to $R^6$ independently represents an alkyl group, an alkenyl group, an alkynyl group, an aryl group, a cyclohydrocarbon group or a heterocyclic group. Each of $R^7$ to $R^{11}$ independently represents an alkyl group, an alkenyl group, an alkynyl group, an aryl group, a cyclohydrocarbon group, a heterocyclic group, an alkoxy group or an aryloxy group. Each of $R^{12}$ to $R^{17}$ independently represents a hydrogen atom, a halogen atom or a monovalent organic group.

Each of the alkyl groups represented by $R^4$ to $R^{11}$ preferably has 1 to 30 carbon atoms, more preferably 1 to 20 carbon atoms and further preferably 1 to 8 carbon atoms. The alkyl groups may be linear or may have a substituent.

Each of the alkenyl groups represented by $R^4$ to $R^{11}$ preferably has 2 to 30 carbon atoms, more preferably 2 to 20 carbon atoms and further preferably 2 to 8 carbon atoms. The alkenyl groups may have a substituent.

Each of the alkynyl groups represented by $R^4$ to $R^{11}$ preferably has 2 to 30 carbon atoms, more preferably 2 to 20 carbon atoms and further preferably 2 to 8 carbon atoms. The alkynyl groups may have a substituent.

Each of the aryl groups represented by $R^1$ to $R^{11}$ preferably has 6 to 30 carbon atoms, more preferably 6 to 20 carbon atoms and further preferably 6 to 10 carbon atoms. The aryl groups may have a substituent.

Each of the cyclohydrocarbon groups represented by $R^4$ to $R^{11}$ preferably has 3 to 30 carbon atoms, more preferably 3 to 20 carbon atoms and further preferably 3 to 10 carbon atoms. The cyclohydrocarbon groups may have a substituent.

Each of the heterocyclic groups represented by $R^4$ to $R^{11}$ preferably has 4 to 30 carbon atoms, more preferably 4 to 20 carbon atoms and further preferably 4 to 10 carbon atoms. The heterocyclic groups may have a substituent. Preferably, the heteroatom contained in the heterocyclic groups is a nitrogen atom, an oxygen atom or a sulfur atom.

Each of the alkoxy groups represented by $R^7$ to $R^{11}$ preferably has 1 to 30 carbon atoms, more preferably 1 to 20 carbon atoms and further preferably 1 to 8 carbon atoms. The alkoxy groups may have any of substituents to be described hereinafter. The alkyl moiety of the alkoxy groups may be an alkenyl group, an alkynyl group, a cyclohydrocarbon group or a nonaromatic heterocyclic group.

Each of the aryloxy groups represented by $R^7$ to $R^{11}$ preferably has 6 to 30 carbon atoms, more preferably 6 to 20 carbon atoms and further preferably 6 to 10 carbon atoms. The aryloxy groups may have any of substituents to be described hereinafter. The aryl moiety of the aryloxy groups may be an aromatic heterocyclic group.

In the formula (III), if appropriate, $R^2$ and $R^3$ may be bonded to each other to thereby form a ring.

In the formula (IV), if appropriate, two or more of $R^4$ to $R^6$ may be bonded to each other to thereby form a ring.

In the formula (V), if appropriate, two or more of $R^7$ to $R^{10}$ may be bonded to each other to thereby form a ring.

In the formula (VI), if appropriate, two or more of $R^{11}$ to $R^{14}$ may be bonded to each other to thereby form a ring.

In the formula (VII), if appropriate, two or more of $R^{15}$ to $R^{17}$ may be bonded to each other to thereby form a ring.

The substituent that may be introduced in any of the above alkyl group, alkenyl group, alkynyl group, aryl group, cyclohydrocarbon group, heterocyclic group, alkoxy group or aryloxy group may be any of monovalent nonmetallic atomic groups excluding hydrogen. Preferred examples of the monovalent nonmetallic atomic groups include a halogen atom (—F, —Br, —Cl or —I), a hydroxyl group, an alkyl group, an aryl group, an alkenyl group, an alkynyl group, an alkoxy group, an aryloxy group, a mercapto group, an alkylthio group, an arylthio group, an alkyldithio group, an aryldithio group, an amino group, an N-alkylamino group, an N,N-dialkylamino group, an N-arylamino group, an N,N-diarylamino group, an N-alkyl-N-arylamino group, an acyloxy group, a carbamoyloxy group, an N-alkylcarbamoyloxy group, an N-arylcarbamoyloxy group, an N,N-dialkylcarbamoyloxy group, an N,N-diarylcarbamoyloxy group, an N-alkyl-N-arylcarbamoyloxy group, an alkylsulfoxy group, an arylsulfoxy group, an acylthio group, an acylamino group, an N-alkylacylamino group, an N-arylacylamino group, a ureido group, an N'-alkylureido group, an N',N'-dialkylureido group, an N'-arylureido group, an N',N'-diarylureido group, an N'-alkyl-N'-arylureido group, an N-alkylureido group, an N-arylureido group, an N'-alkyl-N-alkylureido group, an N'-alkyl-N-arylureido group, an N',N'-dialkyl-N-alkylureido group, an N',N'-dialkyl-N-arylureido group, an N'-aryl-N-alkylureido group, an N'-aryl-N-arylureido group, an N',N'-diaryl-N-alkylureido group, an N',N'-diaryl-N-arylureido group, an N'-alkyl-N'-aryl-N-alkylureido group, an N'-alkyl-N'-aryl-N-arylureido group, an alkoxycarbonylamino group, an aryloxycarbonylamino group, an N-alkyl-N-alkoxycarbonylamino group, an N-alkyl-N-aryloxycarbonylamino group, an N-aryl-N-alkoxycarbonylamino group, an N-aryl-N-aryloxycarbonylamino group, a formyl group, an acyl group, a carboxyl group or its conjugate base group (hereinafter referred to as "carboxylate"), an alkoxycarbonyl group, an aryloxycarbonyl group, a carbamoyl group, an N-alkylcarbamoyl group, an N,N-dialkylcarbamoyl group, an N-arylcarbamoyl group, an N,N-diarylcarbamoyl group, an N-alkyl-N-arylcarbamoyl group, an alkylsulfinyl group, an arylsulfinyl group, an alkylsulfonyl group, an arylsulfonyl group, a sulfo group (—$SO_3H$) or its conjugate base group (hereinafter referred to as "sulfonate group"), an alkoxysulfonyl group, an aryloxysulfonyl group, a sulfinamoyl group, an N-alkylsulfinamoyl group, an N,N-dialkylsulfinamoyl group, an N-arylsulfinamoyl group, an N,N-diarylsulfinamoyl group, an N-alkyl-N-arylsulfinamoyl group, a sulfamoyl group, an N-alkylsulfamoyl group, an N,N-dialkylsulfamoyl group, an N-arylsulfamoyl group, an N,N-diarylsulfamoyl group, an N-alkyl-N-arylsulfamoyl group, an N-acylsulfamoyl group or its conjugate base group, an N-alkylsulfonylsulfamoyl group (—$SO_2NHSO_2$(alkyl)) or its conjugate base group, an N-arylsulfonylsulfamoyl group (—$SO_2NHSO_2$(aryl)) or its conjugate base group, an N-alkylsulfonylcarbamoyl group (—$CONHSO_2$(alkyl)) or its conjugate base group, an N-arylsulfonylcarbamoyl group (—$CONHSO_2$(aryl)) or its conjugate base group, a silyl group, an alkoxysilyl group (—$Si(Oalkyl)_3$), an aryloxysilyl group (—$Si(Oaryl)_3$), a hydroxysilyl group (—$Si(OH)_3$) or its conjugate base group, a phosphono group (—$PO_3H_2$) or its conjugate base group (hereinafter referred to as "phosphonate group"), a dialkylphosphono group (—$PO_3(alkyl)_2$), a diarylphosphono group (—$PO_3(aryl)_2$), an alkylarylphosphono group (—$PO_3$(alkyl)(aryl)), a monoalkylphosphono group (—$PO_3H$(alkyl)) or its conjugate base group (hereinafter referred to as "alkylphosphonate group"), a monoarylphosphono group (—$PO_3H$(aryl)) or its conjugate base group (hereinafter referred to as "arylphosphonate group"), a phosphonooxy group (—$OPO_3H_2$) or its conjugate base group (hereinafter referred to as "phosphonateoxy group"), a dialkylphosphonooxy group (—$OPO_3(alkyl)_2$), a diarylphosphonooxy group (—$OPO_3(aryl)_2$), an alkylarylphosphonooxy group (—$OPO_3$(alkyl)(aryl)), a monoalkylphosphonooxy group (—$OPO_3H$(alkyl)) or its conjugate base group (hereinafter referred to as "alkylphosphonateoxy group"), a monoarylphosphonooxy group (—$OPO_3H$(aryl)) or its conjugate base group (hereinafter referred to as "arylphosphonateoxy group"), a cyano group and a nitro group. These substituents may further be substituted with these substituents. Moreover, if appropriate, these substituents may form rings.

Each of $R^{12}$ to $R^{17}$ independently represents a hydrogen atom, a halogen atom or a monovalent organic group.

As the halogen atom represented $R^{12}$ to $R^{17}$, there can be mentioned a fluorine atom, a chlorine atom, a bromine atom or an iodine atom. Of these, a fluorine atom, a chlorine atom and a bromine atom are preferred.

The monovalent organic groups represented by $R^{12}$ to $R^{17}$ include an alkyl group, an alkenyl group, an alkynyl group, an aryl group, a cyclohydrocarbon group, a heterocyclic group, an alkoxy group, an aryloxy group, an acyl group, an alkoxycarbonyl group, an acyloxy group, —$SO_3$—$R^a$, —$NR^bR^c$, a cyano group, —$SiR^dR^eR^f$, —$SOR^g$, —$SO_2R^g$ and a nitro group. $R^a$ represents an alkyl group, an alkenyl group, an alkynyl group, an aryl group, an arylalkyl group or a quaternary ammonium. Each of $R^b$, $R^c$ and $R^g$ independently represents an alkyl group, an alkenyl group, an alkynyl group, an aryl group, a cyclohydrocarbon group or a heterocyclic group. Each of $R^d$ to $R^f$ independently represents an alkyl group, an alkenyl group, an alkynyl group, an aryl group, a cyclohydrocarbon group, a heterocyclic group, an alkoxy group or an aryloxy group.

The alkyl group, alkenyl group, alkynyl group, aryl group, cyclohydrocarbon group, heterocyclic group, alkoxy group and aryloxy group represented by $R^{12}$ to $R^{17}$ are as defined above with respect to those represented by $R^7$ to $R^{11}$. The preferred scopes thereof are also the same. Further, these groups may have the above-mentioned substituents.

The acyl group or alkoxycarbonyl group represented by $R^{12}$ to $R^{17}$ at its carbon chain moiety preferably has 1 to 30 carbon atoms, especially preferably 1 to 12 carbon atoms. The acyl group or alkoxycarbonyl group may be linear or may have any of the above-mentioned substituents.

The acyloxy group represented by $R^{12}$ to $R^{17}$ preferably has 1 to 30 carbon atoms, especially preferably 1 to 12 carbon atoms. The acyloxy group may be linear or may have any of the above-mentioned substituents.

The $R^a$ of the —$SO_3$—$R^a$ represented the by $R^{12}$ to $R^{17}$ is preferably a hydrogen atom, any of the above alkyl groups that may have a substituent, any of the above aryl groups that may have a substituent, a lithium atom, a sodium atom or a potassium atom.

The alkyl group, alkenyl group, alkynyl group, aryl group, cyclohydrocarbon group and heterocyclic group represented by the $R^b$ or $R^c$ of —$NR^bR^c$ are as defined above with respect to those represented by $R^7$ to $R^{11}$. The preferred scopes thereof are also the same. Further, these groups may have the above-mentioned substituents.

The alkyl group, alkenyl group, alkynyl group, aryl group, cyclohydrocarbon group, heterocyclic group, alkoxy group and aryloxy group represented by the $R^d$ to $R^f$ of —$SiR^dR^eR^f$ are as defined above with respect to those represented by $R^7$ to $R^{11}$. The preferred scopes thereof are also the same. Further, these groups may have the above-mentioned substituents.

The alkyl group, alkenyl group, alkynyl group, aryl group, cyclohydrocarbon group and heterocyclic group represented by the $R^g$ of —$SOR^g$ and —$SO_2R^g$ are as defined above with respect to those represented by $R^7$ to $R^{11}$. The preferred scopes thereof are also the same. Further, these groups may have the above-mentioned substituents.

As preferred particular examples of the counter cations of the general formulae (II) to (VII), there can be mentioned, for example, those of the structures of formulae Ca-1 to Ca-41 below.

Ca-1

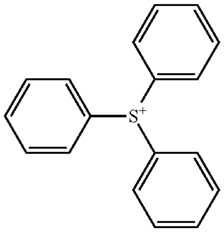

Ca-2

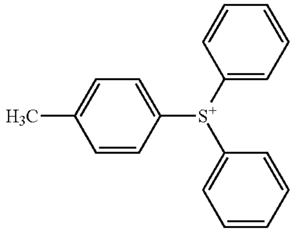

Ca-3

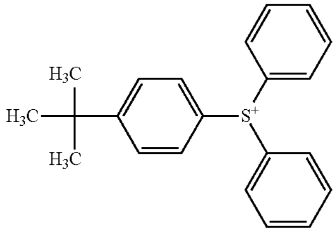

-continued

Ca-4

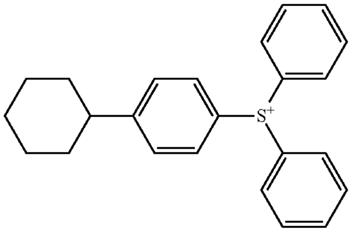

Ca-5

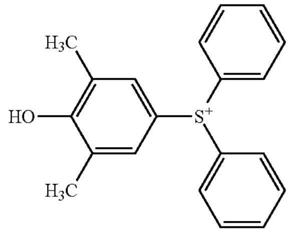

Ca-6

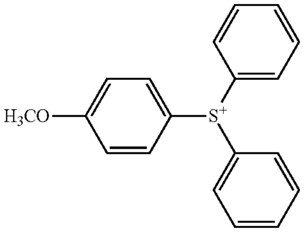

Ca-7

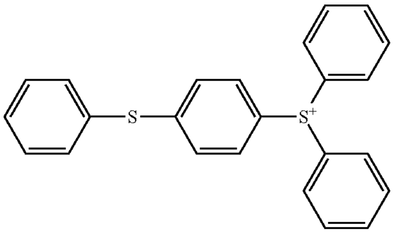

Ca-8

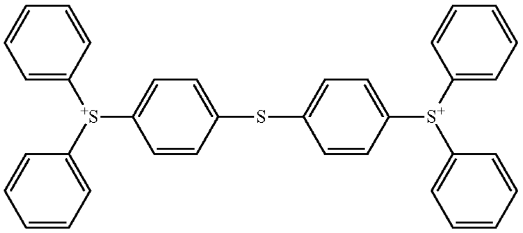

Ca-9

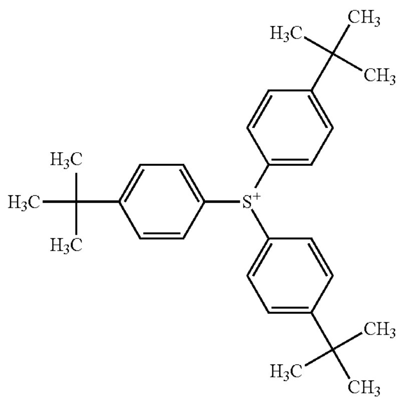

-continued
Ca-10
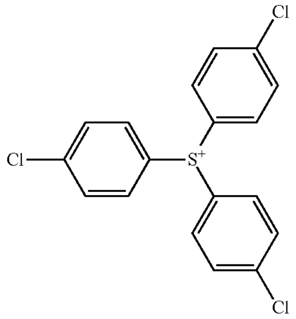
Ca-11
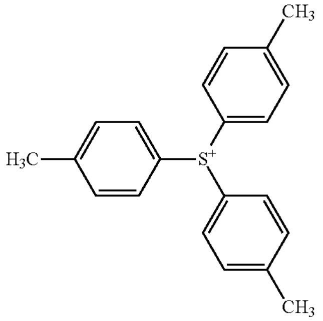
Ca-12
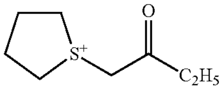
Ca-13
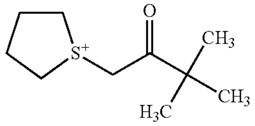
Ca-14
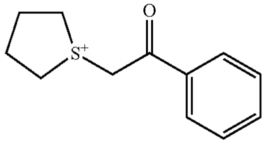
Ca-15
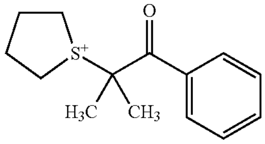
Ca-16
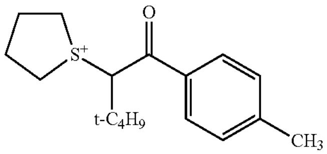
Ca-17
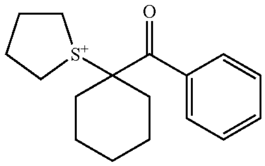
-continued
Ca-18
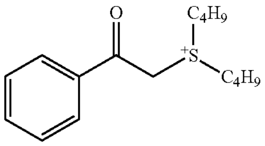
Ca-19
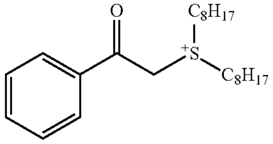
Ca-20
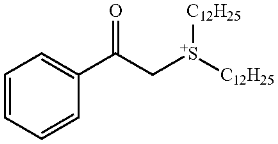
Ca-21
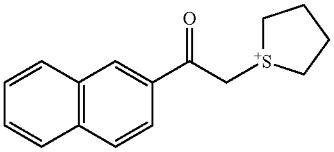
Ca-22
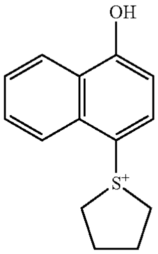
Ca-23
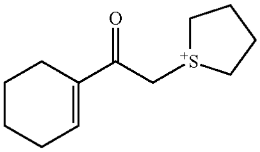
Ca-24
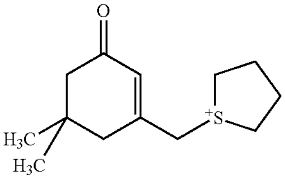
Ca-25
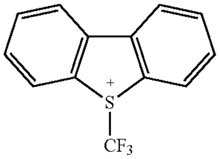

-continued

Ca-26

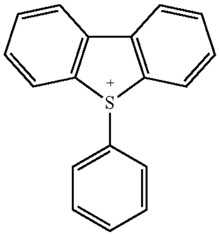

Ca-27

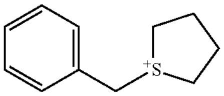

Ca-28

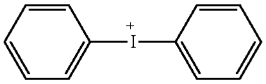

Ca-29

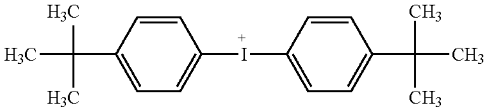

Ca-30

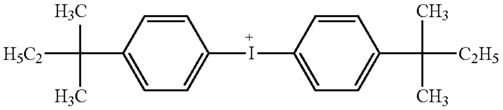

Ca-31

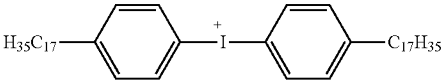

Ca-32

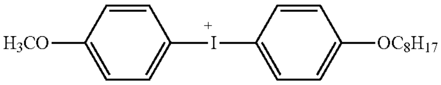

Ca-33

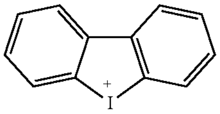

Ca-34

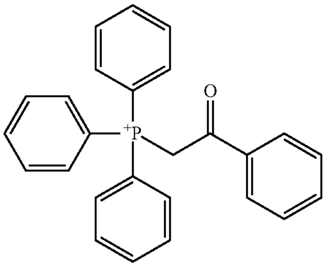

Ca-35

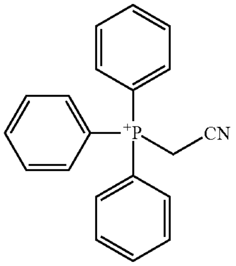

-continued

Ca-36

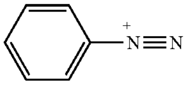

Ca-37

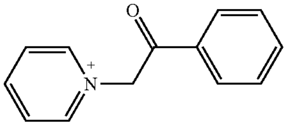

Ca-38

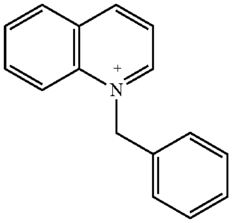

Ca-39

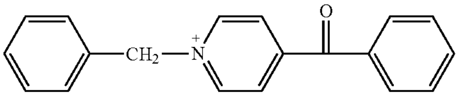

Ca-40

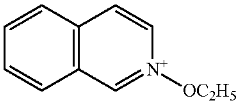

Ca-41

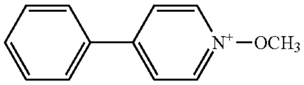

Furthermore, as organic onium ions preferred from the viewpoint of outgas suppression, there can be mentioned the cations having the structures of general formula (VIII) below.

(VIII)

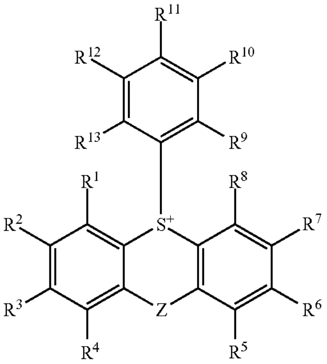

In the general formula (VIII), each of $R^1$ to $R^{13}$ independently represents a hydrogen atom or a substituent, provided that at least one of $R^1$ to $R^{13}$ is a substituent containing an alcoholic hydroxyl group.

Z represents a single bond or a bivalent connecting group.

In the present invention, the alcoholic hydroxyl group refers to a hydroxyl group bonded to a carbon atom of an alkyl group.

When $R^1$ to $R^{13}$ represent substituents containing an alcoholic hydroxyl group, it is preferred for the $R^1$ to $R^{13}$ to represent the groups of the formula -W-Y, wherein Y represents a hydroxyl-substituted alkyl group and W represents a single bond or a bivalent connecting group.

As the alkyl group represented by Y, there can be mentioned a methyl group, an ethyl group, a propyl group, an isopropyl group, an n-butyl group, an isobutyl group, a sec-butyl group, a pentyl group, a neopentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an eicosyl group, a cyclopropyl group, a cyclopentyl group, a cyclohexyl group, an adamantyl group, a norbornyl group, a boronyl group or the like. Of these, an ethyl group, a propyl group, an isopropyl group, an n-butyl group, an isobutyl group and a sec-butyl group are preferred. An ethyl group, a propyl group and an isopropyl group are more preferred. Especially preferably, Y contains the structure of $—CH_2CH_2OH$.

The bivalent connecting group represented by W is not particularly limited. For example, as the bivalent connecting group, there can be mentioned a bivalent group as obtained by replacing with a single bond any hydrogen atom of a monovalent group, such as an alkoxy group, an acyloxy group, a carbamoyloxy group, an alkoxycarbonyloxy group, an aryloxycarbonyloxy group, an acylamino group, an aminocarbonylamino group, an alkoxycarbonylamino group, an aryloxycarbonylamino group, a sulfamoylamino group, an alkyl- or arylsulfonylamino group, an alkylthio group, an arylthio group, a sulfamoyl group, an alkyl- or arylsulfinyl group, an alkyl- or arylsulfonyl group, an acyl group, an aryloxycarbonyl group, an alkoxycarbonyl group or a carbamoyl group.

W is preferably a single bond, or a bivalent group as obtained by replacing with a single bond any hydrogen atom of a group selected from among an alkoxy group, an acyloxy group, an acylamino group, an alkyl- or arylsulfonylamino group, an alkylthio group, an alkylsulfonyl group, an acyl group, an alkoxycarbonyl group and a carbamoyl group. More preferably, W is a single bond, or a bivalent group as obtained by replacing with a single bond any hydrogen atom of a group selected from among an acyloxy group, an alkylsulfonyl group, an acyl group and an alkoxycarbonyl group.

When $R^1$ to $R^{13}$ represent substituents containing an alcoholic hydroxyl group, the number of carbon atoms contained in each of the substituents is preferably in the range of 2 to 10, more preferably 2 to 6 and further preferably 2 to 4.

Each of the substituents containing an alcoholic hydroxyl group represented by $R^1$ to $R^{13}$ may have two or more alcoholic hydroxyl groups. The number of alcoholic hydroxyl groups contained in each of the substituents containing an alcoholic hydroxyl group represented by $R^1$ to $R^{13}$ is in the range of 1 to 6, preferably 1 to 3 and more preferably 1.

The number of alcoholic hydroxyl groups contained in any of the compounds of the general formula (VIII) as the total of those of $R^1$ to $R^{13}$ is in the range of 1 to 10, preferably 1 to 6 and more preferably 1 to 3.

When $R^1$ to $R^{13}$ do not contain any alcoholic hydroxyl group, each of $R^1$ to $R^{13}$ independently represents a hydrogen atom or a substituent. The substituent is not particularly limited. For example, as the substituent, there can be mentioned a halogen atom, any of alkyl groups (including a cycloalkyl group, a bicycloalkyl group and a tricycloalkyl group), any of alkenyl groups (including a cycloalkenyl group and a bicycloalkenyl group), an alkynyl group, an aryl group, a heterocyclic group, a cyano group, a nitro group, a carboxyl group, an alkoxy group, an aryloxy group, a silyloxy group, a heterocyclic oxy group, an acyloxy group, a carbamoyloxy group, an alkoxycarbonyloxy group, an aryloxycarbonyloxy group, any of amino groups (including an anilino group), an ammonio group, an acylamino group, an aminocarbonylamino group, an alkoxycarbonylamino group, an aryloxycarbonylamino group, a sulfamoylamino group, an alkyl- or arylsulfonylamino group, a mercapto group, an alkylthio group, an arylthio group, a heterocyclic thio group, a sulfamoyl group, a sulfo group, an alkyl- or arylsulfinyl group, an alkyl- or arylsulfonyl group, an acyl group, an aryloxycarbonyl group, an alkoxycarbonyl group, a carbamoyl group, an aryl- or heterocyclic azo group, an imido group, a phosphine group, a phosphinyl group, a phosphinyloxy group, a phosphinylamino group, a phosphono group, a silyl group, a hydrazino group, a ureido group, a boronic acid residue ($—B(OH)_2$), a phosphato group ($—OPO(OH)_2$), a sulfato group ($—OSO_3H$) or any of other substituents known in the art.

Any two adjacent to each other of $R^1$ to $R^{13}$ can cooperate with each other so as to form a ring (an aromatic or nonaromatic cyclohydrocarbon or heterocycle which can form a condensed polycycle through further combination; as such, there can be mentioned, for example, a benzene ring, a naphthalene ring, an anthracene ring, a phenanthrene ring, a fluorene ring, a triphenylene ring, a naphthacene ring, a biphenyl ring, a pyrrole ring, a furan ring, a thiophene ring, an imidazole ring, an oxazole ring, a thiazole ring, a pyridine ring, a pyrazine ring, a pyrimidine ring, a pyridazine ring, an indolizine ring, an indole ring, a benzofuran ring, a benzothiophene ring, an isobenzofuran ring, a quinolizine ring, a quinoline ring, a phthalazine ring, a naphthyridine ring, a quinoxaline ring, a quinoxazoline ring, an isoquinoline ring, a carbazole ring, a phenanthridine ring, an acridine ring, a phenanthroline ring, a thianthrene ring, a chromene ring, a xanthene ring, a phenoxathiin ring, a phenothiazine ring or a phenazine ring).

When $R^1$ to $R^{13}$ do not contain any alcoholic hydroxyl group, each of $R^1$ to $R^{13}$ preferably represents a hydrogen atom, a halogen atom, any of alkyl groups (including a cycloalkyl group, a bicycloalkyl group and a tricycloalkyl group), any of alkenyl groups (including a cycloalkenyl group and a bicycloalkenyl group), an alkynyl group, an aryl group, a cyano group, a carboxyl group, an alkoxy group, an aryloxy group, an acyloxy group, a carbamoyloxy group, an acylamino group, an aminocarbonylamino group, an alkoxycarbonylamino group, an aryloxycarbonylamino group, a sulfamoylamino group, an alkyl- or arylsulfonylamino group, an alkylthio group, an arylthio group, a sulfamoyl group, an alkyl- or arylsulfonyl group, an aryloxycarbonyl group, an alkoxycarbonyl group, a carbamoyl group, an imido group, a silyl group or a ureido group.

When $R^1$ to $R^{13}$ do not contain any alcoholic hydroxyl group, each of $R^1$ to $R^{13}$ more preferably represents a hydrogen atom, a halogen atom, any of alkyl groups (including a cycloalkyl group, a bicycloalkyl group and a tricycloalkyl group), a cyano group, an alkoxy group, an acyloxy group, an acylamino group, an aminocarbonylamino group, an alkoxycarbonylamino group, an alkyl- or arylsulfonylamino group, an alkylthio group, a sulfamoyl group, an alkyl- or arylsulfonyl group, an alkoxycarbonyl group or a carbamoyl group.

When $R^1$ to $R^{13}$ do not contain any alcoholic hydroxyl group, especially preferably, each of $R^1$ to $R^{13}$ represents a hydrogen atom, any of alkyl groups (including a cycloalkyl group, a bicycloalkyl group and a tricycloalkyl group), a halogen atom or an alkoxy group.

In the general formula (VIII), at least one of $R^1$ to $R^{13}$ contains an alcoholic hydroxyl group. Preferably, at least one of $R^9$ to $R^{13}$ contains an alcoholic hydroxyl group.

Z represents a single bond or a bivalent connecting group. The bivalent connecting group is, for example, an alkylene group, an arylene group, a carbonyl group, a sulfonyl group, a carbonyloxy group, a carbonylamino group, a sulfonylamido group, an ether group, a thioether group, an amino group, a disulfide group, an acyl group, an alkylsulfonyl group, —CH═CH—, —C≡C—, an aminocarbonylamino group, an aminosulfonylamino group or the like. The bivalent connecting group may have a substituent. The same substituents as mentioned above with respect to $R^1$ to $R^{13}$ can be employed. Preferably, Z is a single bond or a substituent exhibiting no electron withdrawing properties, such as an alkylene group, an arylene group, an ether group, a thioether group, an amino group, —CH═CH—, an aminocarbonylamino group or an aminosulfonylamino group. More preferably, Z is a single bond, an ether group or a thioether group. Most preferably, Z is a single bond.

Specific examples of the onium ions of the general formula (VIII) will be shown below, which are however nonlimiting.

(A1)

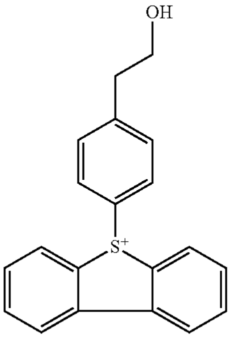

(A2)

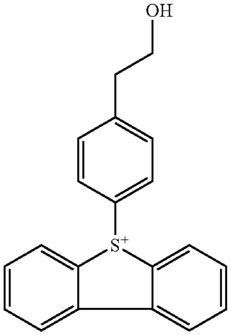

(A3)

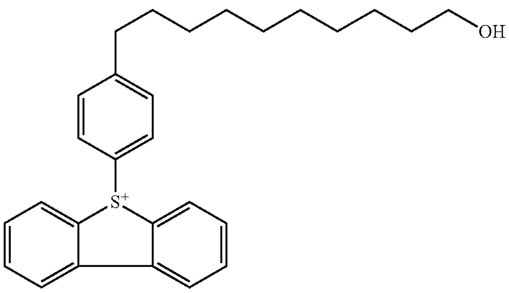

-continued (A4)

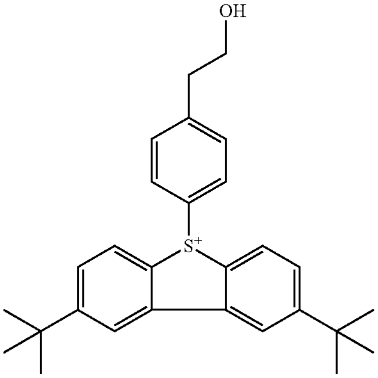

(A5)

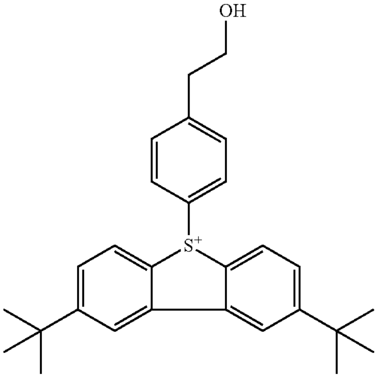

(A6)

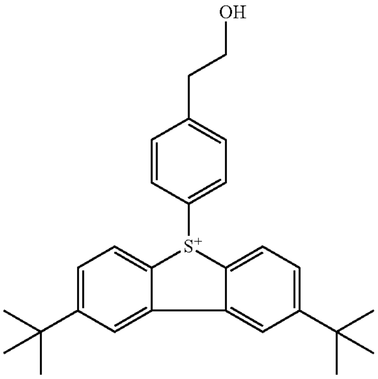

(A7)

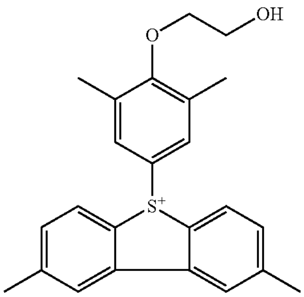

-continued
(A8)
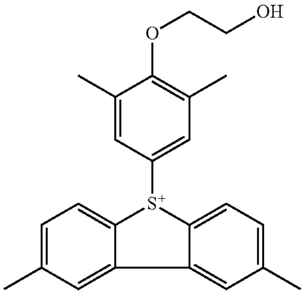
(A9)
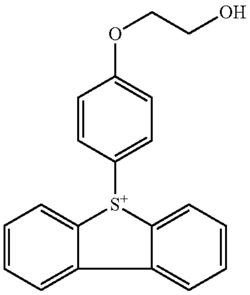
(A10)
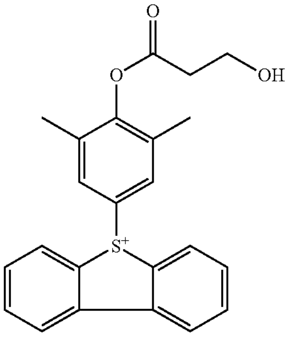
(A11)
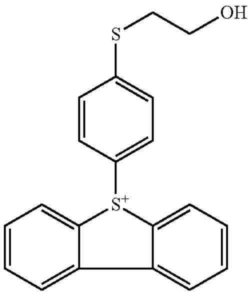
(A12)
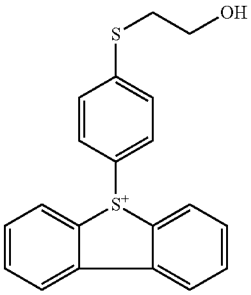
-continued
(A13)
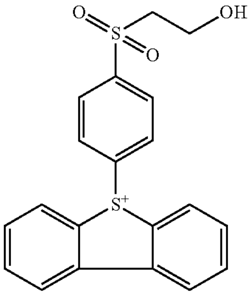
(A14)
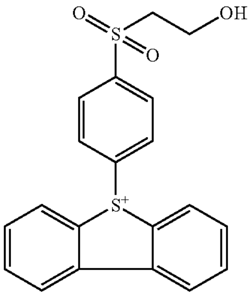
(A15)
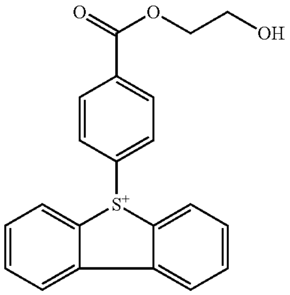
(A16)
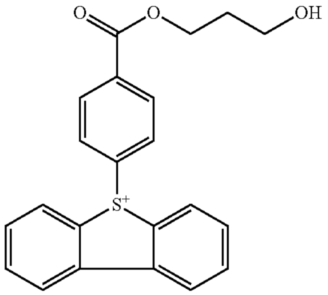
(A17)
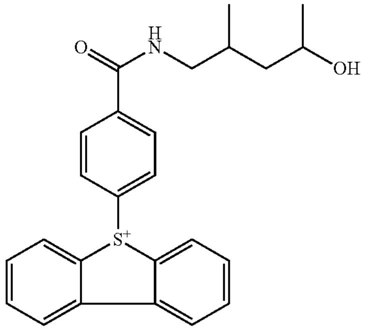

(A18)
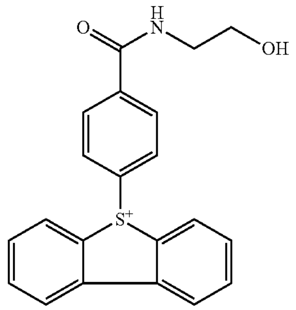
(A19)
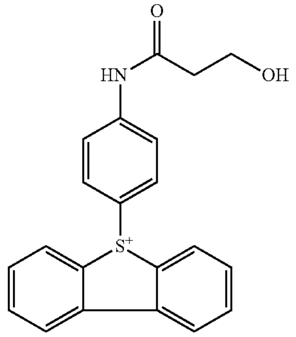
(A20)
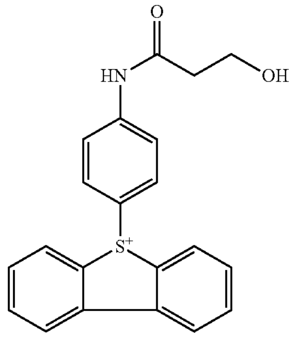
(A21)
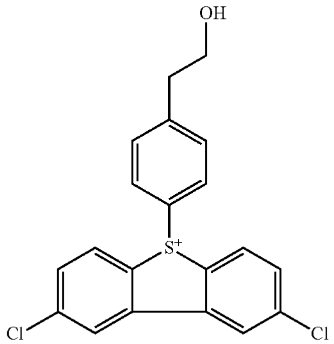
(A22)
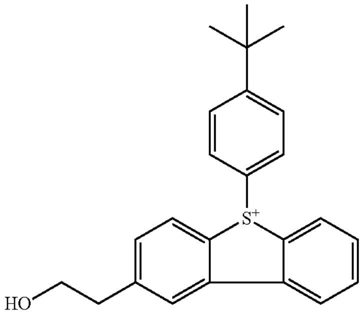
(A23)
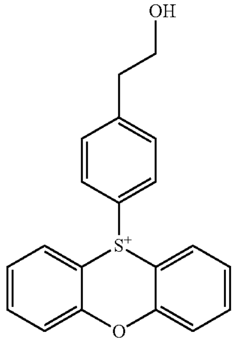
(A24)
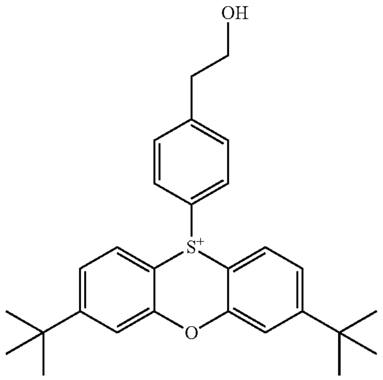
(A25)
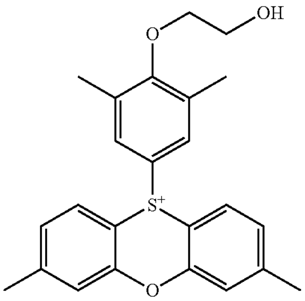

-continued
(A26)
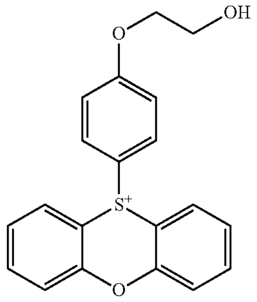
(A27)
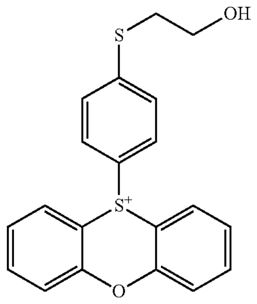
(A28)
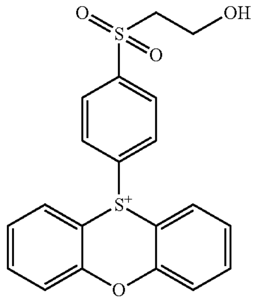
(A29)
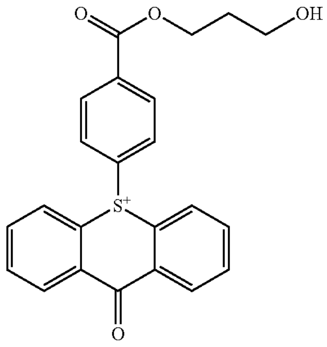
(A30)
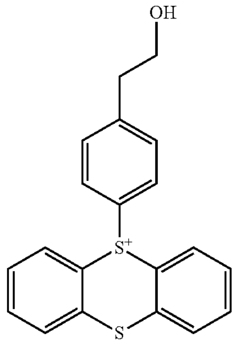
-continued
(A31)
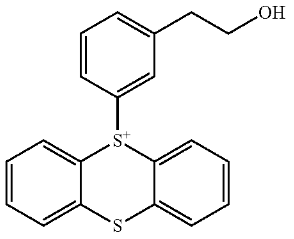
(A32)
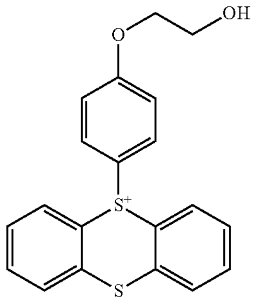
(A33)
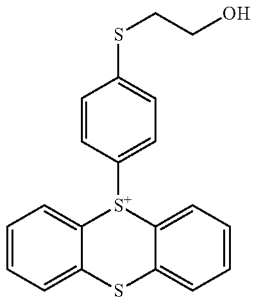
(A34)
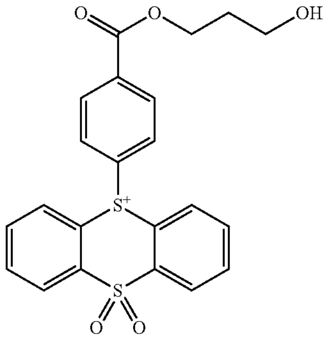
(A35)
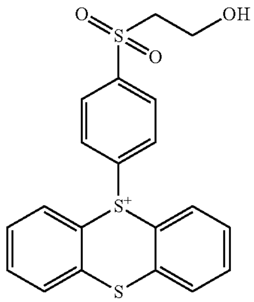

-continued (A36)

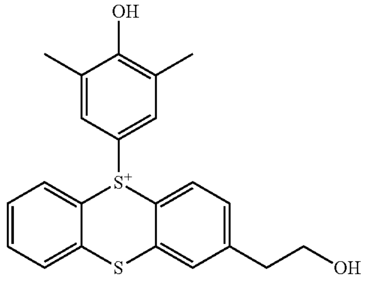

The total amount of compounds (A1) of the general formula (I) added, based on the total solid content of the photosensitive composition is preferably in the range of 0.1 to 40 mass %, more preferably 0.5 to 35 mass % and further preferably 3 to 30 mass %.

The molecular weight of any of the compounds (A1) of the general formula (I) is preferably in the range of 200 to 2000, especially preferably 400 to 1000.

The compounds (A1) of the general formula (I) can be synthesized by, for example, a method of sulfonating an aromatic compound of cyclic aliphatic skeleton. For example, the compounds substituted with a cycloalkyl group (Cy) according to the present invention can be synthesized by the following scheme.

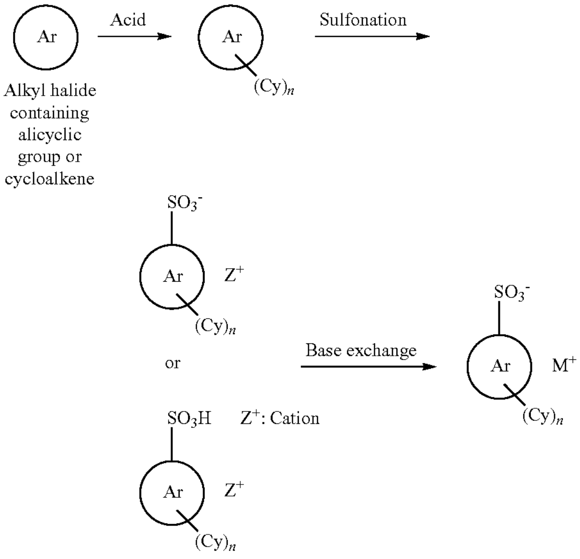

The sulfonation reaction can be carried out by use of any of reagents, such as chlorosulfonic acid (hydrolysis therewith), sulfuric acid, fuming sulfuric acid, $SO_3$, an $SO_3$ complex and a sulfite salt.

With respect to the counter cations, the conversion to desired cation $M^+$ can be effected by, for example, a conversion method using an ion exchange resin or a generally known anion exchange method as described in JP-A-6-184170, etc.

[2] Compound that when Exposed to Actinic Rays or Radiation, Generates an Acid (Acid Generator A2)

The photosensitive composition of the present invention may contain, together with the acid generator (A1), another acid generator. Hereinafter, the acid generator other than the acid generator (A1) will be referred to as an "acid generator (A2)."

As the acid generator (A2), use can be made of a member appropriately selected from among a photoinitiator for photocationic polymerization, a photoinitiator for photoradical polymerization, a photo-achromatic agent and photo-discoloring agent for dyes, any of generally known compounds that when exposed to actinic rays or radiation, generate an acid, employed in microresists, etc., and mixtures thereof.

For example, as the acid generator, there can be mentioned a diazonium salt, a phosphonium salt, a sulfonium salt, an iodonium salt, an imide sulfonate, an oxime sulfonate, diazosulfone, disulfone or o-nitrobenzyl sulfonate.

Further, use can be made of compounds obtained by introducing any of the above groups or compounds that when exposed to actinic rays or radiation, generate an acid in a polymer principal chain or side chain, for example, compounds described in U.S. Pat. No. 3,849,137, DE 3914407, JP-A' s-63-26653, 55-164824, 62-69263, 63-146038, 63-163452, 62-153853, 63-146029, etc.

Furthermore, use can be made of compounds that when exposed to light, generate an acid described in U.S. Pat. No. 3,779,778 and EP 126,712.

As preferred compounds among the acid generators, there can be mentioned those of the following general formulae (ZI), (ZII) and (ZIII).

ZI

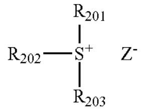

ZII

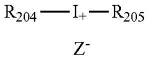

ZIII

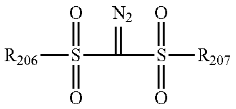

In the above general formula (ZI), each of $R_{201}$, $R_{202}$ and $R_{203}$ independently represents an organic group.

The number of carbon atoms of the organic group represented by $R_{201}$, $R_{202}$ and $R_{203}$ is generally in the range of 1 to 30, preferably 1 to 20.

Two of $R_{201}$ to $R_{203}$ may be bonded with each other to thereby form a ring structure, and the ring within the same may contain an oxygen atom, a sulfur atom, an ester bond, an amido bond or a carbonyl group. As the group formed by bonding of two of $R_{201}$ to $R_{203}$, there can be mentioned an alkylene group (for example, a butylene group or a pentylene group).

$Z^-$ represents a normucleophilic anion.

As the normucleophilic anion represented by $Z^-$, there can be mentioned, for example, a sulfonate anion, a carboxylate anion, a sulfonylimido anion, a bis(alkylsulfonyl)imido anion, a tris(alkylsulfonyl)methyl anion or the like.

The normucleophilic anion means an anion whose capability of inducing a nucleophilic reaction is extremely low and is an anion capable of inhibiting any temporal decomposition by intramolecular nucleophilic reaction. This would realize an enhancement of the temporal stability of the resist.

As the sulfonate anion, there can be mentioned, for example, an aliphatic sulfonate anion, an aromatic sulfonate anion, a camphor sulfonate anion or the like.

As the carboxylate anion, there can be mentioned, for example, an aliphatic carboxylate anion, an aromatic carboxylate anion, an aralkyl carboxylate anion or the like.

The aliphatic moiety of the aliphatic sulfonate anion may be an alkyl group or a cycloalkyl group, being preferably an alkyl group having 1 to 30 carbon atoms or a cycloalkyl group having 3 to 30 carbon atoms. As such, there can be mentioned, for example, a methyl group, an ethyl group, a propyl group, an isopropyl group, an n-butyl group, an isobutyl group, a sec-butyl group, a pentyl group, a neopentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an eicosyl group, a cyclopropyl group, a cyclopentyl group, a cyclohexyl group, an adamantyl group, a norbornyl group, a boronyl group or the like.

As a preferred aromatic group of the aromatic sulfonate anion, there can be mentioned an aryl group having 6 to 14 carbon atoms, for example, a phenyl group, a tolyl group, a naphthyl group or the like.

The alkyl group, cycloalkyl group and aryl group of the aliphatic sulfonate anion and aromatic sulfonate anion may have a substituent. As the substituent of the alkyl group, cycloalkyl group and aryl group of the aliphatic sulfonate anion and aromatic sulfonate anion, there can be mentioned, for example, a nitro group, a halogen atom (fluorine atom, chlorine atom, bromine atom or iodine atom), a carboxyl group, a hydroxyl group, an amino group, a cyano group, an alkoxy group (preferably having 1 to 5 carbon atoms), a cycloalkyl group (preferably having 3 to 15 carbon atoms), an aryl group (preferably having 6 to 14 carbon atoms), an alkoxycarbonyl group (preferably having 2 to 7 carbon atoms), an acyl group (preferably having 2 to 12 carbon atoms), an alkoxycarbonyloxy group (preferably having 2 to 7 carbon atoms) or the like. The aryl group or ring structure of these groups may further have an alkyl group (preferably having 1 to 15 carbon atoms) as its substituent.

As the aliphatic moiety of the aliphatic carboxylate anion, there can be mentioned the same alkyl groups and cycloalkyl groups as mentioned with respect to the aliphatic sulfonate anion.

As the aromatic group of the aromatic carboxylate anion, there can be mentioned the same aryl groups as mentioned with respect to the aromatic sulfonate anion.

As a preferred aralkyl group of the aralkyl carboxylate anion, there can be mentioned an aralkyl group having 6 to 12 carbon atoms, for example, a benzyl group, a phenethyl group, a naphthylmethyl group, a naphthylethyl group, a naphthylbutyl group or the like.

The alkyl group, cycloalkyl group, aryl group and aralkyl group of the aliphatic carboxylate anion, aromatic carboxylate anion and aralkyl carboxylate anion may have a substituent. As the substituent of the alkyl group, cycloalkyl group, aryl group and aralkyl group of the aliphatic carboxylate anion, aromatic carboxylate anion and aralkyl carboxylate anion, there can be mentioned, for example, the same halogen atom, alkyl group, cycloalkyl group, alkoxy group, alkylthio group, etc. as mentioned with respect to the aromatic sulfonate anion.

As the sulfonylimido anion, there can be mentioned, for example, a saccharin anion.

The alkyl group of the bis(alkylsulfonyl)imido anion and tris(alkylsulfonyl)methyl anion is preferably an alkyl group having 1 to 5 carbon atoms. As such, there can be mentioned, for example, a methyl group, an ethyl group, a propyl group, an isopropyl group, an n-butyl group, an isobutyl group, a sec-butyl group, a pentyl group, a neopentyl group or the like. As a substituent of these alkyl groups, there can be mentioned a halogen atom, an alkyl group substituted with a halogen atom, an alkoxy group, an alkylthio group or the like. An alkyl group substituted with a fluorine atom is preferred.

As the other normucleophilic anions, there can be mentioned, for example, phosphorus fluoride, boron fluoride, antimony fluoride and the like.

The normucleophilic anion represented by $Z^-$ is preferably selected from among an aliphatic sulfonate anion substituted at its $\alpha$-position of sulfonic acid with a fluorine atom, an aromatic sulfonate anion substituted with a fluorine atom or a group having a fluorine atom, a bis(alkylsulfonyl)imido anion whose alkyl group is substituted with a fluorine atom and a tris(alkylsulfonyl)methide anion whose alkyl group is substituted with a fluorine atom. More preferably, the normucleophilic anion is a perfluorinated aliphatic sulfonate anion having 4 to 8 carbon atoms or a benzene sulfonate anion having a fluorine atom. Still more preferably, the normucleophilic anion is a nonafluorobutane sulfonate anion, a perfluorooctane sulfonate anion, a pentafluorobenzene sulfonate anion or a 3,5-bis(trifluoromethyl)benzene sulfonate anion.

As the organic groups represented by $R_{201}$, $R_{202}$ and $R_{203}$, there can be mentioned, for example, groups corresponding to the following compounds (ZI-1), (ZI-2) and (ZI-3).

Appropriate use may be made of compounds with two or more of the structures of the general formula (ZI). For example, use may be made of compounds having a structure wherein at least one of $R_{201}$ to $R_{203}$ of a compound of the general formula (ZI) is bonded with at least one of $R_{201}$ to $R_{203}$ of another compound of the general formula (ZI).

As preferred (ZI) components, there can be mentioned the following compounds (ZI-1), (ZI-2), (ZI-3) and (ZI-4).

The compounds (ZI-1) are arylsulfonium compounds of the general formula (ZI) wherein at least one of $R_{201}$ to $R_{203}$ is an aryl group, namely, compounds containing an arylsulfonium as a cation.

In the arylsulfonium compounds, all of the $R_{201}$ to $R_{203}$ may be aryl groups. It is also appropriate that the $R_{201}$ to $R_{203}$ are partially an aryl group and the remainder is an alkyl group or a cycloalkyl group.

As the arylsulfonium compounds, there can be mentioned, for example, a triarylsulfonium compound, a diarylalkylsulfonium compound, an aryldialkylsulfonium compound, a diarylcycloalkylsulfonium compound and an aryldicycloalkylsulfonium compound.

The aryl group of the arylsulfonium compounds is preferably a phenyl group or a naphthyl group, more preferably a phenyl group. The aryl group may be one having a heterocyclic structure containing an oxygen atom, nitrogen atom, sulfur atom or the like. As the aryl group having a heterocyclic structure, there can be mentioned, for example, a pyrrole residue (group formed by loss of one hydrogen atom from pyrrole), a furan residue (group formed by loss of one hydrogen atom from furan), a thiophene residue (group formed by loss of one hydrogen atom from thiophene), an indole residue (group formed by loss of one hydrogen atom from indole), a benzofuran residue (group formed by loss of one hydrogen atom from benzofuran), a benzothiophene residue (group formed by loss of one hydrogen atom from benzothiophene) or the like. When the arylsulfonium compound has two or more aryl groups, the two or more aryl groups may be identical to or different from each other.

The alkyl group or cycloalkyl group contained in the arylsulfonium compound according to necessity is preferably a linear or branched alkyl group having 1 to 15 carbon atoms or a cycloalkyl group having 3 to 15 carbon atoms. As such, there can be mentioned, for example, a methyl group, an ethyl group, a propyl group, an n-butyl group, a sec-butyl group, a t-butyl group, a cyclopropyl group, a cyclobutyl group, a cyclohexyl group or the like.

The aryl group, alkyl group or cycloalkyl group represented by $R_{201}$ to $R_{203}$ may have as its substituent an alkyl group (for example, 1 to 15 carbon atoms), cycloalkyl group (for example, 3 to 15 carbon atoms), an aryl group (for example, 6 to 14 carbon atoms), an alkoxy group (for example, 1 to 15 carbon atoms), a halogen atom, a hydroxyl group or a phenylthio group. Preferred substituents are a linear or branched alkyl group having 1 to 12 carbon atoms, a cycloalkyl group having 3 to 12 carbon atoms and a linear, branched or cyclic alkoxy group having 1 to 12 carbon atoms. More preferred substituents are an alkyl group having 1 to 4 carbon atoms and an alkoxy group having 1 to 4 carbon atoms. The substituents may be contained in any one of the three $R_{201}$ to $R_{203}$, or alternatively may be contained in all three of $R_{201}$ to $R_{203}$. When $R_{201}$ to $R_{203}$ represent an aryl group, the substituent preferably lies at the p-position of the aryl group.

Now, the compounds (ZI-2) will be described.

The compounds (ZI-2) are compounds of the formula (ZI) wherein each of $R_{201}$ to $R_{203}$ independently represents an organic group having no aromatic ring. The aromatic rings include an aromatic ring having a heteroatom.

The organic group having no aromatic ring represented by $R_{201}$ to $R_{203}$ generally has 1 to 30 carbon atoms, preferably 1 to 20 carbon atoms.

Preferably, each of $R_{201}$ to $R_{203}$ independently represents an alkyl group, a cycloalkyl group, an allyl group or a vinyl group. More preferred groups are a linear or branched 2-oxoalkyl group, a 2-oxocycloalkyl group and an alkoxycarbonylmethyl group. Especially preferred is a linear or branched 2-oxoalkyl group.

As preferred alkyl groups and cycloalkyl groups represented by $R_{201}$ to $R_{203}$, there can be mentioned a linear or branched alkyl group having 1 to 10 carbon atoms (for example, a methyl group, an ethyl group, a propyl group, a butyl group or a pentyl group) and a cycloalkyl group having 3 to 10 carbon atoms (a cyclopentyl group, a cyclohexyl group or a norbornyl group). As more preferred alkyl groups, there can be mentioned a 2-oxoalkyl group and an alkoxycarbonylmethyl group. As more preferred cycloalkyl group, there can be mentioned a 2-oxocycloalkyl group.

The 2-oxoalkyl group may be linear or branched. A group having >C═O at the 2-position of the alkyl group is preferred.

The 2-oxocycloalkyl group is preferably a group having >C═O at the 2-position of the cycloalkyl group.

As preferred alkoxy groups of the alkoxycarbonylmethyl group, there can be mentioned alkoxy groups having 1 to 5 carbon atoms (a methoxy group, an ethoxy group, a propoxy group, a butoxy group and a pentoxy group).

The $R_{201}$ to $R_{203}$ may be further substituted with a halogen atom, an alkoxy group (for example, 1 to 5 carbon atoms), a hydroxyl group, a cyano group or a nitro group.

The compounds (ZI-3) are those represented by the following general formula (ZI-3) which have a phenacylsulfonium salt structure.

(ZI-3)

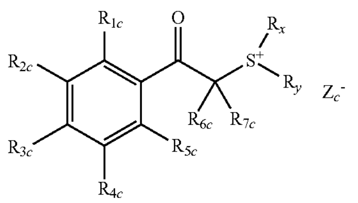

In the general formula (ZI-3), each of $R_{1c}$ to $R_{5c}$ independently represents a hydrogen atom, an alkyl group, a cycloalkyl group, an alkoxy group or a halogen atom.

Each of $R_{6c}$ and $R_{7c}$ independently represents a hydrogen atom, an alkyl group or a cycloalkyl group.

Each of $R_x$ and $R_y$ independently represents an alkyl group, a cycloalkyl group, an allyl group or a vinyl group.

Any two or more of $R_{1c}$ to $R_{5c}$, and $R_{6c}$ and $R_{7c}$, and $R_x$ and $R_y$ may be bonded with each other to thereby form a ring structure. This ring structure may contain an oxygen atom, a sulfur atom, an ester bond or an amido bond. As the group formed by bonding of any two or more of $R_{1c}$ to $R_{5c}$, and $R_{6c}$ and $R_{7c}$, and $R_x$ and $R_y$, there can be mentioned a butylene group, a pentylene group or the like.

$Zc^-$ represents a normucleophilic anion. There can be mentioned the same normucleophilic anions as mentioned with respect to the $Z^-$ of the general formula (ZI).

The alkyl group represented by $R_{1c}$ to $R_{7c}$ may be linear or branched. As such, there can be mentioned, for example, an alkyl group having 1 to 20 carbon atoms, preferably a linear or branched alkyl group having 1 to 12 carbon atoms (for example, a methyl group, an ethyl group, a linear or branched propyl group, a linear or branched butyl group or a linear or branched pentyl group). As the cycloalkyl group, there can be mentioned, for example, a cycloalkyl group having 3 to 8 carbon atoms (for example, a cyclopentyl group or a cyclohexyl group).

The alkoxy group represented by $R_{1c}$ to $R_{5c}$ may be linear, or branched, or cyclic. As such, there can be mentioned, for example, an alkoxy group having 1 to 10 carbon atoms, preferably a linear or branched alkoxy group having 1 to 5 carbon atoms (for example, a methoxy group, an ethoxy group, a linear or branched propoxy group, a linear or branched butoxy group or a linear or branched pentoxy group) and a cycloalkoxy group having 3 to 8 carbon atoms (for example, a cyclopentyloxy group or a cyclohexyloxy group).

Preferably, any one of $R_{1c}$ to $R_{5c}$ is a linear or branched alkyl group, a cycloalkyl group or a linear, branched or cyclic alkoxy group. More preferably, the sum of carbon atoms of $R_{1c}$ to $R_{5c}$ is in the range of 2 to 15. Accordingly, there can be attained an enhancement of solvent solubility and inhibition of particle generation during storage.

As the alkyl groups and cycloalkyl groups represented by $R_x$ and $R_y$, there can be mentioned the same alkyl groups and cycloalkyl groups as mentioned with respect to $R_{1c}$ to $R_{7c}$. Among them, a 2-oxoalkyl group, a 2-oxocycloalkyl group and an alkoxycarbonylmethyl group are preferred.

As the 2-oxoalkyl group and 2-oxocycloalkyl group, there can be mentioned groups having >C═O at the 2-position of the alkyl group and cycloalkyl group represented by $R_{1c}$ to $R_{7c}$.

Regarding the alkoxy group of the alkoxycarbonylmethyl group, there can be mentioned the same alkoxy groups as mentioned with respect to $R_{1c}$ to $R_{5c}$.

Each of $R_x$ and $R_y$ is preferably an alkyl group or cycloalkyl group having preferably 4 or more carbon atoms. The alkyl group or cycloalkyl group has more preferably 6 or more carbon atoms and still more preferably 8 or more carbon atoms.

The compounds (ZI-4) are those of general formula (ZI-4) below.

(ZI-4)

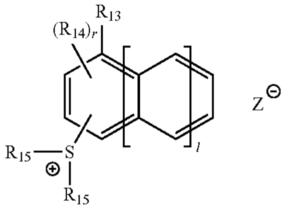

In the general formula (ZI-4), $R_{13}$ represents a hydrogen atom, a fluorine atom, a hydroxyl group, an alkyl group, a cycloalkyl group, an alkoxy group or an alkoxycarbonyl group.

$R_{14}$, each independently in the presence of two or more groups, represents an alkyl group, a cycloalkyl group, an alkoxy group, an alkylsulfonyl group or a cycloalkylsulfonyl group.

Each of $R_{15}$s independently represents an alkyl group, a cycloalkyl group, a phenyl group or a naphthyl group, provided that the two $R_{15}$s may be bonded to each other to thereby form a ring.

In the formula, 1 is an integer of 0 to 2, and r is an integer of 0 to 10.

$Z^-$ represents a normucleophilic anion. As such, there can be mentioned any of the same normucleophilic anions as mentioned with respect to the $Z^-$ of the general formula (ZI).

In the general formula (ZI-4), the alkyl groups represented by $R_{13}$, $R_{14}$ and $R_{15}$ may be linear or branched and preferably each have 1 to 10 carbon atoms. As such, there can be mentioned a methyl group, an ethyl group, an n-propyl group, an i-propyl group, an n-butyl group, a 2-methylpropyl group, a 1-methylpropyl group, a t-butyl group, an n-pentyl group, a neopentyl group, an n-hexyl group, an n-heptyl group, an n-octyl group, a 2-ethylhexyl group, an n-nonyl group, an n-decyl group and the like. Of these alkyl groups, a methyl group, an ethyl group, an n-butyl group, a t-butyl group and the like are preferred.

As the cycloalkyl groups represented by $R_{13}$, $R_{14}$ and $R_{15}$, there can be mentioned cyclopropyl, cyclobutyl, cyclopentyl, cyclohexyl, cycloheptyl, cyclooctyl, cyclododecanyl, cyclopentenyl, cyclohexenyl, cyclooctadienyl and the like. Cyclopropyl, cyclopentyl, cyclohexyl and cyclooctyl are especially preferred.

The alkoxy groups represented by $R_{13}$ and $R_{14}$ may be linear or branched and preferably each have 1 to 10 carbon atoms. As such, there can be mentioned, for example, a methoxy group, an ethoxy group, an n-propoxy group, an i-propoxy group, an n-butoxy group, a 2-methylpropoxy group, a 1-methylpropoxy group, a t-butoxy group, an n-pentyloxy group, a neopentyloxy group, an n-hexyloxy group, an n-heptyloxy group, an n-octyloxy group, a 2-ethylhexyloxy group, an n-nonyloxy group, an n-decyloxy group and the like. Of these alkoxy groups, a methoxy group, an ethoxy group, an n-propoxy group, an n-butoxy group and the like are preferred.

The alkoxycarbonyl group represented by $R_{13}$ may be linear or branched and preferably has 2 to 11 carbon atoms. As such, there can be mentioned, for example, a methoxycarbonyl group, an ethoxycarbonyl group, an n-propoxycarbonyl group, an i-propoxycarbonyl group, an n-butoxycarbonyl group, a 2-methylpropoxycarbonyl group, a 1-methylpropoxycarbonyl group, a t-butoxycarbonyl group, an n-pentyloxycarbonyl group, a neopentyloxycarbonyl group, an n-hexyloxycarbonyl group, an n-heptyloxycarbonyl group, an n-octyloxycarbonyl group, a 2-ethylhexyloxycarbonyl group, an n-nonyloxycarbonyl group, an n-decyloxycarbonyl group and the like. Of these alkoxycarbonyl groups, a methoxycarbonyl group, an ethoxycarbonyl group, an n-butoxycarbonyl group and the like are preferred.

The alkylsulfonyl and cycloalkylsulfonyl groups represented by $R_{14}$ may be linear, branched or cyclic and preferably each have 1 to 10 carbon atoms. As such, there can be mentioned, for example, a methanesulfonyl group, an ethanesulfonyl group, an n-propanesulfonyl group, an n-butanesulfonyl group, a tert-butanesulfonyl group, an n-pentanesulfonyl group, a neopentanesulfonyl group, an n-hexanesulfonyl group, an n-heptanesulfonyl group, an n-octanesulfonyl group, a 2-ethylhexanesulfonyl group, an n-nonanesulfonyl group, an n-decanesulfonyl group, a cyclopentanesulfonyl group, a cyclohexanesulfonyl group and the like. Of these alkylsulfonyl and cycloalkylsulfonyl groups, a methanesulfonyl group, an ethanesulfonyl group, an n-propanesulfonyl group, an n-butanesulfonyl group, a cyclopentanesulfonyl group, a cyclohexanesulfonyl group and the like are preferred.

In the formula, r is preferably 0 to 2.

In the general formula (ZI-4), the phenyl groups represented by $R_{15}$ may be substituted. As such, there can be mentioned, for example, a phenyl group or a phenyl group substituted with a linear, branched or cyclic alkyl group having 1 to 10 carbon atoms (for example, a phenyl group, an o-tolyl group, a m-tolyl group, a p-tolyl group, 2,3-dimethylphenyl group, 2,4-dimethylphenyl group, 2,5-dimethylphenyl group, 2,6-dimethylphenyl group, 3,4-dimethylphenyl group, 3,5-dimethylphenyl group, 2,4,6-trimethylphenyl group, 4-ethylphenyl group, 4-t-butylphenyl group, 4-cyclohexylphenyl group or 4-fluorophenyl group), or the phenyl group or the alkyl-substituted phenyl group having at least one hydrogen atom thereof substituted with at least one group selected from a hydroxyl group, a carboxyl group, a cyano group, a nitro group, an alkoxy group, an alkoxyalkyl group, an alkoxycarbonyl group, an alkoxycarbonyloxy group or the like.

With respect to the above substituents of the phenyl group or the alkyl-substituted phenyl group, as the alkoxy group, there can be mentioned, for example, a linear, branched or cyclic alkoxy group having 1 to 20 carbon atoms, such as a methoxy group, an ethoxy group, an n-propoxy group, an i-propoxy group, an n-butoxy group, a 2-methylpropoxy group, a 1-methylpropoxy group, a t-butoxy group, a cyclopentyloxy group or a cyclohexyloxy group.

As the alkoxyalkyl group, there can be mentioned, for example, a linear, branched or cyclic alkoxyalkyl group having 2 to 21 carbon atoms, such as a methoxymethyl group, an ethoxymethyl group, a 1-methoxyethyl group, a 2-methoxyethyl group, a 1-ethoxyethyl group or a 2-ethoxyethyl group.

As the alkoxycarbonyl group, there can be mentioned, for example, a linear, branched or cyclic alkoxycarbonyl group having 2 to 21 carbon atoms, such as a methoxycarbonyl group, an ethoxycarbonyl group, an n-propoxycarbonyl group, an i-propoxycarbonyl group, an n-butoxycarbonyl group, a 2-methylpropoxycarbonyl group, a 1-methylpropoxycarbonyl group, a t-butoxycarbonyl group, a cyclopentyloxycarbonyl group or a cyclohexyloxycarbonyl group.

As the alkoxycarbonyloxy group, there can be mentioned, for example, a linear, branched or cyclic alkoxycarbonyloxy group having 2 to 21 carbon atoms, such as a methoxycarbonyloxy group, an ethoxycarbonyloxy group, an n-propoxycarbonyloxy group, an i-propoxycarbonyloxy group, an n-butoxycarbonyloxy group, a t-butoxycarbonyloxy group, a cyclopentyloxycarbonyloxy group or a cyclohexyloxycarbonyloxy group.

As the optionally substituted phenyl groups represented by $R_{15}$ in the general formula (ZI-4), a phenyl group, 4-cyclohexylphenyl group, 4-t-butylphenyl group, 4-methoxyphenyl group and 4-t-butoxyphenyl group are preferred.

As the optionally substituted naphthyl groups represented by $R_{15}$, there can be mentioned, for example, a naphthyl group or a naphthyl group substituted with a linear, branched or cyclic alkyl group having 1 to 10 carbon atoms (for example, 1-naphthyl group, 2-methyl-1-naphthyl group, 3-methyl-1-naphthyl group, 4-methyl-1-naphthyl group, 5-methyl-1-naphthyl group, 6-methyl-1-naphthyl group, 7-methyl-1-naphthyl group, 8-methyl-1-naphthyl group, 2,3-dimethyl-1-naphthyl group, 2,4-dimethyl-1-naphthyl group, 2,5-dimethyl-1-naphthyl group, 2,6-dimethyl-1-naphthyl group, 2,7-dimethyl-1-naphthyl group, 2,8-dimethyl-1-naphthyl group, 3,4-dimethyl-1-naphthyl group, 3,5-dimethyl-1-naphthyl group, 3,6-dimethyl-1-naphthyl group, 3,7-dimethyl-1-naphthyl group, 3,8-dimethyl-1-naphthyl group, 4,5-dimethyl-1-naphthyl group, 5,8-dimethyl-1-naphthyl group, 4-ethyl-1-naphthyl group, 2-naphthyl group, 1-methyl-2-naphthyl group, 3-methyl-2-naphthyl group or 4-methyl-2-naphthyl group) or the naphthyl group or the alkyl-substituted naphthyl group having at least one hydrogen atom thereof substituted with at least one group selected from a hydroxyl group, a carboxyl group, a cyano group, a nitro group, an alkoxy group, an alkoxyalkyl group, an alkoxycarbonyl group, an alkoxycarbonyloxy group or the like.

With respect to the above substituents, as the alkoxy group, the alkoxyalkyl group, the alkoxycarbonyl group and the alkoxycarbonyloxy group, the same groups as mentioned with respect to the above phenyl groups and the above alkyl-substituted phenyl groups can be exemplified.

As the optionally substituted naphthyl groups represented by $R_{15}$ in the general formula (ZI-4), 1-naphthyl group, 1-(4-methoxynaphthyl) group, 1-(4-ethoxynaphthyl) group, 1-(4-n-propoxynaphthyl) group, 1-(4-n-butoxynaphthyl) group, 2-(7-methoxynaphtyl) group, 2-(7-ethoxynaphtyl) group, 2-(7-n-propoxynaphtyl) group and 2-(7-n-butoxynaphtyl) group are preferred.

The cyclic structure that may be formed by the bonding of the two $R_{15}$s to each other is preferably a 5- or 6-membered ring, especially a 5-membered ring (namely, a tetrahydrothiophene ring) formed by two bivalent $R_{15}$s in cooperation with the sulfur atom of the general formula (ZI-4). The bivalent $R_{15}$s may have substituents. As such substituents, there can be mentioned, for example, a hydroxyl group, a carboxyl group, a cyano group, a nitro group, an alkoxy group, an alkoxyalkyl group, an alkoxycarbonyl group, an alkoxycarbonyloxy group and the like as mentioned above. It is especially preferred for the $R_{15}$ of the general formula (ZI-4) to be a methyl group, an ethyl group, a phenyl group, 4-methoxyphenyl group, the above-mentioned bivalent group allowing two $R_{15}$s to be bonded to each other so as to form a tetrahydrothiophene ring structure in cooperation with the sulfur atom of the general formula (ZI-4), or the like.

Preferred specific examples of the cations of the compounds of the general formula (ZI-4) will be shown below.

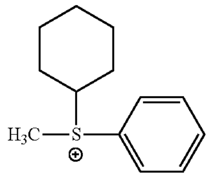
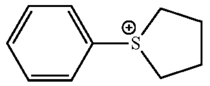
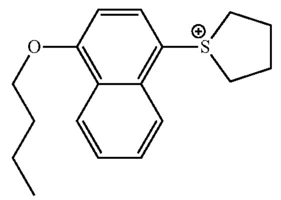
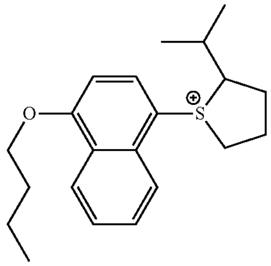
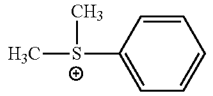
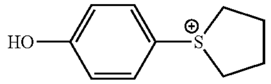
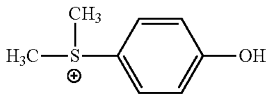
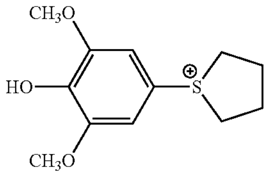
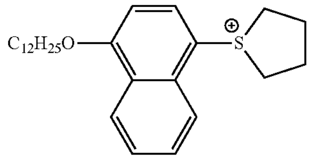
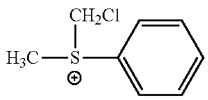
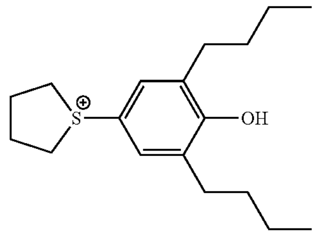
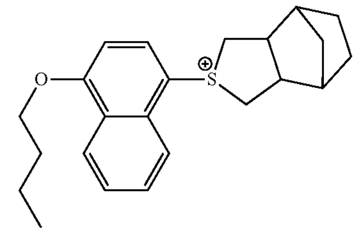
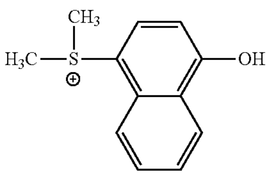
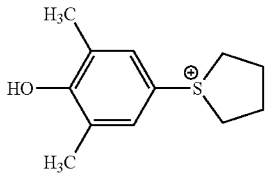
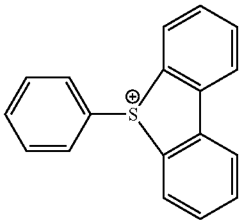
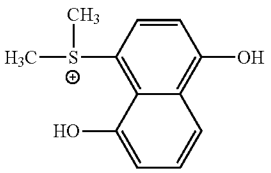

-continued

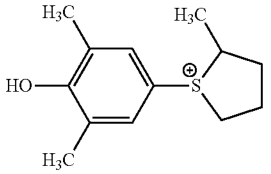

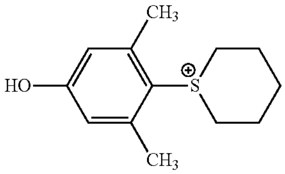

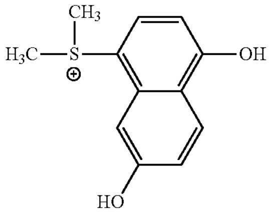

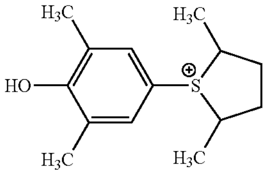

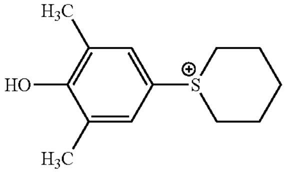

In the general formulae (ZII) and (ZIII), each of $R_{204}$ to $R_{207}$ independently represents an aryl group, an alkyl group or a cycloalkyl group.

The aryl group represented by $R_{204}$ to $R_{207}$ is preferably a phenyl group or a naphthyl group, more preferably a phenyl group. The aryl group represented by $R_{204}$ to $R_{207}$ may be one having a heterocyclic structure containing an oxygen atom, nitrogen atom, sulfur atom or the like. As the aryl group having a heterocyclic structure, there can be mentioned, for example, a pyrrole residue (group formed by loss of one hydrogen atom from pyrrole), a furan residue (group formed by loss of one hydrogen atom from furan), a thiophene residue (group formed by loss of one hydrogen atom from thiophene), an indole residue (group formed by loss of one hydrogen atom from indole), a benzofuran residue (group formed by loss of one hydrogen atom from benzofuran), a benzothiophene residue (group formed by loss of one hydrogen atom from benzothiophene) or the like.

As preferred alkyl groups and cycloalkyl groups represented by $R_{204}$ to $R_{207}$, there can be mentioned a linear or branched alkyl group having 1 to 10 carbon atoms (for example, a methyl group, an ethyl group, a propyl group, a butyl group or a pentyl group) and a cycloalkyl group having 3 to 10 carbon atoms (a cyclopentyl group, a cyclohexyl group or a norbornyl group).

The aryl group, alkyl group and cycloalkyl group represented by $R_{204}$ to $R_{207}$ may have a substituent. As a possible substituent on the aryl group, alkyl group and cycloalkyl group represented by $R_{204}$ to $R_{207}$, there can be mentioned, for example, an alkyl group (for example, 1 to 15 carbon atoms), a cycloalkyl group (for example, 3 to 15 carbon atoms), an aryl group (for example, 6 to 15 carbon atoms), an alkoxy group (for example, 1 to 15 carbon atoms), a halogen atom, a hydroxyl group, a phenylthio group or the like.

$Z^-$ represents a normucleophilic anion. As such, there can be mentioned the same normucleophilic anions as mentioned with respect to the $Z^-$ of the general formula (ZI).

As the acid generators, there can be further mentioned the compounds of the following general formulae (ZIV), (ZV) and (ZVI).

ZIV $$Ar_3—SO_2—SO_2—Ar_4$$

ZV

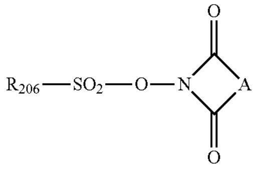

ZVI

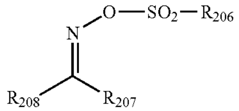

In the general formulae (ZIV) to (ZVI), each of $Ar_3$ and $Ar_4$ independently represents an aryl group.

Each of $R_{206}$, $R_{207}$ and $R_{208}$ independently represents an alkyl group, a cycloalkyl group or an aryl group.

A represents an alkylene group, an alkenylene group or an arylene group.

Among the acid generators, the compounds of the general formulae (ZI) to (ZIII) are more preferred.

As a preferred acid generator, there can be mentioned a compound that generates an acid having one sulfonate group or imido group. As a more preferred acid generator, there can be mentioned a compound that generates a monovalent perfluoroalkanesulfonic acid, a compound that generates a monovalent aromatic sulfonic acid substituted with a fluorine atom or fluorine-atom-containing group, or a compound that generates a monovalent imidic acid substituted with a fluorine atom or fluorine-atom-containing group. As a still more preferred acid generator, there can be mentioned any of sulfonium salts of fluorinated alkanesulfonic acid, fluorinated benzenesulfonic acid or fluorinated imidic acid. With respect to practicable acid generators, it is especially preferred for the generated acid to be a fluorinated alkanesulfonic acid, fluorinated benzenesulfonic acid or fluorinated imidic acid of −1 or below pKa. By the use thereof, an enhancement of sensitivity can be attained.

Especially preferred examples of the acid generators are as follows.

(z1)

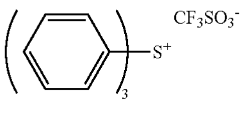

(z2)

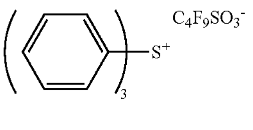

-continued
(z3)
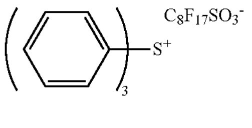
(z4)
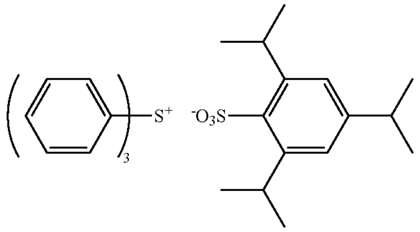
(z5)
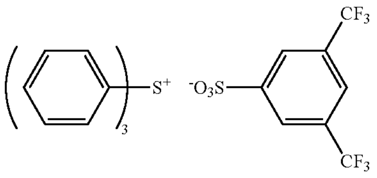
(z6)
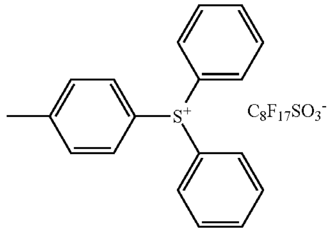
(z7)
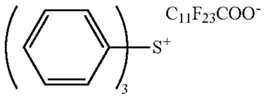
(z8)
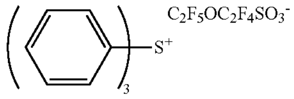
(z9)
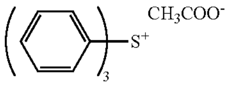
(z10)
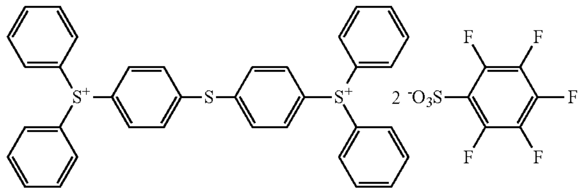
(z11)
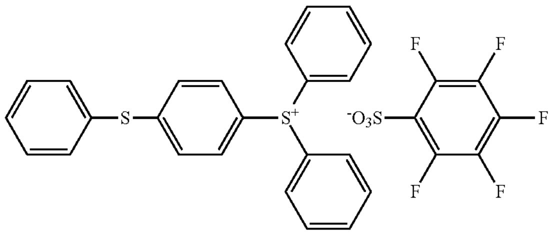
(z12)
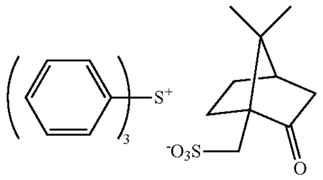
(z13)
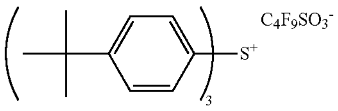
(z14)
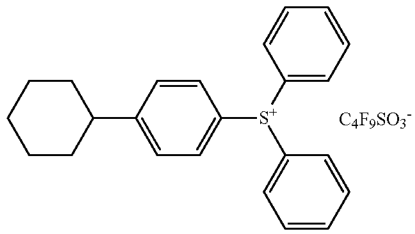
(z15)
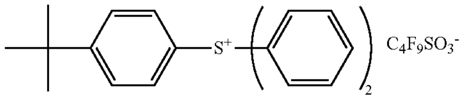
(z16)
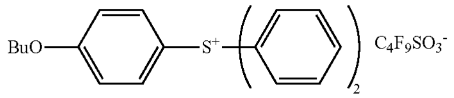
(z17)
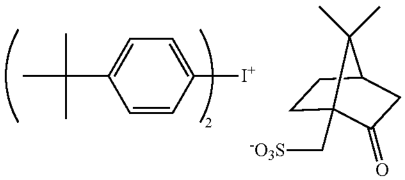
(z18)
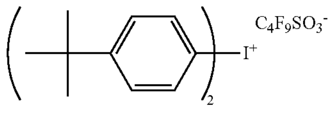

-continued
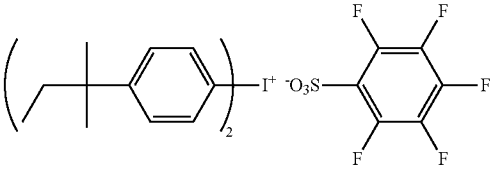
(z19)
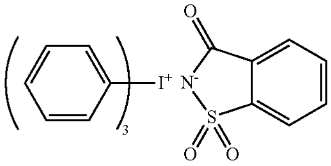
(z20)
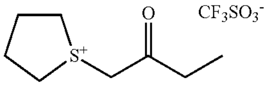
(z21)
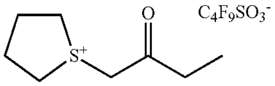
(z22)
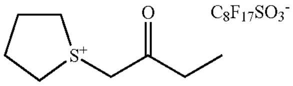
(z23)
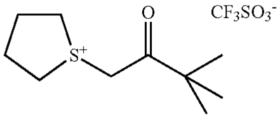
(z24)
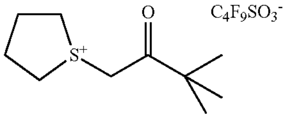
(z25)
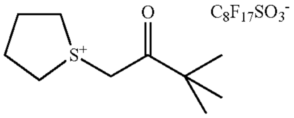
(z26)
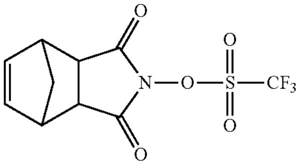
(z27)
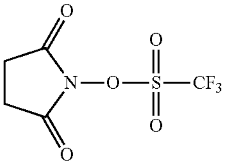
(z28)
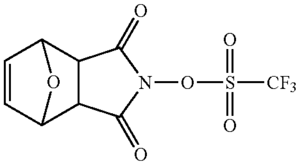
(z29)
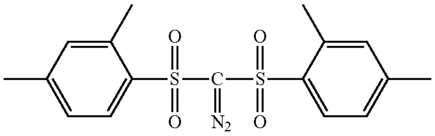
(z30)
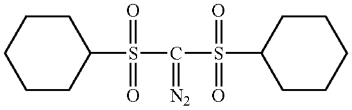
(z31)
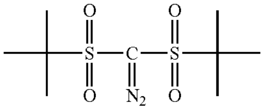
(z32)
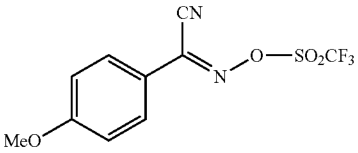
(z33)
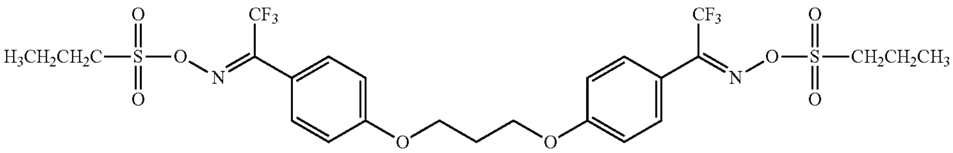
(z34)
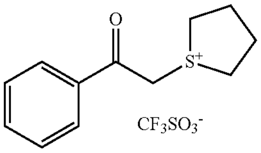
(z35)
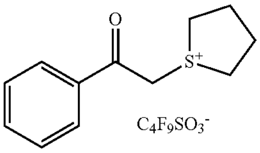
(z36)

-continued
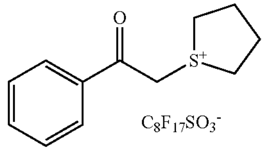
(z37)
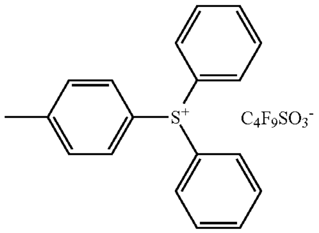
(z38)
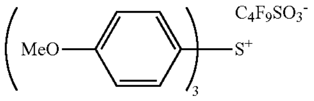
(z39)
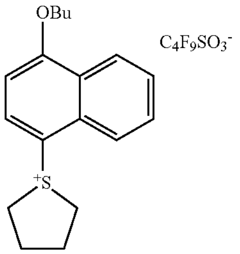
(z40)
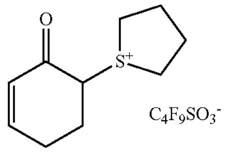
(z41)
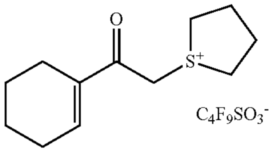
(z42)
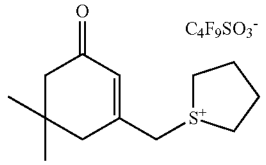
(z43)
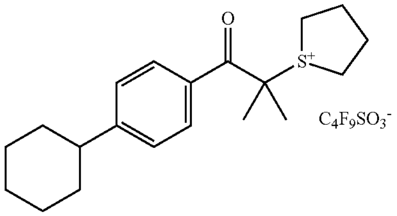
(z44)
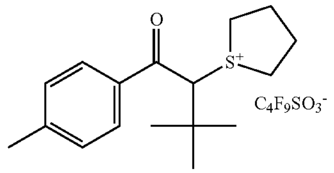
(z45)
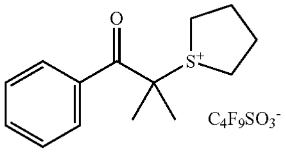
(z46)
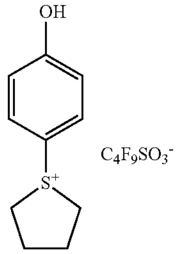
(z47)
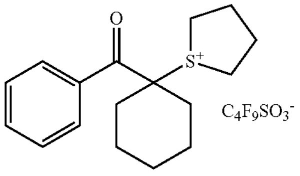
(z48)
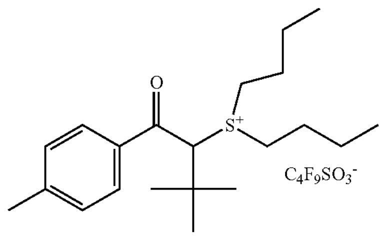
(z49)
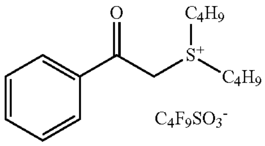
(z50)

-continued
(z51)
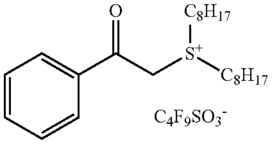
(z52)
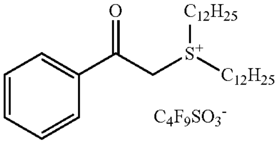
(z53)
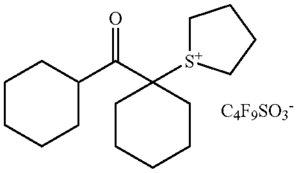
(z54)
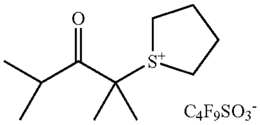
(z55)
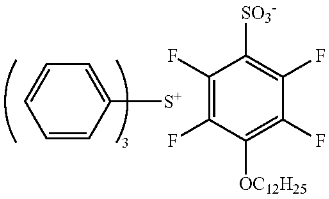
(z56)
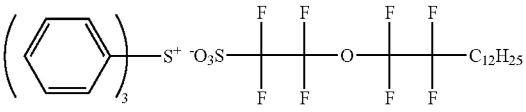
(z58)
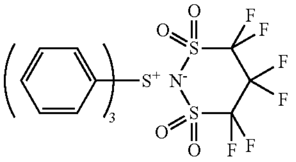
(z57)
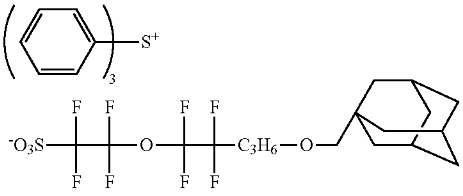
(z59)
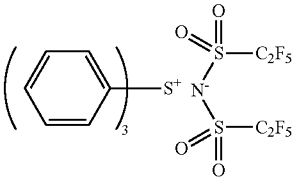
(z60)
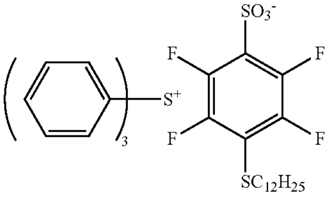
(z61)
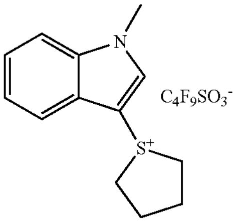
(z62)
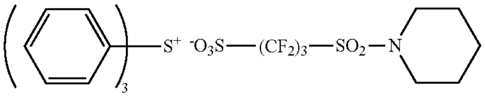
(z63)
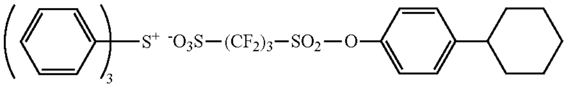
(z64)
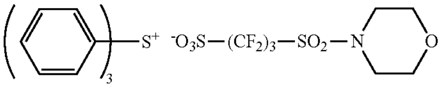
(z65)
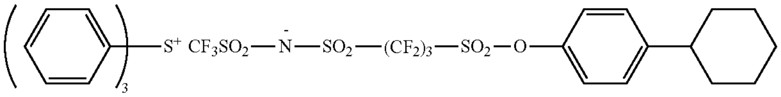

The acid generators (A2) can also be used either individually or in combination.

The amount of acid generator (A2) added, based on the acid generator (A1), is generally 100 mass % or less, preferably 80 mass % or less and more preferably 60 mass % or less.

[3] Resin (B) that is Decomposed by the Action of an Acid to Thereby Exhibit an Increased Solubility in an Alkali Developer The resin (B) that is decomposed by the action of an acid to thereby exhibit an increased solubility in an alkali developer for use in the positive photosensitive composition of the present invention is a resin having, in its principal chain or side chain or both thereof, a group (acid-decomposable group) that is decomposed by the action of an acid to thereby generate an alkali-soluble group. Among them, a resin having an acid-decomposable group in its side chain is preferred.

The acid-decomposable group is preferably a group resulting from substitution of the hydrogen atom of an alkali-soluble group, such as a —COOH group or an —OH group, with an acid-eliminable group.

In the present invention, the acid-decomposable group is preferably an acetal group or a tertiary ester group.

The matrix resin for bonding of the acid-decomposable group as a side chain is an alkali-soluble resin having, in its side chain, an —OH or —COOH group. For example, there can be mentioned the alkali-soluble resins to be described hereinafter.

The alkali dissolution rate of the alkali-soluble resin as measured in a 0.261 N tetramethylammonium hydroxide (TMAH) (23° C.) is preferably 17 nm/sec or greater. The alkali dissolution rate is especially preferably 33 nm/sec or greater.

The alkali-soluble resins especially preferred from this viewpoint include alkali-soluble resins having hydroxystyrene structural units, such as o-, m- or p-poly(hydroxystyrene) and copolymers thereof, hydrogenated poly(hydroxystyrene), halogenated or alkylated poly(hydroxystyrene), poly(hydroxystyrene) having its part O-alkylated or O-acylated, styrene-hydroxystyrene copolymer, α-methylstyrene-hydroxystyrene copolymer and hydrogenated novolak resin and include alkali-soluble resins having carboxylated repeating units, such as those of (meth)acrylic acid and norbornene carboxylic acid.

As repeating units having an acid-decomposable group preferred in the present invention, there can be mentioned, for example, repeating units derived from t-butoxycarbonyloxystyrene, a 1-alkoxyethoxystyrene and a (meth)acrylic acid tertiary alkyl ester. Repeating units derived from a 2-alkyl-2-adamantyl (meth)acrylate and a dialkyl(1-adamantyl)methyl (meth)acrylate are more preferred.

The component (B) for use in the present invention can be obtained by reaction of a precursor of acid-decomposable group with an alkali-soluble resin or by copolymerization of an alkali-soluble resin monomer having an acid-decomposable group bonded thereto with various monomers, as disclosed in, for example, EP 254853 and JP-A' s 2-25850, 3-223860 and 4-251259. When the positive photosensitive composition of the present invention is exposed to KrF excimer laser beams, electron beams, X-rays or high-energy light rays of 50 nm or less wavelength (EUV, etc.), it is preferred for the resin as the component (B) to have hydroxystyrene repeating units. More preferably, the component (B) resin is a copolymer of hydroxystyrene/hydroxystyrene protected by an acid-decomposable group or a copolymer of hydroxystyrene/(meth)acrylic acid tertiary alkyl ester.

In particular, the resin is preferably, for example, one having any of the repeating structures of general formula (I) below.

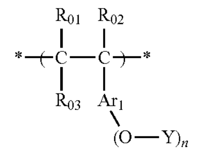

(1)

In the formula, each of $R_{01}$, $R_{02}$ and $R_{03}$ independently represents a hydrogen atom, an alkyl group, a cycloalkyl group, a halogen atom, a cyano group or an alkoxycarbonyl group.

$Ar_1$ represents an aromatic ring group. Alternatively, $R_{03}$ and $Ar_1$ may be simultaneously alkylene groups and bonded to each other so as to form a 5-membered or 6-membered ring in cooperation with —C—C—.

In the formula, each of n Y's independently represents a hydrogen atom or a group that is eliminated by the action of an acid, provided that at least one of the Y's is a group that is eliminated by the action of an acid.

In the formula, n is an integer of 1 to 4, preferably 1 or 2 and more preferably 1.

As preferred alkyl groups represented by $R_{01}$ to $R_{03}$ in the general formula, there can be mentioned optionally substituted alkyl groups having up to 20 carbon atoms, such as a methyl group, an ethyl group, a propyl group, an isopropyl group, an n-butyl group, a sec-butyl group, a hexyl group, a 2-ethylhexyl group, an octyl group and a dodecyl group. Alkyl groups having up to 8 carbon atoms are more preferred.

The alkyl groups contained in the alkoxycarbonyl groups are preferably the same as the above-mentioned alkyl groups represented by $R_{01}$ to $R_{03}$.

The cycloalkyl groups may be monocyclic or polycyclic. As preferred examples thereof, there can be mentioned optionally substituted monocyclic alkyl groups having 3 to 8 carbon atoms, such as a cyclopropyl group, a cyclopentyl group and a cyclohexyl group.

As the halogen atom, there can be mentioned a fluorine atom, a chlorine atom, a bromine atom or an iodine atom. A fluorine atom is preferred.

As preferred alkylene groups represented by $R_{03}$, there can be mentioned those having 1 to 8 carbon atoms, such as a methylene group, an ethylene group, a propylene group, a butylene group, a hexylene group and an octylene group.

The aromatic ring group represented by $Ar_t$ is preferably an optionally substituted aromatic ring group having 6 to 14 carbon atoms. In particular, there can be mentioned a benzene ring, a toluene ring, a naphthalene ring or the like.

In the formula, each of n Y's independently represents a hydrogen atom or a group that is eliminated by the action of an acid, provided that at least one of the n Y's is a group that is eliminated by the action of an acid.

As the group (Y) that is eliminated by the action of an acid, there can be mentioned, for example, $—C(R_{36})(R_{37})(R_{38})$, $—O(=O)—O—C(R_{36})(R_{37})(R_{38})$, $—C(R_{01})(R_{02})(OR_{39})$, $—C(R_{01})(R_{02})—O(=O)—O—C(R_{36})(R_{37})(R_{38})$, $—CH(R_{36})(Ar)$ or the like.

In the formulae, each of $R_{36}$ to $R_{39}$ independently represents an alkyl group, a cycloalkyl group, an aryl group, an aralkyl group or an alkenyl group. $R_{36}$ and $R_{37}$ may be bonded with each other to thereby form a ring structure.

Each of $R_{01}$ and $R_{02}$ independently represents a hydrogen atom, an alkyl group, a cycloalkyl group, an aryl group, an aralkyl group or an alkenyl group.

Ar represents an aryl group.

The alkyl groups represented by $R_{36}$ to $R_{39}$ and $R_{01}$ and $R_{02}$ each preferably have 1 to 8 carbon atoms. For example, there can be mentioned a methyl group, an ethyl group, a propyl group, an n-butyl group, a sec-butyl group, a hexyl group, an octyl group and the like.

The cycloalkyl groups represented by $R_{36}$ to $R_{39}$ and $R_{01}$ and $R_{02}$ may be monocyclic or polycyclic. The monocyclic alkyl groups are preferably cycloalkyl groups having 3 to 8 carbon atoms. As such, there can be mentioned, for example, a cyclopropyl group, a cyclobutyl group, a cyclopentyl group, a cyclohexyl group, a cyclooctyl group and the like. The polycyclic alkyl groups are preferably cycloalkyl groups having 6 to 20 carbon atoms. As such, there can be mentioned, for example, an adamantyl group, a norbornyl group, an isobornyl group, a camphonyl group, a dicyclopentyl group, an α-pinel group, a tricyclodecanyl group, a tetracyclododecyl group, an androstanyl group and the like. With respect to these, the carbon atoms of each of the cycloalkyl groups may be partially substituted with a heteroatom, such as an oxygen atom.

The aryl groups represented by $R_{36}$ to $R_{39}$, $R_{01}$ and $R_{02}$ and Ar each preferably have 6 to 10 carbon atoms. For example, there can be mentioned a phenyl group, a naphthyl group, an anthryl group and the like.

The aralkyl groups represented by $R_{36}$ to $R_{39}$, $R_{01}$ and $R_{02}$ each preferably have 7 to 12 carbon atoms. For example, there can be mentioned a benzyl group, a phenethyl group, a naphthylmethyl group and the like.

The alkenyl groups represented by $R_{36}$ to $R_{39}$, $R_{01}$ and $R_{02}$ each preferably have 2 to 8 carbon atoms. For example, there can be mentioned a vinyl group, an allyl group, a butenyl group, a cyclohexenyl group and the like.

The ring formed by mutual bonding of $R_{36}$ and $R_{37}$ may be monocyclic or polycyclic. The monocyclic structure is preferably a cycloalkane structure having 3 to 8 carbon atoms. As such, there can be mentioned, for example, a cyclopropane structure, a cyclobutane structure, a cyclopentane structure, a cyclohexane structure, a cycloheptane structure, a cyclooctane structure or the like. The polycyclic structure is preferably a cycloalkane structure having 6 to 20 carbon atoms. As such, there can be mentioned, for example, an adamantane structure, a norbornane structure, a dicyclopentane structure, a tricyclodecane structure, a tetracyclododecane structure or the like. With respect to these, the carbon atoms of each of the cycloalkane structure may be partially substituted with a heteroatom, such as an oxygen atom.

Each of the groups represented by $R_{36}$ to $R_{39}$, $R_{01}$, $R_{02}$, $R_{03}$, Ar and $Ar_1$ may have a substituent. As the substituent, there can be mentioned, for example, an alkyl group, a cycloalkyl group, an aryl group, an amino group, an amido group, a ureido group, a urethane group, a hydroxyl group, a carboxyl group, a halogen atom, an alkoxy group, a thioether group, an acyl group, an acyloxy group, an alkoxycarbonyl group, a cyano group, a nitro group or the like. Preferably, the number of carbon atoms of each of the substituents is up to 8.

The group (Y) that is eliminated by the action of an acid more preferably has any of the structures of general formula (2) below.

(2)

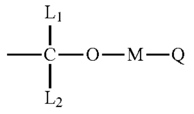

In the formula, each of $L_1$ and $L_2$ independently represents a hydrogen atom, an alkyl group, a cycloalkyl group, an aryl group or an aralkyl group.

M represents a single bond or a bivalent connecting group.

Q represents an alkyl group, a cycloalkyl group, an alicyclic group optionally containing a heteroatom, an aromatic ring group optionally containing a heteroatom, an amino group, an ammonium group, a mercapto group, a cyano group or an aldehyde group.

At least two of Q, M and $L_1$ may be bonded to each other to thereby form a 5-membered or 6-membered ring.

The alkyl groups represented by $L_1$ and $L_2$ are, for example, alkyl groups having 1 to 8 carbon atoms. As preferred examples thereof, there can be mentioned a methyl group, an ethyl group, a propyl group, an n-butyl group, a sec-butyl group, a hexyl group and an octyl group.

The cycloalkyl groups represented by $L_1$ and $L_2$ are, for example, cycloalkyl groups having 3 to 15 carbon atoms. As preferred examples thereof, there can be mentioned a cyclopentyl group, a cyclohexyl group, a norbornyl group and an adamantyl group.

The aryl groups represented by $L_1$ and $L_2$ are, for example, aryl groups having 6 to 15 carbon atoms. As preferred examples thereof, there can be mentioned a phenyl group, a tolyl group, a naphthyl group, an anthryl group and the like.

The aralkyl groups represented by $L_1$ and $L_2$ are, for example, those having 6 to 20 carbon atoms. There can be mentioned a benzyl group, a phenethyl group and the like.

The bivalent connecting group represented by M is, for example, an alkylene group (e.g., a methylene group, an ethylene group, a propylene group, a butylene group, a hexylene group, an octylene group, etc.), a cycloalkylene group (e.g., a cyclopentylene group, a cyclohexylene group, etc.), an alkenylene group (e.g., an ethylene group, a propenylene group, a butenylene group, etc.), an arylene group (e.g., a phenylene group, a tolylene group, a naphthylene group, etc.), —S—, —O—, —CO—, —$SO_2$—, —$N(R_0)$— or a bivalent connecting group resulting from combination of these groups. $R_0$ represents a hydrogen atom or an alkyl group (for example, an alkyl group having 1 to 8 carbon atoms; in particular, there can be mentioned a methyl group, an ethyl group, a propyl group, an n-butyl group, a sec-butyl group, a hexyl group, an octyl group or the like).

The alkyl group and cycloalkyl group represented by Q are the same as those mentioned above as $L_1$ and $L_2$.

As the alicyclic group and aromatic ring group contained in the alicyclic group optionally containing a heteroatom and aromatic ring group optionally containing a heteroatom represented by Q, there can be mentioned, for example, the cycloalkyl group and aryl group mentioned above as $L_1$ and $L_2$. Preferably, each of the alicyclic group and aromatic ring group has 3 to 15 carbon atoms.

As the alicyclic group containing a heteroatom and aromatic ring group containing a heteroatom, there can be mentioned, for example, groups having a heterocyclic structure, such as thiirane, cyclothiorane, thiophene, furan, pyrrole, benzothiophene, benzofuran, benzopyrrole, triazine, imidazole, benzimidazole, triazole, thiadiazole, thiazole and pyrrolidone. However, the alicyclic groups and aromatic ring groups are not limited to these as long as the ring is formed by carbon and a heteroatom or by heteroatoms. As the 5-membered or 6-membered ring that may be formed by mutual bonding of at least two of Q, M and $L_1$, there can be mentioned the 5-membered or 6-membered ring resulting from mutual bonding of at least two of Q, M and $L_1$ so as to form, for example, a propylene group or a butylene group and subsequent formation of a ring containing an oxygen atom.

In the general formula (2), each of the groups represented by $L_1$, $L_2$, M and Q may have a substituent.

As the substituent, there can be mentioned, for example, those mentioned above as being optionally introduced in $R_{36}$ to $R_{39}$, $R_{01}$, $R_{02}$, $R_{03}$, Ar and $Ar_1$. Preferably, the number of carbon atoms of each of the substituents is up to 8.

The groups of the formula -M-Q are preferably groups having 1 to 30 carbon atoms, more preferably groups having 5 to 20 carbon atoms. From the viewpoint of outgas suppression, it is especially preferred for the number of carbon atoms to be 6 or greater.

Specific examples of the components (B) for use in the present invention will be shown below, which however in no way limit the scope of the present invention.

(R-1)

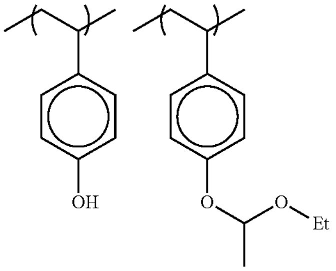

(R-2)

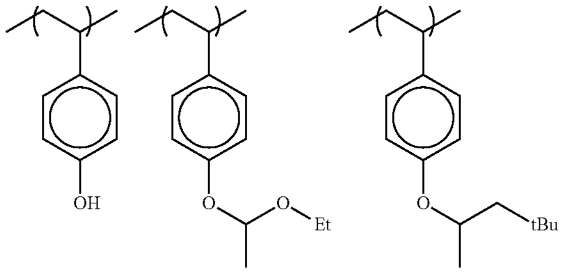

(R-3)

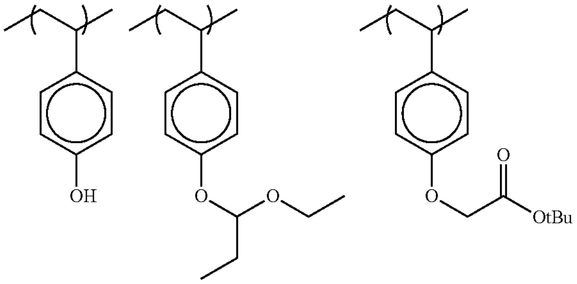

-continued (R-4)

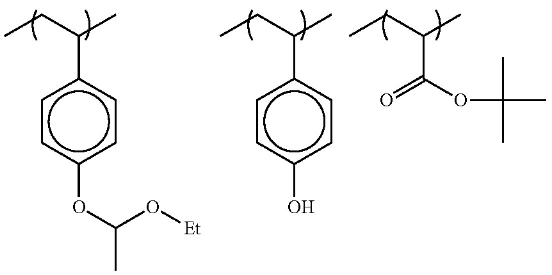

(R-5)

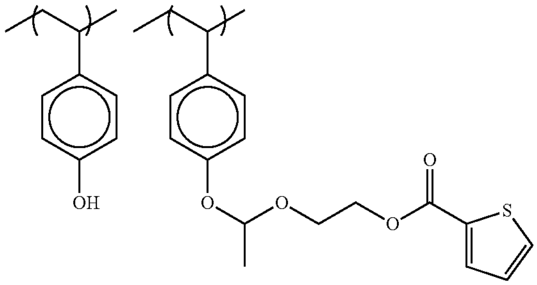

(R-6)

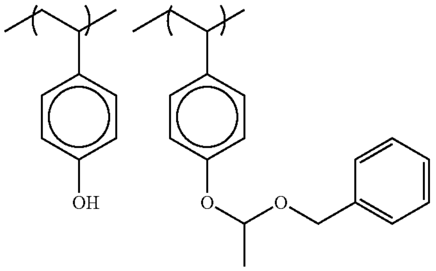

(R-7)

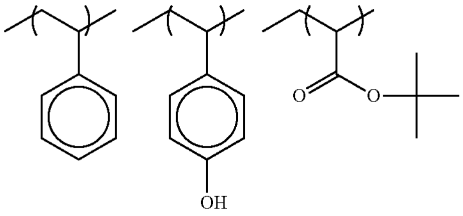

(R-8)

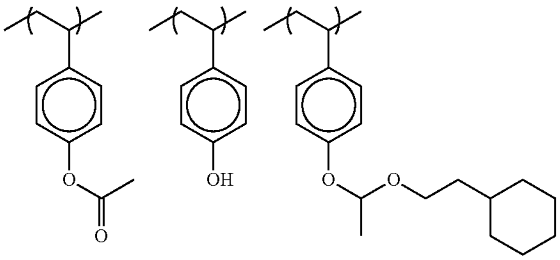

-continued
(R-9)
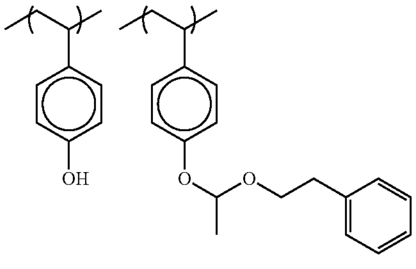
(R-10)
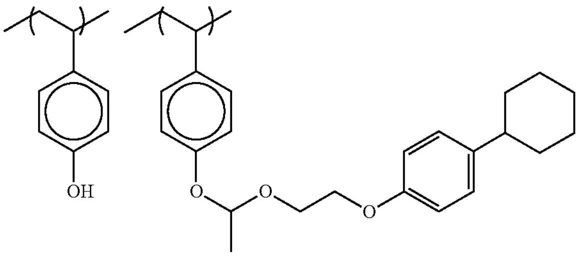
(R-11)
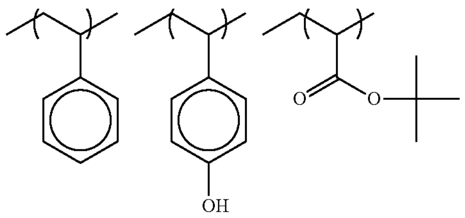
(R-12)
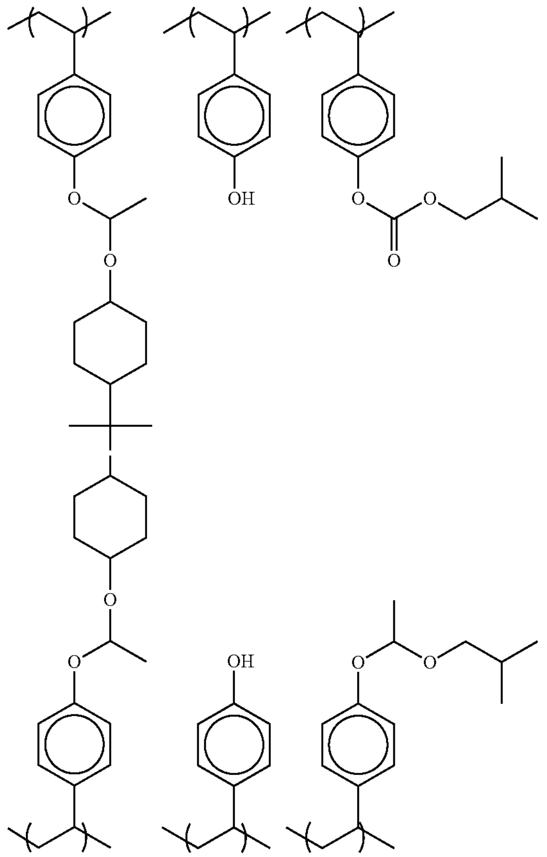
-continued
(R-13)
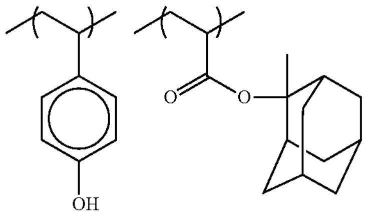
(R-14)
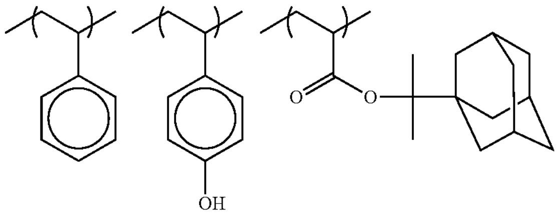
(R-15)
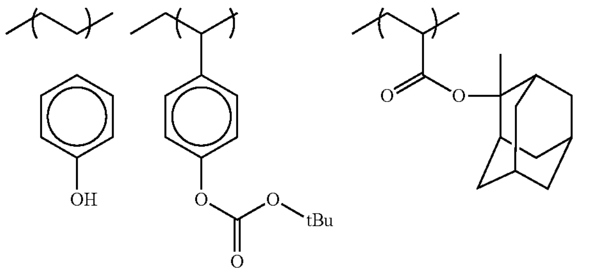
(R-16)
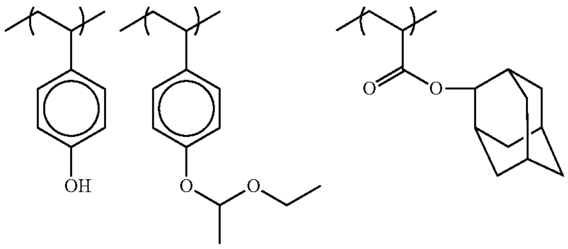
(R-17)
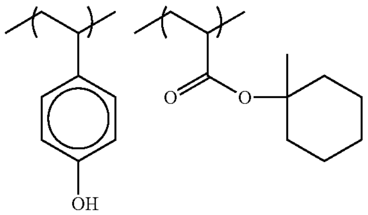
R-18
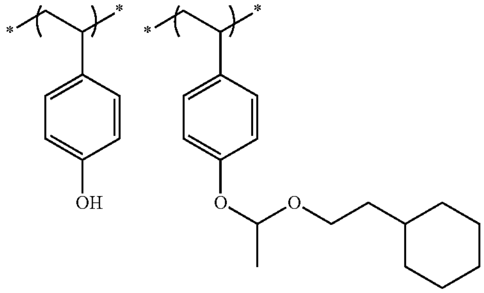

-continued

R-19

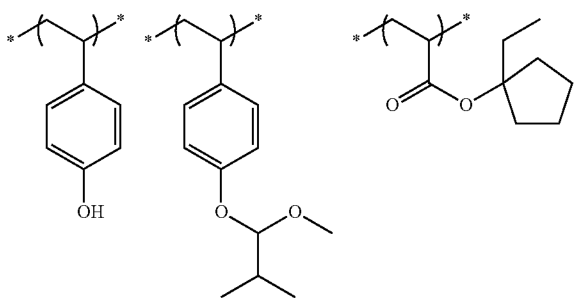

R-20

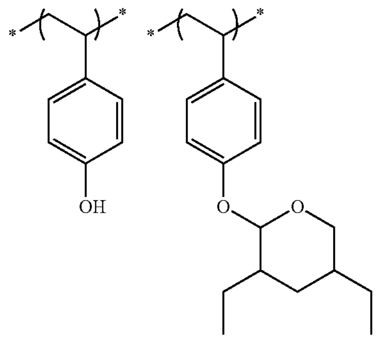

R-21

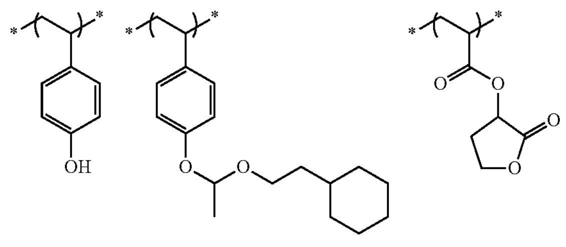

In the above specific examples, tBu represents a t-butyl group.

The content of acid-decomposable group is expressed by the formula B/(B+S) wherein B refers to the number of acid-decomposable groups contained in the resin and S refers to the number of alkali-soluble groups not protected by any acid-eliminable group. The content is preferably in the range of 0.01 to 0.7, more preferably 0.05 to 0.50 and further preferably 0.05 to 0.40.

When the positive photosensitive composition of the present invention is exposed to ArF excimer laser beams, it is preferred for the resin as the component (B) to be a resin that has an alicyclic hydrocarbon structure of a single ring or multiple rings and that is decomposed by the action of an acid to thereby exhibit an increased solubility in an alkali developer.

The resin that has an alicyclic hydrocarbon structure of a single ring or multiple rings and that is decomposed by the action of an acid to thereby exhibit an increased solubility in an alkali developer (hereinafter also referred to as "alicyclic hydrocarbon based acid-decomposable resin") is preferably a resin having at least one member selected from the group consisting of the repeating units having partial structures containing the alicyclic hydrocarbons of general formulae (pI) to (pV) below and the repeating units of general formula (II-AB) below.

(pI)

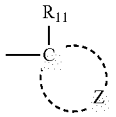

(pII)

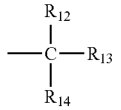

(pIII)

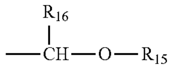

(pIV)

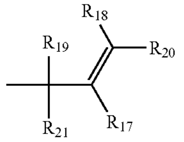

(pV)

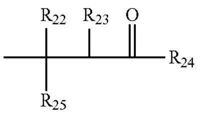

In the general formulae (pI) to (pV), $R_{11}$ represents a methyl group, an ethyl group, an n-propyl group, an isopropyl group, an n-butyl group, an isobutyl group or a sec-butyl group, and Z represents an atomic group required for formation of a cycloalkyl group in cooperation with a carbon atom.

Each of $R_{12}$ to $R_{16}$ independently represents a cycloalkyl group or a linear or branched alkyl group having 1 to 4 carbon atoms, provided that at least one of $R_{12}$ to $R_{14}$ or either $R_{15}$ or $R_{16}$ represents a cycloalkyl group.

Each of $R_{17}$ to $R_{21}$ independently represents a hydrogen atom or a cycloalkyl group or a linear or branched alkyl group having 1 to 4 carbon atoms, provided that at least one of $R_{17}$ to $R_{21}$ represents a cycloalkyl group. Either $R_{19}$ or $R^{21}$ represents a cycloalkyl group or a linear or branched alkyl group having 1 to 4 carbon atoms.

Each of $R_{22}$ to $R_{25}$ independently represents a hydrogen atom or a cycloalkyl group or a linear or branched alkyl group having 1 to 4 carbon atoms, provided that at least one of $R_{22}$ to $R_{25}$ represents a cycloalkyl group. $R_{23}$ and $R_{24}$ may be bonded to each other to thereby form a ring.

(II-AB)

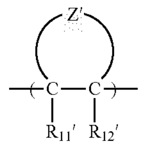

In the general formula (II-AB), each of $R_{11}'$ and $R_{12}'$ independently represents a hydrogen atom, a cyano group, a halogen atom or an alkyl group.

Z' represents an atomic group for formation of an alicyclic structure wherein two bonded carbon atoms (C—C) are contained.

Further preferably, the general formula (II-AB) is either general formula (II-AB1) or general formula (II-AB2) below.

(II-AB1)

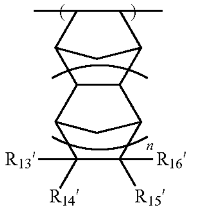

(II-AB2)

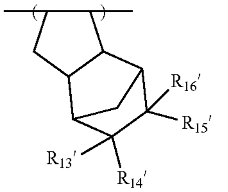

In the general formulae (II-AB1) and (II-AB2), each of $R_{13}$' to $R_{16}$' independently represents a hydrogen atom, a halogen atom, a cyano group, a hydroxyl group, —COOH, —$COOR_5$, a group that is decomposed by the action of an acid, —C(═O)—X-A'—$R_{17}$', an alkyl group or a cycloalkyl group. At least two of $R_{13}$' to $R_{16}$' may be bonded to each other to thereby form a ring.

In the above formula, $R_5$ represents an alkyl group, a cycloalkyl group or a group with a lactone structure.

X represents an oxygen atom, a sulfur atom, —NH—, —$NHSO_2$— or —$NHSO_2NH$—.

A' represents a single bond or a bivalent connecting group.

$R_{17}$' represents —COOH, —$COOR_5$, —CN, a hydroxyl group, an alkoxy group, —CO—NH—$R_6$, —CO—NH—$SO_2$—$R_6$ or a group with a lactone structure.

$R_6$ represents an alkyl group or a cycloalkyl group.

n is 0 or 1.

In the general formulae (pI) to (pV), each of the alkyl groups represented by $R_{12}$ to $R_{25}$ is a linear or branched alkyl group having 1 to 4 carbon atoms. As such, there can be mentioned, for example, a methyl group, an ethyl group, a propyl group, an n-butyl group, a sec-butyl group, a t-butyl group or the like.

The cycloalkyl groups represented by $R_{11}$ to $R_{25}$ and the cycloalkyl group formed by Z and a carbon atom may be monocyclic or polycyclic. In particular, there can be mentioned groups of a monocyclo, bicyclo, tricyclo or tetracyclo structure or the like having 5 or more carbon atoms. The number of carbon atoms thereof is preferably in the range of 6 to 30, especially preferably 7 to 25. These cycloalkyl groups may have substituents.

As preferred cycloalkyl groups, there can be mentioned an adamantyl group, a noradamantyl group, a decalin residue, a tricyclodecanyl group, a tetracyclododecanyl group, a norbornyl group, a cedrol group, a cyclopentyl group, a cyclohexyl group, a cycloheptyl group, a cyclooctyl group, a cyclodecanyl group and a cyclododecanyl group. As more preferred cycloalkyl groups, there can be mentioned an adamantyl group, a norbornyl group, a cyclohexyl group, a cyclopentyl group, a tetracyclododecanyl group and a tricyclodecanyl group.

These alkyl groups and cycloalkyl groups may further have substituents. As substituents that can be introduced in the alkyl groups and cycloalkyl groups, there can be mentioned an alkyl group (1 to 4 carbon atoms), a halogen atom, a hydroxyl group, an alkoxy group (1 to 4 carbon atoms), a carboxyl group and an alkoxycarbonyl group (2 to 6 carbon atoms). These alkyl groups, alkoxy groups, alkoxycarbonyl groups, etc. may further have substituents. As substituents that can be further introduced in the alkyl groups, alkoxy groups, alkoxycarbonyl groups, etc., there can be mentioned a hydroxyl group, a halogen atom and an alkoxy group.

The structures of the general formulae (pI) to (pV) employed in the above resin can be used for the protection of the alkali-soluble groups. As the alkali-soluble groups, there can be mentioned various groups generally known in this technical field.

In particular, there can be mentioned, for example, structures resulting from replacement of a hydrogen atom of a carboxylic acid group, sulfonic acid group, phenol group or thiol group with any of the structures of the general formulae (pI) to (pV). Structures resulting from replacement of a hydrogen atom of a carboxylic acid group or sulfonic acid group with any of the structures of the general formulae (pI) to (pV) are preferred.

As preferred repeating units having any of the alkali-soluble groups protected by the structures of the general formulae (pI) to (pV), there can be mentioned those of general formula (pA) below.

(pA)

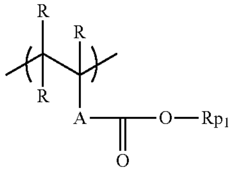

In the general formula (pA), R represents a hydrogen atom, a halogen atom or a linear or branched alkyl group having 1 to 4 carbon atoms. Two or more R's may be identical to or different from each other.

A represents any one or a combination of two or more groups selected from the group consisting of a single bond, an alkylene group, an ether group, a thioether group, a carbonyl group, an ester group, an amido group, a sulfonamido group, a urethane group and a urea group. A single bond is preferred.

Pp1 represents any of the groups of the above general formulae (pI) to (pV).

The repeating units of the general formula (pA) are most preferably those derived from a 2-alkyl-2-adamantyl (meth) acrylate and a dialkyl(1-adamantyl)methyl (meth)acrylate.

Specific examples of the repeating units of the general formula (pA) will be shown below.

1

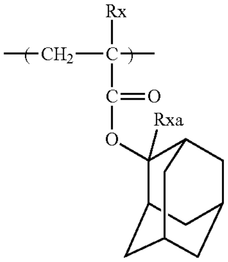

-continued
2
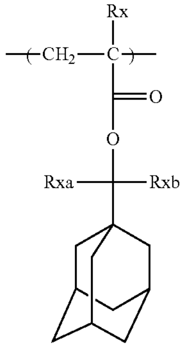
3
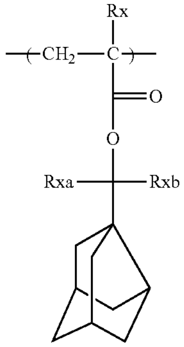
4
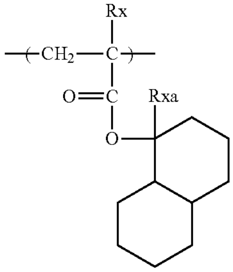
5
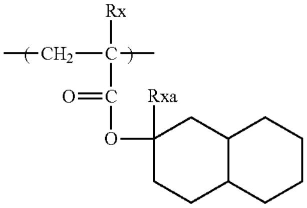
6
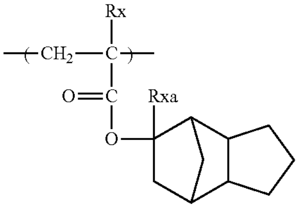
7
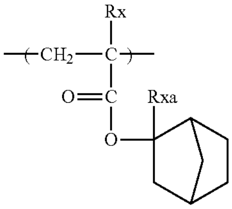
-continued
8
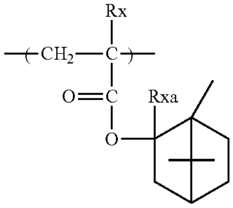
9
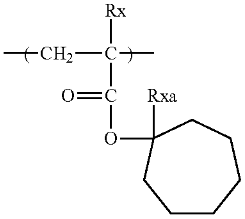
10
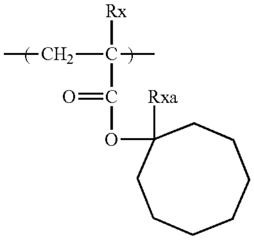
11
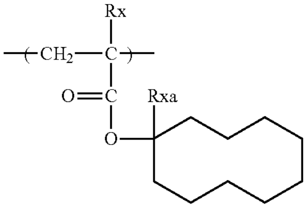
12
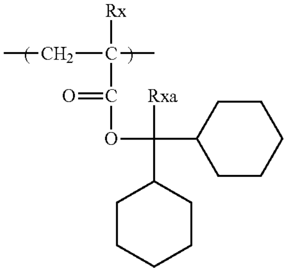
13
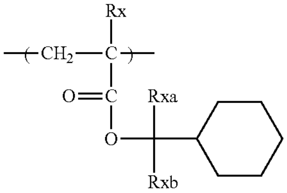
14
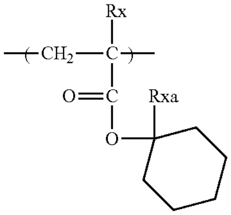

-continued

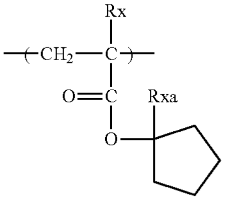

15

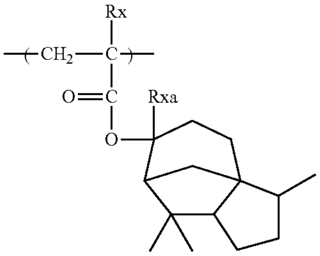

16

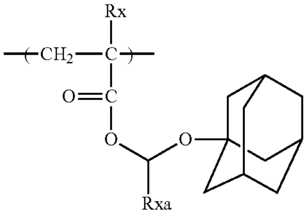

17

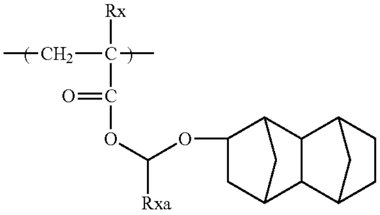

18

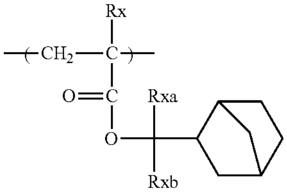

19

In the above structural formulae, Rx represents H, $CH_3$, $CF_3$ or $CH_2OH$. Each of Rxa and Rxb independently represents an alkyl group having 1 to 4 carbon atoms. In the general formula (II-AB), the halogen atoms represented by $R_{11}'$ and $R_{12}'$ include a chlorine atom, a bromine atom, a fluorine atom, an iodine atom, etc.

The alkyl groups represented by $R_{11}'$ and $R_{12}'$ are preferably linear or branched alkyl groups each having 1 to 10 carbon atoms. For example, there can be mentioned a methyl group, an ethyl group, an n-propyl group, an isopropyl group, a linear or branched butyl, pentyl, hexyl or heptyl group, and the like.

The atomic group for formation of the alicyclic structure represented by Z' is an atomic group capable of providing the resin with a repeating unit of optionally substituted alicyclic hydrocarbon. The atomic group is especially preferably one capable of providing a bridged alicyclic structure for formation of a bridged alicyclic hydrocarbon repeating unit.

The provided alicyclic hydrocarbon skeleton can be the same as that of the cycloalkyl groups represented by $R_{12}$ to $R_{25}$ in the general formulae (pII) to (pV).

The alicyclic hydrocarbon skeleton may have a substituent. As the substituent, there can be mentioned any of the atoms or groups represented by $R_{13}'$ to $R_{16}'$ in the general formulae (II-AB1) and (II-AB2).

In the alicyclic hydrocarbon based acid-decomposable resin according to the present invention, the group that is decomposed by the action of an acid can have at least one repeating unit selected from among the repeating units having partial structures containing the alicyclic hydrocarbons of the general formulae (pI) to (pV), the repeating units of general formula (II-AB) and the repeating units of copolymer components to be described below.

Any of the various substituents that can be introduced in $R_{13}'$ to $R_{16}'$ in the general formulae (II-AB1) and (II-AB2) can be a substituent for the atomic groups for formation of the alicyclic structures of the general formula (II-AB) or the atomic groups Z for formation of the bridged alicyclic structures.

Specific examples of the repeating units of the above general formulae (II-AB1) and (II-AB2) will be shown below, which however in no way limit the scope of the present invention.

[II-1]

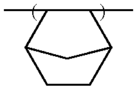

[II-2]

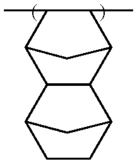

[II-3]

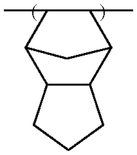

[II-4]

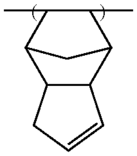

[II-5]

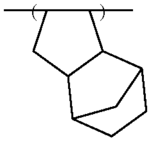

[II-6]

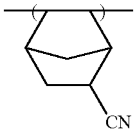

[II-7]

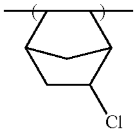

-continued
[II-8]
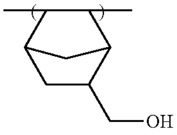
[II-9]
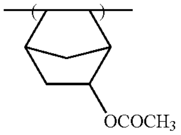
[II-10]
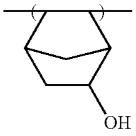
[II-11]
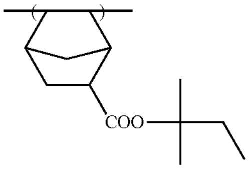
[II-12]
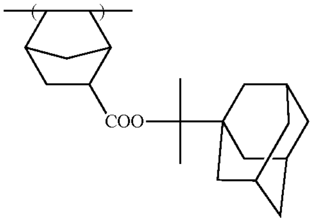
[II-13]
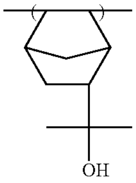
[II-14]
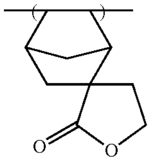
[II-15]
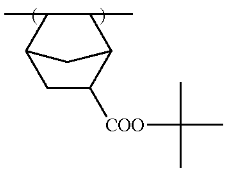
[II-16]
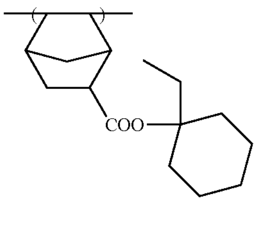
-continued
[II-17]
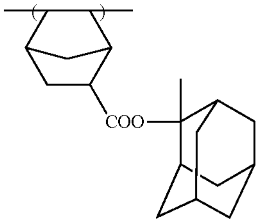
[II-18]
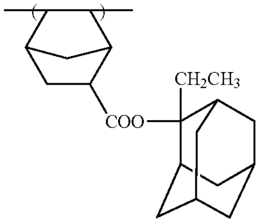
[II-19]
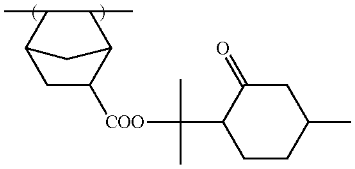
[II-20]
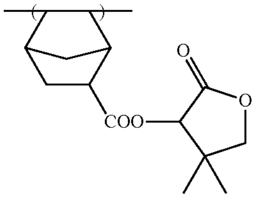
[II-21]
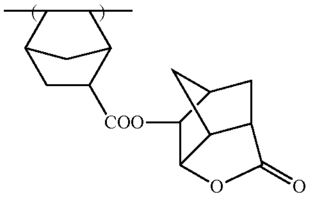
[II-22]
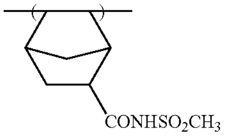
[II-23]
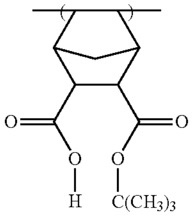

-continued

[II-24]

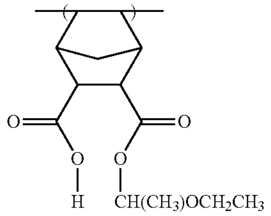

[II-25]

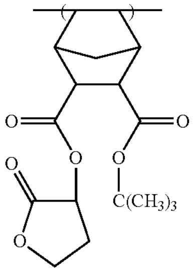

[II-26]

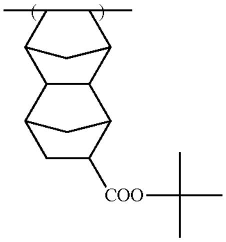

[II-27]

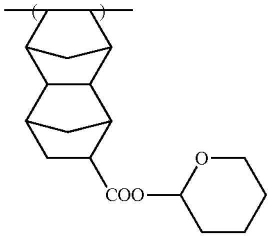

[II-28]

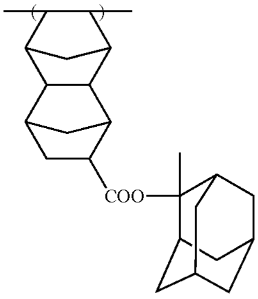

[II-29]

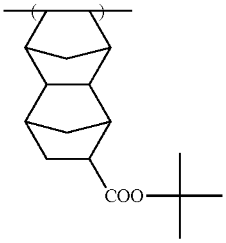

-continued

[II-30]

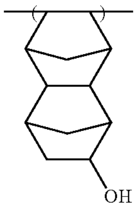

[II-31]

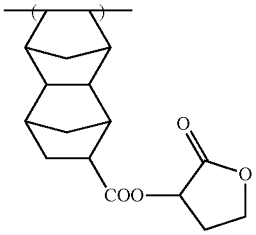

[II-32]

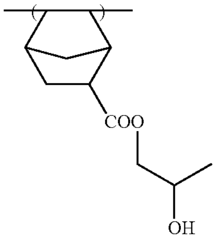

It is preferred for the alicyclic hydrocarbon based acid-decomposable resin according to the present invention to have a repeating unit having a lactone group. Any lactone groups can be employed as long as a lactone structure is possessed therein. However, groups with a 5 to 7-membered ring lactone structure are preferred, and those resulting from condensation of lactone structures of a 5 to 7-membered ring with other cyclic structures effected in a fashion to form a bicyclo structure or Spiro structure are especially preferred. More preferably, the alicyclic hydrocarbon based acid-decomposable resin according to the present invention has a repeating unit having a lactone structure represented by any of general formulae (LC1-1) to (LC1-16) below. The groups with lactone structures may be directly bonded to the principal chain of the resin. Preferred lactone structures are those of the formulae (LC1-1), (LC1-4), (LC1-5), (LC1-6), (LC1-13) and (LC1-14). The use of these specified lactone structures would realize improvement in the line edge roughness and development defect.

LC-1-1

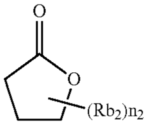

LC1-2

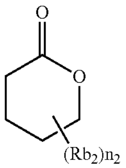

-continued

LC1-3

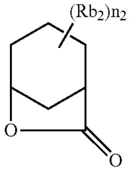

LC1-4

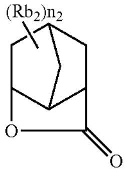

LC1-5

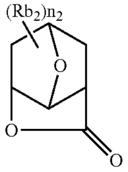

LC1-6

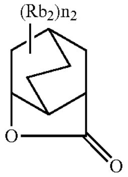

LC1-7

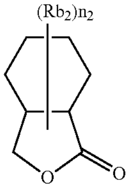

LC1-8

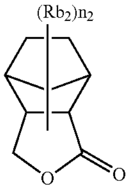

LC1-9

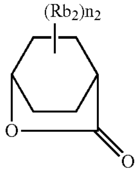

LC1-10

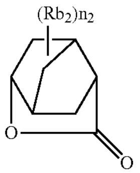

-continued

LC1-11

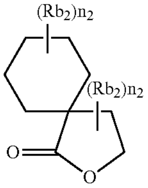

LC1-12

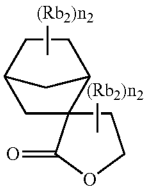

LC1-13

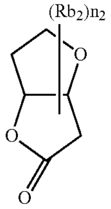

LC1-14

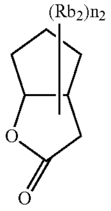

LC1-15

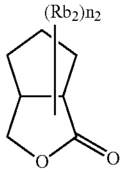

LC1-16

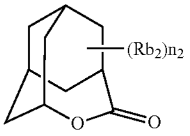

The presence of a substituent ($Rb_2$) on the portion of the lactone structure is optional. As preferred substituents ($Rb_2$), there can be mentioned an alkyl group having 1 to 8 carbon atoms, a cycloalkyl group having 3 to 7 carbon atoms, an alkoxy group having 1 to 8 carbon atoms, an alkoxycarbonyl group having 1 to 8 carbon atoms, a carboxyl group, a halogen atom, a hydroxyl group, a cyano group, an acid-decomposable group and the like. In the formulae, $n_2$ is an integer of 0 to 4. When $n_2$ is an integer of 2 or greater, the plurality of present substituents ($Rb_2$) may be identical to or different from each other. Further, the plurality of present substituents ($Rb_2$) may be bonded to each other to thereby form a ring.

As the repeating units having the groups with lactone structures of any of the general formulae (LC1-1) to (LC1-16), there can be mentioned the repeating units of the general formulae (II-AB1) and (II-AB2) wherein at least one of R13' to R16' has any of the groups of the general formulae (LC1-1) to (LC1-16) (for example, the $R_5$ of —$COOR_5$ represents any of the groups of the general formulae (LC1-1) to (LC1-16)) as well as the repeating units of general formula (AI) below.

(AI)

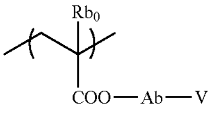

In the general formula (AI), $Rb_0$ represents a hydrogen atom, a halogen atom or an alkyl group having 1 to 4 carbon atoms.

As the alkyl group represented by $Rb_0$, there can be mentioned, for example, a methyl group, an ethyl group, a propyl group, an n-butyl group, a sec-butyl group, a t-butyl group or the like. The alkyl group represented by $Rb_0$ may have a substituent. As preferred substituents that may be introduced in the alkyl group represented by $Rb_0$, there can be mentioned, for example, a hydroxyl group and a halogen atom.

As the halogen atom represented by $Rb_0$, there can be mentioned a fluorine atom, a chlorine atom, a bromine atom or an iodine atom. The $Rb_0$ is preferably a hydrogen atom or a methyl group.

Ab represents an alkylene group, a bivalent connecting group with an alicyclic hydrocarbon structure of a single ring or multiple rings, a single bond, an ether group, an ester group, a carbonyl group, a carboxyl group or a bivalent connecting group resulting from combination of these. A single bond and a connecting group of the formula $-Ab_1-CO_2-$ are preferred.

$Ab_1$ is a linear or branched alkylene group or a cycloalkylene group of a single ring or multiple rings, being preferably a methylene group, an ethylene group, a cyclohexyl residue, an adamantyl residue or a norbornyl residue.

V represents any of the groups of the general formulae (LC1-1) to (LC1-16).

The repeating unit having a lactone structure is generally present in the form of optical isomers. Any of the optical isomers may be used. It is both appropriate to use a single type of optical isomer alone and to use a plurality of optical isomers in the form of a mixture. When a single type of optical isomer is mainly used, the optical purity (ee) thereof is preferably 90 or higher, more preferably 95 or higher.

Specific examples of the repeating units having groups with lactone structures will be shown below, which however in no way limit the scope of the present invention.

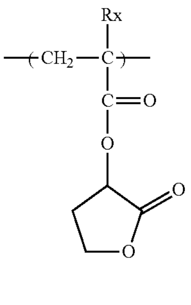

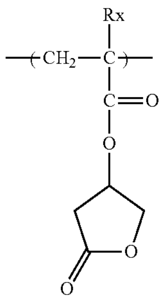

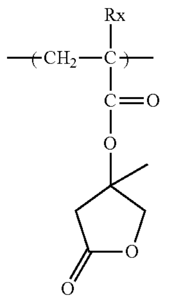

-continued

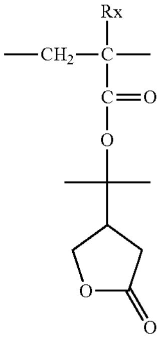

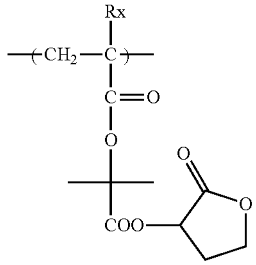

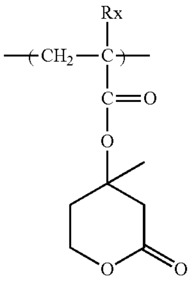

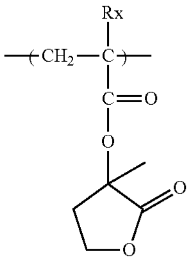

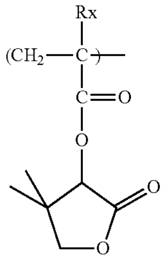

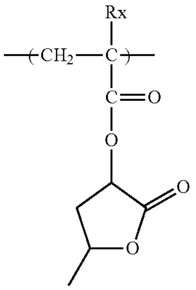

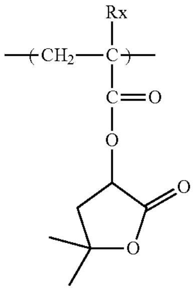

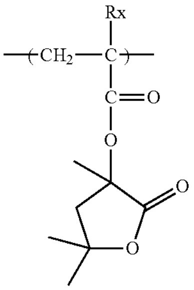

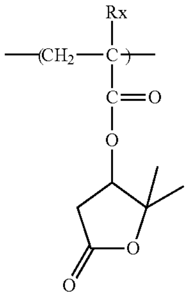

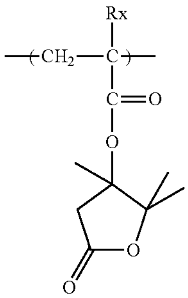

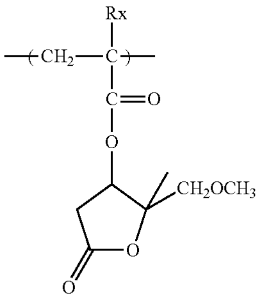

-continued
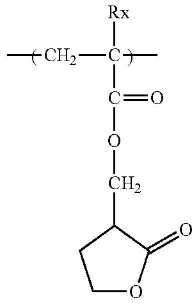
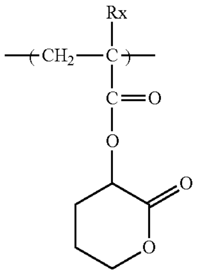
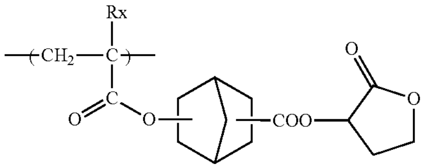
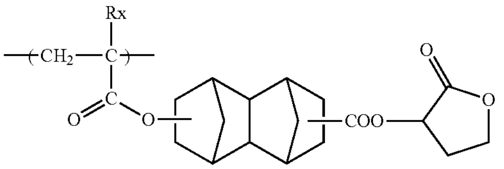
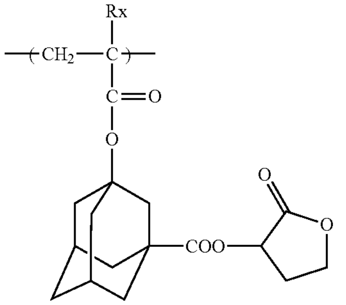
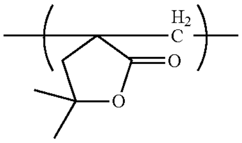
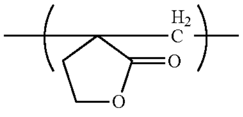
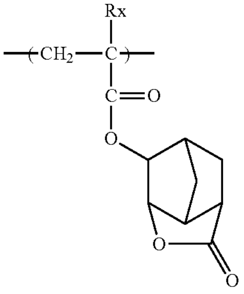
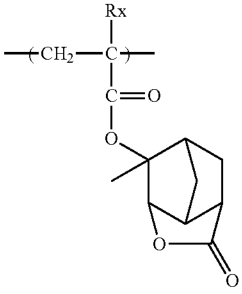
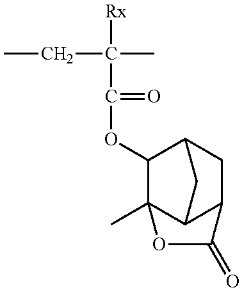
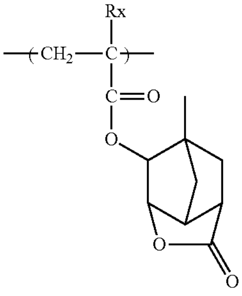
-continued
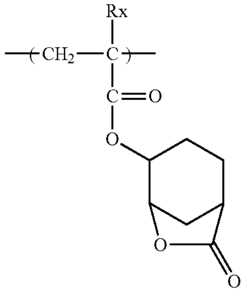
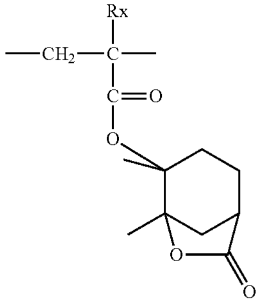
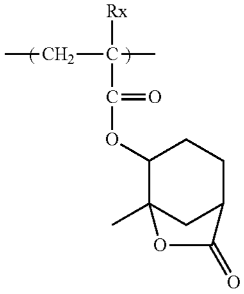
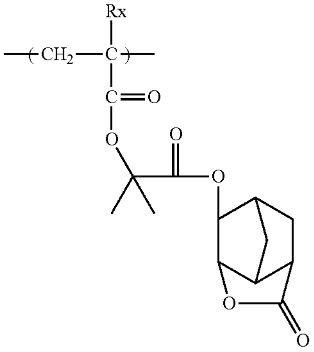
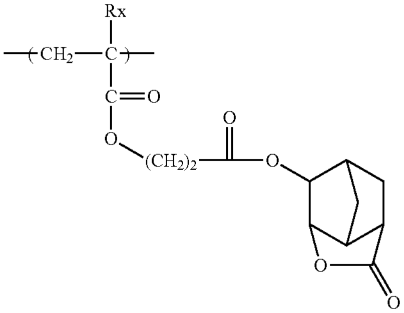
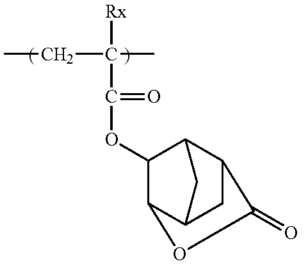
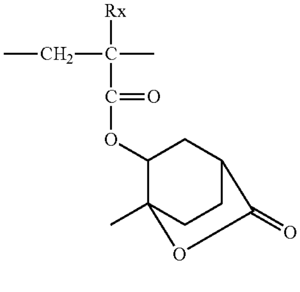
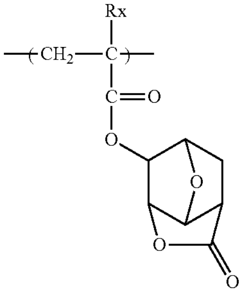

-continued
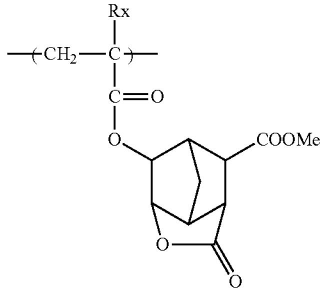
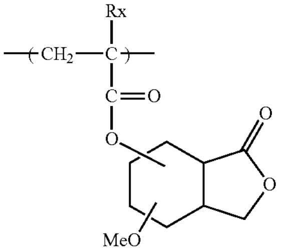
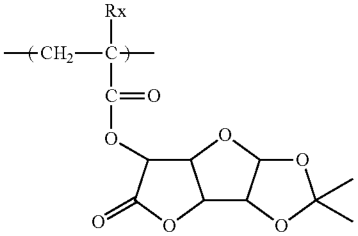
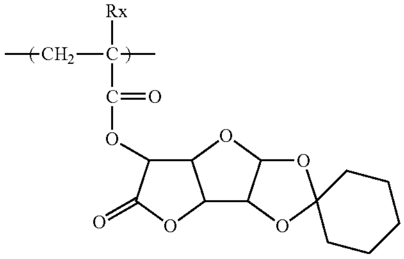
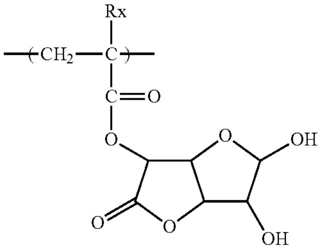
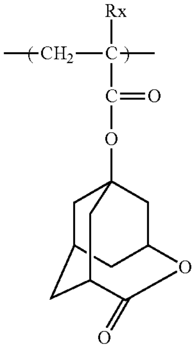
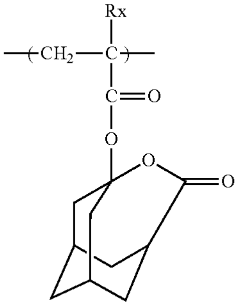
-continued
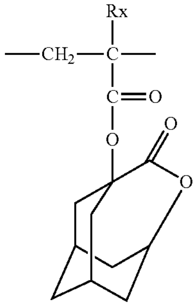
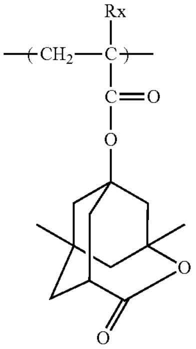
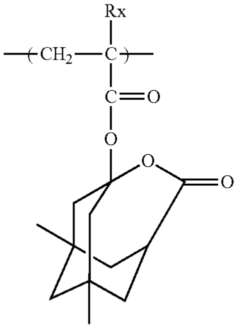
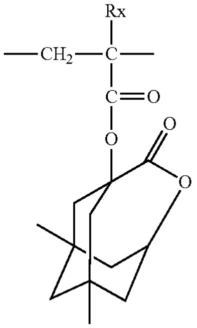
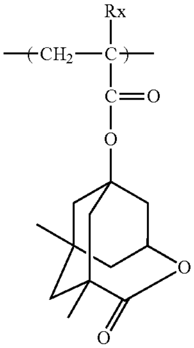
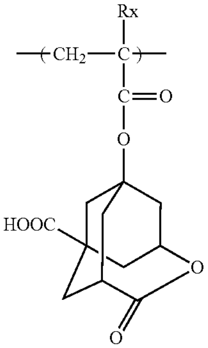
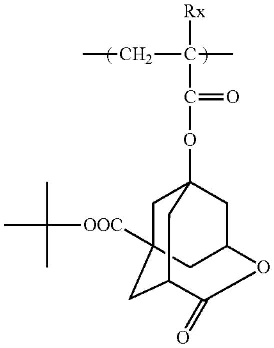
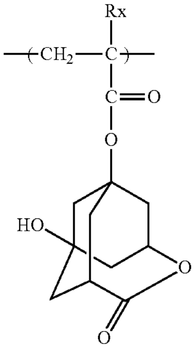

-continued

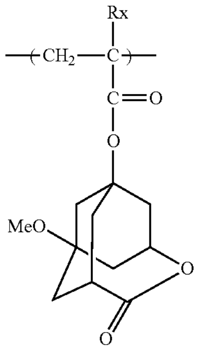

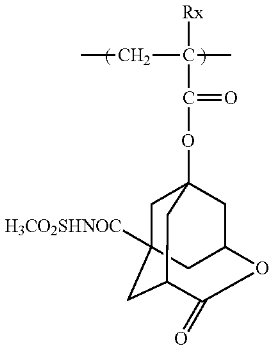

It is preferred for the alicyclic hydrocarbon based acid-decomposable resin according to the present invention to have a repeating unit having an alicyclic hydrocarbon structure substituted with a polar group. The containment of this repeating unit would realize enhancements of adhesion to substrate and developer affinity. The polar group is preferably a hydroxyl group or a cyano group.

The hydroxyl group as the polar group constitutes an alcoholic hydroxyl group.

As the alicyclic hydrocarbon structure substituted with a polar group, there can be mentioned, for example, any of the structures of general formulae (VIIa) and (VIIb) below.

(VIIa)

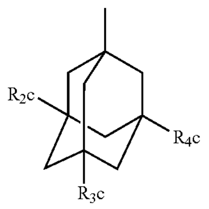

(VIIb)

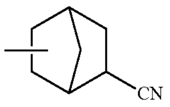

In the general formula (VIIa), each of $R_2c$ to $R_4c$ independently represents a hydrogen atom, a hydroxyl group or a cyano group, provided that at least one of the $R_2c$ to $R_4c$ represents a hydroxyl group or a cyano group. Preferably, one or two of the $R_2c$ to $R_4c$ are hydroxyl groups and the remainder is a hydrogen atom. More preferably, two of the $R_2c$ to $R_4c$ are hydroxyl groups and the remainder is a hydrogen atom.

The groups of the general formula (VIIa) preferably have a dihydroxy form or monohydroxy form, more preferably a dihydroxy form.

As the repeating units having the groups of the general formula (VIIa) or (VIIb), there can be mentioned the repeating units of the general formulae (II-AB1) and (II-AB2) wherein at least one of R13' to R16' has any of the groups of the general formula (VIIa) or (VIIb) (for example, the $R_5$ of $—COOR_5$ represents any of the groups of the general formula (VIIa) or (VIIb)) as well as the repeating units of general formula (AIIa) or (AIIb) below.

(AIIa)

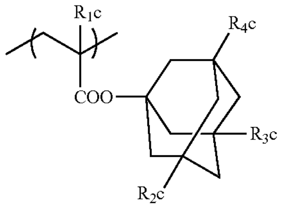

(AIIb)

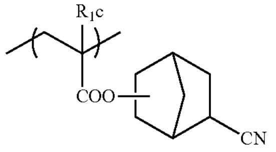

In the general formulae (AIIa) and (AIIb), $R_1c$ represents a hydrogen atom, a methyl group, a trifluoromethyl group or a hydroxymethyl group.

$R_2c$ to $R_4c$ have the same meaning as those of the general formula (VIIa).

Specific examples of the repeating units having an alicyclic hydrocarbon structure substituted with a polar group, expressed by the general formula (AIIa) or (AIIb) will be shown below, which however in no way limit the scope of the present invention.

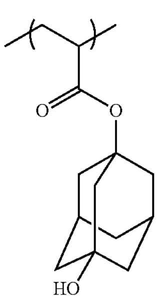

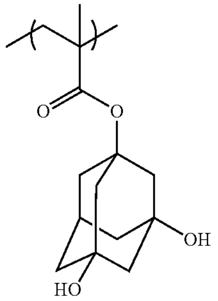

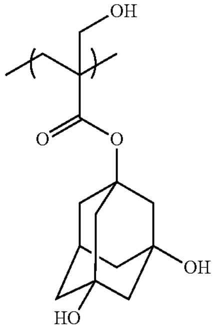

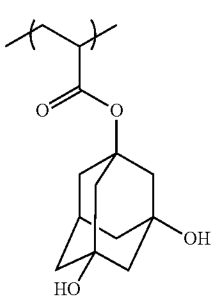

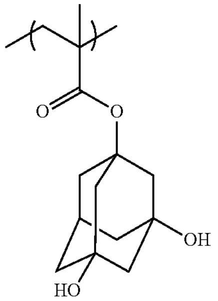

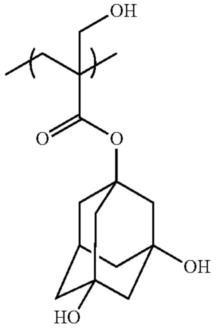

-continued

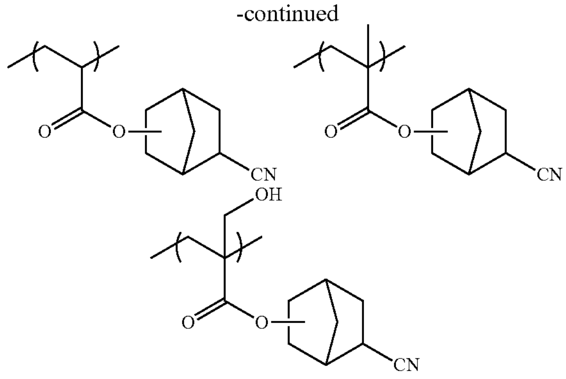

The alicyclic hydrocarbon based acid-decomposable resin according to the present invention may have any of the repeating units of general formula (VIII) below.

(VIII)

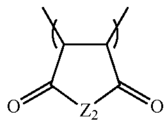

In the general formula (VIII), $Z_2$ represents —O— or —N($R_{41}$)—. $R_{41}$ represents a hydrogen atom, a hydroxyl group, an alkyl group or —$OSO_2$—$R_{42}$. $R_{42}$ represents an alkyl group, a cycloalkyl group or a camphor residue. The alkyl groups represented by $R_{41}$ and $R_{42}$ may be substituted with, for example, a halogen atom (preferably a fluorine atom).

Specific examples of the repeating units of the general formula (VIII) will be shown below, which however in no way limit the scope of the present invention.

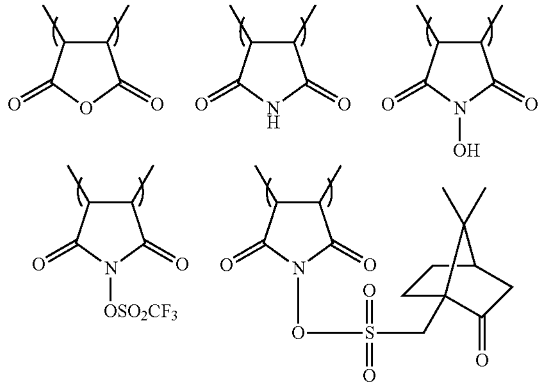

It is preferred for the alicyclic hydrocarbon based acid-decomposable resin according to the present invention to contain a repeating unit having an alkali-soluble group, especially a repeating unit having a carboxyl group. The introduction of the repeating unit having an alkali-soluble group would increase the resolving power in contact hole usage. The repeating unit having a carboxyl group is preferably either a repeating unit wherein the carboxyl group is directly bonded to the principal chain of a resin such as a repeating unit of acrylic acid or methacrylic acid or a repeating unit wherein the carboxyl group is bonded via a connecting group to the principal chain of a resin. The connecting group may have a cyclohydrocarbon structure of a single ring or multiple rings. The repeating unit of acrylic acid or methacrylic acid is most preferred.

The alicyclic hydrocarbon based acid-decomposable resin according to the present invention may have a repeating unit having 1 to 3 groups of general formula (F1) below. This would realize an enhancement of line edge roughness.

(F1)

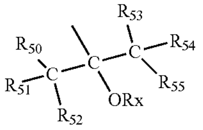

In the general formula (F1), each of $R_{50}$ to $R_{55}$ independently represents a hydrogen atom, a fluorine atom or an alkyl group, provided that at least one of $R_{50}$ to $R_{55}$ is a fluorine atom or an alkyl group whose at least one hydrogen atom is replaced with a fluorine atom.

Rx represents a hydrogen atom or an organic group (preferably, an acid-decomposable protective group, an alkyl group, a cycloalkyl group, an acyl group or an alkoxycarbonyl group).

The alkyl groups represented by $R_{50}$ to $R_{55}$ may be substituted with a halogen atom such as a fluorine atom, a cyano group or the like. Alkyl groups having 1 to 3 carbon atoms are preferred. As such, there can be mentioned, for example, a methyl group or a trifluoromethyl group.

It is preferred for all of $R_{50}$ to $R_{55}$ to represent a fluorine atom.

The organic group represented by Rx is preferably an acid-decomposable protective group or an optionally substituted alkyl group, cycloalkyl group, acyl group, alkylcarbonyl group, alkoxycarbonyl group, alkoxycarbonylmethyl group, alkoxymethyl group or 1-alkoxyethyl group.

As preferred repeating units having the groups of the general formula (F1), there can be mentioned those of general formula (F2) below.

(F2)

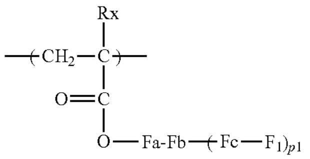

In the general formula (F2), Rx represents a hydrogen atom, a halogen atom or an alkyl group having 1 to 4 carbon atoms. The alkyl group represented by Rx may have a substituent, which is preferably a hydroxyl group or a halogen atom.

Fa represents a single bond or a linear or branched alkylene group, preferably a single bond.

Fb represents a monocyclic or polycyclic hydrocarbon group.

Fc represents a single bond or a linear or branched alkylene group, preferably a single bond or a methylene group.

$F_1$ represents any of the groups of the general formula (F1).

$p_1$ is an integer of 1 to 3.

The cyclohydrocarbon group represented by Fb is preferably a cyclopentyl group, a cyclohexyl group or a norbornyl group.

Specific examples of the repeating units with the structures of the general formula (F1) will be shown below.

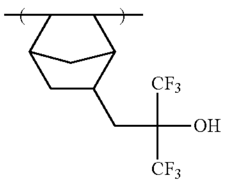

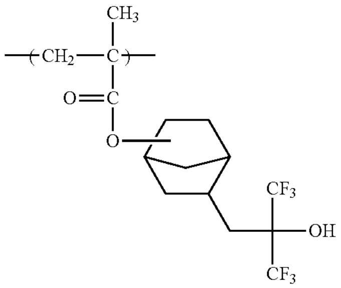

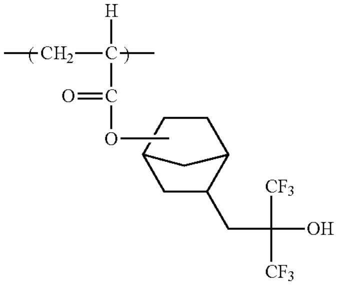

The alicyclic hydrocarbon based acid-decomposable resin according to the present invention may have a repeating unit The resin (A) may have, in addition to the foregoing repeating structural units, various repeating structural units for the purpose of regulating the dry etching resistance, standard developer adaptability, substrate adhesion, resist profile and generally required properties of the resist such as resolving power, heat resistance and sensitivity.

As such repeating structural units, there can be mentioned those corresponding to the following monomers, which however are nonlimiting.

The use of such repeating structural units would allow fine regulation of the required properties of the alicyclic hydrocarbon based acid-decomposable resin, especially:

(1) solubility in application solvents, (2) film forming easiness (glass transition point), (3) alkali developability, (4) film thinning (selections of hydrophilicity/hydrophobicity and alkali-soluble group), (5) adhesion of unexposed area to substrate, (6) dry etching resistance, etc.

As appropriate monomers, there can be mentioned, for example, a compound having an unsaturated bond capable of addition polymerization, selected from among acrylic esters, methacrylic esters, acrylamides, methacrylamides, allyl compounds, vinyl ethers, vinyl esters and the like.

In addition, any unsaturated compound capable of addition polymerization that is copolymerizable with monomers corresponding to the above various repeating structural units may be copolymerized therewith.

The molar ratios of individual repeating structural units contained in the alicyclic hydrocarbon based acid-decomposable resin are appropriately determined from the viewpoint of regulation of not only the dry etching resistance of the resist but also the standard developer adaptability, substrate adhesion, resist profile and generally required properties of the resist such as the resolving power, heat resistance and sensitivity.

Preferred forms of the alicyclic hydrocarbon based acid-decomposable resins according to the present invention are as follows.

(1) Resins having repeating units with the partial structures containing alicyclic hydrocarbons of the general formulae (pI) to (pV) (side chain type), preferably resins having repeating units of (meth)acrylate with the structures of the general formulae (pI) to (pV).

(2) Resins having the repeating units of the general formula (II-AB) (principal chain type). The resins (2) above include, for example, the following.

(3) Resins having the repeating units of the general formula (II-AB), a maleic anhydride derivative structure and a (meth) acrylate structure (hybrid type).

In the alicyclic hydrocarbon based acid-decomposable resin, the content of repeating units having acid-decomposable groups, based on all the repeating structural units, is preferably in the range of 10 to 60 mol %, more preferably 20 to 50 mol % and further preferably 25 to 40 mol %.

In the alicyclic hydrocarbon based acid-decomposable resin, the content of repeating units with the partial structures containing alicyclic hydrocarbons of the general formulae (pI) to (pV), based on all the repeating structural units, is preferably in the range of 25 to 70 mol %, more preferably 35 to 65 mol % and further preferably 40 to 60 mol %.

In the alicyclic hydrocarbon based acid-decomposable resin, the content of repeating units of the general formula (II-AB), based on all the repeating structural units, is preferably in the range of 10 to 60 mol %, more preferably 15 to 55 mol % and further preferably 20 to 50 mol %.

The content of repeating units having lactone groups, based on all the repeating structural units, is preferably in the range of 10 to 70 mol %, more preferably 20 to 60 mol % and further preferably 25 to 60 mol %.

The content of repeating units having alicyclic hydrocarbon structures substituted with polar groups, based on all the repeating structural units, is preferably in the range of 1 to 40 mol %, more preferably 5 to 30 mol % and further preferably 5 to 20 mol %.

The content of repeating structural units derived from the above further copolymerization component monomers in the resin can be appropriately determined in conformity with desired resist performance. In general, however, the above content based on the total molar quantity being the sum of repeating structural units with the partial structures containing alicyclic hydrocarbons of the general formulae (pI) to (pV) and repeating units of the general formula (II-AB) is preferably 99 mol % or less, more preferably 90 mol % or less and further preferably 80 mol % or less.

When the composition of the present invention is one for ArF exposure, it is preferred for the resin to have no aromatic group from the viewpoint of transparency to ArF beams.

In the alicyclic hydrocarbon based acid-decomposable resin for use in the present invention, preferably, all the repeating units consist of (meth)acrylate repeating units. Illustratively, use can be made of any of a resin wherein all the repeating units consist of a methacrylate, a resin wherein all the repeating units consist of an acrylate and a resin wherein all the repeating units consist of a methacrylate/acrylate mixture. However, it is preferred for the acrylate repeating units to account for 50 mol % or less based on all the repeating units.

More preferably, the resin is a ternary copolymer containing 25 to 50% of repeating units with the partial structures containing alicyclic hydrocarbons of the general formulae (pI) to (pV), 25 to 50% of repeating units with the above lactone structures and 5 to 30% of repeating units with the above alicyclic hydrocarbon structures substituted with a polar group, or a quaternary copolymer further containing 5 to 20% of repeating units having a carboxyl group or the structures of the general formula (F1).

The alicyclic hydrocarbon based acid-decomposable resin for use in the present invention can be synthesized by conventional techniques (for example, radical polymerization). As general synthetic methods, there can be mentioned, for example, a batch polymerization method in which monomer species and an initiator are dissolved in a solvent and heated so as to accomplish polymerization and a dropping polymerization method in which a solution of monomer species and initiator is dropped into a heated solvent over a period of 1 to 10 hours. The dropping polymerization method is preferred. As a reaction solvent, there can be mentioned, for example, an ether, such as tetrahydrofuran, 1,4-dioxane or diisopropyl ether; a ketone, such as methyl ethyl ketone or methyl isobutyl ketone; an ester solvent, such as ethyl acetate; an amide solvent, such as dimethylformamide or dimethylacetamide; or a solvent capable of dissolving the composition of the present invention, such as propylene glycol monomethyl ether acetate, propylene glycol monomethyl ether or cyclohexanone, to be hereinafter described. It is preferred to perform the polymerization with the use of the same solvent as employed in the photosensitive composition of the present invention. This would inhibit any particle generation during storage.

The polymerization reaction is preferably carried out in an atmosphere of inert gas, such as nitrogen or argon. The polymerization is initiated by the use of a commercially available radical initiator (azo initiator, peroxide, etc.) as a polymerization initiator. Among the radical initiators, an azo initiator is preferred. An azo initiator having an ester group, a cyano group or a carboxyl group is especially preferred. As preferred initiators, there can be mentioned azobisisobutyronitrile, azobisdimethylvaleronitrile, dimethyl 2,2'-azobis(2-methylpropionate) and the like. According to necessity, a supplementation of initiator or divided addition thereof may be effected. After the completion of the reaction, the reaction mixture is poured into a solvent. The desired polymer is recovered by a method for powder or solid recovery, etc. The concentration during the reaction is in the range of 5 to 50 mass %, preferably 10 to 30 mass %. The reaction temperature is generally in the range of 10° to 150° C., preferably 30° to 120° C. and more preferably 50° to 100° C.

When the composition of the present invention is used in an upper resist of a multilayer resist, it is preferred for the resin as the component (B) to contain a silicon atom.

As the resin that contains a silicon atom and is decomposed by the action of an acid to thereby exhibit an increased solubility in an alkali developer, use can be made of a resin containing a silicon atom in at least one of its principal chain and side chain. As a resin having a siloxane structure in its side chain, there can be mentioned, for example, a copolymer from an olefin monomer having a silicon atom in its side chain, maleic anhydride and a (meth)acrylic acid monomer having an acid-decomposable group in its side chain.

The resin having a silicon atom is preferably one having a trialkylsilyl structure or a monocyclic or polycyclic siloxane structure. More preferably, the resin is one having a repeating unit having any of the structures of general formulae (SS-1) to (SS-4) below. It is especially preferred to employ a resin having a vinyl or allyl repeating unit or (meth)acrylic ester repeating unit having any of the structures of the general formulae (SS-1) to (SS-4).

SS-1

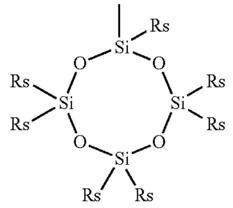

SS-2

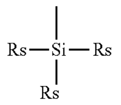

SS-3

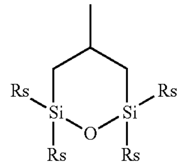

SS-4

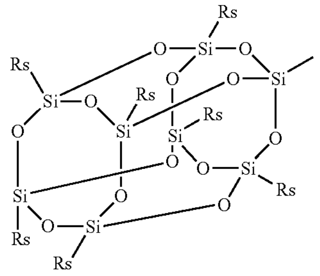

In the general formulae (SS-1) to (SS-4), Rs represents an alkyl group having 1 to 5 carbon atoms, preferably a methyl group or an ethyl group.

It is preferred for the resin having a silicon atom to have two or more different siliconized repeating units. More preferably, the resin has both a repeating unit (Sa) having 1 to 4 silicon atoms and a repeating unit (Sb) having 5 to 10 silicon atoms. Further preferably, the resin has at least one repeating unit having any of the structures of the general formulae (SS-1) to (SS-3) and a repeating unit having any of the structures of the general formula (SS-4).

When the positive photosensitive composition of the present invention is exposed to $F_2$ excimer laser beams, it is preferred for the resin as the component (B) to be a resin that has a structure having its polymer skeleton principal chain and/or side chain substituted with a fluorine atom and that is decomposed by the action of an acid to thereby exhibit an increased solubility in an alkali developer (hereinafter also referred to as "fluorinated acid-decomposable resin"). More preferably, the resin is one having in its 1-position a fluorine atom or a hydroxyl group substituted with a fluoroalkyl group, or having in its 1-position a fluorine atom or a group consisting of a fluoroalkyl-substituted hydroxyl group protected by an acid-decomposable group. Especially preferably, the resin is one having a hexafluoro-2-propanol structure or a structure in which the hydroxyl group of hexafluoro-2-propanol is protected by an acid-decomposable group. The introduction of a fluorine atom would realize an enhancement of transparency to far ultraviolet rays, especially $F_2$ (157 nm) beams.

As preferred fluorinated acid-decomposable resins, there can be mentioned, for example, resins having at least one of the repeating units of general formulae (FA) to (FG) below.

(FA)

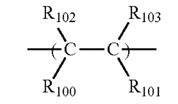

(FB)

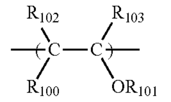

(FC)

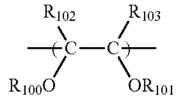

(FD)

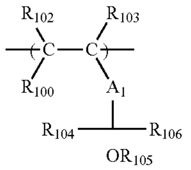

(FE)

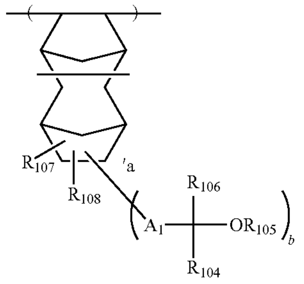

(FF)

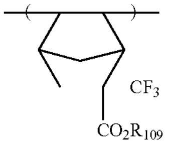

(FG)

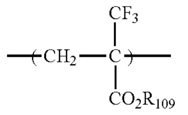

In the above general formulae, each of $R_{100}$ to $R_{103}$ represents a hydrogen atom, a fluorine atom, an alkyl group or an aryl group. Each of $R_{104}$ and $R_{106}$ represents a hydrogen atom, a fluorine atom or an alkyl group, provided that at least one of $R_{104}$ and $R_{106}$ is a fluorine atom or a fluoroalkyl group. Preferably, $R_{104}$ and $R_{106}$ simultaneously represent trifluoromethyl groups.

$R_{105}$ represents a hydrogen atom, an alkyl group, a cycloalkyl group, an acyl group, an alkoxycarbonyl group or a group that is decomposed by the action of an acid.

$A_1$ represents a single bond or a bivalent connecting group, for example, an alkylene group, a cycloalkylene group, an alkenylene group, an arylene group, —COO—, —COO—, —CON($R_{24}$)— or a connecting group containing two or more of these. $R_{24}$ represents a hydrogen atom or an alkyl group.

Each of $R_{107}$ and $R_{108}$ represents a hydrogen atom, a halogen atom, an alkyl group, an alkoxy group, an alkoxycarbonyl group or a group that is decomposed by the action of an acid.

$R_{109}$ represents a hydrogen atom, an alkyl group, a cycloalkyl group or a group that is decomposed by the action of an acid.

In the formulae, b is 0, 1 or 2.

In the general formulae (FA) and (FC), $R_{100}$ and $R_{101}$ may form a ring via an optionally fluorinated alkylene group (1 to 5 carbon atoms).

The repeating units of the general formulae (FA) to (FG) have at least one, preferably three or more fluorine atoms per repeating unit.

In the general formulae (FA) and (FC), as preferred alkyl groups, there can be mentioned, for example, alkyl groups having 1 to 8 carbon atoms, such as a methyl group, an ethyl group, a propyl group, an n-butyl group, a sec-butyl group, a hexyl group, a 2-ethylhexyl group or an octyl group.

The cycloalkyl groups may be monocyclic or polycyclic. As preferred monocyclic alkyl groups, there can be mentioned cycloalkyl groups having 3 to 8 carbon atoms, such as a cyclopropyl group, a cyclopentyl group, a cyclohexyl group, a cycloheptyl group and a cyclooctyl group. As preferred polycyclic alkyl groups, there can be mentioned cycloalkyl groups having 6 to 20 carbon atoms, such as an adamantyl group, a norbornyl group, an isobornyl group, a camphonyl group, a dicyclopentyl group, an α-pinel group, a tricyclodecanyl group, a tetracyclododecyl group, an androstanyl group and the like. With respect to these, the carbon atoms of the monocyclic or polycyclic alkyl groups may be substituted with heteroatoms, such as an oxygen atom.

As preferred fluoroalkyl groups, there can be mentioned, for example, fluoroalkyl groups having 1 to 12 carbon atoms, such as a trifluoromethyl group, a perfluoroethyl group, a perfluoropropyl group, a perfluorobutyl group, a perfluorohexyl group, a perfluorooctyl group, a perfluorooctylethyl group, a perfluorododecyl group and the like.

As preferred aryl groups, there can be mentioned, for example, aryl groups having 6 to 15 carbon atoms, such as a phenyl group, a tolyl group, a dimethylphenyl group, a 2,4,6-trimethylphenyl group, a naphthyl group, an anthryl group, a 9,10-dimethoxy anthryl group and the like.

As preferred alkoxy groups, there can be mentioned, for example, alkoxy groups having 1 to 8 carbon atoms, such as a methoxy group, an ethoxy group, an n-propoxy group, an isopropoxy group, a butoxy group, a pentoxy group, an allyloxy group, an octoxy group and the like.

As preferred acyl groups, there can be mentioned, for example, acyl groups having 1 to 10 carbon atoms, such as a formyl group, an acetyl group, a propanoyl group, a butanoyl group, a pivaloyl group, an octanoyl group, a benzoyl group and the like.

As alkoxycarbonyl groups, there can be mentioned an i-propoxycarbonyl group, a t-butoxycarbonyl group, a t-amyloxycarbonyl group, a 1-methyl-1-cyclohexyloxycarbonyl group and the like. Secondary alkoxycarbonyl groups are preferred, and tertiary alkoxycarbonyl groups are more preferred.

As the halogen atom, there can be mentioned, for example, a fluorine atom, a chlorine atom, a bromine atom, an iodine atom or the like.

As preferred alkylene groups, there can be mentioned alkylene groups having 1 to 8 carbon atoms, such as a methylene group, an ethylene group, a propylene group, a butylene group, a hexylene group and an octylene group As preferred alkenylene groups, there can be mentioned alkenylene groups having 2 to 6 carbon atoms, such as an ethenylene group, a propenylene group and a butenylene group.

As preferred cycloalkylene groups, there can be mentioned cycloalkylene groups having 5 to 8 carbon atoms, such as a cyclopentylene group and a cyclohexylene group.

As preferred arylene groups, there can be mentioned arylene groups having 6 to 15 carbon atoms, such as a phenylene group, a tolylene group and a naphthylene group.

These groups may have a substituent. As the substituent, there can be mentioned, for example, one having an active hydrogen, such as an alkyl group, a cycloalkyl group, an aryl group, an amino group, an amido group, a ureido group, a urethane group, a hydroxyl group or a carboxyl group as well as a halogen atom (a fluorine atom, a chlorine atom, a bromine atom or an iodine atom), an alkoxy group (a methoxy group, an ethoxy group, a propoxy group, a butoxy group or the like), a thioether group, an acyl group (an acetyl group, a propanoyl group, a benzoyl group or the like), an acyloxy group (an acetoxy group, a propanoyloxy group, a benzoyloxy group or the like), an alkoxycarbonyl group (a methoxycarbonyl group, an ethoxycarbonyl group, a propoxycarbonyl group or the like), a cyano group, a nitro group or the like.

The above-mentioned alkyl group, cycloalkyl group and aryl group are the same as described hereinbefore. Further, the alkyl group may be substituted with a fluorine atom or a cycloalkyl group.

As the group that is contained in the fluorinated acid-decomposable resin according to the present invention and decomposed by the action of an acid to thereby exhibit alkali solubility, there can be mentioned, for example, $-O-C(R_{36})(R_{37})(R_{38})$, $-O-C(R_{36})(R_{37})(OR_{39})$, $-O-COO-C(R_{36})(R_{37})(R_{38})$, $-O-C(R_{01})(R_{02})COO-C(R_{36})(R_{37})(R_{38})$, $-COO-C(R_{36})(R_{37})(R_{38})$, $-COO-C(R_{36})(R_{37})(OR_{39})$ or the like.

In the formulae, each of $R_{36}$ to $R_{39}$ represents an alkyl group, a cycloalkyl group, an aryl group, an aralkyl group or an alkenyl group. Each of $R_{01}$ and $R_{02}$ represents a hydrogen atom, an alkyl group, a cycloalkyl group, an alkenyl group (a vinyl group, an allyl group, a butenyl group, a cyclohexenyl group or the like), an aralkyl group (a benzyl group, a phenethyl group, a naphthylmethyl group or the like) or an aryl group.

As preferred specific examples, there can be mentioned an ether or ester group of a tertiary alkyl such as a t-butyl group, a t-amyl group, a 1-alkyl-1-cycloalkyl group, a 2-alkyl-2-adamantyl group, a 2-adamantyl-2-propyl group or a 2-(4-methylcyclohexyl)-2-propyl group, an acetal or acetal ester group of, for example, a 1-alkoxy-1-ethoxy group or a tetrahydropyranyl group, a t-alkyl carbonate group, a t-alkylcarbonylmethoxy group and the like.

Specific examples of the repeating structural units of the general formulae (FA) to (FG) will be shown below, which however in no way limit the scope of the present invention.

(F-1)

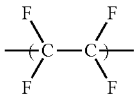

(F-2)

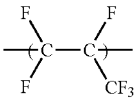

-continued (F-3)

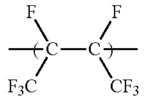

(F-4)

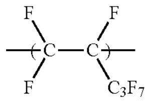

(F-5)

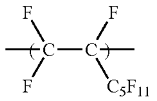

(F-6)

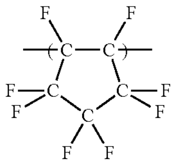

(F-7)

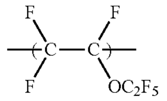

(F-8)

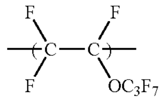

(F-9)

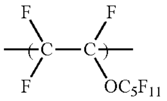

(F-10)

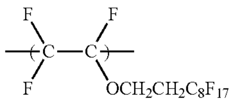

(F-11)

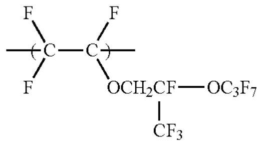

(F-12)

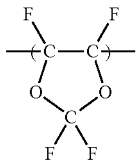

(F-13)

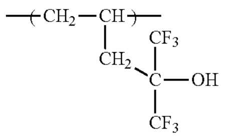

(F-14)

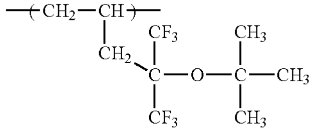

-continued
(F-15)
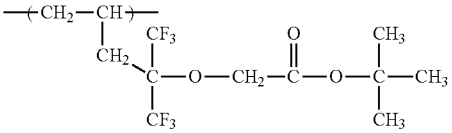
(F-16)
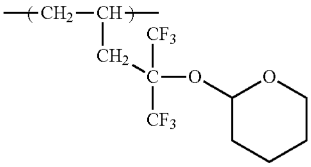
(F-17)
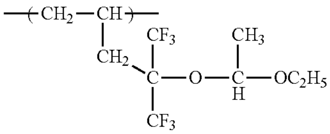
(F-18)
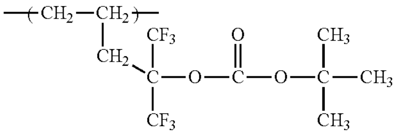
(F-19)
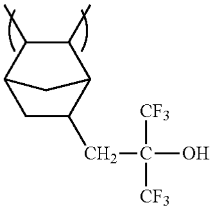
(F-20)
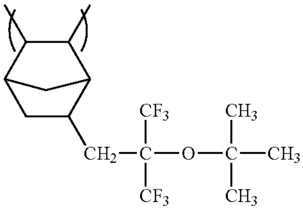
(F-21)
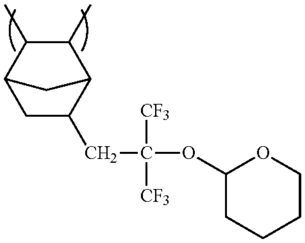
(F-22)
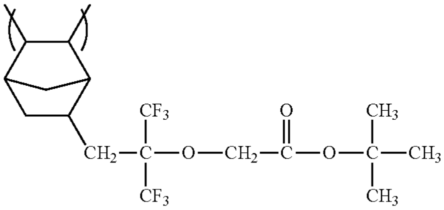
-continued
(F-23)
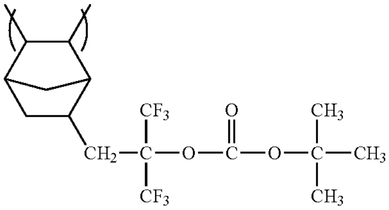
(F-24)
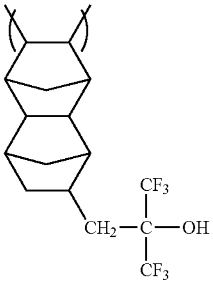
(F-25)
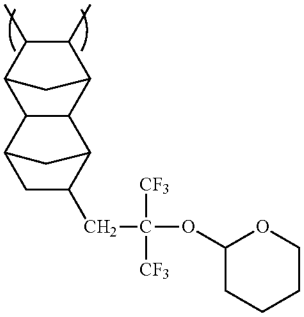
(F-26)
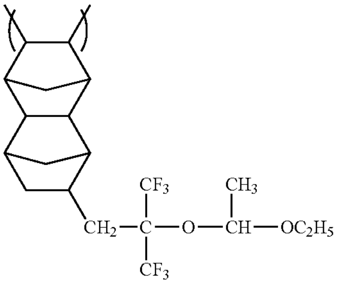
(F-27)
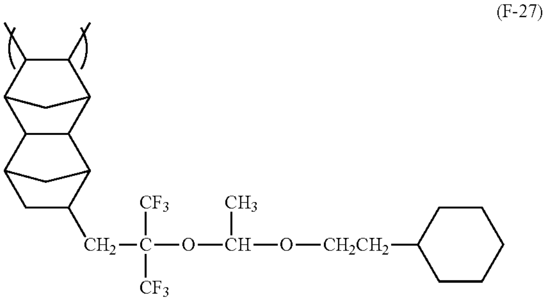

-continued
(F-28)
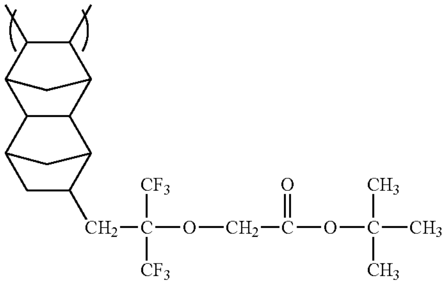
(F-29)
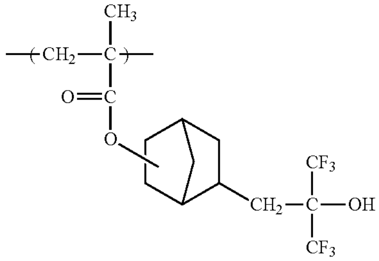
(F-30)
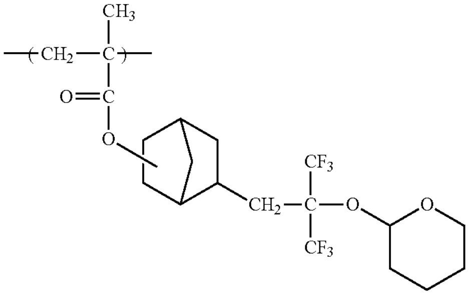
(F-31)
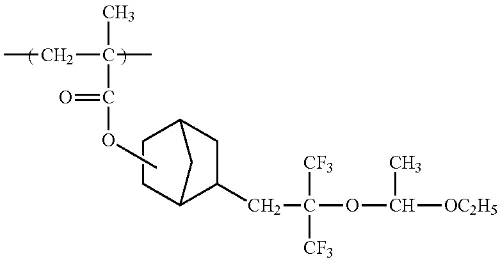
(F-32)
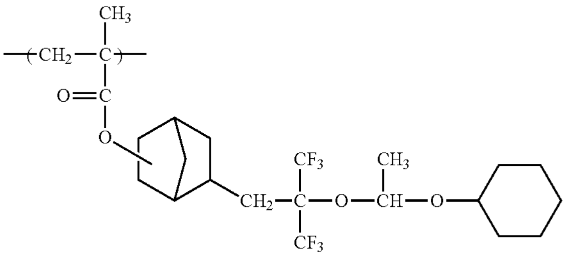
-continued
(F-33)
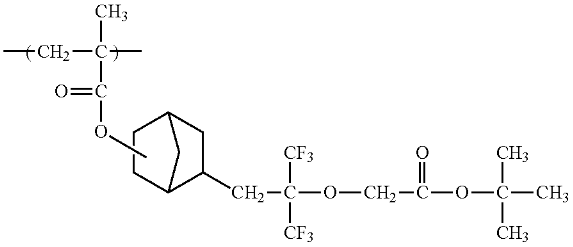
(F-34)
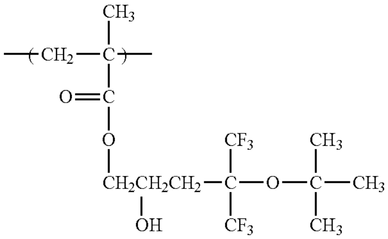
(F-35
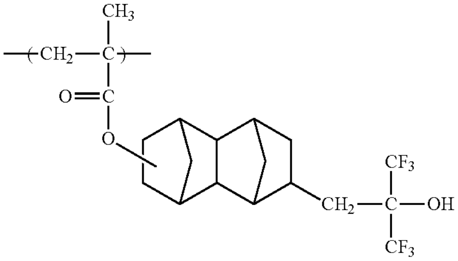
(F-36)
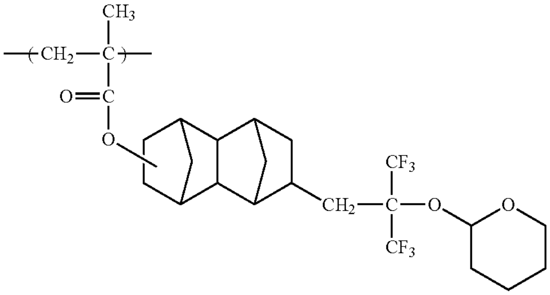
(F-37)
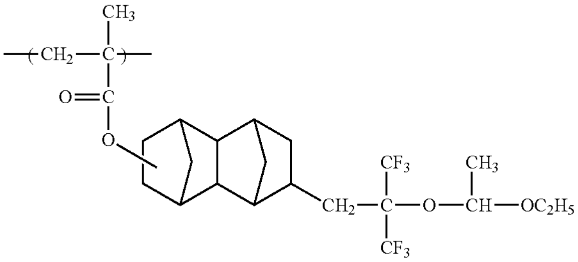

-continued
(F-38)
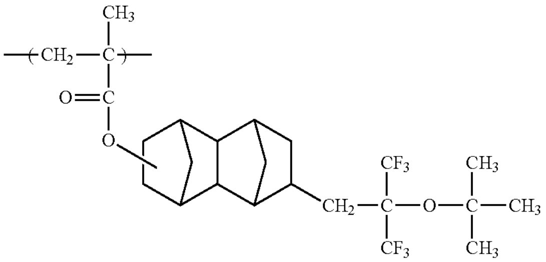
(F-39)
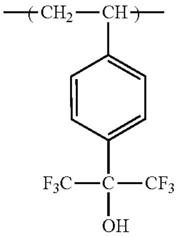
(F-40)
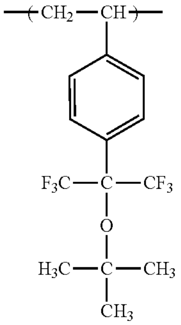
(F-41)
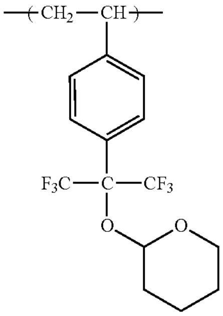
(F-42)
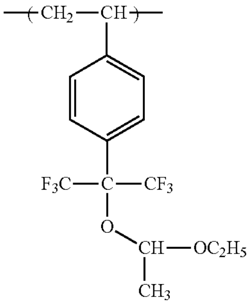
-continued
(F-43)
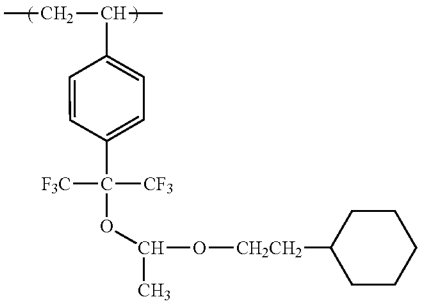
(F-44)
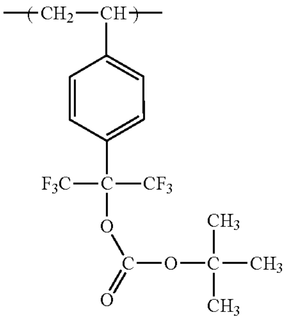
(F-45)
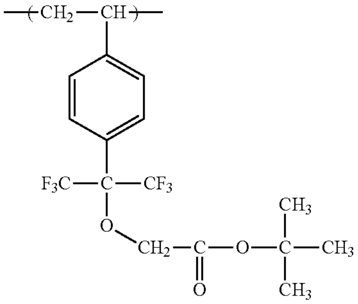
(F-46)
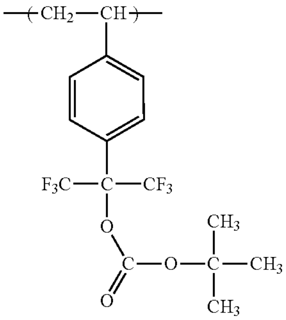
(F-47)
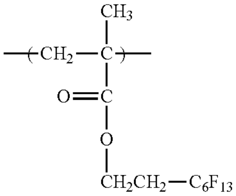

-continued
(F-48)
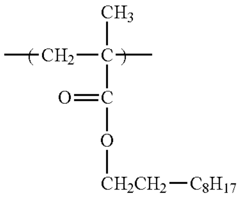
(F-49)
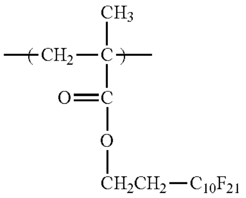
(F-50)
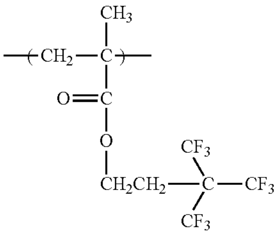
(F-51)
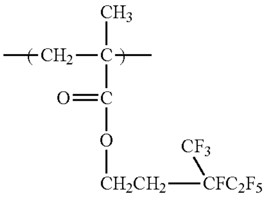
(F-52)
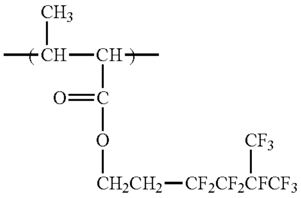
(F-53)
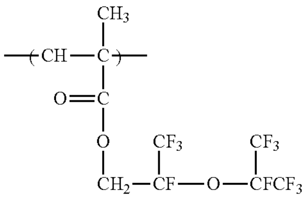
(F-54)
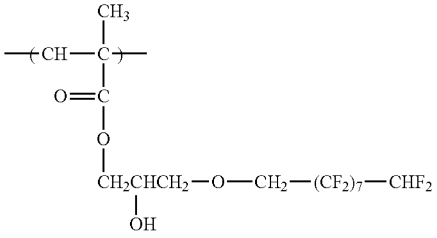
-continued
(F-55)
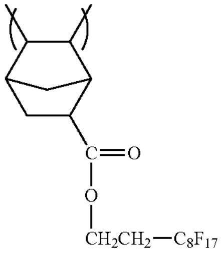
(F-56)
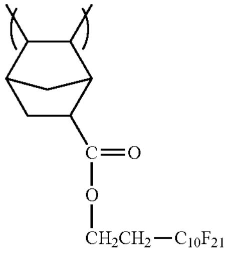
(F-57)
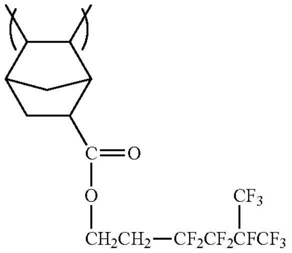
(F-58)
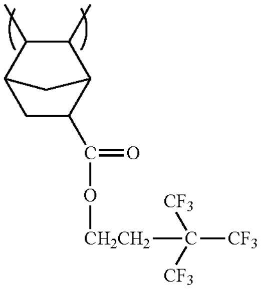
(F-59)
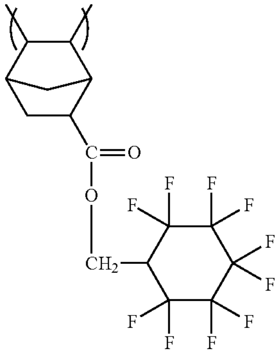

-continued (F-60)

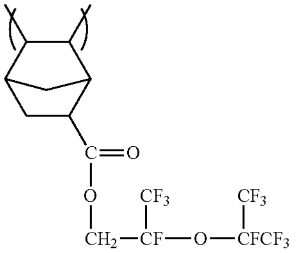

(F-61)

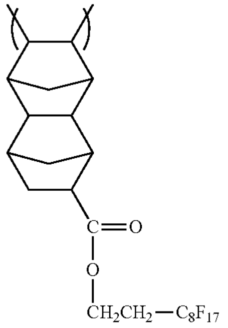

(F-62)

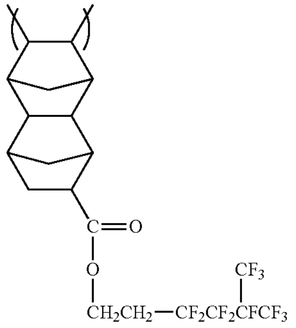

(F-63)

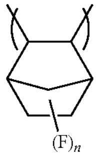

$n = 8$ (F-64)

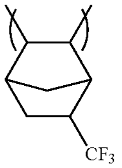

(F-65)

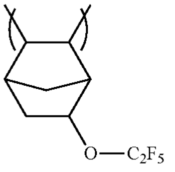

The total content of repeating units employed among those of the general formulae (FA) to (FG), based on all the repeating units of the resin, is generally in the range of 10 to 80 mol %, preferably 30 to 70 mol % and more preferably 35 to 65 mol %.

The fluorinated acid-decomposable resin may further have a repeating structural unit other than the foregoing repeating structural units that is obtained by copolymerization with other polymerizable monomers for the purpose of enhancing the performance of the resist of the present invention.

The employable comonomers include the following. For example, use may be made of a compound having an unsaturated bond capable of addition polymerization, other than those mentioned above, selected from among acrylic esters, acrylamides, methacrylic esters, methacrylamides, allyl compounds, vinyl ethers, vinyl esters, styrenes, crotonic esters and the like.

From the viewpoint of enhancement of dry etching resistance, regulation of alkali solubility, enhancement of substrate adhesion, etc., it is preferred for the fluorinated acid-decomposable resin to contain not only the repeating unit having a fluorine atom but also another repeating unit as a copolymer component. Preferred other repeating units include:

(1) any of the repeating units having alicyclic hydrocarbon structures of the general formulae (pI) to (pV) and (II-AB), for example, repeating units 1 to 23 and repeating units [II-1] to [II-32], preferably repeating units 1 to 19 wherein Rx is CF3;

(2) any of the repeating units having lactone structures of the general formulae (Lc) and (V-1) to (V-5), for example, the repeating units shown hereinbefore as examples thereof, especially the repeating units with the groups of the general formulae (Lc) and (V-1) to (V-4) shown hereinbefore as examples thereof; and (3) any of the repeating units of general formulae (XV), (XVI) and (XVII) below, for example, formulae (C-1) to (C-15) below derived from maleic anhydride, a vinyl ether and a cyanated vinyl compound. It is optional for these other repeating units to contain a fluorine atom.

(XV)

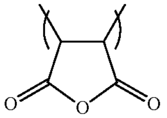

(XVI)

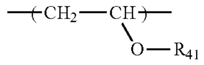

(XVII)

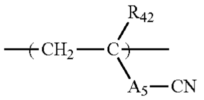

In the formulae, $R_{41}$ represents an alkyl group, a cycloalkyl group, an aralkyl group or an aryl group. The alkyl group represented by $R_{41}$ may be substituted with an aryl group.

$R_{42}$ represents a hydrogen atom, a halogen atom, a cyano group or an alkyl group.

$A_5$ represents a single bond, a bivalent alkylene, alkenylene, cycloalkylene or arylene group, or —O—CO—$R_{22}$—, —CO—O—$R_{23}$—, or —CO—N($R_{24}$)—$R_{25}$—.

$R_{22}$, $R_{23}$ and $R_{25}$ may be identical to or different from each other. Each thereof represents a single bond or a bivalent alkylene, alkenylene, cycloalkylene or arylene group wherein an ether group, an ester group, an amido group, a urethane group or a ureido group may be introduced.

$R_{24}$ represents a hydrogen atom, an alkyl group, a cycloalkyl group, an aralkyl group or an aryl group.

Examples of employable substituents are the same as those of the general formulae (FA) to (FG) above.

Specific examples of the repeating structural units of the general formulae (XV) to (XVII) will be shown below, which however in no way limit the scope of the present invention.

(C-1)

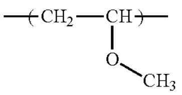

(C-2)

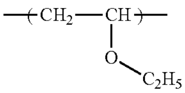

(C-3)

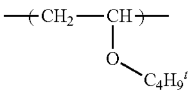

(C-4)

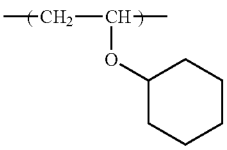

(C-5)

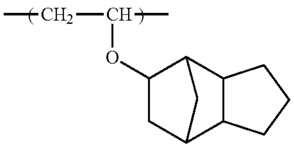

(C-6)

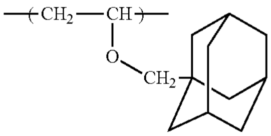

(C-7)

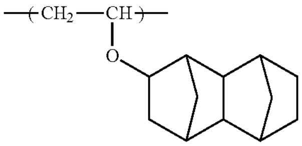

(C-8)

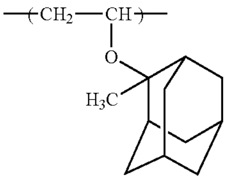

(C-9)

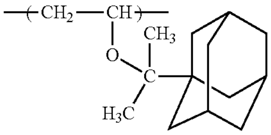

(C-10)

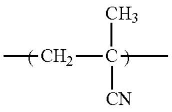

-continued (C-11)

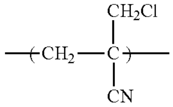

(C-12)

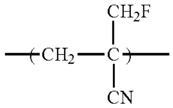

(C-13)

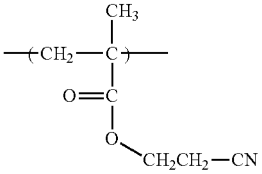

(C-14)

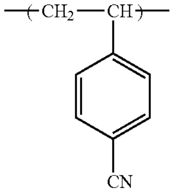

(C-15)

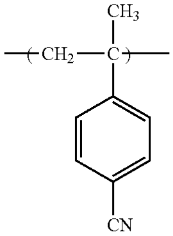

In practical use, the sum of repeating units of the general formulae (XV) to (XVII) and other repeating units, based on all the repeating units of the resin, is generally in the range of 0 to 70 mol %, preferably 10 to 60 mol % and further preferably 20 to 50 mol %.

In the fluorinated acid-decomposable resin, the acid-decomposable group may be contained in any of the repeating units of the resin.

The content of repeating units having acid-decomposable groups, based on all the repeating units, is preferably in the range of 10 to 70 mol %, more preferably 20 to 60 mol % and further preferably 30 to 60 mol %.

The fluorinated acid-decomposable resin can be synthesized by radical polymerization in substantially the same manner as for the alicyclic hydrocarbon based acid-decomposable resin.

The weight average molecular weight of the resin as the component (B) in terms of polystyrene molecular weight measured by GPC is preferably in the range of 2000 to 200,000. Causing the weight average molecular weight to be 2000 or greater would realize enhancements of thermal stability and dry etching performance. On the other hand, causing the weight average molecular weight to be 200,000 or less would realize an enhancement of developability and would also, due to a viscosity lowering, enhance film forming properties. The weight average molecular weight is more preferably from 2500 to 50,000 and further preferably from 3000 to 20,000. In the micropattern formation using electron beams, X-rays or high-energy rays of 50 nm or less wavelength (EUV, etc.), the weight average molecular weight is most preferably from 3000 to 10,000. The thermal stability, resolving power, development defect, etc. of the composition can be simultaneously satisfied by regulating the molecular weight. The dispersity (Mw/Mn) of the resin as the component (B) is preferably in the range of 1.0 to 3.0, more preferably 1.2 to 2.5 and further preferably 1.2 to 1.6. The line edge roughness performance can be enhanced by regulating the dispersity so as to fall within an appropriate range.

In the actinic ray-sensitive or radiation-sensitive resin composition of the present invention, the ratio of resin as the component (B) contained in the whole composition, based on the total solid content of the composition, is preferably in the range of 40 to 99.9 mass %, more preferably 50 to 95 mass % and further preferably 60 to 93 mass %.

[4] Resin (C) Soluble in Alkali Developer

Hereinafter, this resin may also be referred to as "component (C)" or "alkali-soluble resin." The alkali dissolution rate of the alkali-soluble resin as measured in a 0.261 N tetramethylammonium hydroxide (TMAH) (23° C.) is preferably 2 nm/sec or higher, especially preferably 20 nm/sec or higher.

As the alkali-soluble resin for use in the present invention, there can be mentioned, for example, a novolak resin, a hydrogenated novolak resin, an acetone-pyrogallol resin, an o-polyhydroxystyrene, a m-polyhydroxystyrene, a p-polyhydroxystyrene, a hydrogenated polyhydroxystyrene, a halogenated or alkylated polyhydroxystyrene, a hydroxystyrene-N-substituted maleimide copolymer, an o/p- and m/p-hydroxystyrene copolymer, a partial O-alkylation product of hydroxyl of polyhydroxystyrene (for example, a 5 to 30 mol % O-methylation product, O-(1-methoxy)ethylation product, O-(1-ethoxy)ethylation product, O-2-tetrahydropyranylation product, O-(t-butoxycarbonyl)methylation product, etc.), an O-acylation product thereof (for example, a 5 to 30 mol % O-acetylation product, O-(t-butoxy)carbonylation product, etc.), a styrene-maleic anhydride copolymer, a styrene-hydroxystyrene copolymer, an α-methylstyrene-hydroxystyrene copolymer, a carboxylated methacrylic resin or its derivative, or a polyvinyl alcohol derivative. However, the alkali-soluble resins are not limited to these.

Especially preferred alkali-soluble resins are a novolak resin, an o-polyhydroxystyrene, a m-polyhydroxystyrene, a p-polyhydroxystyrene, a copolymer of these polyhydroxystyrenes, an alkylated polyhydroxystyrene, a partial O-alkylation product or O-acylation product of polyhydroxystyrene, a styrene-hydroxystyrene copolymer and an α-methylstyrene-hydroxystyrene copolymer.

The above novolak resin can be obtained by addition condensation of a given monomer as a main component with an aldehyde conducted in the presence of an acid catalyst.

The weight average molecular weight of the alkali-soluble resin is 2000 or greater, preferably from 5000 to 200,000 and more preferably 5000 to 100,000.

Herein, the weight average molecular weight is in terms of polystyrene molecular weight measured by gel permeation chromatography.

In the present invention, two or more types of alkali-soluble resins (C) may be used in combination.

The amount of alkali-soluble resin added, based on the solid contents of the whole photosensitive composition, is in the range of 40 to 97 mass %, preferably 60 to 90 mass %.

[5] Dissolution Inhibiting Compound of 3000 or Less Molecular Weight (E) that is Decomposed by the Action of an Acid to Thereby Increase the Solubility in an Alkali Developer Hereinafter, this compound is also referred to as "component (E)" or "Dissolution inhibiting compound."

From the viewpoint of preventing any lowering of 220 nm or shorter transmission, the dissolution inhibiting compound of 3000 or less molecular weight (E) that is decomposed by the action of an acid to thereby increase the solubility in an alkali developer is preferably an alicyclic or aliphatic compound containing an acid-decomposable group, such as any of cholic acid derivatives having an acid-decomposable group described in Proceeding of SPIE, 2724, 355 (1996). The acid-decomposable group and alicyclic structure are the same as described above with respect to the alicyclic hydrocarbon based acid-decomposable resin.

When the photosensitive composition of the present invention is exposed to a KrF excimer laser or irradiated with electron beams, preferred use is made of a compound containing a structure resulting from substitution of the phenolic hydroxyl group of a phenol compound with an acid-decomposable group. The phenol compound preferably contains 1 to 9 phenol skeletons, more preferably 2 to 6 phenol skeletons.

In the present invention, the molecular weight of each of the dissolution inhibiting compounds is 3000 or less, preferably 300 to 3000 and more preferably 500 to 2500.

The amount of dissolution inhibiting compound added is preferably in the range of 3 to 50 mass %, more preferably 5 to 40 mass % based on the solid contents of the photosensitive composition.

Specific examples of the dissolution inhibiting compounds will be shown below, which however in no way limit the scope of the present invention.

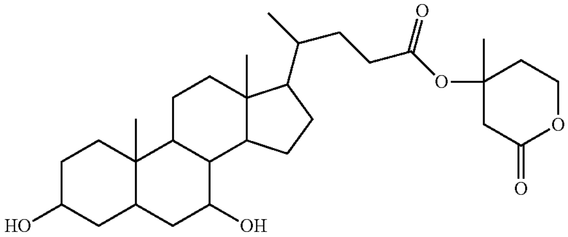

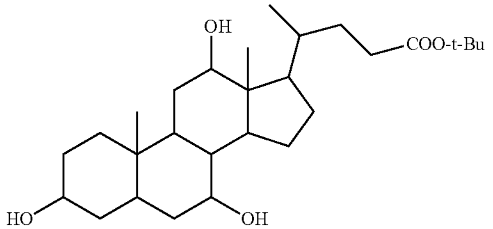

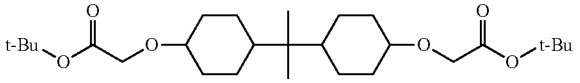

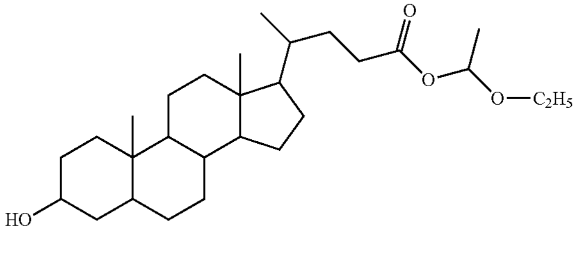

-continued

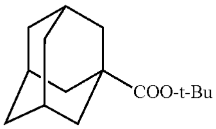

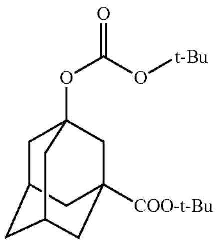

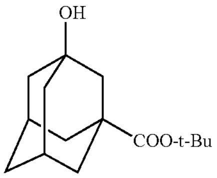

[6] Acid Crosslinking Agent (D) Capable of Crosslinking with the Alkali-Soluble Resin by the Action of an Acid Hereinafter, this agent is also referred to as "component (D)" or "crosslinking agent."

A crosslinking agent is used in the negative photosensitive composition of the present invention.

Any crosslinking agent can be used as long as it is a compound capable of crosslinking with the resin soluble in an alkali developer by the action of an acid. However, compounds (1) to (3) below are preferred.

(1) A hydroxymethylated form, alkoxymethylated or acyloxymethylated form of phenol derivative.

(2) A compound having an N-hydroxymethyl group, an N-alkoxymethyl group or an N-acyloxymethyl group.

(3) A compound having an epoxy group.

The alkoxymethyl group preferably has 6 or less carbon atoms, and the acyloxymethyl group preferably has 6 or less carbon atoms.

Those especially preferred among these crosslinking agents will be shown below.

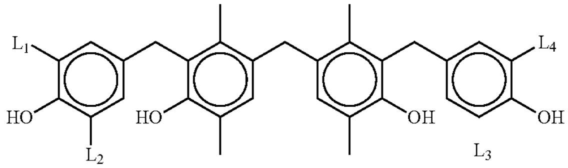

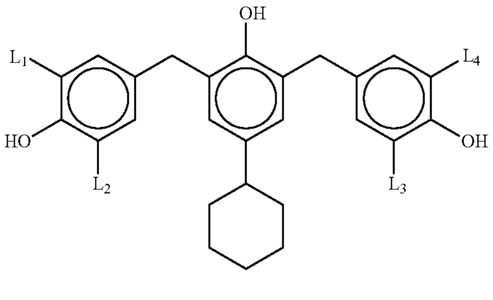

-continued

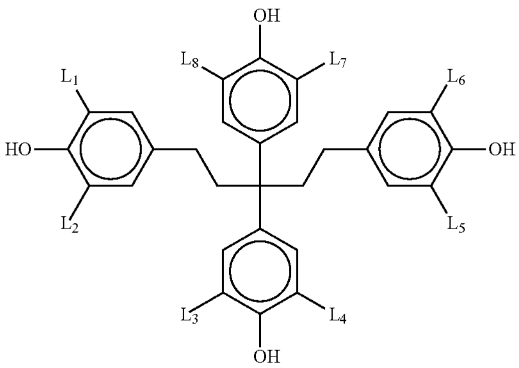

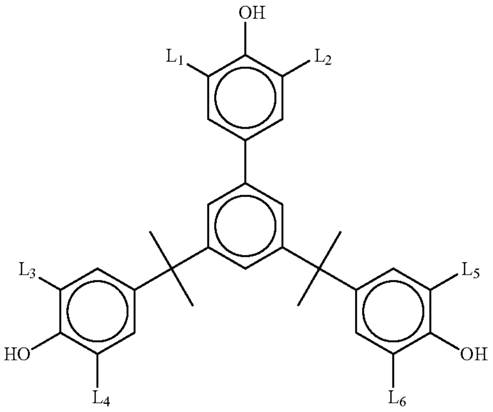

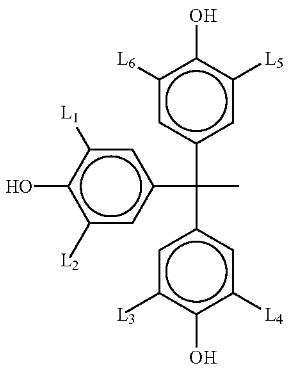

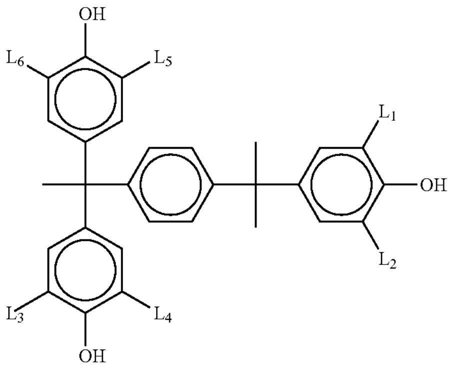

-continued

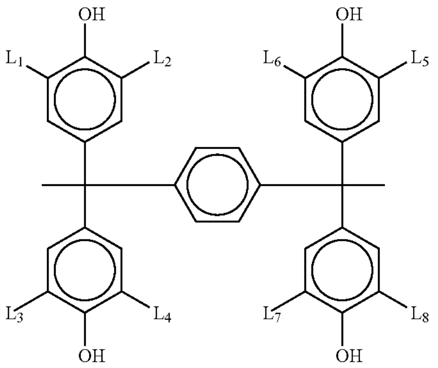

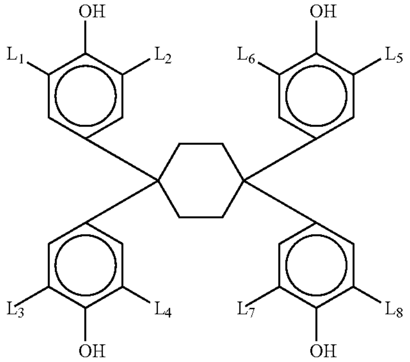

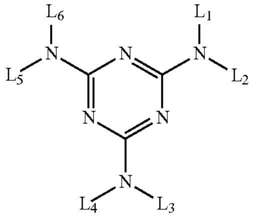

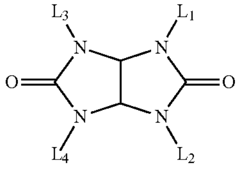

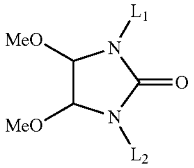

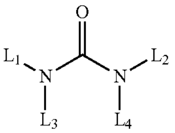

In the formulae, $L_1$ to $L_8$ may be identical to or different from each other, and each thereof represents a hydrogen atom, a hydroxymethyl group, a methoxymethyl group, an ethoxymethyl group or an alkyl group having 1 to 6 carbon atoms.

The crosslinking agent is generally added in an amount of 3 to 70 mass %, preferably 5 to 50 mass %, based on the solid content of the photosensitive composition.

[7] Basic Compound (F)

The resist composition of the present invention preferably contains a basic compound in order to reduce any performance change over time from exposure to bake. The role of the basic compound is to quench any deprotection reaction by the acid generated by exposure, and the diffusivity and basicity thereof would influence the substantial diffusivity of the acid.

As preferred structures, there can be mentioned basic compounds with the structures of formulae (A) to (E) below and ammonium salts.

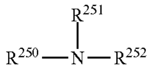

(A)

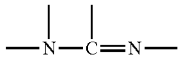

(B)

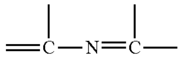

(C)

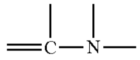

(D)

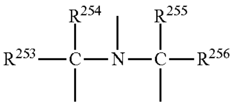

(E)

In the formulae, each of $R^{250}$, $R^{251}$ and $R^{252}$ independently represents a hydrogen atom, an alkyl group (preferably having 1 to 20 carbon atoms), a cycloalkyl group (preferably having 3 to 20 carbon atoms) or an aryl group (preferably having 6 to 20 carbon atoms). $R^{251}$ and $R^{252}$ may be bonded to each other to thereby form a ring.

These groups may have substituents. The alkyl group and cycloalkyl group having substituents are preferably an aminoalkyl group having 1 to 20 carbon atoms, an aminocycloalkyl group having 3 to 20 carbon atoms, a hydroxyalkyl group having 1 to 20 carbon atoms and a hydroxycycloalkyl group having 3 to 20 carbon atoms.

These groups may contain an oxygen atom, a sulfur atom or a nitrogen atom in the alkyl chain thereof.

In the formulae, each of $R^{253}$, $R^{254}$, $R^{255}$ and $R^{256}$ independently represents an alkyl group (preferably having 1 to 6 carbon atoms) or a cycloalkyl group (preferably having 3 to 6 carbon atoms).

As preferred compounds, there can be mentioned guanidine, aminopyrrolidine, pyrazole, pyrazoline, piperazine, aminomorpholine, aminoalkylmorpholines, piperidine and the like. These may have substituents. As further preferred compounds, there can be mentioned compounds with an imidazole structure, a diazabicyclo structure, an onium hydroxide structure, an onium carboxylate structure, a trialkylamine structure, an aniline structure or a pyridine structure, alkylamine derivatives having a hydroxyl group and/or an ether bond, aniline derivatives having a hydroxyl group and/or an ether bond and the like. As the compounds with an imidazole structure, there can be mentioned imidazole, 2,4,5-triphenylimidazole, benzimidazole and the like. As the compounds with a diazabicyclo structure, there can be mentioned 1,4-diazabicyclo[2,2,2]octane, 1,5-diazabicyclo[4,3,0]non-5-ene, 1,8-diazabicyclo[5,4,0]undec-7-ene and the like. As the compounds with an onium hydroxide structure, there can be mentioned triarylsulfonium hydroxides, phenacylsulfonium hydroxide, and sulfonium hydroxides having a 2-oxoalkyl group such as triphenylsulfonium hydroxide, tris(t-butylphenyl)sulfonium hydroxide, bis(t-butylphenyl)iodonium hydroxide, phenacylthiophenium hydroxide, 2-oxopropylthiophenium hydroxide and the like. As the compounds with an onium carboxylate structure, there can be mentioned those having a carboxylate at the anion moiety of the compounds with an onium hydroxide structure, for example, acetate, adamantane-1-carboxylate, perfluoroalkyl carboxylates and the like. As the compounds with a trialkylamine structure, there can be mentioned tri(n-butyl)amine, tri(n- octyl)amine and the like. As the aniline compounds, there can be mentioned 2,6-diisopropylaniline, N,N-dimethylaniline and the like. As the alkylamine derivatives having a hydroxyl group and/or an ether bond, there can be mentioned ethanolamine, diethanolamine, triethanolamine, tris(methoxyethoxyethyl)amine and the like. As the aniline derivatives having a hydroxyl group and/or an ether bond, there can be mentioned N,N-bis(hydroxyethyl)aniline and the like.

Further, as basic compounds, there can be mentioned at least one nitrogenous compound selected from among an amine compound having a phenoxy group, an ammonium salt compound having a phenoxy group, an amine compound having a sulfonic ester group and an ammonium salt compound having a sulfonic ester group.

As the amine compound, use can be made of primary, secondary and tertiary amine compounds. An amine compound having at least one alkyl group bonded to the nitrogen atom thereof is preferred. Among the amine compounds, a tertiary amine compound is more preferred. In the amine compounds, as long as at least one alkyl group (preferably having 1 to 20 carbon atoms) is bonded to the nitrogen atom, a cycloalkyl group (preferably having 3 to 20 carbon atoms) or an aryl group (preferably having 6 to 12 carbon atoms) besides the alkyl group may be bonded to the nitrogen atom.

In the amine compounds, it is preferred for the alkyl chain thereof to contain an oxygen atom, thereby forming an oxyalkylene group. The number of oxyalkylene groups in each molecule is one or more, preferably 3 to 9, and more preferably 4 to 6. The oxyalkylene group is preferably an oxyethylene group ($—CH_2CH_2O—$) or an oxypropylene group ($—CH(CH_3)CH_2O—$ or $—CH_2CH_2CH_2O—$), more preferably an oxyethylene group.

In the ammonium salt compounds, as long as at least one alkyl group (preferably having 1 to 20 carbon atoms) is bonded to the nitrogen atom, a cycloalkyl group (preferably having 3 to 20 carbon atoms) or an aryl group (preferably having 6 to 12 carbon atoms) besides the alkyl group may be bonded to the nitrogen atom.

In the ammonium salt compounds, it is preferred for the alkyl chain thereof to contain an oxygen atom, thereby forming an oxyalkylene group. The number of oxyalkylene groups in each molecule is one or more, preferably 3 to 9 and more preferably 4 to 6. The oxyalkylene group is preferably an oxyethylene group ($—CH_2CH_2O—$) or an oxypropylene group ($—CH(CH_3)CH_2O—$ or $—CH_2CH_2CH_2O—$), more preferably an oxyethylene group.

As the anion of the ammonium salt compounds, there can be mentioned a halogen atom, a sulfonate, a borate, a phosphate, a hydroxide or the like. Of these, a hydroxide is preferred. Among halogen atoms, chloride, bromide and iodide are especially preferred. Among sulfonates, an organic sulfonate having 1 to 20 carbon atoms is especially preferred. As the organic sulfonate, there can be mentioned an aryl sulfonate and an alkyl sulfonate having 1 to 20 carbon atoms. The alkyl group of the alkyl sulfonate may have a substituent. As the substituent, there can be mentioned, for example, fluorine, chlorine, bromine, an alkoxy group, an acyl group, an aryl group or the like. As specific examples of the alkyl sulfonates, there can be mentioned methane sulfonate, ethane sulfonate, butane sulfonate, hexane sulfonate, octane sulfonate, benzyl sulfonate, trifluoromethane sulfonate, pentafluoroethane sulfonate, nonafluorobutane sulfonate and the like. As the aryl group of the aryl sulfonate, there can be mentioned a benzene ring, a naphthalene ring or an anthracene ring. The benzene ring, naphthalene ring or anthracene ring may have a substituent. As preferred substituents, there can be mentioned a linear or branched alkyl group having 1 to 6 carbon atoms and a cycloalkyl group having 3 to 6 carbon atoms. As specific examples of the linear or branched alkyl groups and cycloalkyl groups, there can be mentioned methyl, ethyl, n-propyl, isopropyl, n-butyl, i-butyl, t-butyl, n-hexyl, cyclohexyl and the like. As other substituents, there can be mentioned an alkoxy group having 1 to 6 carbon atoms, a halogen atom, cyano, nitro, an acyl group, an acyloxy group and the like.

The amine compound having a phenoxy group can be obtained by first heating a primary or secondary amine having a phenoxy group and a haloalkyl ether so as to effect a reaction therebetween, subsequently adding an aqueous solution of a strong base, such as sodium hydroxide, potassium hydroxide or a tetraalkylammonium, and thereafter carrying out an extraction with an organic solvent, such as ethyl acetate or chloroform. Alternatively, the amine compound having a phenoxy group can be obtained by first heating a primary or secondary amine and a haloalkyl ether having a phenoxy group at its terminus so as to effect a reaction therebetween, subsequently adding an aqueous solution of a strong base, such as sodium hydroxide, potassium hydroxide or a tetraalkylammonium, and thereafter carrying out an extraction with an organic solvent, such as ethyl acetate or chloroform.

From the viewpoint of sensitivity, roughness and stability, an ammonium salt compound is preferred among the various basic compounds. A quaternary ammonium salt compound in its hydroxide form is most preferred.

These basic compounds may be used either individually or in combination.

The molecular weight of the basic compounds is preferably in the range of 250 to 1000, more preferably 250 to 800 and further preferably 400 to 800.

The amount of basic compound contained in the composition, based on the total solid content of the composition, is preferably in the range of 1.0 to 8.0 mass %, more preferably 1.5 to 5.0 mass % and further preferably 2.0 to 4.0 mass.

[8] Fluorinated and/or Siliconized Surfactant (G)

Preferably, the photosensitive composition of the present invention further contains any one, or two or more members, of fluorinated and/or siliconized surfactants (fluorinated surfactant, siliconized surfactant and surfactant containing both fluorine and silicon atoms).

The photosensitive composition of the present invention when containing the fluorinated and/or siliconized surfactant would, in the use of an exposure light source of 250 nm or below, especially 220 nm or below, realize favorable sensitivity and resolving power and produce a resist pattern of less adhesion and development defects.

As the fluorinated and/or siliconized surfactants, there can be mentioned, for example, those described in JP-A' s 62-36663, 61-226746, 61-226745, 62-170950, 63-34540, 7-230165, 8-62834, 9-54432, 9-5988 and 2002-277862 and U.S. Pat. Nos. 5,405,720, 5,360,692, 5,529,881, 5,296,330, 5,436,098, 5,576,143, 5,294,511 and 5,824,451. Any of the following commercially available surfactants can be used as is.

As useful commercially available surfactants, there can be mentioned, for example, fluorinated or siliconized surfactants, such as Eftop EF301 and EF303 (produced by Shin-Akita Kasei Co., Ltd.), Florad FC 430 and 431 (produced by Sumitomo 3M Ltd.), Megafac F171, F173, F176, F189 and R08 (produced by Dainippon Ink & Chemicals, Inc.), Surflon S-382, SC101, 102, 103, 104, 105 and 106 (produced by Asahi Glass Co., Ltd.) and Troy Sol S-366 (produced by Troy Chemical Co., Ltd.). Further, polysiloxane polymer KP-341 (produced by Shin-Etsu Chemical Co., Ltd.) can be employed as the siliconized surfactant.

As the surfactants, besides the above publicly known surfactants, use can be made of a surfactant based on a polymer having a fluorinated aliphatic group derived from a fluorinated aliphatic compound produced by a telomerization technique (also called a telomer process) or an oligomerization technique (also called an oligomer process). The fluorinated aliphatic compound can be synthesized by the process described in JP-A-2002-90991.

The polymer having a fluorinated aliphatic group is preferably a copolymer from a monomer having a fluorinated aliphatic group and a poly(oxyalkylene) acrylate and/or poly (oxyalkylene) methacrylate, which copolymer may have an irregular distribution or may result from block copolymerization. As the poly(oxyalkylene) group, there can be mentioned a poly(oxyethylene) group, a poly(oxypropylene) group, a poly(oxybutylene) group or the like. Further, use can be made of a unit having alkylene groups of different chain lengths in a single chain, such as poly(oxyethylene-oxypropylene-oxyethylene block concatenation) or poly(oxyethylene-oxypropylene block concatenation). Moreover, the copolymer from a monomer having a fluorinated aliphatic group and a poly (oxyalkylene) acrylate (or methacrylate) is not limited to two-monomer copolymers and may be a three or more monomer copolymer obtained by simultaneous copolymerization of two or more different monomers having a fluorinated aliphatic group, two or more different poly(oxyalkylene) acrylates (or methacrylates), etc.

For example, as a commercially available surfactant, there can be mentioned Megafac F178, F-470, F-473, F-475, F-476 or F-472 (produced by Dainippon Ink & Chemicals, Inc.). Further, there can be mentioned a copolymer from an acrylate (or methacrylate) having a $C_6F_{13}$ group and a poly(oxyalkylene) acrylate (or methacrylate), a copolymer from an acrylate (or methacrylate) having a $C_6F_{13}$ group, poly(oxyethylene) acrylate (or methacrylate) and poly(oxypropylene) acrylate (or methacrylate), a copolymer from an acrylate (or methacrylate) having a $C_8F_{17}$ group and a poly(oxyalkylene) acrylate (or methacrylate), a copolymer from an acrylate (or methacrylate) having a $C_8F_{17}$ group, poly(oxyethylene) acrylate (or methacrylate) and poly(oxypropylene) acrylate (or methacrylate), or the like.

The amount of fluorinated and/or siliconized surfactant used is preferably in the range of 0.0001 to 2 mass %, more preferably 0.001 to 1 mass % based on the total mass (excluding solvents) of the photosensitive composition.

[9] Organic Solvent (H)

Before the use of the photosensitive composition of the present invention, the foregoing components are dissolved in a given organic solvent.

As useful organic solvents, there can be mentioned, for example, ethylene dichloride, cyclohexanone, cyclopentanone, 2-heptanone, γ-butyrolactone, methyl ethyl ketone, ethylene glycol monomethyl ether, ethylene glycol monoethyl ether, 2-methoxyethyl acetate, ethylene glycol monoethyl ether acetate, propylene glycol monomethyl ether, propylene glycol monomethyl ether acetate, toluene, ethyl acetate, methyl lactate, ethyl lactate, methyl methoxypropionate, ethyl ethoxypropionate, methyl pyruvate, ethyl pyruvate, propyl pyruvate, N,N-dimethylformamide, dimethyl sulfoxide, N-methylpyrrolidone, tetrahydrofuran and the like.

The solvents having a ketone structure include a linear ketone solvent and a cycloketone solvent. Compounds having 5 to 8 carbon atoms in total are preferred from the viewpoint of high coatability.

As the linear ketone solvent, there can be mentioned, for example, 2-heptanone, methyl ethyl ketone, methyl isobutyl ketone or the like. Of these, 2-heptanone is preferred.

As the cycloketone solvent, there can be mentioned, for example, cyclopentanone, 3-methyl-2-cyclopentanone, cyclohexanone, 2-methylcyclohexanone, 2,6-dimethylcyclohexanone, cycloheptanone, cyclooctanone, isophorone or the like. Cyclohexanone and cycloheptanone are preferred.

The solvents having a ketone structure are preferably used either alone or as a mixture with another solvent. As the mixed solvent (joint solvent), there can be mentioned a propylene glycol monoalkyl ether carboxylate, an alkyl lactate, a propylene glycol monoalkyl ether, an alkyl alkoxypropionate, a lactone compound or the like.

As the propylene glycol monoalkyl ether carboxylate, there can be mentioned, for example, propylene glycol monomethyl ether acetate, propylene glycol monomethyl ether propionate, propylene glycol monoethyl ether acetate or the like.

As the alkyl lactate, there can be mentioned, for example, methyl lactate, ethyl lactate or the like.

As the propylene glycol monoalkyl ether, there can be mentioned, for example, propylene glycol monomethyl ether, propylene glycol monoethyl ether or the like.

As the alkyl alkoxypropionate, there can be mentioned, for example, methyl methoxypropionate, ethyl methoxypropionate, methyl ethoxypropionate, ethyl ethoxypropionate or the like.

As the lactone compound, there can be mentioned, for example, γ-butyrolactone or the like.

As preferred joint solvents, there can be mentioned a propylene glycol monoalkyl ether carboxylate, an alkyl lactate and a propylene glycol monoalkyl ether. A more preferred joint solvent is propylene glycol monomethyl ether acetate.

A solvent with a boiling point as high as 200° C. or higher, such as ethylene carbonate or propylene carbonate, may be mixed into the solvent for use in order to attain enhancements of film thickness uniformity and development defect performance.

The amount of high-boiling-point solvent added, based on the total mass of solvents, is generally in the range of 0.1 to 15 mass %, preferably 0.5 to 10 mass % and more preferably 1 to 5 mass %.

In the present invention, a photosensitive composition having a solid content of generally 3 to 25 mass %, preferably 5 to 22 mass % and more preferably 5 to 15 mass % is prepared by use of solvents individually, preferably in combination.

[10] Other Additive (I)

The photosensitive composition of the present invention may further according to necessity contain a dye, a plasticizer, a surfactant other than the above-mentioned component (G), a photosensitizer, a compound capable of accelerating the dissolution in a developer, etc.

The compound capable of accelerating the dissolution in a developer that can be employed in the present invention is a low-molecular compound of 1000 or less molecular weight having two or more phenolic OH groups or one or more carboxyl groups. When a carboxyl group is contained, an alicyclic or aliphatic compound is preferred.

The amount of dissolution accelerating compound added, based on the mass of the resin as component (B) or resin as component (C), is preferably in the range of 2 to 50 mass %, more preferably 5 to 30 mass %. It is preferred for the amount to be up to 50 mass % from the viewpoint of suppression of any development residue and prevention of any pattern distortion at development.

The above phenolic compound of 1000 or less molecular weight can be easily synthesized by persons of ordinary skill in the art to which the present invention pertains while consulting the processes described in, for example, JP-A' s 4-122938 and 2-28531, U.S. Pat. No. 4,916,210 and EP 219294.

As the carboxylated alicyclic or aliphatic compound, there can be mentioned, for example, a carboxylic acid derivative of steroid structure such as cholic acid, deoxycholic acid or lithocholic acid, an adamantanecarboxylic acid derivative, adamantanedicarboxylic acid, cyclohexanecarboxylic acid, cyclohexanedicarboxylic acid or the like. These are however nonlimiting.

In the present invention, surfactants other than the above fluorinated and/or siliconized surfactants (G) can also be added to the composition. In particular, there can be mentioned nonionic surfactants, such as a polyoxyethylene alkyl ether, a polyoxyethylene alkylallyl ether, a polyoxyethylene-polyoxypropylene block copolymer, a sorbitan aliphatic ester, a polyoxyethylene sorbitan aliphatic ester or the like.

These surfactants may be added either individually or in combination.

[11] Method of Forming Pattern

The photosensitive composition of the present invention is used in such a manner that the above components are dissolved in a given organic solvent, preferably the above mixed solvent, and applied onto a given support in the following manner.

For example, the photosensitive composition is applied onto a substrate, such as one for use in the production of precision integrated circuit elements (e.g., silicon/silicon dioxide coating), by appropriate application means, such as a spinner or coater, and dried to thereby form a photosensitive film. In advance, the substrate may be provided with an anti-reflection film known in the art.

The photosensitive film is exposed through a given mask to actinic rays or radiation, preferably baked (heated), and developed. Accordingly, a desirable pattern can be obtained.

In the stage of irradiation with actinic rays or radiation, exposure (liquid immersion exposure) may be carried out after filling the interstice between the photosensitive film and a lens with a liquid of refractive index higher than that of air. This would realize an enhancement of resolving power.

As the actinic rays or radiation, there can be mentioned infrared rays, visible light, ultraviolet rays, far ultraviolet rays, X-rays, electron beams or the like. Among them, preferred use is made of far ultraviolet rays of especially 250 nm or less, more especially 220 nm or less wavelength, such as a KrF excimer laser (248 nm), an ArF excimer laser (193 nm) and an $F_2$ excimer laser (157 nm), as well as X-rays, electron beams and the like. More preferred use is made of an ArF excimer laser, an $F_2$ excimer laser, EUV (13 nm) and electron beams.

(Liquid Immersion Exposure)

When the photosensitive composition of the present invention is subjected to liquid immersion exposure, from the viewpoint of enhancement of resolving power, it is preferred for the photosensitive composition to be used with a film thickness of 30 to 250 nm. More preferably, the photosensitive composition is used with a film thickness of 30 to 100 nm. This film thickness can be attained by regulating the solid content of the photosensitive composition within an appropriate range so as to cause the composition to have an appropriate viscosity, thereby improving the applicability and film forming property.

The total solid content of the photosensitive composition is generally in the range of 1 to 10 mass %, preferably 1 to 8 mass % and more preferably 1.0 to 6.0 mass %.

When the photosensitive composition of the present invention is subjected to liquid immersion exposure, the photosensitive composition is used in such a manner that the above components are dissolved in a given organic solvent, preferably the above mixed solvent, and applied onto a given support in the following manner.

Illustratively, the photosensitive composition is applied onto a substrate, such as one for use in the production of precision integrated circuit elements (e.g., silicon/silicon dioxide coating), by appropriate application means, such as a spinner or coater, at an arbitrary thickness (generally 30 to 500 nm). After the application, according to necessity, the resist film is washed with water for liquid immersion. The washing time is generally in the range of 5 seconds to 5 minutes.

Subsequently, the applied photosensitive composition is dried by spin or bake to thereby form a photosensitive film (hereinafter also referred to as a resist film). Thereafter, the photosensitive film is exposed through a mask for pattern formation or the like and through a water for liquid immersion (liquid immersion exposure). For example, the exposure is carried out in a state in which the interstice between the resist film and an optical lens is filled with the water for liquid immersion. The exposure intensity, although can be appropriately set, is generally in the range of 1 to 100 mJ/cm$^2$. After the exposure, according to necessity, the resist film is washed with the liquid for liquid immersion. The washing time is generally in the range of 5 seconds to 5 minutes. The washed resist film is preferably spun or/and baked, developed and rinsed. Accordingly, a desirable pattern can be obtained. The bake is preferred, and the bake temperature is generally in the range of 30° to 300° C. From the viewpoint of the PED, it is preferred to shorten the time from the exposure to the bake operation.

As an exposure light, use is made of far ultraviolet rays of preferably 250 nm or shorter, more preferably 220 nm or shorter wavelength. In particular, there can be mentioned a KrF excimer laser (248 nm), an ArF excimer laser (193 nm), an $F_2$ excimer laser (157 nm), X-rays or the like.

It is assumed that any change in performance realized by the application of the resist to liquid immersion exposure would result from the contact of the surface of the resist with the liquid for liquid immersion.

The liquid for liquid immersion for use in the liquid immersion exposure will be described below.

The liquid for liquid immersion preferably consists of a liquid being transparent in exposure wavelength whose temperature coefficient of refractive index is as low as possible so as to ensure minimization of any distortion of optical image projected on the resist. Especially in the use of an ArF excimer laser (wavelength: 193 nm) as an exposure light source, it is preferred to use water from not only the above viewpoints but also the viewpoints of easy procurement and easy handling.

Further, from the viewpoint of refractive index increase, use can be made of a medium of 1.5 or higher refractive index. Such a medium may be an aqueous solution or an organic solvent.

In the use of water as the liquid for liquid immersion, a slight proportion of additive (liquid) that would not dissolve the resist layer on a wafer and would be negligible with respect to its influence on any optical coat for an under surface of lens element may be added in order to not only decrease the surface tension of water but also increase a surface activating power. The additive is preferably an aliphatic alcohol with a refractive index approximately equal to that of water, for example, methyl alcohol, ethyl alcohol, isopropyl alcohol or the like. The addition of an alcohol with a refractive index approximately equal to that of water is advantageous in that even when the alcohol component is evaporated from water to thereby cause a change of content concentration, the change of refractive index of the liquid as a whole can be minimized. On the other hand, when a substance being opaque in 193 nm rays or an impurity whose refractive index is greatly different from that of water is mixed therein, the mixing would invite a distortion of optical image projected on the resist. Accordingly, it is preferred to use distilled water as the liquid immersion water. Furthermore, use may be made of pure water having been filtered through an ion exchange filter or the like.

Desirably, the electrical resistance of the water is 18.3 MQcm or higher, and the TOC (organic matter concentration) thereof is 20 ppb or below. Prior deaeration of the water is desired.

Raising the refractive index of the liquid for liquid immersion would enable an enhancement of lithography performance. From this viewpoint, an additive suitable for refractive index increase may be added to the water, or heavy water ($D_2O$) may be used in place of water.

For the prevention of direct contact of the resist film with the liquid for liquid immersion, a film that is highly insoluble in the liquid for liquid immersion (hereinafter also referred to as a "top coat") may be provided between the resist film from the photosensitive composition of the present invention and the liquid for liquid immersion. The functions to be fulfilled by the top coat are applicability to an upper layer portion of the resist, transparency in radiation of especially 193 nm and being highly insoluble in the liquid for liquid immersion. Preferably, the top coat does not mix with the resist and is uniformly applicable to an upper layer of the resist.

From the viewpoint of 193 nm transparency, the top coat preferably consists of a polymer containing no aromatic moiety. As such, there can be mentioned, for example, a hydrocarbon polymer, an acrylic ester polymer, polymethacrylic acid, polyacrylic acid, polyvinyl ether, a siliconized polymer, a fluoropolymer or the like.

At the detachment of the top coat, use may be made of a developer, or a separate peeling agent may be used. The peeling agent preferably consists of a solvent being less in the permeation into the resist. Detachability by an alkali developer is preferred from the viewpoint of simultaneous attainment of the detachment step with the development processing step for the resist. The top coat is preferred to be acidic from the viewpoint of detachment with the use of an alkali developer. However, from the viewpoint of non-intermixability with the resist, the top coat may be neutral or alkaline.

The less the difference in refractive index between the top coat and the liquid for liquid immersion, the higher the resolving power. When an ArF excimer laser (wavelength: 193 nm) is used as an exposure light source, as water is preferably used as the liquid for liquid immersion, it is preferred for the top coat for ArF liquid immersion exposure to have a refractive index close to that of water (1.44). Moreover, from the viewpoint of transparency and refractive index, it is preferred to reduce the thickness of the resist film.

When an organic solvent is used as the liquid for liquid immersion, the top coat is preferably one that is soluble in water.

When the resist film consisting of the photosensitive composition of the present invention is exposed through a liquid immersion medium, in place of the top coat, a hydrophobic resin (HR) may be added to the resist composition. This would bring about uneven localization of the hydrophobic resin (HR) on the surface layer of the resist film. When the liquid immersion medium is water, there would be attained an increase of receding contact angle on the surface of the resist film with reference to water upon formation of the resist film and accordingly an enhancement of the liquid immersion water tracking property. The hydrophobic resin (HR) is not limited as long as the receding contact angle on the surface is increased by the addition of the resin. However, it is preferred for the resin to have at least either a fluorine atom or a silicon atom. The receding contact angle of the resist film is preferably in the range of 60° to 90°, more preferably 70° or greater. The amount of hydrophobic resin added can be appropriately regulated so that the receding contact angle of the resist film falls within the above range. However, the addition amount is preferably in the range of 0.1 to 10 mass %, more preferably 0.1 to 5 mass % based on the total solid content of the resist composition. Although the hydrophobic resin (HR) is unevenly localized on the interface as mentioned above, as different from surfactants, the hydrophobic resin does not necessarily have to have a hydrophilic group in its molecule and does not need to contribute toward uniform mixing of polar/nonpolar substances.

The fluorine atom or silicon atom of the hydrophobic resin (HR) may be introduced either in the principal chain of the resin or as a substituent in the side chain thereof.

The hydrophobic resin (HR) is preferably a resin having, as a partial structure having a fluorine atom, an alkyl group having a fluorine atom, a cycloalkyl group having a fluorine atom or an aryl group having a fluorine atom.

As the hydrophobic resin (HR), a variety of resins known in the art can be employed without any particular limitation.

In the development step, an alkali developer is used as follows. As the alkali developer for the resist composition, use can be made of any of alkaline aqueous solutions of an inorganic alkali such as sodium hydroxide, potassium hydroxide, sodium carbonate, sodium silicate, sodium metasilicate or aqueous ammonia, a primary amine such as ethylamine or n-propylamine, a secondary amine such as diethylamine or di-n-butylamine, a tertiary amine such as triethylamine or methyldiethylamine, an alcoholamine such as dimethylethanolamine or triethanolamine, a quaternary ammonium salt such as tetramethylammonium hydroxide or tetraethylammonium hydroxide, a cycloamine such as pyrrole or piperidine, or the like.

Before the use of the above alkali developer, appropriate amounts of an alcohol and a surfactant may be added thereto.

The alkali concentration of the alkali developer is generally in the range of 0.1 to 20 mass %.

The pH value of the alkali developer is generally in the range of 10.0 to 15.0.

EXAMPLE

The present invention will be described in greater detail below with reference to its examples. However, the subject matter of the present invention is in no way limited to these examples.

<Synthesis of acid generator A1>

(1) Synthesis of compound A1-1

<Synthesis of Tricyclohexylbenzene>

Aluminum chloride amounting to 6.83 g was added to 20.0 g of benzene and agitated while cooling at 3° C. Then, 40.4 g of cyclohexyl chloride was slowly dropped thereinto. After the completion of the dropping, the mixture was agitated at room temperature for 5 hours and poured into ice water. An organic layer was extracted by use of ethyl acetate, and the obtained organic layer was distilled at 40° C. under reduced pressure and further at 170° C. under reduced pressure. The resultant matter was cooled to room temperature, and 50 ml of acetone was poured thereinto to thereby carry out recrystallization. The crystal obtained by the recrystallization was collected by filtration. Thus, 14 g of tricyclohexylbenzene was obtained.

<Synthesis of Sodium Tricyclohexylbenzenesulfonate>

Tricyclohexylbenzene amounting to 30 g was dissolved in 50 ml of methylene chloride, and agitated while cooling at 3° C. Then, 15.2 g of chlorosulfonic acid was slowly dropped thereinto. After the completion of the dropping, the mixture was agitated at room temperature for 5 hours, and 10 g of ice was poured thereinto. Further, 40 g of a 50% aqueous solution of sodium hydroxide was poured into the mixture, and 20 g of ethanol was added thereto. The mixture was agitated at 50° C. for 1 hour, and any undissolved matter was removed by filtration. Vacuum distillation was carried out at 40° C., and separated crystals were collected by filtration. The crystals were washed with hexane. Thus, 30 g of sodium 1,3,5-tricyclohexylbenzenesulfonate was obtained.

<Synthesis of Compound A1-1>

Triphenylsulfonium bromide A amounting to 4.0 g was dissolved in 20 ml of methanol, and 5.0 g of sodium 1,3,5-tricyclohexylbenzenesulfonate dissolved in 20 ml of methanol was added thereto. The mixture was agitated at room temperature for 2 hours, and 50 ml of ion exchanged water was added thereto. Extraction with chloroform was carried out, and the thus obtained organic layer was washed with water. Vacuum distillation thereof was carried out at 40° C., and the thus obtained crystals were recrystallized with a methanol/ethyl acetate solvent. Thus, 5.0 g of compound A1-1 was obtained.

$^1$H-NMR (400 MHz, $CDCl_3$) δ=7.85 (d, 6H), 7.68 (t, 3H), 7.59 (t, 6H), 6.97 (s, 2H), 4.36-4.27 (m, 2H), 2.48-2.38 (m, 1H), 1.97-1.16 (m, 30H)

(2) Synthesis of Compound A1-2

Compound A1-2 amounting to 4.0 g was obtained in the same manner as in the synthesis of the compound A1-1 except that 4.0 g of triphenylsulfonium bromide A was changed to 4.5 g of the following sulfonium salt B, and that 5.0 g of sodium 1,3,5-tricyclohexylbenzenesulfonate was changed to 4.0 g of sodium 1,4-dicyclohexylbenzenesulfonate.

(B)

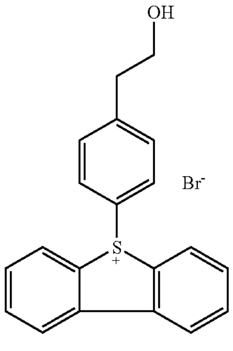

$^1$H-NMR (400 MHz, $CDCl_3$) δ=8.30 (d, 2H), 8.15 (d, 2H), 7.92 (s, 1H), 7.80 (t, 2H), 7.67 (d, 2H), 7.57 (t, 2H), 7.31 (d, 2H), 7.23 (d, 1H), 7.09 (d, 1H), 3.96-3.86 (m, 1H), 3.75 (t, 2H), 2.80 (t, 2H), 2.44-2.37 (m, 1H), 1.95-1.16 (m, 30H)

(3) Synthesis of Compound A1-3

Compound A1-3 amounting to 4.0 g was obtained in the same manner as in the synthesis of the compound A1-1 except that 4.0 g of triphenylsulfonium bromide A was changed to 4.5 g of the above sulfonium salt B.

$^1$H-NMR (400 MHz, $CDCl_3$) δ=8.35 (d, 2H), 8.11 (d, 2H), 7.79 (t, 2H), 7.74 (d, 2H), 7.57 (t, 2H), 7.31 (d, 2H), 6.98 (s, 2H), 4.32-4.23 (m, 2H), 3.79 (t, 2H), 2.82 (t, 2H), 2.37-2.46 (m, 1H), 1.97-1.16 (m, 30H)

(4) Synthesis of Compound A1-4

Compound A1-4 amounting to 4.0 g was obtained in the same manner as in the synthesis of the compound A1-1 except that 4.0 g of triphenylsulfonium bromide A was changed to 4.5 g of the following iodonium salt C.

(C)

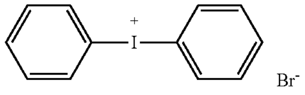

$^1$H-NMR (400 MHz, $CDCl_3$) δ=7.91 (d, 4H), 7.57 (t, 2H), 7.41 (t, 4H), 6.98 (s, 2H), 4.13-4.01 (m, 2H), 2.47-2.37 (m, 1H), 1.94-1.15 (m, 30H)

(5) Synthesis of Compound A1-5

Compound A1-5 amounting to 5.5 g was obtained in the same manner as in the synthesis of the compound A1-1 except that 5.0 g of sodium 1,3,5-tricyclohexylbenzenesulfonate was changed to 5.8 g of the following compound D.

(D)

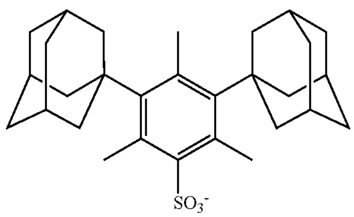

$^1$H-NMR (400 MHz, $CDCl_3$) δ=7.91 (d, 4H), 7.57 (t, 2H), 7.41 (t, 4H), 6.98 (s, 2H), 4.13-4.01 (m, 2H), 2.47-2.37 (m, 1H), 1.94-1.15 (m, 30H)

(6) Synthesis of Compound A1-6

Compound A1-6 amounting to 3.5 g was obtained in the same manner as in the synthesis of the compound A1-1 except that 4.0 g of triphenylsulfonium bromide A was changed to 4.8 g of the following compound E.

(E)

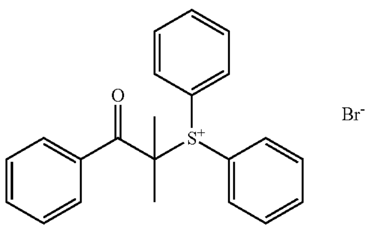

The structure of compound A1-6 was confirmed by $^1$H-NMR (400 MHz, $CDCl_3$).

(7) Synthesis of Compound A1-7

Compound A1-7 amounting to 5.0 g was obtained in the same manner as in the synthesis of the compound A1-1 except that 5.0 g of sodium 1,3,5-tricyclohexylbenzenesulfonate was changed to 6.0 g of the following sodium tetracyclohexylbenzenesulfonate F.

(F)

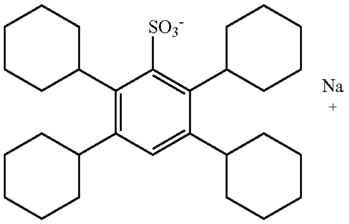

The structure of compound A1-7 was confirmed by $^1$H-NMR (400 MHz, $CDCl_3$).

(8) Synthesis of Compound A1-8

Compound A1-8 amounting to 6.0 g was obtained in the same manner as in the synthesis of the compound A1-1 except that 5.0 g of sodium 1,3,5-tricyclohexylbenzenesulfonate was changed to 6.0 g of the following compound G.

(G)

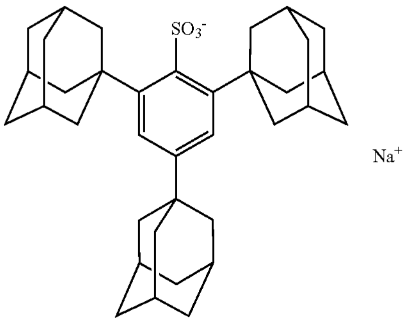

The structure of compound A1-8 was confirmed by $^1$H-NMR (400 MHz, $CDCl_3$).

(9) Synthesis of Compound A1-9

Compound A1-9 amounting to 4.0 g was obtained in the same manner as in the synthesis of the compound A1-1 except that 4.0 g of triphenylsulfonium bromide A was changed to 4.0 g of the following sulfonium salt H.

(H)

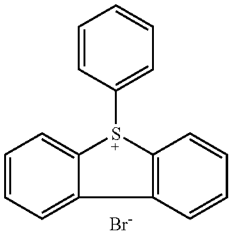

The structure of compound A1-9 was confirmed by $^1$H-NMR (400 MHz, $CDCl_3$).

(10) Synthesis of Compound A1-10

Compound A1-10 amounting to 4.0 g was obtained in the same manner as in the synthesis of the compound A1-1 except that 4.0 g of triphenylsulfonium bromide A was changed to 4.5 g of the above sulfonium salt B, and that 5.0 g of sodium 1,3,5-tricyclohexylbenzenesulfonate was changed to 5.0 g of the following sodium 1,2,4-tricyclohexylbenzenesulfonate I.

(I)

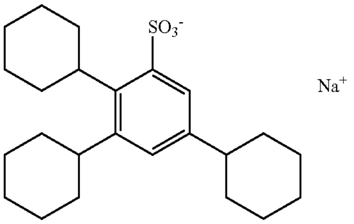

$^1$H-NMR (400 MHz, $CDCl_3$) δ=8.38 (d, 2H), 8.11 (d, 2H), 7.91 (s, 1H), 7.80 (t, 2H), 7.75 (d, 2H), 7.60 (t, 2H), 7.35 (d, 2H), 7.15 (s, 1H), 3.93-3.85 (m, 1H), 3.80 (t, 2H), 2.83 (t, 2H), 2.76-2.63 (m, 2H), 1.97-1.16 (m, 30H)

(11) Synthesis of Compound A1-11

Compound A1-11 amounting to 3.2 g was obtained in the same manner as in the synthesis of the compound A1-1 except that 5.0 g of sodium 1,3,5-tricyclohexylbenzenesulfonate was changed to 4.7 g of sodium 2,4-biscyclohexylmethoxy benzenesulfonate.

(12) Synthesis of Compound A1-12

Compound A1-12 amounting to 3.1 g was obtained in the same manner as in the synthesis of the compound A1-1 except that 5.0 g of sodium 1,3,5-tricyclohexylbenzenesulfonate was changed to 4.0 g of sodium 2,6-dicyclohexylbenzenesulfonate.

(13) Synthesis of Compound A1-13

Compound A1-13 amounting to 4.1 g was obtained in the same manner as in the synthesis of the compound A1-1 except that 5.0 g of sodium 1,3,5-tricyclohexylbenzenesulfonate was changed to 4.4 g of sodium 2,4-bis(cyclohexyloxy)benzenesulfonate.

(14) Synthesis of Compound A1-14

Compound A1-14 amounting to 4.0 g was obtained in the same manner as in the synthesis of the compound A1-1 except that 4.0 g of triphenylsulfonium bromide A was changed to 4.3 g of 1-(4-butoxy-naphthalen-1-yl) tetrahydrothiophenium bromide.

(15) Synthesis of Compound A1-15

Compound A1-15 amounting to 4.4 g was obtained in the same manner as in the synthesis of the compound A1-1 except that 4.0 g of triphenylsulfonium bromide A was changed to 5.0 g of 5-(propoxy-phenyl)-thianthren-5-ium bromide.

(16) Synthesis of Compound A1-16

Compound A1-16 amounting to 4.4 g was obtained in the same manner as in the synthesis of the compound A1-1 except that 4.0 g of triphenylsulfonium bromide A was changed to 4.8 g of (4-t-butoxy-phenyl)-diphenylsulfonium bromide.

(17) Synthesis of Compound A1-17

Compound A1-17 amounting to 3.4 g was obtained in the same manner as in the synthesis of the compound A1-1 except that 4.0 g of triphenylsulfonium bromide A was changed to 3.5 g of 1-(4-t-butylphenyl)tetrahydrothiophenium bromide.

(18) Synthesis of Compound A1-18

Compound A1-18 amounting to 4.4 g was obtained in the same manner as in the synthesis of the compound A1-1 except that 4.0 g of triphenylsulfonium bromide A was changed to 5.5 g of (4-isopropylphenyl)-(2-methoxycarbonylphenyl)-(4-methoxyphenyl)-sulfonium bromide.

(19) Synthesis of Compound A1-19

Compound A1-19 amounting to 5.4 g was obtained in the same manner as in the synthesis of the compound A1-1 except that 4.0 g of triphenylsulfonium bromide A was changed to 9.0 g of tris(4-t-butoxy-carbonyloxy-3,5-dimethylphenyl) sulfonium bromide The formulae of the compounds A1-1 to A1-19 obtained by the above synthesizing methods together with comparative compounds 1 to 4 are shown below.
A1-1
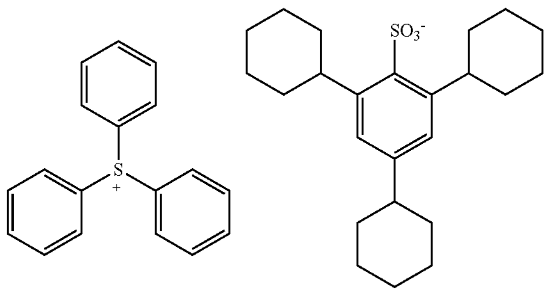
A1-2
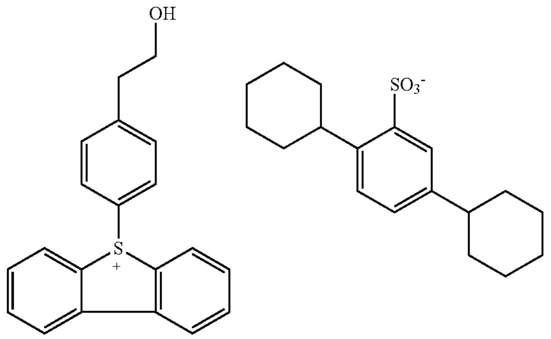
A1-3
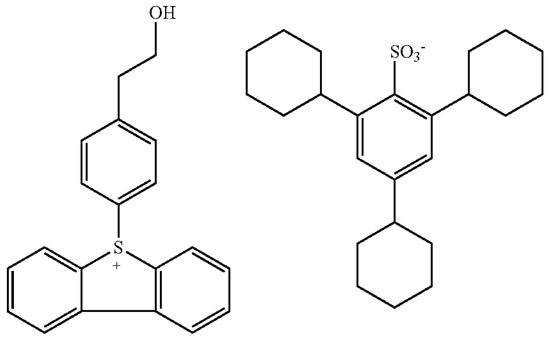
A1-4
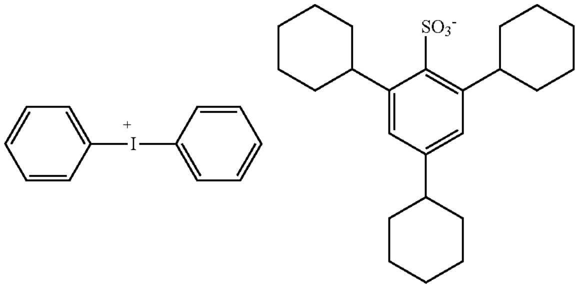
-continued
A1-5
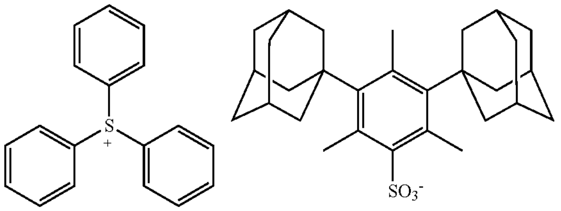
A1-6
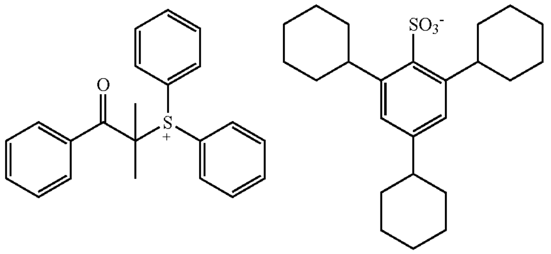
A1-7
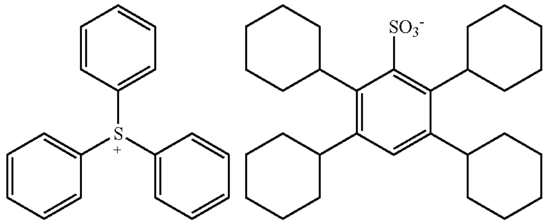
A1-8
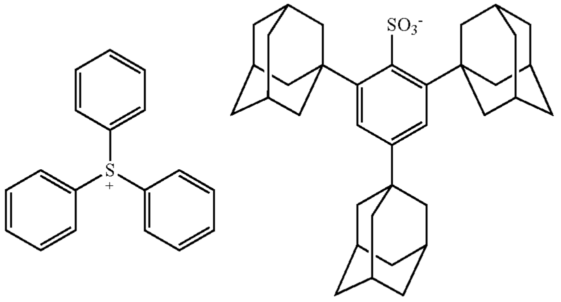
A1-9
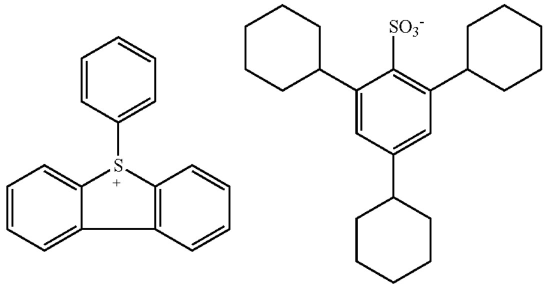

-continued
A1-10
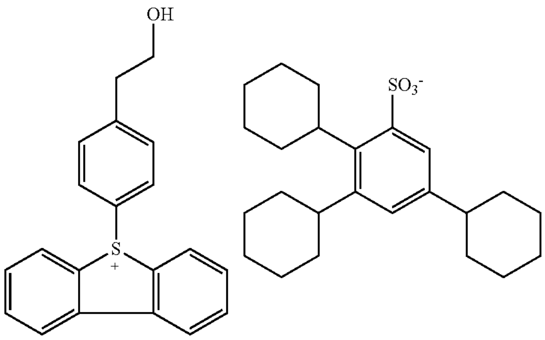
A1-11
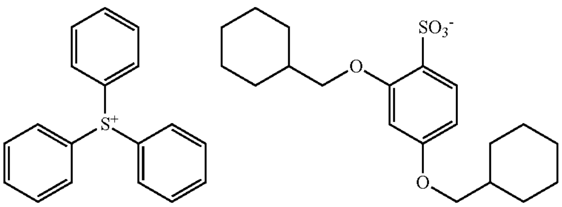
A1-12
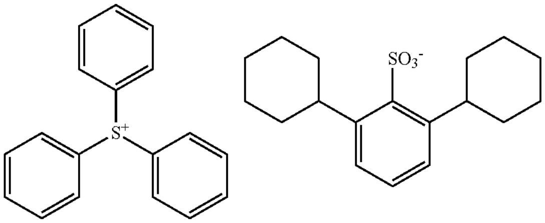
A1-13
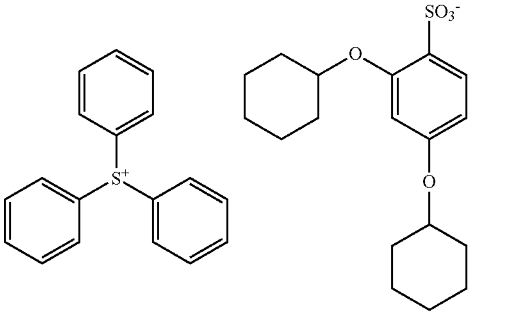
A1-14
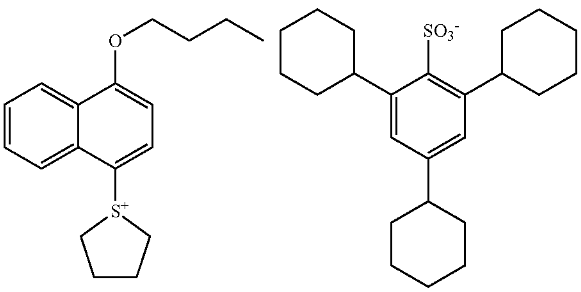
-continued
A1-15
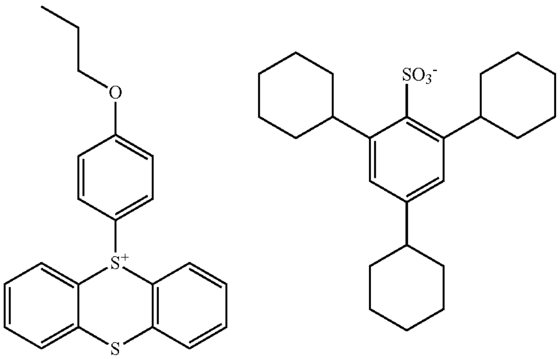
A1-16
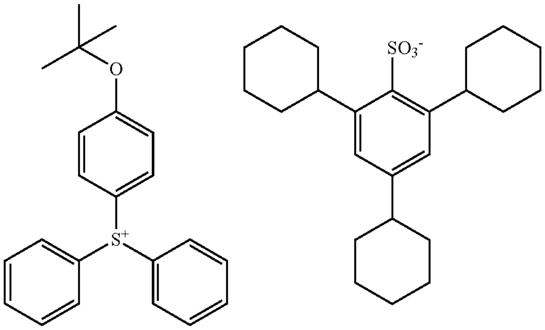
A1-17
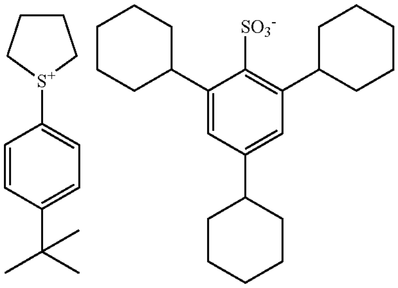
A1-18
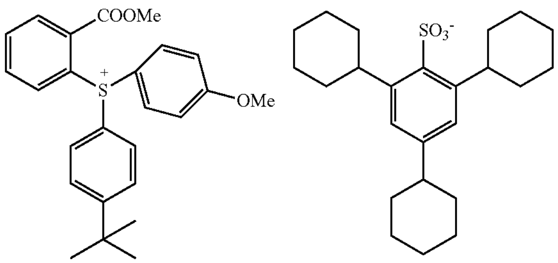

-continued

A1-19

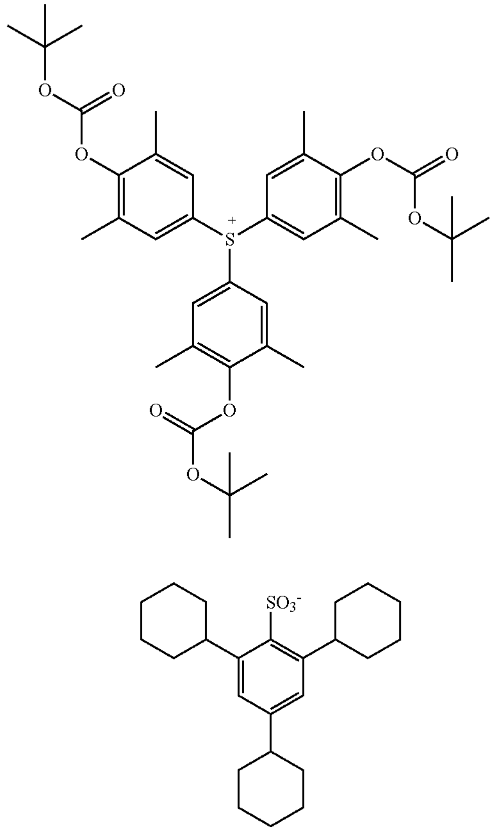

Comparative compound 1

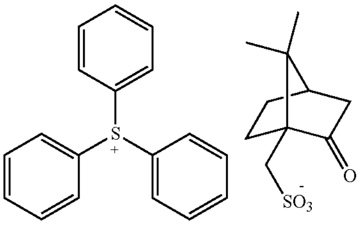

Comparative compound 2

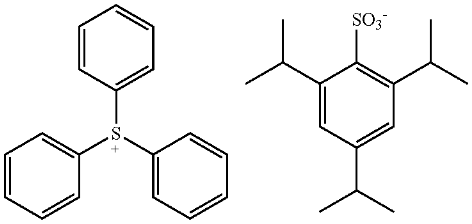

Comparative compound 3

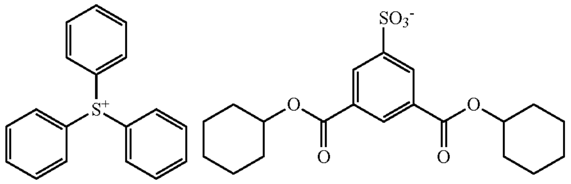

-continued

Comparative compound 4

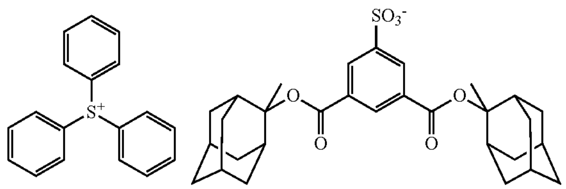

<Resin (B)>

Among the following resins (RA-1) to (RA-25), resins (RA-1), (RA-20), (RA-23) and (RA-25) below were used as the resin (B) in the following Examples. The numeral appearing on the right side of each repeating unit refers to the molar ratio thereof. Mw means the weight average molecular weight, and Mw/Mn refers to the dispersity of molecular weight. These are applicable hereinafter.

(RA-1)

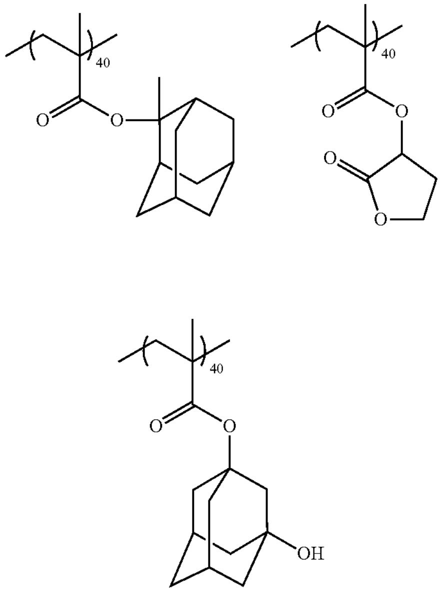

Mw = 10700
Mw/Mn = 1.81

(RA-20)

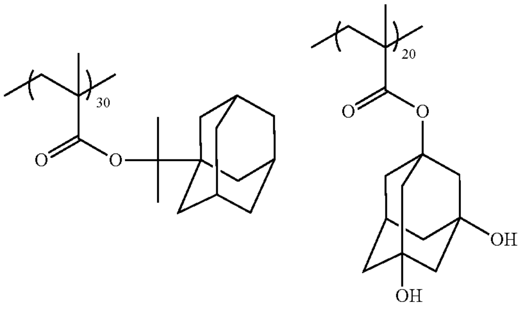

-continued

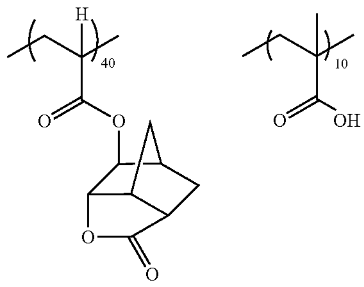

Mw = 7600
Mw/Mn = 1.76

(RA-23)

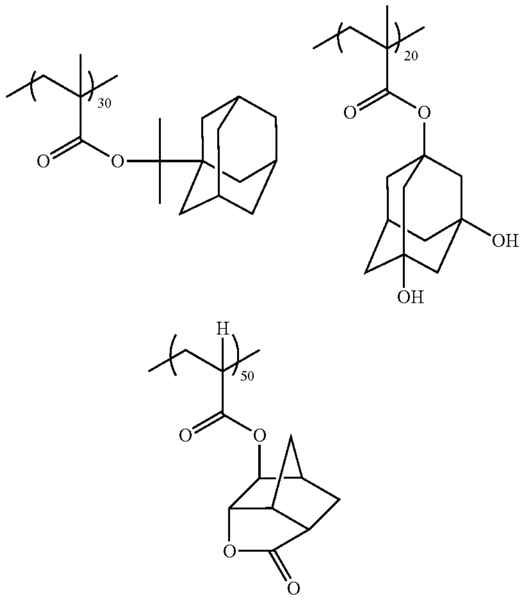

Mw = 8500
Mw/Mn = 1.77

(RA-25)

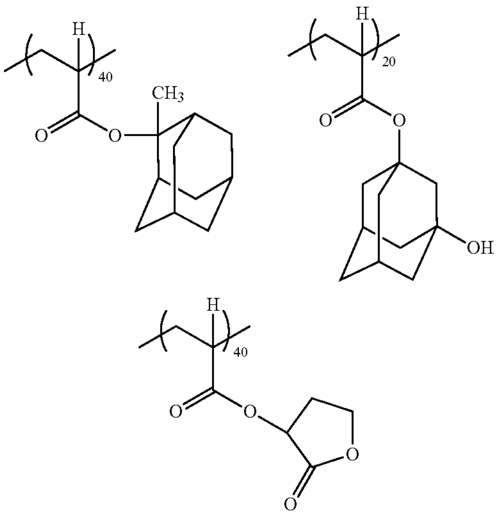

Mw = 20800
Mw/Mn = 2.25

Example A

Examples 1A to 14A and Comparative Examples 1A and 2A

<Preparation of Resist>

Referring to Table 1 below, with respect to each of the resists, the individual components were dissolved in the solvent, thereby obtaining a solution of 12 mass % solid content. This solution was passed through a polytetrafluoroethylene filter of 0.1 μm pore size, thereby obtaining a positive resist solution. The thus obtained positive resist solutions were evaluated by the following methods, and the results are given in Table 1.

<Evaluation of Resist>

An antireflection film DUV-42 produced by Brewer Science Inc. was uniformly applied at a thickness of 60 nm onto a silicon substrate having undergone a hexamethyldisilazane treatment by use of a spin coater, and dried on a hot plate at 100° C. for 90 seconds. Further drying was carried out by heating at 190° C. for 240 seconds. Thereafter, each of the positive resist solutions was applied thereonto by use of a spin coater and dried at 120° C. for 90 seconds, thereby obtaining a 0.25 μm resist film.

The obtained resist film was exposed through a mask by use of an ArF excimer laser stepper (manufactured by ISI, NA=0.6). Immediately after the exposure, the resist film was heated on a hot plate at 120° C. for 90 seconds. Thereafter, the resist film was developed with a 2.38 mass % aqueous tetramethylammonium hydroxide solution at 23° C. for 60 seconds, rinsed with pure water for 30 seconds and dried. Thus, an intended line pattern was obtained.

[Sensitivity, Resolving Power (γ)]

Surface exposure was carried out while changing the exposure intensity by 0.5 mJ at a time within the range of 10 to 40 $mJ/cm^2$, and the exposed film was baked at 110° C. for 90 seconds. Thereafter, using a 2.38 mass % aqueous tetramethylammonium hydroxide (TMAH) solution, the dissolution rate at each of the exposure intensities was measured, thereby obtaining a sensitivity curve.

The sensitivity was defined as the exposure intensity at which the dissolution rate of the resist was saturated on the sensitivity curve. Dissolution contrast (γ value) was calculated from the gradient of the straight line portion of the sensitivity curve. The larger the γ value, the greater the excellence in dissolution contrast.

[Line Edge Roughness]

At arbitrary 30 points in a 50 μm region in the longitudinal direction of a 150 nm line pattern at the exposure intensity realizing the above sensitivity, the distance from a reference line on which edges were to be present was measured by means of a scanning electron microscope (model S-9220, manufactured by Hitachi, Ltd.). The standard deviation of measurements was determined, and 3σ was computed.

[Pattern Profile]

The optimum exposure intensity refers to the exposure intensity that reproduces a line-and-space mask pattern of 150 nm line width. The profile at the optimum exposure intensity was observed by means of a scanning electron microscope (SEM).

TABLE 1

| ArF positive exposure | | | | | | | | | | | |
|---|---|---|---|---|---|---|---|---|---|---|---|
| | (A1) Acid generator (0.2 g) | (A2) Acid generator (0.2 g) | (B) Resin (10 g) | (F) Basic compound (0.02 g) | (G) Surfactant (0.1 mass %)* | (H) Solvent (mass ratio) | Sensitivity ($mJ/cm^2$) | Resolving power (γ) | Roughness (nm) | Pattern profile |
| Ex. 1A | A1-1 | Z | RA-20 | C-1 | W-1 | A1/B1 (6/4) | 24.0 | 6.2 | 4.0 | Rectangle |
| Ex. 2A | A1-2 | Z | RA-20 | C-1 | W-1 | A2/B2 (6/4) | 24.0 | 6.2 | 5.0 | Rectangle |
| Ex. 3A | A1-3 | Z | RA-20 | C-1 | W-1 | A3/B1 (6/4) | 22.0 | 6.2 | 4.0 | Rectangle |
| Ex. 4A | A1-4 | Z | RA-20 | C-1 | W-1 | A4/B1 (6/4) | 24.0 | 6.0 | 4.0 | Rectangle |
| Ex. 5A | A1-5 | Z | RA-20 | C-1 | W-1 | A1/B2 (6/4) | 25.0 | 6.0 | 4.5 | Rectangle |
| Ex. 6A | A1-6 | Z | RA-20 | C-1 | W-1 | A1/B1 (6/4) | 24.0 | 6.0 | 4.0 | Rectangle |
| Ex. 7A | A1-7 | Z | RA-20 | C-1 | W-1 | A1/B1 (6/4) | 24.0 | 6.0 | 3.8 | Rectangle |
| Ex. 8A | A1-8 | Z | RA-20 | C-1 | W-1 | A1/B1 (6/4) | 25.0 | 6.0 | 4.0 | Rectangle |
| Ex. 9A | A1-9 | Z | RA-20 | C-1 | W-1 | A1/B1 (6/4) | 24.0 | 6.0 | 4.0 | Rectangle |
| Ex. 10A | A1-10 | Z | RA-20 | C-2 | W-1 | A1/B1 (6/4) | 20.0 | 7.0 | 4.0 | Rectangle |
| Ex. 11A | A1-11 | Z | RA-20 | C-3 | W-1 | A1/B1 (6/4) | 22.0 | 7.0 | 4.0 | Rectangle |
| Ex. 12A | A1-12 | Z | RA-23 | C-1 | W-2 | A1/B1 (6/4) | 20.0 | 6.2 | 4.0 | Rectangle |
| Ex. 13A | A1-13 | Z | RA-25 | C-1 | W-3 | A1/B1 (6/4) | 25.0 | 6.0 | 4.0 | Rectangle |
| Ex. 14A | A1-14 | Z | RA-1 | C-1 | W-4 | A1/B1 (6/4) | 25.0 | 6.0 | 4.0 | Rectangle |
| Ex. 15A | A1-11 | Z | RA-20 | C-1 | W-1 | A1/B1 (6/4) | 24.0 | 6.2 | 4.0 | Rectangle |
| Ex. 16A | A1-12 | Z | RA-20 | C-1 | W-1 | A2/B2 (6/4) | 24.0 | 6.2 | 5.0 | Rectangle |
| Ex. 17A | A1-13 | Z | RA-20 | C-1 | W-1 | A3/B1 (6/4) | 22.0 | 6.2 | 4.0 | Rectangle |
| Ex. 18A | A1-14 | Z | RA-20 | C-1 | W-1 | A4/B1 (6/4) | 24.0 | 6.0 | 4.0 | Rectangle |
| Ex. 19A | A1-15 | Z | RA-20 | C-1 | W-1 | A1/B2 (6/4) | 25.0 | 6.0 | 4.5 | Rectangle |
| Ex. 20A | A1-16 | Z | RA-20 | C-1 | W-1 | A1/B1 (6/4) | 24.0 | 6.0 | 4.0 | Rectangle |
| Ex. 21A | A1-17 | Z | RA-20 | C-1 | W-1 | A1/B1 (6/4) | 24.0 | 6.0 | 3.8 | Rectangle |
| Ex. 22A | A1-18 | Z | RA-20 | C-1 | W-1 | A1/B1 (6/4) | 25.0 | 6.0 | 4.0 | Rectangle |
| Ex. 23A | A1-19 | Z | RA-20 | C-1 | W-1 | A1/B1 (6/4) | 24.0 | 6.0 | 4.0 | Rectangle |
| Comp. 1A | Comp. Compound 1 | Z | RA-20 | C-1 | W-1 | A1/B1 (6/4) | 25.0 | 3.3 | 8.0 | Taper |
| Comp. 2A | Comp. Compound 2 | Z | RA-20 | C-1 | W-1 | A1/B1 (6/4) | 25.0 | 3.2 | 8.0 | Taper |
| Comp. 3A | Comp. Compound 3 | Z | RA-20 | C-8 | W-1 | A1/B1 (6/4) | 20.0 | 7.0 | 4.0 | Rectangle |
| Comp. 4A | Comp. Compound 4 | Z | RA-20 | C-8 | W-1 | A1/B1 (6/4) | 20.0 | 7.0 | 4.0 | Rectangle |

*based on the total solid content of the resist composition

The employed components are as follows.

[Acid Generator]

The acid generator (A1) according to the present invention is one mentioned hereinbefore by way of example.

The jointly used acid generator (A2) is a compound Z shown below.

Z

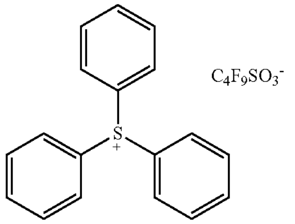

[Basic Compound]

Of the following compounds, compounds C-1, C-8 and C-12 were used.

C-1: 2,4,5-triphenylimidazole,

C-2: tetrabutylammonium hydroxide, and

C-3: 1,5-diazabicyclo[4.3.0]non-5-ene.

[Surfactant]

W-1: Megafac F176 (produced by Dainippon Ink & Chemicals, Inc.) (fluorinated),

W-2: Megafac R08 (produced by Dainippon Ink & Chemicals, Inc.) (fluorinated and siliconized), W-3: polysiloxane polymer KP-341 (produced by Shin-Etsu Chemical Co., Ltd.) (siliconized), and W-4: Troy Sol S-366 (produced by Troy Chemical Co., Ltd.).

[Solvent]

A1: propylene glycol monomethyl ether acetate,

A2: 2-heptanone,

A3: cyclohexanone,

A4: γ-butyrolactone,

B1: propylene glycol monomethyl ether, and

B2: ethyl acetate.

It is apparent from the results of Table 1 that in the employment of ArF exposure, the photosensitive composition of the present invention excels in the sensitivity, γ-value and pattern profile.

Example B

A resist solution was prepared according to exactly the same procedure as in Example A except that 0.06 g of the polymer shown below was added to the photosensitive composition of the Example 1A. The resist solution was applied in the same manner, thereby obtaining a resist film. The obtained resist film was patternwise exposed through a liquid for liquid immersion (pure water) by use of an ArF excimer laser liquid immersion scanner (manufactured by ASML, XT1250i, NA0.85), thereby attaining the same pattern formation as in Example A. It was ascertained that in all of the sensitivity, resolving power (γ), line edge roughness and pattern profile, the same evaluation results were obtained on the obtained patterns.

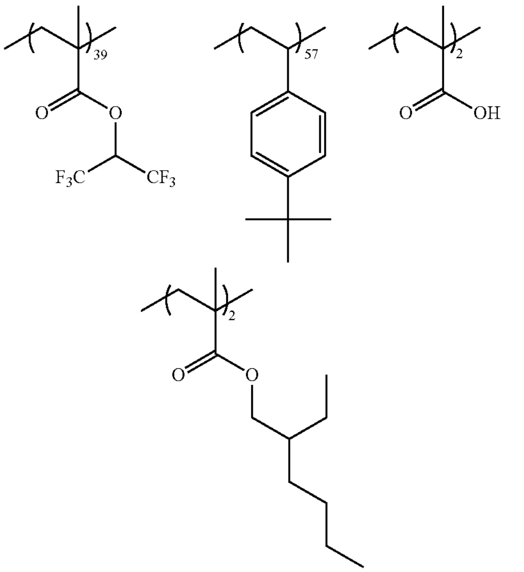

Weight-average molecular 4500
Dispersity 1.4

Example C

Examples 1C to 16C and Comparative Examples 1C and 2C

<Preparation of Resist>

Referring to Table 2 below, with respect to each of the resists, the individual components were dissolved in the solvent and passed through a polytetrafluoroethylene filter of 0.1 μm pore size, thereby obtaining a positive resist solution of 14 mass % solid content.

<Evaluation of Resist>

Each of the obtained positive resist solutions was uniformly applied onto a silicon substrate having undergone a hexamethyldisilazane treatment by use of a spin coater, and heated and dried on a hot plate at 120° C. for 90 seconds, thereby obtaining a 0.4 μm resist film.

The obtained resist film was patternwise exposed through a line-and-space mask by use of a KrF excimer laser stepper (NA=0.63). Immediately after the exposure, the resist film was heated on a hot plate at 110° C. for 90 seconds. Thereafter, the resist film was developed with a 2.38 mass % aqueous tetramethylammonium hydroxide solution at 23° C. for 60 seconds, rinsed with pure water for 30 seconds and dried. Thus, an intended line pattern was obtained.

[Sensitivity, Resolving Power (γ)]

Surface exposure was carried out while changing the exposure intensity by 0.5 mJ at a time within the range of 10 to 40 mJ/cm$^2$, and the exposed film was baked at 110° C. for 90 seconds. Thereafter, using a 2.38 mass % aqueous tetramethylammonium hydroxide (TMAH) solution, the dissolution rate at each of the exposure intensities was measured, thereby obtaining a sensitivity curve.

The sensitivity was defined as the exposure intensity at which the dissolution rate of the resist was saturated on the sensitivity curve. Dissolution contrast (γ value) was calculated from the gradient of the straight line portion of the sensitivity curve. The larger the γ value, the greater the excellence in dissolution contrast.

[Line Edge Roughness]

At arbitrary 30 points in a 50 μm region in the longitudinal direction of a 180 nm line pattern at the exposure intensity realizing the above sensitivity, the distance from a reference line on which edges were to be present was measured by means of a scanning electron microscope (model S-9220, manufactured by Hitachi, Ltd.). The standard deviation of measurements was determined, and 3σ was computed.

[Pattern Profile]

The optimum exposure intensity refers to the exposure intensity that reproduces a line-and-space mask pattern of 180 nm line width. The profile at the optimum exposure intensity was observed by means of a scanning electron microscope (SEM).

The evaluation results are given in Table 2.

TABLE 2

| KrF positive exposure | | | | | | | | | | |
|---|---|---|---|---|---|---|---|---|---|---|
| | (A1) Acid generator | (A2) Acid generator (0.1 g) | (B) Resin (10 g) | (F) Basic compound (0.02 g) | (G) Surfactant (0.1 mass %)* | (H) Solvent (mass ratio) | Sensitivity (mJ/cm$^2$) | Resolving power (γ) | Roughness (nm) | Pattern profile |
| Ex. 1C | A1-1 (0.3 g) | — | R-18 (H) | C-1 | W-1 | A1/B1 (6/4) | 20.0 | 6.1 | 4.0 | Rectangle |
| Ex. 2C | A1-2 (0.3 g) | — | R-18 (H) | C-1 | W-1 | A2/B2 (6/4) | 20.0 | 6.0 | 5.0 | Rectangle |
| Ex. 3C | A1-3 (0.3 g) | — | R-18 (H) | C-1 | W-2 | A3/B1 (6/4) | 15.0 | 6.5 | 4.0 | Rectangle |
| Ex. 4C | A1-4 (0.3 g) | — | R-18 (H) | C-1 | W-3 | A4/B1 (6/4) | 20.0 | 5.5 | 4.0 | Rectangle |
| Ex. 5C | A1-5 (0.3 g) | — | R-18 (H) | C-1 | W-1 | A1/B2 (6/4) | 20.0 | 6.0 | 4.5 | Rectangle |
| Ex. 6C | A1-6 (0.3 g) | — | R-18 (H) | C-1 | W-1 | A1/B1 (6/4) | 20.0 | 5.5 | 4.0 | Rectangle |
| Ex. 7C | A1-7 (0.3 g) | — | R-18 (H) | C-1 | W-4 | A1/B1 (6/4) | 20.0 | 6.0 | 3.8 | Rectangle |
| Ex. 8C | A1-8 (0.3 g) | — | R-18 (H) | C-1 | W-2 | A1/B1 (6/4) | 22.0 | 6.0 | 4.0 | Rectangle |
| Ex. 9C | A1-9 (0.3 g) | — | R-18 (H) | C-1 | W-3 | A1/B1 (6/4) | 18.0 | 6.0 | 4.0 | Rectangle |
| Ex. 10C | A1-1 (0.3 g) | — | R-2 | C-1 | W-1 | A1/B1 (6/4) | 20.0 | 6.0 | 5.0 | Rectangle |

TABLE 2-continued

| KrF positive exposure | | | | | | | | | | |
|---|---|---|---|---|---|---|---|---|---|---|
| | (A1) Acid generator | (A2) Acid generator (0.1 g) | (B) Resin (10 g) | (F) Basic compound (0.02 g) | (G) Surfactant (0.1 mass %)* | (H) Solvent (mass ratio) | Sensitivity ($mJ/cm^2$) | Resolving power (γ) | Roughness (nm) | Pattern profile |
| Ex. 11C | A1-1 (0.2 g) | Z | R-8 | C-1 | W-1 | A1/B1 (6/4) | 22.0 | 6.0 | 4.5 | Rectangle |
| Ex. 12C | A1-1 (0.2 g) | Z | R-14 | C-1 | W-1 | A1/B1 (6/4) | 22.0 | 6.0 | 4.5 | Rectangle |
| Ex. 13C | A1-1 (0.2 g) | Z | R-17 | C-1 | W-2 | A1/B1 (6/4) | 22.0 | 6.0 | 4.5 | Rectangle |
| Ex. 14C | A1-1 (0.3 g) | — | R-18 | C-2 | W-3 | A1/B1 (6/4) | 18.0 | 6.5 | 4.0 | Rectangle |
| Ex. 15C | A1-1 (0.2 g) | Z | R-2 | C-1 | W-4 | A1/B1 (6/4) | 20.0 | 6.3 | 4.5 | Rectangle |
| Ex. 16C | A1-1 (0.2 g) | Z33 | R-2 | C-1 | W-1 | A1/B1 (6/4) | 20.0 | 6.3 | 4.0 | Rectangle |
| Ex. 17C | A1-10 (0.3 g) | — | R-18 (H) | C-1 | W-1 | A2/B2 (6/4) | 20.0 | 6.1 | 4.0 | Rectangle |
| Ex. 18C | A1-11 (0.3 g) | — | R-18 (H) | C-1 | W-1 | A2/B2 (6/4) | 21.0 | 5.2 | 5.0 | Rectangle |
| Ex. 19C | A1-12 (0.3 g) | — | R-18 (H) | C-1 | W-1 | A3/B1 (6/4) | 21.0 | 5.5 | 5.5 | Rectangle |
| Ex. 20C | A1-13 (0.3 g) | — | R-18 (H) | C-1 | W-1 | A4/B1 (6/4) | 22.0 | 5.3 | 5.2 | Rectangle |
| Ex. 21C | A1-14 (0.3 g) | — | R-18 (H) | C-1 | W-1 | A1/B2 (6/4) | 18.0 | 6.1 | 4.5 | Rectangle |
| Ex. 22C | A1-15 (0.3 g) | — | R-18 (H) | C-1 | W-1 | A1/B1 (6/4) | 22.0 | 6.0 | 4.5 | Rectangle |
| Ex. 23C | A1-16 (0.3 g) | — | R-18 (H) | C-1 | W-1 | A1/B1 (6/4) | 22.0 | 6.0 | 4.5 | Rectangle |
| Ex. 24C | A1-17 (0.3 g) | — | R-18 (H) | C-1 | W-1 | A1/B1 (6/4) | 22.0 | 6.0 | 4.5 | Rectangle |
| Ex. 25C | A1-18 (0.3 g) | — | R-18 (H) | C-1 | W-1 | A1/B1 (6/4) | 22.0 | 6.0 | 4.5 | Rectangle |
| Ex. 26C | A1-19 (0.3 g) | — | R-18 (H) | C-1 | W-1 | A1/B1 (6/4) | 20.0 | 6.0 | 4.5 | Rectangle |
| Ex. 27C | A1-1 (0.3 g) | — | R-18 (L) | C-2 | W-1 | A1/B1 (6/4) | 18.0 | 7.0 | 3.5 | Rectangle |
| Ex. 28C | A1-1 (0.3 g) | — | R-10 (H) | C-1 | W-1 | A1/B1 (6/4) | 18.0 | 6.0 | 4.0 | Rectangle |
| Ex. 29C | A1-1 (0.3 g) | — | R-10 (L) | C-1 | W-1 | A1/B1 (6/4) | 18.0 | 7.0 | 3.5 | Rectangle |
| Ex. 30C | A1-1 (0.3 g) | — | R-19 | C-1 | W-1 | A1/B1 (6/4) | 18.0 | 6.0 | 4.0 | Rectangle |
| Ex. 31C | A1-1 (0.3 g) | — | R-20 | C-1 | W-1 | A1/B1 (6/4) | 18.0 | 6.1 | 4.0 | Rectangle |
| Ex. 32C | A1-1 (0.3 g) | — | R-21 | C-1 | W-1 | A1/B1 (6/4) | 18.0 | 6.5 | 3.5 | Rectangle |
| Comp. 1C | Comp. Compound 1 (0.3 g) | — | R-2 | C-1 | W-1 | A1/B1 (6/4) | 23.5 | 3.5 | 7.8 | Taper |
| Comp. 2C | Comp. Compound 2 (0.3 g) | — | R-2 | C-1 | W-1 | A1/B1 (6/4) | 23.0 | 3.5 | 7.8 | Taper |
| Comp. 3C | Comp. Compound 3 (0.3 g) | — | R-2 | C-1 | W-1 | A1/B1 (6/4) | 20.0 | 4.5 | 7.0 | Taper |
| Comp. 4C | Comp. Compound 4 (0.3 g) | — | R-2 | C-1 | W-1 | A1/B1 (6/4) | 20.0 | 4.5 | 7.0 | Taper |

*based on the total solid content of the resist composition

The resins (R-2), (R-8), (R-14), (R-17), (R-10(H)), (R-10 (L)), (R-18(H)), (R-18(L)), (R-19), (R-20) and (R-21) appearing in Table 2 are resins shown hereinbefore by way of example. With respect to each of these resins, the molar ratio of individual repeating units and the weight average molecular weight are given in Table 3.

TABLE 3

| Resin | Molar ratio of repeating units (corresponding to individual repeating units in order from the left) | Weight-average Molecular Weight (Mw) |
|---|---|---|
| R-2 | 60/20/20 | 12000 |
| R-8 | 60/20/20 | 12000 |
| R-14 | 60/15/25 | 12000 |
| R-17 | 80/20 | 15000 |
| R-10 (H) | 60/40 | 10000 |
| R-10 (L) | 60/40 | 4000 |
| R-18 (H) | 60/40 | 10000 |
| R-18 (L) | 60/40 | 4000 |
| R-19 | 60/20/20 | 12000 |
| R-20 | 60/40 | 12000 |
| R-21 | 60/20/20 | 12000 |

It is apparent from the results of Table 2 that the photosensitive composition of the present invention exhibits excellent performance as a positive resist composition employed in KrF excimer laser exposure.

Example D

Examples 1D to 15D and Comparative Examples 1D and 2D

<Preparation of Resist>

Referring to Table 4 below, with respect to each of the resists, the individual components were dissolved in the solvent and passed through a polytetrafluoroethylene filter of 0.1 μm pore size, thereby obtaining a negative resist solution of 14 mass % solid content. The thus obtained negative resist solutions were evaluated in the same manner as in the Example C (KrF positive exposure). The results are given in Table 4.

TABLE 4

| KrF negative exposure | | | | | | | | | | | | |
|---|---|---|---|---|---|---|---|---|---|---|---|---|
| | (A1) Acid generator (0.3 g) | (A2) Acid generator (0.1 g) | (C) Resin (10 g) | (D) Cross-linking agent (3.0 g) | (F) Basic compound (0.02 g) | (G) Surfactant (0.1 mass %)* | (H) Solvent (mass ratio) | Sensitivity (mJ/cm$^2$) | Resolving power γ | Roughness (nm) | Pattern profile |
| Ex. 1D | A1-1 | — | P-3 | CL-1 | C-1 | W-1 | A1/B1 (6/4) | 21.0 | 6.3 | 10.2 | Rectangle |
| Ex. 2D | A1-2 | — | P-3 | CL-1 | C-1 | W-2 | A2/B2 (6/4) | 21.0 | 6.0 | 14.0 | Rectangle |
| Ex. 3D | A1-3 | — | P-3 | CL-1 | C-1 | W-3 | A3/B1 (6/4) | 18.0 | 6.5 | 10.0 | Rectangle |
| Ex. 4D | A1-4 | — | P-3 | CL-1 | C-1 | W-1 | A4/B1 (6/4) | 21.0 | 5.5 | 10.2 | Rectangle |
| Ex. 5D | A1-5 | — | P-3 | CL-1 | C-1 | W-3 | A1/B2 (6/4) | 21.0 | 5.5 | 13.0 | Rectangle |
| Ex. 6D | A1-6 | — | P-3 | CL-1 | C-1 | W-2 | A1/B1 (6/4) | 21.0 | 5.5 | 10.2 | Rectangle |
| Ex. 7D | A1-7 | — | P-3 | CL-1 | C-1 | W-4 | A1/B1 (6/4) | 21.0 | 6.3 | 9.5 | Rectangle |
| Ex. 8D | A1-8 | — | P-3 | CL-1 | C-1 | W-2 | A1/B1 (6/4) | 21.0 | 6.3 | 10.2 | Rectangle |
| Ex. 9D | A1-9 | — | P-3 | CL-1 | C-1 | W-1 | A1/B1 (6/4) | 19.0 | 6.3 | 10.2 | Rectangle |
| Ex. 10D | A1-1 | — | P-2 | CL-1 | C-1 | W-1 | A1/B1 (6/4) | 22.0 | 6.3 | 10.2 | Rectangle |
| Ex. 11D | A1-1 | — | P-1 | CL-1 | C-1 | W-1 | A1/B1 (6/4) | 22.0 | 6.3 | 10.2 | Rectangle |
| Ex. 12D | A1-1 | — | P-1 | CL-3 | C-1 | W-1 | A1/B1 (6/4) | 21.0 | 6.3 | 10.2 | Rectangle |
| Ex. 13D | A1-1 | — | P-2 | CL-2 | C-1 | W-1 | A1/B1 (6/4) | 21.0 | 6.3 | 10.2 | Rectangle |
| Ex. 14D | A1-1 | — | P-3 | CL-1 | C-2 | W-1 | A1/B1 (6/4) | 21.0 | 6.3 | 10.2 | Rectangle |
| Ex. 15D | A1-1 | Z2 | P-3 | CL-1 | C-1 | W-1 | A1/B1 (6/4) | 20.0 | 6.3 | 10.2 | Rectangle |
| Ex. 16D | A1-10 | — | P-3 | CL-1 | C-1 | W-1 | A1/B1 (6/4) | 21.0 | 6.2 | 10.0 | Rectangle |
| Ex. 17D | A1-11 | — | P-3 | CL-1 | C-1 | W-1 | A1/B1 (6/4) | 22.0 | 5.5 | 15.0 | Rectangle |
| Ex. 18D | A1-12 | — | P-3 | CL-1 | C-1 | W-1 | A1/B1 (6/4) | 22.0 | 5.2 | 15.0 | Rectangle |
| Ex. 19D | A1-13 | — | P-3 | CL-1 | C-1 | W-1 | A1/B1 (6/4) | 21.0 | 5.2 | 14.0 | Rectangle |
| Ex. 20D | A1-14 | — | P-3 | CL-1 | C-1 | W-1 | A1/B1 (6/4) | 22.0 | 6.2 | 10.0 | Rectangle |

TABLE 4-continued

| KrF negative exposure | | | | | | | | | | | | |
|---|---|---|---|---|---|---|---|---|---|---|---|---|
| | (A1) Acid generator (0.3 g) | (A2) Acid generator (0.1 g) | (C) Resin (10 g) | (D) Cross-linking agent (3.0 g) | (F) Basic compound (0.02 g) | (G) Surfactant (0.1 mass %)* | (H) Solvent (mass ratio) | Sensitivity ($mJ/cm^2$) | Resolving power γ | Roughness (nm) | Pattern profile |
| Ex. 21D | A1-15 | — | P-3 | CL-1 | C-1 | W-1 | A1/B1 (6/4) | 21.0 | 6.2 | 10.2 | Rectangle |
| Ex. 22D | A1-16 | — | P-3 | CL-1 | C-1 | W-1 | A1/B1 (6/4) | 21.0 | 6.0 | 10.2 | Rectangle |
| Ex. 23D | A1-17 | — | P-3 | CL-1 | C-1 | W-1 | A1/B1 (6/4) | 21.0 | 6.2 | 10.0 | Rectangle |
| Ex. 24D | A1-18 | — | P-3 | CL-1 | C-1 | W-1 | A1/B1 (6/4) | 22.0 | 6.2 | 10.0 | Rectangle |
| Ex. 25D | A1-19 | — | P-3 | CL-1 | C-1 | W-1 | A1/B1 (6/4) | 22.0 | 6.2 | 11.0 | Rectangle |
| Comp. 1D | Comp. compound 1 | — | P-1 | CL-1 | C-1 | W-1 | A1/B1 (6/4) | 24.0 | 4.0 | 16.3 | Taper |
| Comp. 2D | Comp. compound 2 | — | P-1 | CL-1 | C-1 | W-1 | A1/B1 (6/4) | 24.0 | 4.2 | 16.3 | Taper |
| Comp. 3D | Comp. compound 3 | — | P-3 | CL-1 | C-1 | W-1 | A1/B1 (6/4) | 24.0 | 4.8 | 16.0 | Taper |
| Comp. 4D | Comp. compound 4 | — | P-3 | CL-1 | C-1 | W-1 | A1/B1 (6/4) | 24.0 | 4.8 | 16.1 | Taper |

*based on the total solid content of the resist composition

The structure, molecular weight and molecular weight distribution of each of the alkali-soluble resins (C) as well as the crosslinking agents appearing in Table 4 will be shown below.

| | | Mw | Mw/Mn |
|---|---|---|---|
| P-1 | 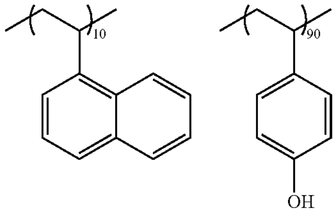 | 16000 | 2.30 |
| P-2 | 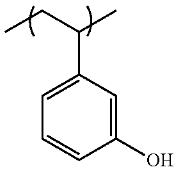 | 12000 | 1.2 |
| P-3 | 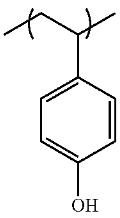 | 6000 | 1.2 |

-continued

| | Mw | Mw/Mn |
|---|---|---|
| VP-5000 (produced by Nippon Soda Co., Ltd.) | | |
| 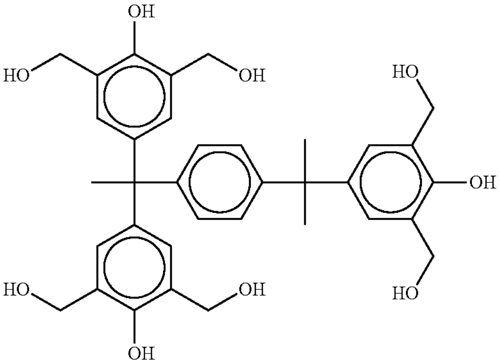 CL-1 | | |
| 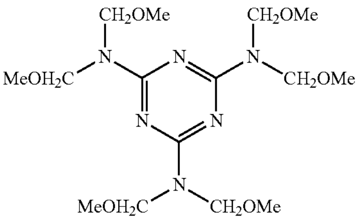 CL-2 | | |
| 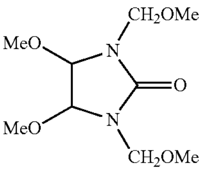 CL-3 | | |

It is apparent from the results of Table 4 that the photosensitive composition of the present invention exhibits excellent performance as a negative resist composition employed in KrF excimer laser exposure.

Example E

Examples 1E to 18E and Comparative Examples 1E and 2E

<Preparation of Resist>

Referring to Table 5 below, with respect to each of the resists, the individual components were dissolved in the solvent and passed through a polytetrafluoroethylene filter of 0.1 μm pore size, thereby obtaining a positive resist solution of 12 mass % solid content.

<Evaluation of Resist>

Each of the obtained positive resist solutions was uniformly applied onto a silicon substrate having undergone a hexamethyldisilazane treatment by use of a spin coater, and heated and dried on a hot plate at 120° C. for 60 seconds, thereby obtaining a 0.3 μm resist film.

The obtained resist film was exposed by use of an electron beams projection lithography equipment manufactured by Nikon Corporation (accelerating voltage 100 keV). Immediately after the exposure, the resist film was heated on a hot plate at 110° C. for 90 seconds. Thereafter, the resist film was developed with a 2.38 mass % aqueous tetramethylammonium hydroxide solution at 23° C. for 60 seconds, rinsed with pure water for 30 seconds and dried. The thus obtained line and space patterns were evaluated in the same manner as in

Example A

Sensitivity, Resolving Power (γ)

Surface exposure was carried out while changing the exposure intensity by 0.1 $\mu C/cm^2$ at a time within the range of 0 to 10 $\mu C/cm^2$, and the exposed film was baked at 110° C. for 90 seconds. Thereafter, using a 2.38 mass % aqueous tetramethylammonium hydroxide (TMAH) solution, the dissolution rate at each of the exposure intensities was measured, thereby obtaining a sensitivity curve.

The sensitivity was defined as the exposure intensity at which the dissolution rate of the resist was saturated on the sensitivity curve. Dissolution contrast (γ value) was calculated from the gradient of the straight line portion of the sensitivity curve. The larger the γ value, the greater the excellence in dissolution contrast.

[Line Edge Roughness]

At arbitrary 30 points in a 50 μm region in the longitudinal direction of a 150 nm line pattern at the exposure intensity realizing the above sensitivity, the distance from a reference line on which edges were to be present was measured by means of a scanning electron microscope (model S-9220, manufactured by Hitachi, Ltd.). The standard deviation of measurements was determined, and 3σ was computed.

[Outgas Performance: Ratio of Change in Film Thickness by Exposure]

Exposure was carried out at the exposure intensity equal to 2.0 times the exposure intensity ($\mu C/cm^2$) at the sensitivity determined by performing a surface exposure by electron beams. The film thickness after the exposure (before post-bake) was measured, and the ratio of change from the film thickness before the exposure was calculated by the following formula.

Ratio of change in film thickness (%)=[(film thickness before exposure−film thickness after exposure)/(film thickness before exposure)]×100

The evaluation results are given in Table 5.

TABLE 5

Electron beam positive exposure

| | (A1) Acid generator | (A2) Acid generator (0.1 g) | (B) Resin | (F) Basic compound (0.02 g) | (G) Surfactant (0.1 mass %)* | (H) Solvent (mass ratio) | Sensitivity ($\mu C/cm^2$) | Resolving power γ | Roughness (nm) | Outgas (%) |
|---|---|---|---|---|---|---|---|---|---|---|
| Ex. 1E | A1-1 (0.3 g) | — | R-18 (H) (10 g) | C-1 | W-1 | A1/B1 (6/4) | 3.5 | 5.6 | 4.1 | 5.8 |
| Ex. 2E | A1-2 (0.3 g) | — | R-18 (H) (10 g) | C-1 | W-1 | A2/B2 (6/4) | 3.5 | 5.4 | 5.0 | 1.8 |
| Ex. 3E | A1-3 (0.3 g) | — | R-18 (H) (10 g) | C-1 | W-2 | A3/B1 (6/4) | 3.0 | 6.0 | 4.1 | 1.2 |
| Ex. 4E | A1-4 (0.3 g) | — | R-18 (H) (10 g) | C-1 | W-3 | A4/B1 (6/4) | 3.5 | 5.0 | 4.1 | 5.9 |
| Ex. 5E | A1-5 (0.3 g) | — | R-18 (H) (10 g) | C-1 | W-1 | A1/B2 (6/4) | 3.5 | 5.0 | 5.0 | 5.8 |
| Ex. 6E | A1-6 (0.3 g) | — | R-18 (H) (10 g) | C-1 | W-1 | A1/B1 (6/4) | 3.5 | 5.0 | 4.1 | 5.8 |
| Ex. 7E | A1-7 (0.3 g) | — | R-18 (H) (10 g) | C-1 | W-4 | A1/B1 (6/4) | 3.5 | 6.0 | 3.5 | 5.8 |
| Ex. 8E | A1-8 (0.3 g) | — | R-18 (H) (10 g) | C-1 | W-2 | A1/B1 (6/4) | 3.5 | 5.6 | 4.1 | 5.9 |
| Ex. 9E | A1-9 (0.3 g) | — | R-18 (H) (10 g) | C-1 | W-3 | A1/B1 (6/4) | 3.3 | 5.6 | 4.1 | 4.0 |
| Ex. 10E | A1-1 (0.3 g) | — | R-2 (10 g) | C-1 | W-1 | A1/B1 (6/4) | 3.5 | 5.6 | 4.5 | 5.4 |
| Ex. 11E | A1-1 (0.2 g) | Z | R-8 (10 g) | C-1 | W-1 | A1/B1 (6/4) | 4.0 | 5.0 | 4.5 | 5.4 |
| Ex. 12E | A1-1 (0.2 g) | Z | R-14 (10 g) | C-1 | W-1 | A1/B1 (6/4) | 4.0 | 5.0 | 4.5 | 5.3 |
| Ex. 13E | A1-1 (0.2 g) | Z | R-17 (10 g) | C-1 | W-2 | A1/B1 (6/4) | 4.0 | 5.0 | 4.5 | 5.4 |

TABLE 5-continued

| Electron beam positive exposure | | | | | | | | | | | |
|---|---|---|---|---|---|---|---|---|---|---|---|
| | (A1) Acid generator | (A2) Acid generator (0.1 g) | (B) Resin | (F) Basic compound (0.02 g) | (G) Surfactant (0.1 mass %)* | (H) Solvent (mass ratio) | Sensitivity (μC/cm$^2$) | Resolving power γ | Roughness (nm) | Outgas (%) |
| Ex. 14E | A1-1 (0.2 g) | — | R-18 (H) (10 g) | C-2 | W-3 | A1/B1 (6/4) | 3.0 | 5.6 | 4.1 | 5.9 |
| Ex. 15E | A1-1 (0.2 g) | Z | R-2 (10 g) | C-1 | W-4 | A1/B1 (6/4) | 3.5 | 5.6 | 4.5 | 5.4 |
| Ex. 16E | A1-1 (0.2 g) | Z33 | R-2 (10 g) | C-1 | W-1 | A1/B1 (6/4) | 3.5 | 6.0 | 4.5 | 5.4 |
| Ex. 17E | A1-1 (1 g) | — | R-18 (H) (9 g) | C-1 | W-1 | A1/B1 (6/4) | 2.5 | 5.6 | 4.3 | 5.4 |
| Ex. 18E | A1-1 (3 g) | — | R-18 (H) (7 g) | C-1 | W-1 | A1/B1 (6/4) | 1.0 | 5.6 | 4.5 | 5.4 |
| Ex. 19E | A1-10 (0.3 g) | — | R-18 (H) (10 g) | C-1 | W-1 | A2/B2 (6/4) | 3.5 | 5.6 | 4.1 | 1.8 |
| Ex. 20E | A1-11 (0.3 g) | — | R-18 (H) (10 g) | C-1 | W-1 | A2/B2 (6/4) | 4.0 | 5.1 | 5.1 | 5.9 |
| Ex. 21E | A1-12 (0.3 g) | — | R-18 (H) (10 g) | C-1 | W-1 | A3/B1 (6/4) | 4.5 | 5.0 | 6.0 | 5.9 |
| Ex. 22E | A1-13 (0.3 g) | — | R-18 (H) (10 g) | C-1 | W-1 | A4/B1 (6/4) | 4.0 | 5.0 | 5.5 | 5.9 |
| Ex. 23E | A1-14 (0.3 g) | — | R-18 (H) (10 g) | C-1 | W-1 | A1/B2 (6/4) | 3.5 | 5.6 | 4.3 | 1.8 |
| Ex. 24E | A1-15 (0.3 g) | — | R-18 (H) (10 g) | C-1 | W-1 | A1/B1 (6/4) | 3.5 | 5.6 | 4.2 | 1.8 |
| Ex. 25E | A1-16 (0.3 g) | — | R-18 (H) (10 g) | C-1 | W-1 | A1/B1 (6/4) | 3.5 | 5.6 | 4.4 | 1.8 |
| Ex. 26E | A1-17 (0.3 g) | — | R-18 (H) (10 g) | C-1 | W-1 | A1/B1 (6/4) | 3.8 | 5.6 | 4.3 | 5.9 |
| Ex. 27E | A1-18 (0.3 g) | — | R-18 (H) (10 g) | C-1 | W-1 | A1/B1 (6/4) | 3.6 | 5.6 | 4.1 | 1.8 |
| Ex. 28E | A1-19 (0.3 g) | — | R-18 (H) (10 g) | C-1 | W-1 | A1/B1 (6/4) | 3.5 | 5.6 | 4.3 | 1.8 |
| Ex. 29E | A1-1 (0.3 g) | — | R-18 (L) (10 g) | C-2 | W-1 | A1/B1 (6/4) | 3.5 | 5.6 | 3.1 | 5.9 |
| Ex. 30E | A1-1 (0.3 g) | — | R-10 (H) (10 g) | C-2 | W-1 | A1/B1 (6/4) | 3.7 | 5.6 | 5.2 | 5.9 |
| Ex. 31E | A1-1 (0.3 g) | — | R-10 (L) (10 g) | C-2 | W-1 | A1/B1 (6/4) | 3.8 | 5.6 | 4.2 | 5.9 |
| Ex. 32E | A1-1 (0.3 g) | — | R-19 (10 g) | C-2 | W-1 | A1/B1 (6/4) | 3.5 | 5.4 | 4.1 | 6.2 |
| Ex. 33E | A1-1 (0.3 g) | — | R-20 (10 g) | C-2 | W-1 | A1/B1 (6/4) | 3.4 | 5.3 | 4.1 | 5.9 |
| Ex. 34E | A1-1 (0.3 g) | — | R-21 (10 g) | C-2 | W-1 | A1/B1 (6/4) | 3.6 | 5.6 | 4.1 | 5.9 |
| Comp. 1E | Comp. Compound 1 (0.3 g) | — | R-2 (10 g) | C-1 | W-1 | A1/B1 (6/4) | 7.1 | 3.8 | 7.3 | 7.8 |
| Comp. 2E | Comp. Compound 2 (0.3 g) | — | R-2 (10 g) | C-1 | W-1 | A1/B1 (6/4) | 7.1 | 3.6 | 7.5 | 7.9 |
| Comp. 3E | Comp. Compound 3 (0.3 g) | — | R-2 (10 g) | C-1 | W-1 | A1/B1 (6/4) | 6.1 | 4.2 | 6.8 | 7.8 |
| Comp. 4E | Comp. Compound 4 (0.3 g) | — | R-2 (10 g) | C-1 | W-1 | A1/B1 (6/4) | 6.1 | 4.2 | 6.8 | 7.7 |

*based on the total solid content of the resist composition

It is apparent from the results of Table 5 that the photosensitive composition of the present invention exhibits excellent performance as a positive resist composition employed in electron beam exposure.

Example F

Examples 1F to 15F and Comparative Examples 1F and 2F

<Preparation of Resist>

Referring to Table 6 below, with respect to each of the resists, the individual components were dissolved in the solvent and passed through a polytetrafluoroethylene filter of 0.1 μm pore size, thereby obtaining a negative resist solution of 12 mass % solid content.

<Evaluation of Resist>

Each of the obtained negative resist solutions was uniformly applied onto a silicon substrate having undergone a hexamethyldisilazane treatment by use of a spin coater, and heated and dried on a hot plate at 120° C. for 60 seconds, thereby obtaining a 0.3 μm resist film.

The obtained resist film was exposed by use of an electron beams projection lithography equipment manufactured by Nikon Corporation (accelerating voltage 100 keV). Immedi ately after the exposure, the resist film was heated on a hot plate at 110° C. for 90 seconds. Thereafter, the resist film was developed with a 2.38 mass % aqueous tetramethylammonium hydroxide solution at 23° C. for 60 seconds, rinsed with pure water for 30 seconds and dried. The thus obtained line and space patterns were evaluated in the same manner as in Example E (electron beam negative exposure).

The evaluation results are given in Table 6.

TABLE 6

Electron beam negative exposure

| | (A1) Acid generator | (A2) Acid generator (0.1 g) | (C) Resin (10 g) | (D) Cross-linking agent (3.0 g) | (F) Basic compound (0.02 g) | (G) Surfactant (0.1 mass %)* | (H) Solvent (mass ratio) | Sensitivity ($\mu C/cm^2$) | Resolving power γ | Roughness (nm) | Outgas (%) |
|---|---|---|---|---|---|---|---|---|---|---|---|
| Ex. 1F | A1-1 (0.3 g) | — | P-3 | CL-1 | C-1 | W-1 | A1/B1 (6/4) | 3.8 | 6.0 | 9.5 | 5.5 |
| Ex. 2F | A1-2 (0.3 g) | — | P-3 | CL-1 | C-1 | W-2 | A2/B2 (6/4) | 3.8 | 6.0 | 10.5 | 1.8 |
| Ex. 3F | A1-3 (0.3 g) | — | P-3 | CL-1 | C-1 | W-3 | A3/B1 (6/4) | 3.0 | 6.5 | 9.5 | 1.5 |
| Ex. 4F | A1-4 (0.3 g) | — | P-3 | CL-1 | C-1 | W-1 | A4/B1 (6/4) | 3.8 | 5.5 | 9.5 | 6.0 |
| Ex. 5F | A1-5 (0.3 g) | — | P-3 | CL-1 | C-1 | W-3 | A1/B2 (6/4) | 3.8 | 6.0 | 10.0 | 5.5 |
| Ex. 6F | A1-6 (0.3 g) | — | P-3 | CL-1 | C-1 | W-2 | A1/B1 (6/4) | 3.8 | 5.5 | 9.5 | 5.5 |
| Ex. 7F | A1-7 (0.3 g) | — | P-3 | CL-1 | C-1 | W-4 | A1/B1 (6/4) | 3.8 | 6.0 | 9.0 | 5.0 |
| Ex. 8F | A1-8 (0.3 g) | — | P-3 | CL-1 | C-1 | W-2 | A1/B1 (6/4) | 3.8 | 6.0 | 9.0 | 5.0 |
| Ex. 9F | A1-9 (0.3 g) | — | P-3 | CL-1 | C-1 | W-1 | A1/B1 (6/4) | 3.5 | 6.3 | 9.0 | 4.5 |
| Ex. 10F | A1-1 (0.3 g) | — | P-2 | CL-1 | C-1 | W-1 | A1/B1 (6/4) | 4.0 | 5.8 | 10.0 | 5.0 |
| Ex. 11F | A1-1 (0.3 g) | — | P-1 | CL-1 | C-1 | W-1 | A1/B1 (6/4) | 4.2 | 5.5 | 10.0 | 5.0 |
| Ex. 12F | A1-1 (0.3 g) | — | P-3 | CL-3 | C-1 | W-1 | A1/B1 (6/4) | 3.5 | 5.6 | 4.1 | 5.8 |
| Ex. 13F | A1-1 (0.3 g) | — | P-23 | CL-2 | C-1 | W-1 | A1/B1 (6/4) | 3.5 | 5.6 | 4.1 | 5.8 |
| Ex. 14F | A1-1 (0.3 g) | — | P-3 | CL-1 | C-2 | W-1 | A1/B1 (6/4) | 3.0 | 5.6 | 4.1 | 5.8 |
| Ex. 15F | A1-1 (0.2 g) | Z2 | P-3 | CL-1 | C-1 | W-1 | A1/B1 (6/4) | 3.5 | 5.6 | 4.1 | 5.8 |
| Ex. 16F | A1-10 (0.2 g) | — | P-3 | CL-1 | C-1 | W-1 | A1/B1 (6/4) | 3.9 | 6.2 | 9.5 | 5.4 |
| Ex. 17F | A1-11 (0.2 g) | — | P-3 | CL-1 | C-1 | W-1 | A1/B1 (6/4) | 3.8 | 5.8 | 10.5 | 5.5 |
| Ex. 18F | A1-12 (0.2 g) | — | P-3 | CL-1 | C-1 | W-1 | A1/B1 (6/4) | 3.7 | 5.5 | 11.5 | 5.2 |
| Ex. 19F | A1-13 (0.2 g) | — | P-3 | CL-1 | C-1 | W-1 | A1/B1 (6/4) | 3.8 | 5.7 | 10.9 | 5.2 |
| Ex. 20F | A1-14 (0.2 g) | — | P-3 | CL-1 | C-1 | W-1 | A1/B1 (6/4) | 3.8 | 6.2 | 9.3 | 5.5 |
| Ex. 21F | A1-15 (0.2 g) | — | P-3 | CL-1 | C-1 | W-1 | A1/B1 (6/4) | 3.7 | 6.2 | 9.4 | 2.5 |
| Ex. 22F | A1-16 (0.2 g) | — | P-3 | CL-1 | C-1 | W-1 | A1/B1 (6/4) | 3.8 | 6.4 | 9.5 | 2.2 |
| Ex. 23F | A1-17 (0.2 g) | — | P-3 | CL-1 | C-1 | W-1 | A1/B1 (6/4) | 3.7 | 6.3 | 9.6 | 5.5 |
| Ex. 24F | A1-18 (0.2 g) | — | P-3 | CL-1 | C-1 | W-1 | A1/B1 (6/4) | 3.8 | 6.1 | 9.5 | 2.5 |
| Ex. 25F | A1-19 (0.2 g) | — | P-3 | CL-1 | C-1 | W-1 | A1/B1 (6/4) | 3.8 | 6.2 | 9.7 | 3.5 |
| Comp. 1F | Comp. compound1 (0.3 g) | — | P-1 | CL-1 | C-1 | W-1 | A1/B1 (6/4) | 7.0 | 4.1 | 15.8 | 7.2 |
| Comp. 2F | Comp. compound2 (0.3 g) | — | P-1 | CL-1 | C-1 | W-1 | A1/B1 (6/4) | 7.0 | 4.1 | 15.9 | 7.3 |
| Comp. 3F | Comp. compound3 (0.3 g) | — | P-3 | CL-1 | C-1 | W-1 | A1/B1 (6/4) | 6.5 | 4.8 | 14.5 | 7.0 |
| Comp. 4F | Comp. compound4 (0.3 g) | — | P-3 | CL-1 | C-1 | W-1 | A1/B1 (6/4) | 6.5 | 4.8 | 14.2 | 7.0 |

*based on the total solid content of the resist composition

It is apparent from the results of Table 6 that the photosensitive composition of the present invention exhibits excellent performance as a negative resist composition employed in electron beam exposure.

Example G

Examples 1G to 5G and Comparative Examples 1G and 2G

<Preparation of Resist>

Referring to Table 7 below, with respect to each of the resists, the individual components were dissolved in the solvent and passed through a polytetrafluoroethylene filter of 0.1 μm pore size, thereby obtaining a positive resist solution of 8 mass % solid content. The thus obtained positive resist solution was evaluated by the following methods.

<Evaluation of Resist>

Each of the obtained positive resist solutions was uniformly applied onto a silicon substrate having undergone a hexamethyldisilazane treatment by use of a spin coater, and heated and dried on a hot plate at 120° C. for 60 seconds, thereby obtaining a 0.15 μm resist film.

[Sensitivity, Resolving Power (γ)]

The obtained resist films were exposed by use of EUV ray (wavelength: 13 nm) while changing the exposure intensity by 0.5 mJ/cm$^2$ at a time, and the exposed film was baked at 110° C. for 90 seconds. Thereafter, using a 2.38 mass % aqueous tetramethylammonium hydroxide (TMAH) solution, the dissolution rate at each of the exposure intensities was measured, thereby obtaining a sensitivity curve.

The sensitivity was defined as the exposure intensity at which the dissolution rate of the resist was saturated on the sensitivity curve. Dissolution contrast (γ value) was calculated from the gradient of the straight line portion of the sensitivity curve. The larger the γ value, the greater the excellence in dissolution contrast.

[Line Edge Roughness]

At arbitrary 30 points in a 50 μm region in the longitudinal direction of a 50 nm line pattern at the exposure intensity realizing the above sensitivity, the distance from a reference line on which edges were to be present was measured by means of a scanning electron microscope (model S-9220, manufactured by Hitachi, Ltd.). The standard deviation of measurements was determined, and 3σ was computed.

[Outgas Performance: Ratio of Change in Film Thickness by Exposure]

Exposure was carried out at the exposure intensity equal to 2.0 times the exposure intensity (mJ/cm$^2$) at the sensitivity determined by performing a surface exposure by EUV. The film thickness after the exposure (before postbake) was measured, and the ratio of change from the film thickness before the exposure was calculated by the following formula.

Ratio of change in film thickness (%)=[(film thickness before exposure−film thickness after exposure)/(film thickness before exposure)]×100

The evaluation results are given in Table 7.

TABLE 7

| EUV positive exposure | | | | | | | | | |
|---|---|---|---|---|---|---|---|---|---|
| | (A1) Acid generator | (B) Resin | (F) Basic compound (0.02 g) | (G) Surfactant (0.1 mass %)* | (H) Solvent (mass ratio) | Sensitivity (mJ/cm$^2$) | Resolving power γ | Roughness (nm) | Outgas (%) |
| Ex. 1G | A1-1 (0.3 g) | R-18 (H) (10 g) | C-1 | W-1 | A1/B1 (6/4) | 15.2 | 6.3 | 5.0 | 6.5 |
| Ex. 2G | A1-2 (0.3 g) | R-18 (H) (10 g) | C-1 | W-1 | A1/B1 (6/4) | 16.3 | 6.5 | 6.0 | 1.8 |
| Ex. 3G | A1-3 (0.3 g) | R-18 (H) (10 g) | C-1 | W-1 | A1/B1 (6/4) | 14.5 | 6.8 | 5.0 | 1.5 |
| Ex. 4G | A1-3 (0.3 g) | R-18 (H) (10 g) | C-2 | W-1 | A1/B1 (6/4) | 14.0 | 6.8 | 4.8 | 1.5 |
| Ex. 5G | A1-3 (2 g) | R-18 (H) (8 g) | C-1 | W-1 | A1/B1 (6/4) | 10.2 | 6.3 | 5.0 | 1.5 |
| Ex. 6G | A1-6 (0.3 g) | R-18 (H) (10 g) | C-1 | W-1 | A1/B1 (6/4) | 12.7 | 6.5 | 6.3 | 5.8 |
| Ex. 7G | A1-7 (0.3 g) | R-18 (H) (10 g) | C-1 | W-4 | A1/B1 (6/4) | 15.2 | 6.6 | 6.0 | 6.3 |
| Ex. 8G | A1-8 (0.3 g) | R-18 (H) (10 g) | C-1 | W-2 | A1/B1 (6/4) | 15.5 | 6.6 | 6.3 | 6.3 |
| Ex. 9G | A1-9 (0.3 g) | R-18 (H) (10 g) | C-1 | W-3 | A1/B1 (6/4) | 15.2 | 6.5 | 6.0 | 5.0 |
| Ex. 10G | A1-10 (0.3 g) | R-18 (H) (10 g) | C-1 | W-1 | A1/B1 (6/4) | 15.9 | 6.6 | 6.3 | 1.4 |
| Ex. 11G | A1-11 (0.3 g) | R-18 (H) (10 g) | C-1 | W-1 | A1/B1 (6/4) | 15.8 | 6.7 | 6.9 | 6.4 |
| Ex. 12G | A1-12 (0.3 g) | R-18 (H) (10 g) | C-1 | W-1 | A1/B1 (6/4) | 15.6 | 6.6 | 7.2 | 6.4 |
| Ex. 13G | A1-13 (0.3 g) | R-18 (H) (10 g) | C-1 | W-1 | A1/B1 (6/4) | 15.8 | 6.6 | 7.0 | 6.4 |
| Ex. 14G | A1-14 (0.3 g) | R-18 (H) (10 g) | C-1 | W-1 | A1/B1 (6/4) | 15.1 | 6.5 | 6.3 | 2.4 |
| Ex. 15G | A1-15 (0.3 g) | R-18 (H) (10 g) | C-1 | W-1 | A1/B1 (6/4) | 15.5 | 6.6 | 6.3 | 1.4 |
| Ex. 16G | A1-16 (0.3 g) | R-18 (H) (10 g) | C-1 | W-1 | A1/B1 (6/4) | 15.1 | 6.7 | 6.5 | 1.4 |
| Ex. 17G | A1-17 (0.3 g) | R-18 (H) (10 g) | C-1 | W-1 | A1/B1 (6/4) | 15.7 | 6.6 | 6.5 | 6.5 |
| Ex. 18G | A1-18 (0.3 g) | R-18 (H) (10 g) | C-1 | W-1 | A1/B1 (6/4) | 15.5 | 6.5 | 6.3 | 1.4 |

TABLE 7-continued

| EUV positive exposure | | | | | | | | | |
|---|---|---|---|---|---|---|---|---|---|
| | (A1) Acid generator | (B) Resin | (F) Basic compound (0.02 g) | (G) Surfactant (0.1 mass %)* | (H) Solvent (mass ratio) | Sensitivity (mJ/cm²) | Resolving power γ | Roughness (nm) | Outgas (%) |
| Ex. 19G | A1-19 (0.3 g) | R-18 (H) (10 g) | C-1 | W-1 | A1/B1 (6/4) | 15.7 | 6.6 | 6.3 | 3.4 |
| Ex. 20G | A1-3 (0.3 g) | R-8 (10 g) | C-1 | W-1 | A1/B1 (6/4) | 15.5 | 6.6 | 6.3 | 4.4 |
| Ex. 21G | A1-3 (0.3 g) | R-14 (10 g) | C-1 | W-1 | A1/B1 (6/4) | 15.5 | 5.6 | 6.3 | 1.3 |
| Ex. 22G | A1-3 (0.3 g) | R-17 (10 g) | C-1 | W-2 | A1/B1 (6/4) | 15.8 | 5.6 | 6.7 | 2.4 |
| Ex. 23G | A1-3 (0.3 g) | R-18 (H) (10 g) | C-8 | W-3 | A1/B1 (6/4) | 15.5 | 5.6 | 6.3 | 1.9 |
| Ex. 24G | A1-3 (0.3 g) | R-2 (10 g) | C-1 | W-4 | A1/B1 (6/4) | 15.2 | 5.7 | 6.9 | 6.4 |
| Ex. 25G | A1-3 (0.3 g) | R-2 (10 g) | C-1 | W-1 | A1/B1 (6/4) | 15.6 | 5.6 | 6.9 | 6.4 |
| Ex. 26G | A1-3 (1 g) | R-18 (H) (9 g) | C-1 | W-1 | A1/B1 (6/4) | 12.5 | 5.6 | 4.3 | 1.4 |
| Ex. 27G | A1-3 (3 g) | R-18 (H) (7 g) | C-1 | W-1 | A1/B1 (6/4) | 10.2 | 6.3 | 4.5 | 1.4 |
| Ex. 28G | A1-11 (0.3 g) | R-18 (H) (10 g) | C-1 | W-1 | A2/B2 (6/4) | 15.0 | 6.1 | 6.1 | 1.9 |
| Ex. 29G | A1-12 (0.3 g) | R-18 (H) (10 g) | C-1 | W-1 | A3/B1 (6/4) | 15.0 | 6.1 | 6.7 | 1.9 |
| Ex. 30G | A1-3 (1 g) | R-18 (L) (10 g) | C-2 | W-1 | A1/B1 (6/4) | 13.2 | 6.7 | 4.5 | 1.9 |
| Ex. 31G | A1-3 (1 g) | R-18 (H) (10 g) | C-2 | W-1 | A1/B1 (6/4) | 13.5 | 6.1 | 6.2 | 1.9 |
| Ex. 32G | A1-3 (1 g) | R-18 (L) (10 g) | C-2 | W-1 | A1/B1 (6/4) | 13.2 | 6.7 | 5.0 | 1.9 |
| Ex. 33G | A1-15 (1 g) | R-19 (10 g) | C-2 | W-1 | A1/B1 (6/4) | 13.2 | 6.6 | 6.3 | 6.5 |
| Ex. 34G | A1-15 (1 g) | R-20 (10 g) | C-2 | W-1 | A1/B1 (6/4) | 13.2 | 6.5 | 6.4 | 1.9 |
| Ex. 35G | A1-16 (1 g) | R-21 (10 g) | C-2 | W-1 | A1/B1 (6/4) | 13.2 | 6.3 | 6.1 | 1.9 |
| Comp. 1G | Comp. Compound 1 (0.3 g) | R-2 (10 g) | C-1 | W-1 | A1/B1 (6/4) | 30.0 | 3.4 | 8.5 | 8.5 |
| Comp. 2G | Comp. Compound 2 (0.3 g) | R-2 (10 g) | C-1 | W-1 | A1/B1 (6/4) | 30.0 | 3.2 | 8.0 | 8.5 |
| Comp. 3G | Comp. Compound 3 (0.3 g) | R-2 (10 g) | C-1 | W-1 | A1/B1 (6/4) | 25.0 | 4.4 | 7.5 | 8.5 |
| Comp. 4G | Comp. Compound 4 (0.3 g) | R-2 (10 g) | C-1 | W-1 | A1/B1 (6/4) | 25.0 | 4.6 | 7.5 | 8.5 |

*based on the total solid content of the resist composition

Example H

Examples 1H to 4H and Comparative Examples 1H and 2H

<Preparation of Resist>

Referring to Table 8 below, with respect to each of the resists, the individual components were dissolved in the solvent and passed through a polytetrafluoroethylene filter of 0.1 μm pore size, thereby obtaining a negative resist solution of 8 mass % solid content. The thus obtained negative resist solution was evaluated by the following methods.

<Evaluation of Resist>

Each of the obtained negative resist solutions was uniformly applied onto a silicon substrate having undergone a hexamethyldisilazane treatment by use of a spin coater, and heated and dried on a hot plate at 120° C. for 60 seconds, thereby obtaining a 0.15 μm resist film.

[Sensitivity, Resolving Power (γ)]

The obtained resist films were exposed by use of EUV ray (wavelength: 13 nm) while changing the exposure intensity by 0.5 mJ/cm² at a time, and the exposed film was baked at 110° C. for 90 seconds. Thereafter, using a 2.38 mass % aqueous tetramethylammonium hydroxide (TMAH) solution, the dissolution rate at each of the exposure intensities was measured, thereby obtaining a sensitivity curve.

Properties were evaluated in the same manner as in Example G (EUV positive exposure).

TABLE 8

| EUV negative exposure | | | | | | | | | | |
|---|---|---|---|---|---|---|---|---|---|---|
| | (A1) Acid generator (0.3 g) | (C) Resin (10 g) | (D) Cross-linking agent (3.0 g) | (F) Basic compound (0.02 g) | (G) Surfactant (0.1 mass %)* | (H) Solvent (mass ratio) | Sensitivity (mJ/cm$^2$) | Resolving power $\gamma$ | Roughness (nm) | Outgas (%) |
| Ex. 1H | A1-1 | P-3 | CL-1 | C-1 | W-1 | A1/B1 (6/4) | 15.3 | 5.0 | 9.2 | 6.5 |
| Ex. 2H | A1-2 | P-3 | CL-1 | C-1 | W-2 | A1/B1 (6/4) | 15.8 | 5.0 | 11.0 | 2.1 |
| Ex. 3H | A1-3 | P-3 | CL-1 | C-1 | W-3 | A1/B1 (6/4) | 14.0 | 5.5 | 9.0 | 1.8 |
| Ex. 4H | A1-3 | P-3 | CL-2 | C-1 | W-1 | A1/B1 (6/4) | 15.3 | 5.0 | 9.5 | 1.9 |
| Comp. 1H | Comp. compound 1 | P-1 | CL-1 | C-1 | W-1 | A1/B1 (6/4) | 31.0 | 3.3 | 15.0 | 8.2 |
| Comp. 2H | Comp. compound 2 | P-1 | CL-1 | C-1 | W-1 | A1/B1 (6/4) | 30.0 | 3.2 | 16.0 | 8.2 |

*based on the total solid content of the resist composition

It is apparent from the results of Tables 7 and 8 that the resist composition of the present invention realizes high sensitivity and high contrast and excels in outgas performance as compared with those of the comparative compositions in the performance evaluation under EUV ray exposure.

What is claimed is:

1. An actinic ray-sensitive or radiation-sensitive resin composition comprising any of the compounds of general formula (I) below;

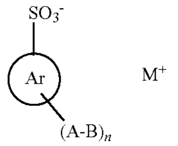

(I)

wherein:

Ar represents a benzene ring that may have a substituent other than the -(A-B) groups and at least one o-position of the benzene ring is substituted with the -(A-B) group;

n is 3;

A represents any one, or a combination of two or more members selected from a single bond, an alkylene group, —O—, —S—, —C(═O)—, —S(═O)—, —S(═O)$_2$— and —OS(═O)$_2$—, provided that —C(═O)O— is excluded;

B represents a group containing a cycloaliphatic group having 4 or more carbon atoms wherein either a tertiary or a quaternary carbon atom is contained, the three -(A-B) groups may be identical to or different from each other and the three -(A-B) groups are substituted at two o-positions and one p-position of the benzene ring; and M$^+$ represents an organic onium ion.

2. The actinic ray-sensitive or radiation-sensitive resin composition according to claim 1, further containing a resin that is decomposed by the action of an acid to thereby exhibit an increased solubility in an alkali developer.

3. The actinic ray-sensitive or radiation-sensitive resin composition according to claim 2, wherein the resin comprises a repeating unit of following general formula (1),

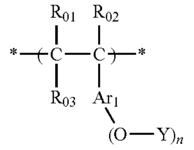

(1)

wherein in formula (1), each of R01, R02 and R03 independently represents a hydrogen atom, an alkyl group, a cycloalkyl group, a halogen atom, a cyano group or an alkoxycarbonyl group;

Ar1 represents an aromatic ring group, or alternatively, R03 and Ar1 may be simultaneously alkylene groups and bonded to each other so as to form a 5-membered or 6-membered ring in cooperation with —C—C—;

each of n Y's independently represents a hydrogen atom or a group that is eliminated by the action of an acid, provided that at least one of the Y's is a group represented by general formula (2) below;

n is an integer of 1 to 4;

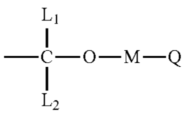

(2)

wherein in formula (2), each of L1 and L2 independently represents a hydrogen atom, an alkyl group, a cycloalkyl group, an aryl group or an aralkyl group;

M represents a single bond or a bivalent connecting group;

Q represents an alkyl group, a cycloalkyl group, an alicyclic group optionally containing a heteroatom, an aromatic ring group optionally containing a heteroatom, an amino group, an ammonium group, a mercapto group, a cyano group or an aldehyde group;

at least two of Q, M and L1 may be bonded to each other to thereby form a 5-membered or 6-membered ring, and wherein the group of the formula -M-Q is a group having 5 to 20 carbon atoms.

4. A method of forming a pattern, comprising the steps of forming the actinic-ray- or radiation-sensitive resin composition according to claim 1 into a film, exposing the film and developing the exposed film.

5. The method of forming a pattern according to claim 4, wherein the exposure is carried out by use of X-rays, electron beams or EUV.

6. The actinic ray-sensitive or radiation-sensitive resin composition according to claim 1, wherein in general formula (I), the three -(A-B) groups are the same.

7. The actinic ray-sensitive or radiation-sensitive resin composition according to claim 1, wherein in general formula (I), A represents a single bond.

8. An actinic ray-sensitive or radiation-sensitive resin composition comprising any of the compounds of general formula (I) below, a resin soluble in an alkali developer and an acid crosslinking agent capable of crosslinking with the resin soluble in an alkali developer by the action of an acid;

(I)

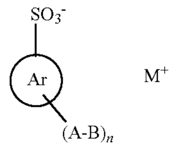

wherein:

- Ar represents a benzene ring that may have a substituent other than the -(A-B) groups and two o-positions of the benzene ring are substituted with the -(A-B) groups;
- n is an integer of 2 to 5;
- A represents any one, or a combination of two or more members selected from a single bond, an alkylene group, —O—, —S—, —C(═O)—, —S(═O)—, $—S(═O)_2—$ and $—OS(═O)_2—$, provided that —C(═O)O— is excluded;
- B represents a group containing a noncyclic hydrocarbon group having 5 or more carbon atoms or a cycloaliphatic group having 4 or more carbon atoms wherein either a tertiary or a quaternary carbon atom is contained,
- the two or more -(A-B) groups may be identical to or different from each other; and
- $M^+$ represents an organic onium ion.

9. The actinic ray-sensitive or radiation-sensitive resin composition according to claim 8, wherein in the general formula (I), B represents a cycloaliphatic group having 4 or more carbon atoms.

10. A method of forming a pattern, comprising the steps of forming the actinic-ray- or radiation-sensitive resin composition according to claim 8 into a film, exposing the film and developing the exposed film.

11. The method of forming a pattern according to claim 10, wherein the exposure is carried out by use of X-rays, electron beams or EUV.

12. The actinic ray-sensitive or radiation-sensitive resin composition according to claim 8, wherein in general formula (I), n=3.

13. The actinic ray-sensitive or radiation-sensitive resin composition according to claim 12, wherein in general formula (I), the three -(A-B) groups are substituted at two o-positions and one p-position of the benzene ring.

14. The actinic ray-sensitive or radiation-sensitive resin composition according to claim 12, wherein in general formula (I), the three -(A-B) groups are the same.

15. The actinic ray-sensitive or radiation-sensitive resin composition according to claim 8, wherein in general formula (I), A represents a single bond.

16. A compound of general formula (I) below;

(I)

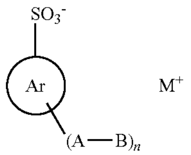

wherein:

- Ar represents an aromatic ring that may have a substituent other than the -(A-B) groups;
- n is an integer of 2 to 5;
- A represents a single bond;
- B represents a group containing a cycloaliphatic group having 4 or more carbon atoms wherein either a tertiary or a quaternary carbon atom is contained,
- the two or more -(A-B) groups may be identical to or different from each other; and
- $M^+$ represents an organic onium ion, and
- wherein a substituent other than -(A-B) groups which aromatic ring Ar in general formula (I) may have is selected from a group consisting of:

alkoxy group, an aryloxy group, an alkylthioxy group, an arylthioxy group, an alkoxycarbonyl group, a phenoxycarbonyl group, and acetoxy group, a liner or branched alkyl group, an alkenyl group, an alkynyl group, an aryl group, an acyl group, a hydroxyl group, a carboxyl group and a sulfonate group.

17. A compound of general formula (I) according to claim 16, wherein two o-positions of the benzene ring are substituted with the -(A-B) groups.

18. A compound of general formula (I) according to claim 16, wherein, n=3.

19. A compound of general formula (I) according to claim 16, wherein the three -(A-B) groups are substituted at two o-positions and one p-position of the benzene ring.

20. A compound of general formula (I) according to claim 16, wherein the three -(A-B) groups are the same.

21. A compound of general formula (I) according to claim 16, wherein the aromatic ring represented by Ar has no substituent other than the -(A-B) groups.

* * * * *